(12) United States Patent
Nguyen et al.

(10) Patent No.: US 8,685,258 B2
(45) Date of Patent: Apr. 1, 2014

(54) SYSTEMS AND METHODS FOR CONVEYING MULTIPLE BLOOD COMPONENTS TO A RECIPIENT

(75) Inventors: Lan T. Nguyen, Vernon Hills, IL (US); Kyungyoon Min, Kildeer, IL (US); Tony Nguyen, Valhalla, NY (US)

(73) Assignee: Fenwal, Inc., Lake Zurich, IL (US)

( * ) Notice: Subject to any disclaimer, the term of this patent is extended or adjusted under 35 U.S.C. 154(b) by 1038 days.

(21) Appl. No.: 12/394,258

(22) Filed: Feb. 27, 2009

(65) Prior Publication Data
US 2009/0211989 A1 Aug. 27, 2009

Related U.S. Application Data

(60) Provisional application No. 61/032,003, filed on Feb. 27, 2008.

(51) Int. Cl.
- *B01D 21/26* (2006.01)
- *A61M 1/38* (2006.01)
- *A61M 1/36* (2006.01)
- *A61M 1/30* (2006.01)
- *A61M 1/02* (2006.01)

(52) U.S. Cl.
CPC ........... *B01D 21/262* (2013.01); *A61M 1/3693* (2013.01); *A61M 1/30* (2013.01); *A61M 1/02* (2013.01); *A61M 1/029* (2013.01); *A61M 1/024* (2013.01); *A61M 1/0209* (2013.01); *A61M 1/38* (2013.01); *A61M 2001/3696* (2013.01); *A61M 2205/128* (2013.01)
USPC ............ 210/782; 210/787; 422/44; 604/5.01; 604/6.11; 604/6.15

(58) Field of Classification Search
USPC ........... 210/782, 787; 422/44; 604/5.01, 6.11, 604/6.15
See application file for complete search history.

(56) References Cited

U.S. PATENT DOCUMENTS

| | | |
|---|---|---|
| 3,244,363 A | 4/1966 | Hein |
| 3,489,145 A | 1/1970 | Judson et al. |
| 4,010,894 A | 3/1977 | Kellogg et al. |
| 4,094,461 A | 6/1978 | Kellogg et al. |
| 4,189,382 A | 2/1980 | Zine, Jr. et al. |
| 4,303,193 A | 12/1981 | Latham, Jr. et al. |
| 4,402,680 A | 9/1983 | Schoendorfer |
| 4,596,657 A | 6/1986 | Wisdom |
| 4,640,785 A | 2/1987 | Carroll et al. |
| 4,647,279 A | 3/1987 | Mulzet et al. |
| 4,708,712 A | 11/1987 | Mulzet |
| 4,713,176 A | 12/1987 | Schoendorfer et al. |
| 4,776,964 A | 10/1988 | Schoendorfer et al. |
| 4,798,577 A | 1/1989 | Brenneman et al. |
| 4,806,252 A | 2/1989 | Brown et al. |
| 4,816,168 A | 3/1989 | Carrol et al. |
| 4,818,418 A | 4/1989 | Saunders |
| 4,834,890 A | 5/1989 | Brown et al. |

(Continued)

*Primary Examiner* — Krishnan S Menon
(74) *Attorney, Agent, or Firm* — Cook Alex Ltd.

(57) ABSTRACT

Systems and methods are provided for conveying an amount of red blood cells and an amount of plasma to a blood source. Blood is conveyed from a blood source into a separation device and the separation device is operated to separate the blood into a layer containing red blood cells and a layer containing plasma. Red blood cells and plasma are removed from the separation device and volumes of the red blood cells and plasma are conveyed to the blood source. The volumes of red blood cells and plasma are alternately conveyed to the blood source for said amounts of red blood cells and plasma.

20 Claims, 68 Drawing Sheets

(56) References Cited

U.S. PATENT DOCUMENTS

| | | | |
|---|---|---|---|
| 4,867,887 | A | 9/1989 | Smith |
| 4,871,462 | A | 10/1989 | Fischel et al. |
| 4,895,666 | A | 1/1990 | Franzen et al. |
| 4,911,833 | A | 3/1990 | Schoendorfer et al. |
| 4,944,883 | A | 7/1990 | Schoendorfer et al. |
| 4,954,264 | A | 9/1990 | Smith |
| 4,957,637 | A | 9/1990 | Cornell |
| 4,957,638 | A | 9/1990 | Smith |
| 4,964,976 | A | 10/1990 | Lysaght et al. |
| 4,981,585 | A | 1/1991 | Kelley et al. |
| 4,985,153 | A | 1/1991 | Kuroda et al. |
| 5,061,381 | A | 10/1991 | Burd |
| 5,071,570 | A | 12/1991 | Shiraki et al. |
| 5,076,911 | A | 12/1991 | Brown et al. |
| 5,100,564 | A | 3/1992 | Pall et al. |
| 5,124,434 | A | 6/1992 | O'Brien |
| 5,147,290 | A * | 9/1992 | Jonsson .................. 604/6.04 |
| 5,173,193 | A | 12/1992 | Schembri |
| 5,186,844 | A | 2/1993 | Burd et al. |
| 5,217,627 | A | 6/1993 | Pall et al. |
| 5,232,437 | A | 8/1993 | Lysaght et al. |
| 5,258,126 | A | 11/1993 | Pall et al. |
| 5,281,342 | A | 1/1994 | Biesel et al. |
| 5,311,980 | A | 5/1994 | Munkner et al. |
| 5,316,540 | A | 5/1994 | McMannis et al. |
| 5,370,802 | A | 12/1994 | Brown |
| 5,386,734 | A | 2/1995 | Pusinelli |
| 5,387,187 | A | 2/1995 | Fell et al. |
| 5,454,958 | A | 10/1995 | Fiehler |
| 5,456,845 | A | 10/1995 | Nishimura et al. |
| 5,458,566 | A | 10/1995 | Herrig et al. |
| 5,494,592 | A | 2/1996 | Latham, Jr. et al. |
| 5,506,333 | A | 4/1996 | O'Brien et al. |
| 5,523,004 | A | 6/1996 | Tanokura et al. |
| 5,545,339 | A | 8/1996 | Bormann et al. |
| 5,547,591 | A | 8/1996 | Hagihara et al. |
| 5,556,557 | A | 9/1996 | O'Brien et al. |
| 5,585,007 | A | 12/1996 | Antanavich et al. |
| 5,603,845 | A | 2/1997 | Holm |
| 5,607,579 | A | 3/1997 | Latham, Jr. et al. |
| 5,616,254 | A | 4/1997 | Pall et al. |
| 5,632,905 | A | 5/1997 | Haynes |
| 5,634,893 | A | 6/1997 | Rishton |
| 5,637,082 | A | 6/1997 | Pages et al. |
| 5,651,766 | A | 7/1997 | Kingsley et al. |
| 5,653,887 | A | 8/1997 | Wahl et al. |
| 5,663,051 | A | 9/1997 | Vlasselaer |
| 5,690,815 | A | 11/1997 | Krasnoff et al. |
| 5,693,232 | A | 12/1997 | Brown et al. |
| 5,702,357 | A | 12/1997 | Bainbridge et al. |
| 5,704,888 | A | 1/1998 | Hlavinka et al. |
| 5,704,889 | A | 1/1998 | Hlavinka et al. |
| 5,707,876 | A | 1/1998 | Levine |
| 5,720,716 | A | 2/1998 | Blakeslee et al. |
| 5,722,926 | A | 3/1998 | Hlavinka et al. |
| 5,722,946 | A | 3/1998 | Mudloff et al. |
| 5,728,060 | A | 3/1998 | Kingsley et al. |
| 5,733,253 | A | 3/1998 | Headley et al. |
| 5,738,796 | A | 4/1998 | Bormann et al. |
| 5,750,025 | A | 5/1998 | Holmes et al. |
| 5,769,811 | A | 6/1998 | Stacey et al. |
| 5,779,660 | A | 7/1998 | Kingsley et al. |
| 5,788,662 | A | 8/1998 | Antanavich et al. |
| 5,792,038 | A | 8/1998 | Hlavinka |
| 5,837,150 | A | 11/1998 | Langley et al. |
| 5,840,502 | A | 11/1998 | Van Vlasselaer |
| 5,849,203 | A | 12/1998 | Brown et al. |
| 5,853,382 | A | 12/1998 | Kingsley et al. |
| 5,855,773 | A | 1/1999 | LaSota |
| 5,858,238 | A | 1/1999 | McRea et al. |
| 5,858,253 | A | 1/1999 | Holm |
| 5,876,321 | A | 3/1999 | Hlavinka et al. |
| 5,876,611 | A | 3/1999 | Shettigar |
| 5,879,280 | A | 3/1999 | Hlavinka et al. |
| 5,882,289 | A | 3/1999 | Sakota et al. |
| 5,904,645 | A | 5/1999 | Hlavinka |
| 5,906,570 | A | 5/1999 | Langley et al. |
| 5,913,768 | A | 6/1999 | Langley et al. |
| 5,939,319 | A | 8/1999 | Hlavinka et al. |
| 5,951,877 | A | 9/1999 | Langley et al. |
| 5,961,842 | A | 10/1999 | Min et al. |
| 5,964,724 | A | 10/1999 | Rivera et al. |
| 5,971,948 | A | 10/1999 | Pages et al. |
| 6,007,509 | A | 12/1999 | Kingsley et al. |
| 6,022,306 | A | 2/2000 | Dumont et al. |
| 6,027,655 | A | 2/2000 | Holm |
| 6,027,657 | A | 2/2000 | Min et al. |
| 6,051,146 | A | 4/2000 | Green et al. |
| 6,053,856 | A | 4/2000 | Hlavinka |
| 6,063,297 | A | 5/2000 | Antanavich et al. |
| 6,071,422 | A | 6/2000 | Hlavinka et al. |
| 6,071,423 | A | 6/2000 | Brown et al. |
| 6,099,491 | A | 8/2000 | Headley et al. |
| 6,102,883 | A | 8/2000 | Kingsley et al. |
| 6,106,727 | A | 8/2000 | Krasnoff et al. |
| 6,113,554 | A | 9/2000 | Gilcher et al. |
| 6,127,656 | A | 10/2000 | Kilmer et al. |
| 6,179,801 | B1 | 1/2001 | Holmes et al. |
| 6,196,987 | B1 | 3/2001 | Holmes et al. |
| 6,200,287 | B1 | 3/2001 | Keller et al. |
| 6,234,989 | B1 | 5/2001 | Brierton et al. |
| 6,251,284 | B1 | 6/2001 | Bishof et al. |
| 6,267,925 | B1 | 7/2001 | Pages |
| 6,296,602 | B1 | 10/2001 | Headley |
| 6,312,607 | B1 | 11/2001 | Brown et al. |
| 6,315,709 | B1 | 11/2001 | Garibaldi et al. |
| 6,322,488 | B1 | 11/2001 | Westberg et al. |
| 6,322,709 | B1 | 11/2001 | Krasnoff et al. |
| 6,334,842 | B1 | 1/2002 | Hlavinka et al. |
| 6,348,156 | B1 | 2/2002 | Vishnoi et al. |
| 6,354,986 | B1 | 3/2002 | Hlavinka et al. |
| 6,361,518 | B1 | 3/2002 | Brierton et al. |
| 6,361,700 | B2 | 3/2002 | Gates et al. |
| 6,379,322 | B1 | 4/2002 | Kingsley et al. |
| 6,387,263 | B1 | 5/2002 | Bhaskar et al. |
| 6,398,972 | B1 | 6/2002 | Blasetti et al. |
| 6,402,702 | B1 | 6/2002 | Gilcher et al. |
| 6,440,372 | B1 | 8/2002 | Pages |
| 6,464,624 | B2 | 10/2002 | Pages |
| 6,471,855 | B1 | 10/2002 | Odak et al. |
| 6,475,175 | B1 | 11/2002 | Rivera et al. |
| 6,497,674 | B1 | 12/2002 | Steele et al. |
| 6,524,231 | B1 | 2/2003 | Westberg et al. |
| 6,537,445 | B2 | 3/2003 | Muller |
| 6,558,307 | B2 | 5/2003 | Headley |
| 6,582,349 | B1 | 6/2003 | Cantu et al. |
| 6,596,180 | B2 | 7/2003 | Baugh et al. |
| 6,605,223 | B2 | 8/2003 | Jorgensen et al. |
| 6,610,002 | B2 | 8/2003 | Dolecek |
| 6,613,009 | B1 | 9/2003 | Bainbridge et al. |
| 6,632,191 | B1 | 10/2003 | Headley et al. |
| 6,641,552 | B1 | 11/2003 | Kingsley et al. |
| 6,649,072 | B2 | 11/2003 | Brandt et al. |
| 6,652,476 | B2 | 11/2003 | Langley et al. |
| 6,695,803 | B1 | 2/2004 | Robinson et al. |
| 6,705,983 | B1 | 3/2004 | Rochat |
| 6,706,008 | B2 | 3/2004 | Vishnoi et al. |
| 6,709,377 | B1 | 3/2004 | Rochat |
| 6,730,055 | B2 | 5/2004 | Bainbridge et al. |
| 6,736,768 | B2 | 5/2004 | Felt et al. |
| 6,743,192 | B1 | 6/2004 | Sakota et al. |
| 6,752,777 | B1 | 6/2004 | Takagi et al. |
| 6,759,007 | B1 * | 7/2004 | Westberg et al. .............. 422/44 |
| 6,773,389 | B2 | 8/2004 | Hlavinka et al. |
| 6,773,413 | B2 | 8/2004 | Keller et al. |
| 6,790,371 | B2 | 9/2004 | Dolecek |
| 6,800,054 | B2 | 10/2004 | Westberg et al. |
| 6,802,982 | B2 | 10/2004 | Brown |
| 6,849,039 | B2 | 2/2005 | Min et al. |
| 6,855,119 | B2 | 2/2005 | Rivera et al. |
| 6,875,191 | B2 | 4/2005 | Smith et al. |
| 6,890,291 | B2 | 5/2005 | Robinson et al. |
| 6,899,666 | B2 | 5/2005 | Brown |
| 6,899,813 | B2 | 5/2005 | Dolecek et al. |

(56) References Cited

U.S. PATENT DOCUMENTS

| | | |
|---|---|---|
| 6,902,539 B2 | 6/2005 | Bainbridge et al. |
| 6,945,948 B2 | 9/2005 | Bainbridge et al. |
| 6,982,038 B2 | 1/2006 | Dolecek et al. |
| 6,994,790 B2 | 2/2006 | Corbin, III et al. |
| 7,008,393 B2 | 3/2006 | Robinson et al. |
| 7,011,761 B2 | 3/2006 | Muller |
| 7,029,430 B2 | 4/2006 | Hlavinka et al. |
| 7,033,512 B2 | 4/2006 | Hlavinka et al. |
| 7,037,428 B1 | 5/2006 | Robinson et al. |
| 7,044,941 B2 | 5/2006 | Mathias et al. |
| 7,087,177 B2 | 8/2006 | Min et al. |
| 7,094,197 B2 | 8/2006 | Hlavinka et al. |
| 7,115,205 B2 | 10/2006 | Robinson et al. |
| 7,166,217 B2 | 1/2007 | Holmes et al. |
| 7,211,037 B2 | 5/2007 | Briggs et al. |
| 7,297,272 B2 | 11/2007 | Min et al. |
| 7,332,125 B2 | 2/2008 | Cianci et al. |
| 2001/0000185 A1 | 4/2001 | Keller et al. |
| 2001/0048892 A1 | 12/2001 | Bainbridge et al. |
| 2001/0051569 A1 | 12/2001 | Headley |
| 2002/0011452 A1 | 1/2002 | Mari et al. |
| 2002/0014462 A1 | 2/2002 | Muller |
| 2002/0020680 A1 | 2/2002 | Jorgensen |
| 2002/0033370 A1 | 3/2002 | Bainbridge et al. |
| 2002/0058575 A1 | 5/2002 | Hlavinka et al. |
| 2002/0090319 A1 | 7/2002 | Vandlik et al. |
| 2002/0104808 A1 | 8/2002 | Blasetti et al. |
| 2002/0128581 A1 | 9/2002 | Vishnoi et al. |
| 2002/0128583 A1 | 9/2002 | Min et al. |
| 2002/0128584 A1 | 9/2002 | Brown et al. |
| 2002/0142909 A1 | 10/2002 | Sakota |
| 2002/0147094 A1 | 10/2002 | Dolecek |
| 2002/0177799 A1 | 11/2002 | Rivera et al. |
| 2002/0183677 A1 | 12/2002 | Chang et al. |
| 2003/0052065 A1 | 3/2003 | Rosiello |
| 2003/0066807 A1 | 4/2003 | Suzuki |
| 2003/0102272 A1 | 6/2003 | Brown |
| 2003/0155312 A1 | 8/2003 | Ivansons et al. |
| 2003/0181305 A1 | 9/2003 | Briggs et al. |
| 2003/0191005 A1 | 10/2003 | Coelho et al. |
| 2003/0195455 A1 | 10/2003 | Bainbridge et al. |
| 2003/0205538 A1 | 11/2003 | Dorian et al. |
| 2003/0211927 A1 | 11/2003 | Cantu et al. |
| 2003/0233064 A1 | 12/2003 | Arm et al. |
| 2004/0026341 A1 | 2/2004 | Hogberg et al. |
| 2004/0065626 A1 | 4/2004 | Woo |
| 2004/0079707 A1 | 4/2004 | Smith et al. |
| 2004/0082459 A1 | 4/2004 | Min et al. |
| 2004/0104182 A1 | 6/2004 | Holmes et al. |
| 2004/0124157 A1 | 7/2004 | Briggs et al. |
| 2004/0127841 A1 | 7/2004 | Briggs |
| 2004/0147865 A1 | 7/2004 | Cianci et al. |
| 2004/0185998 A1 | 9/2004 | Hlavinka et al. |
| 2004/0195190 A1 | 10/2004 | Min et al. |
| 2004/0222168 A1 | 11/2004 | Frey et al. |
| 2004/0230152 A1 | 11/2004 | Bainbridge et al. |
| 2004/0236263 A1 | 11/2004 | Van Waeg et al. |
| 2004/0245189 A1 | 12/2004 | Robinson et al. |
| 2004/0249332 A1 | 12/2004 | Bainbridge et al. |
| 2004/0256318 A1 | 12/2004 | Iida et al. |
| 2005/0010158 A1 | 1/2005 | Brugger et al. |
| 2005/0029190 A1 | 2/2005 | Effenhauser et al. |
| 2005/0045567 A1 | 3/2005 | Holmes et al. |
| 2005/0082237 A1 | 4/2005 | Dolecek et al. |
| 2005/0137516 A1 | 6/2005 | Min et al. |
| 2005/0203469 A1 | 9/2005 | Bobroff et al. |
| 2006/0043007 A1 | 3/2006 | Tarumi et al. |
| 2006/0058167 A1 | 3/2006 | Ragusa et al. |
| 2006/0067857 A1 | 3/2006 | Samolyk |
| 2006/0186061 A1 | 8/2006 | Briggs et al. |
| 2006/0189469 A1 | 8/2006 | Briggs et al. |
| 2006/0226090 A1 | 10/2006 | Robinson et al. |
| 2007/0140898 A1 | 6/2007 | Olsen et al. |
| 2007/0140899 A1 | 6/2007 | Olsen et al. |

\* cited by examiner

FIG. 16
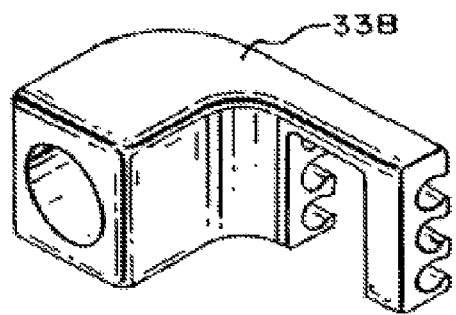
FIG. 17
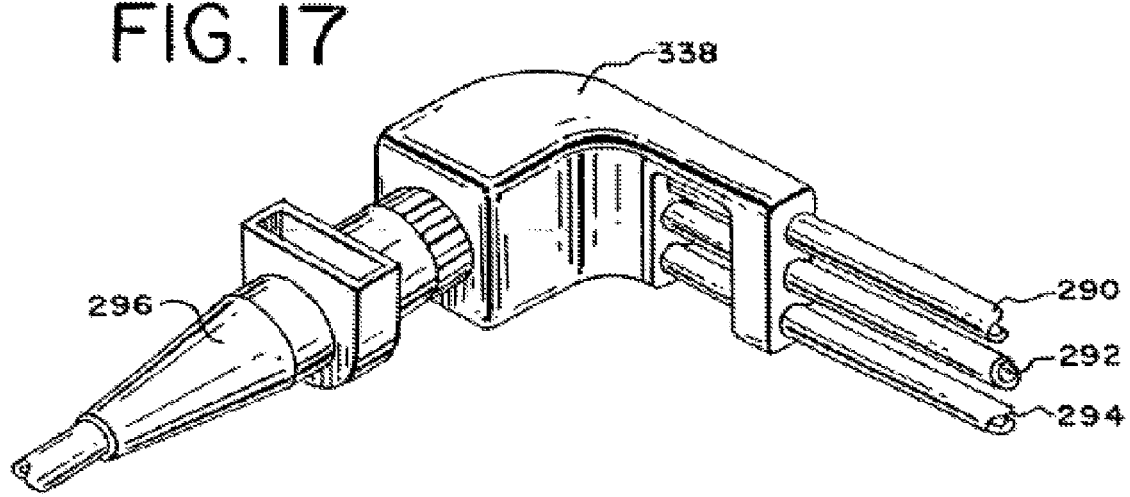
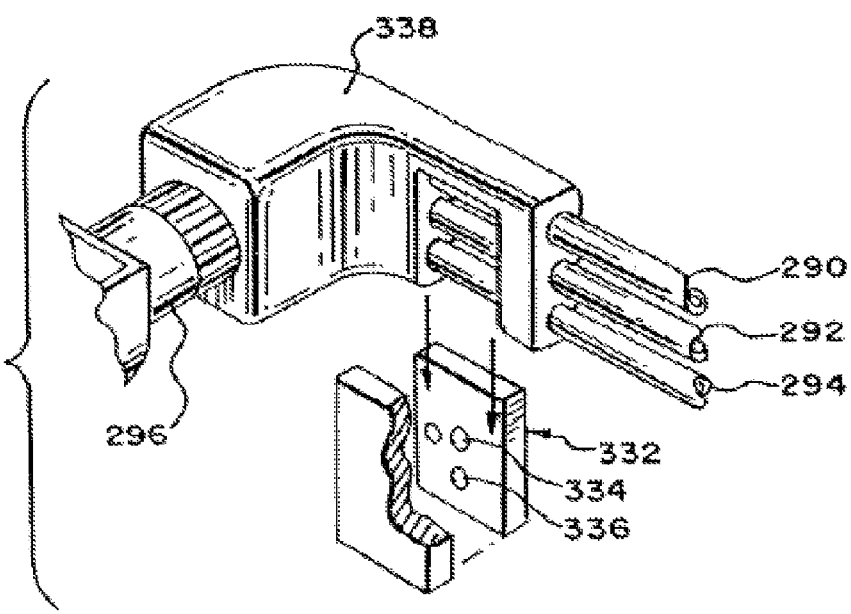
FIG. 18

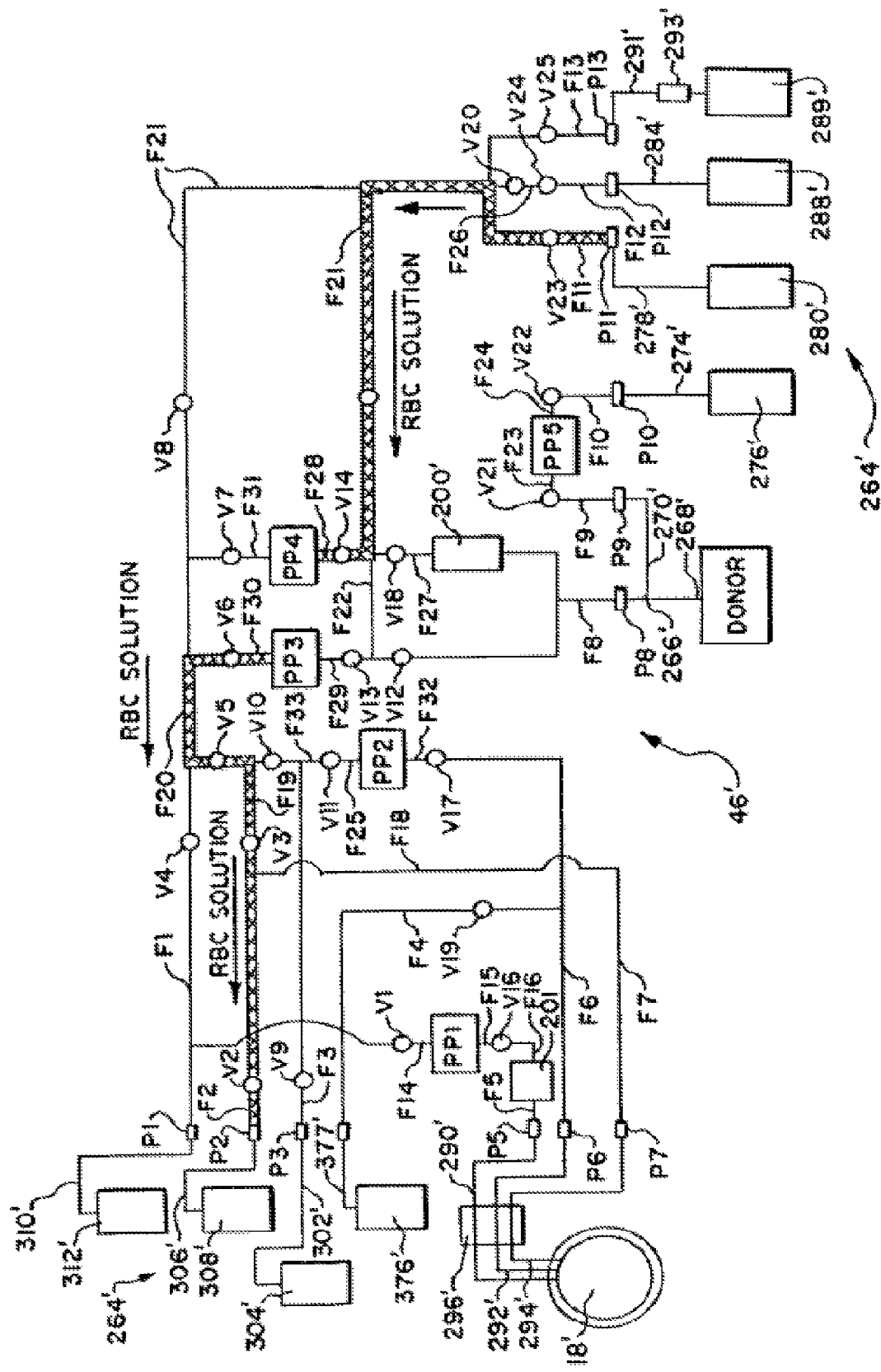

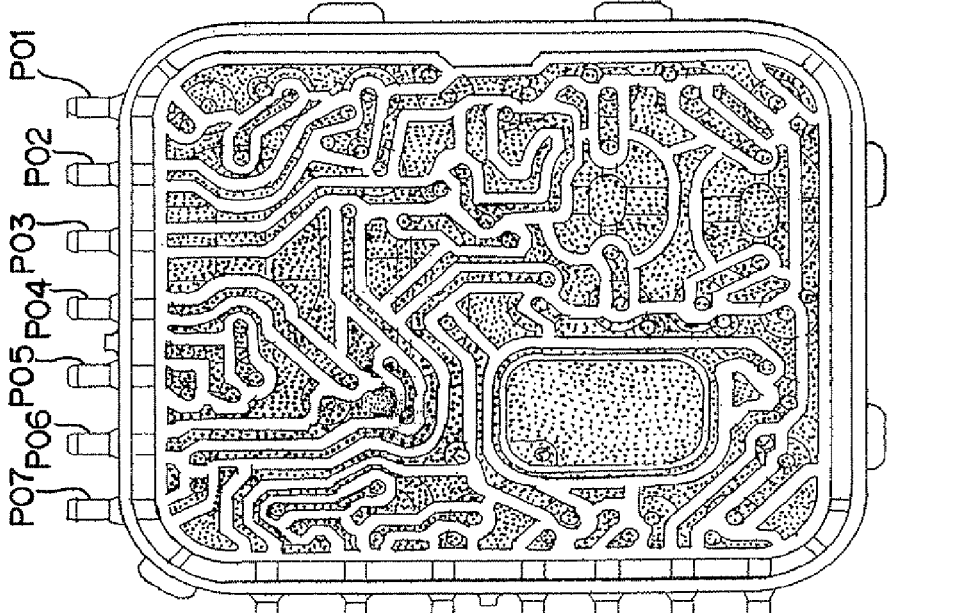
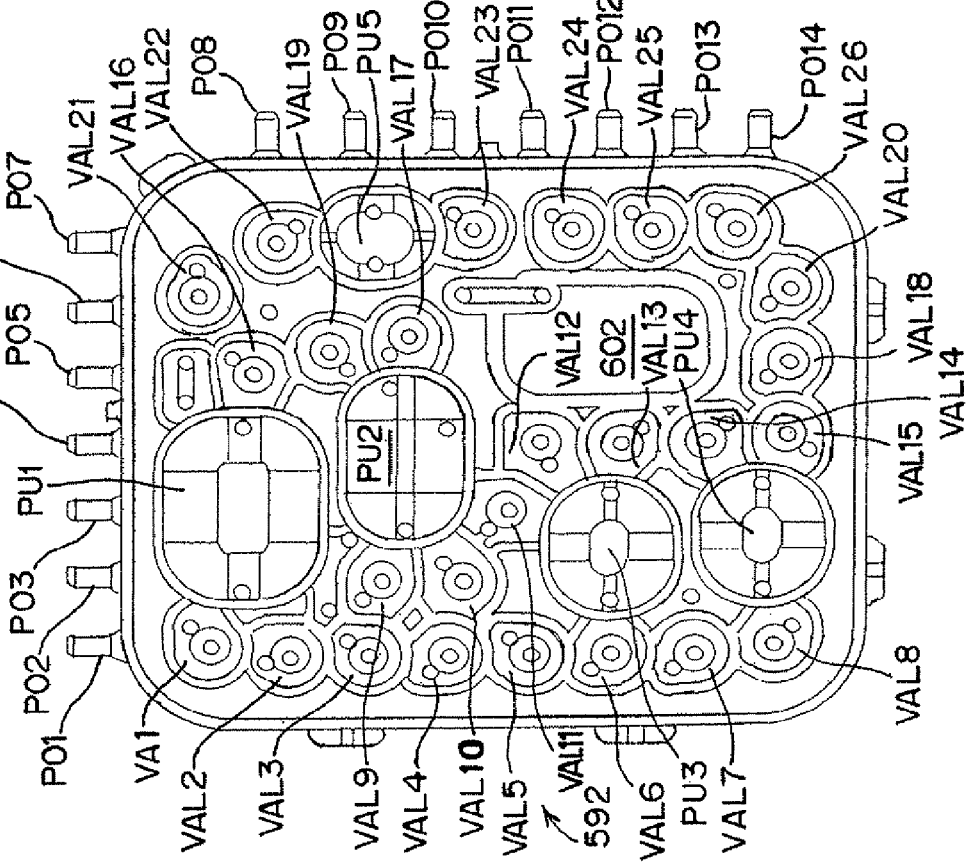

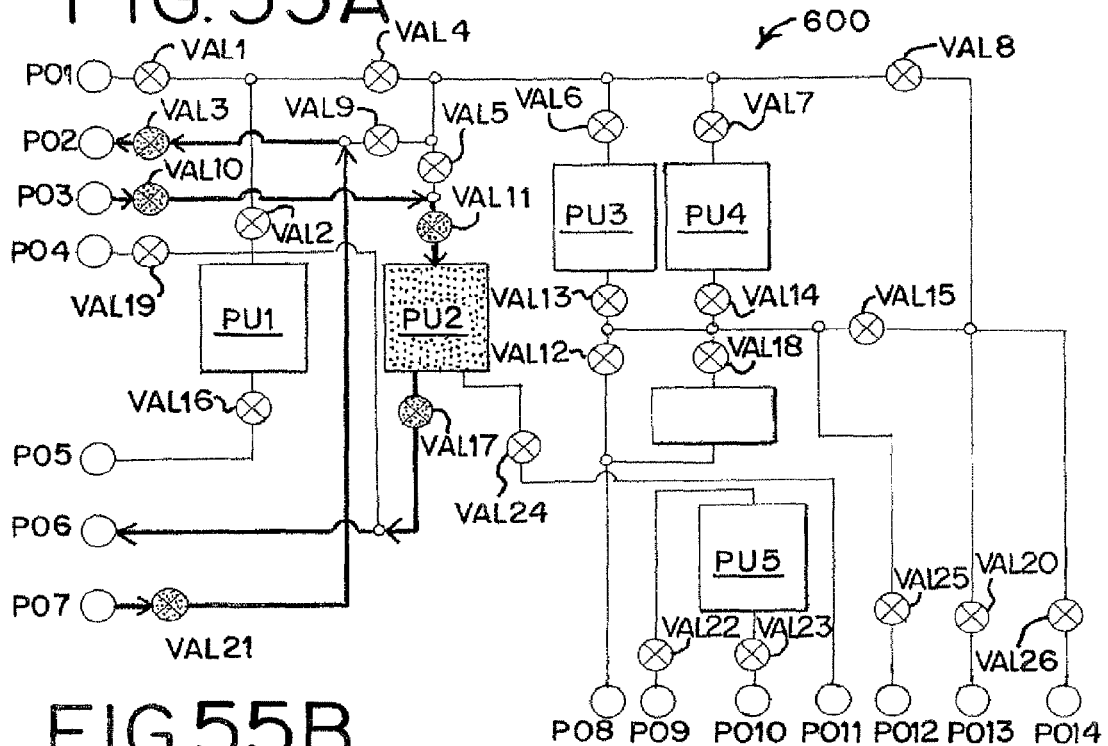
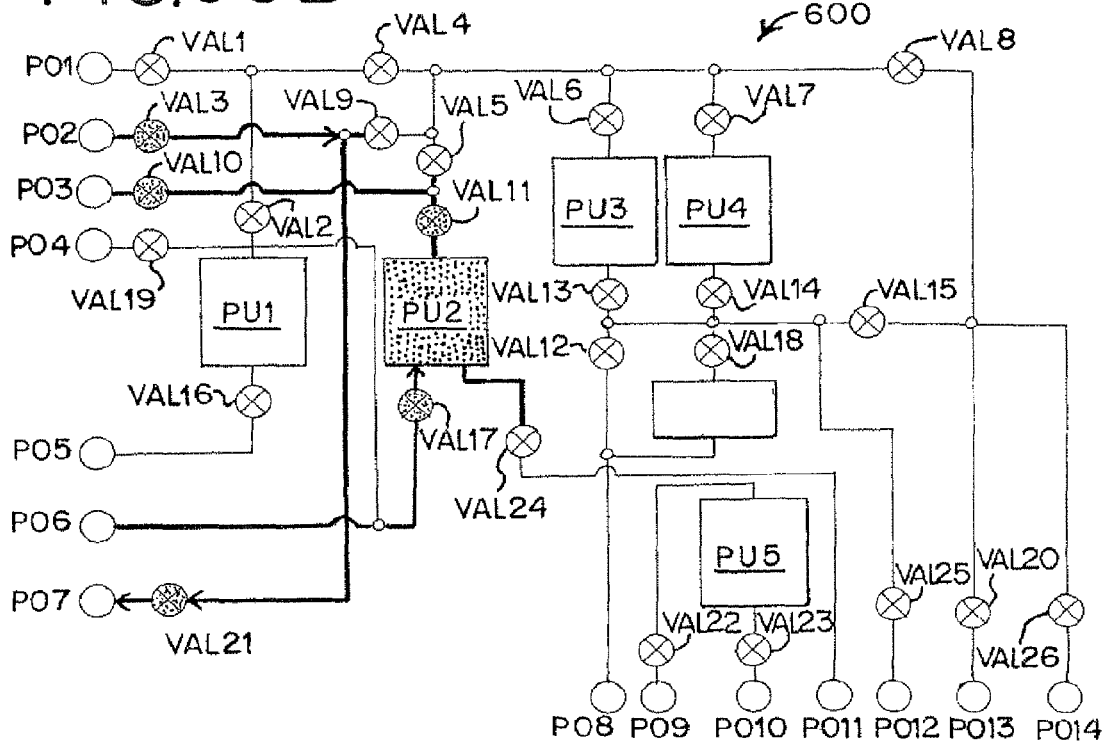

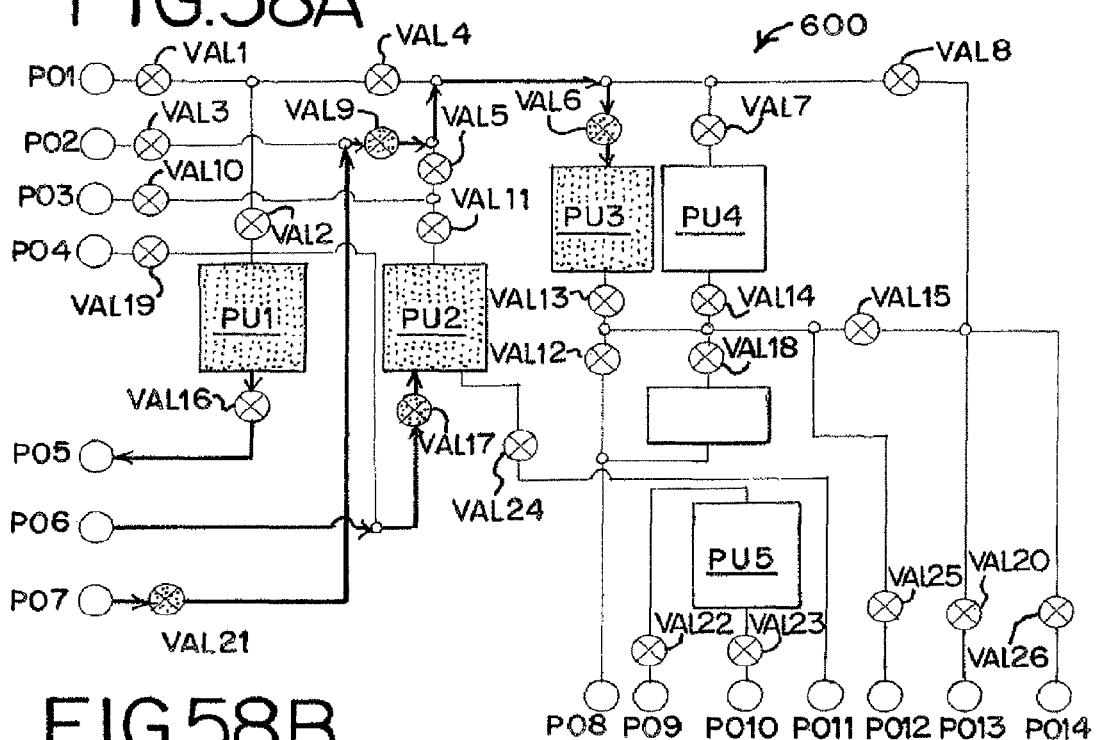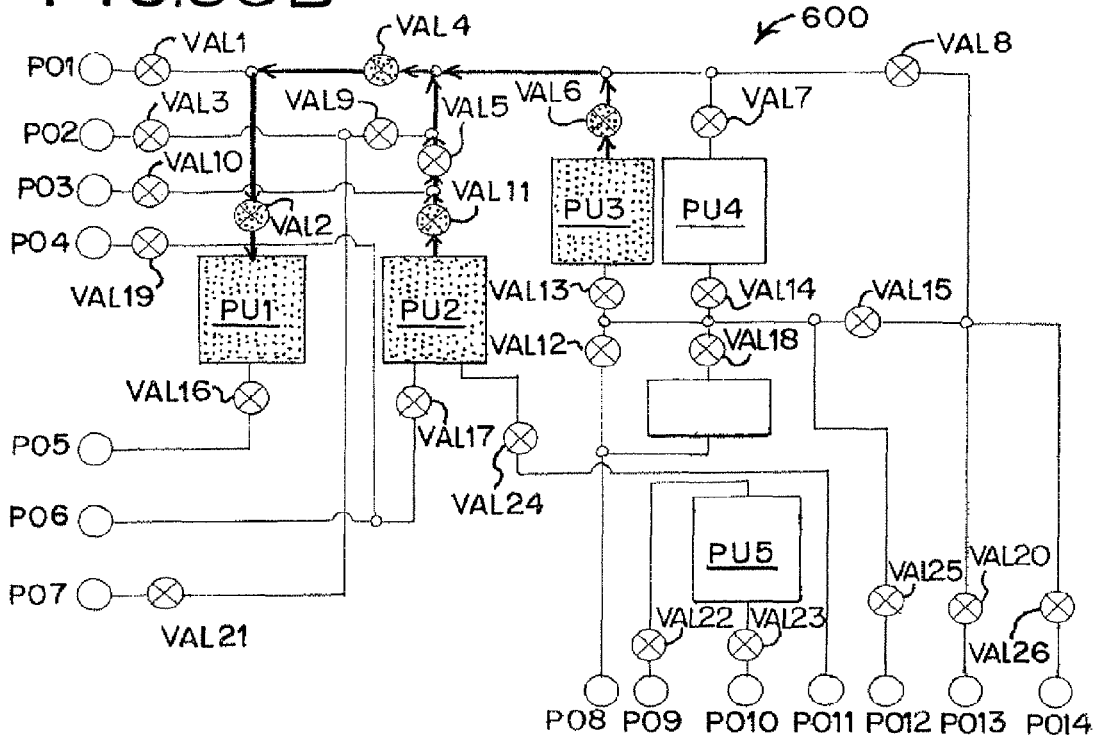

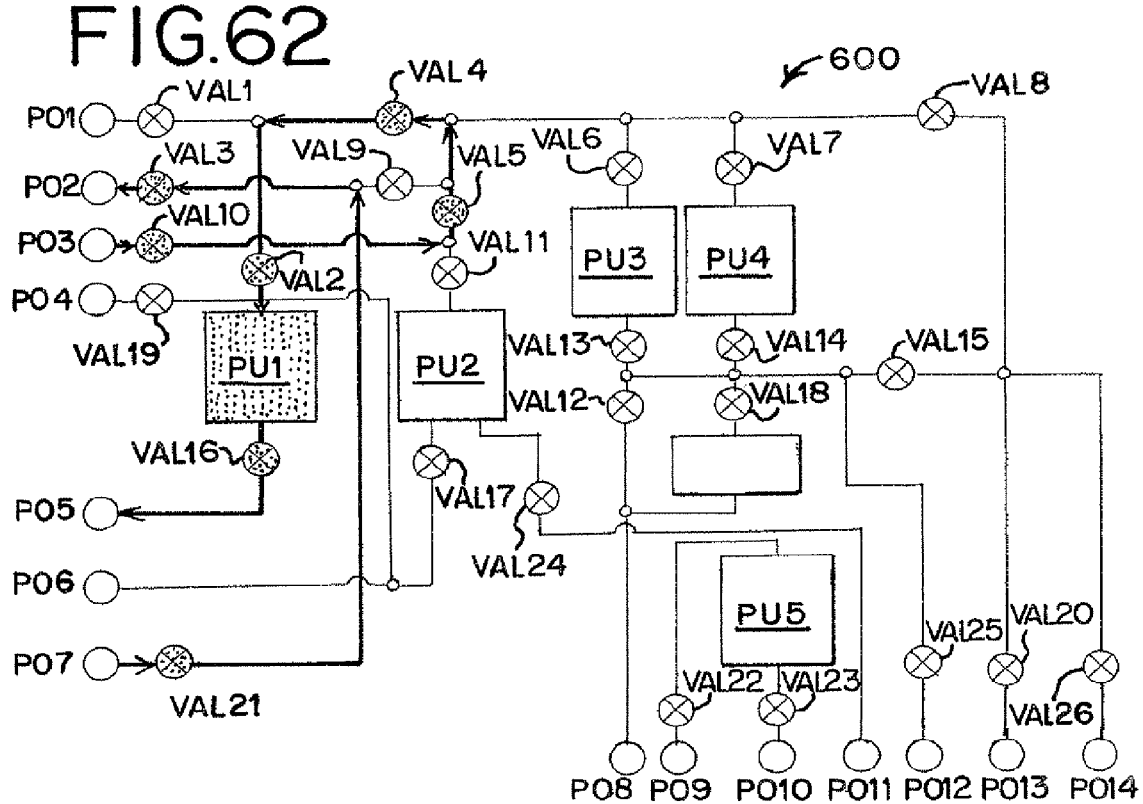

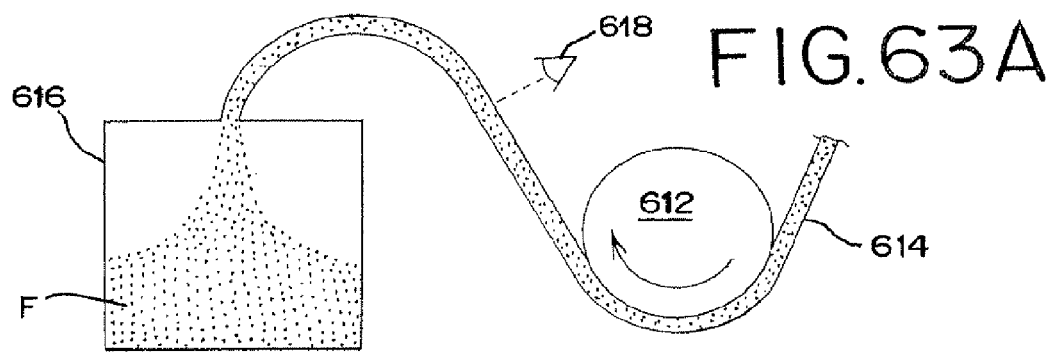
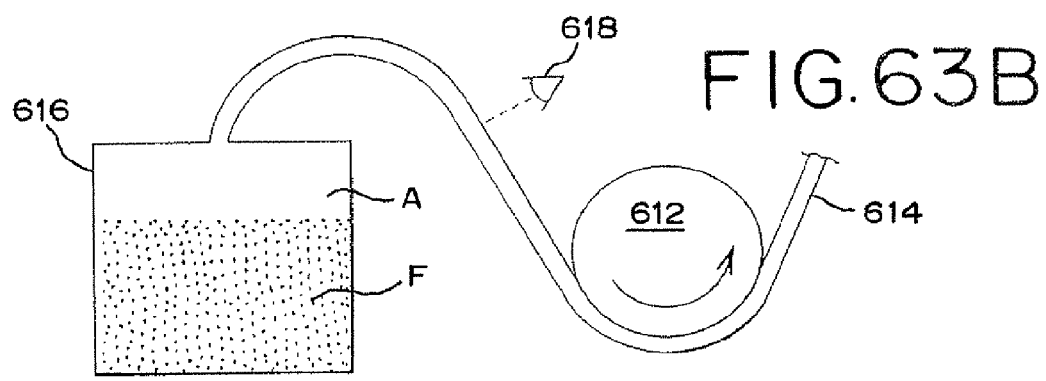
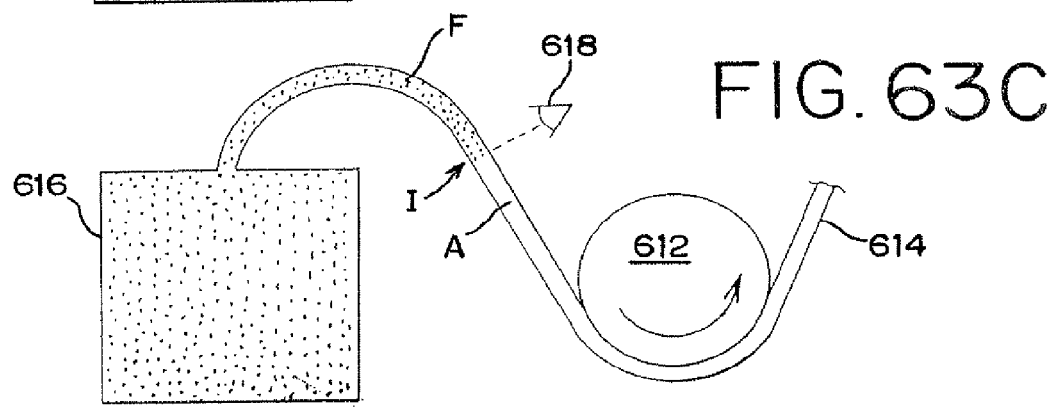
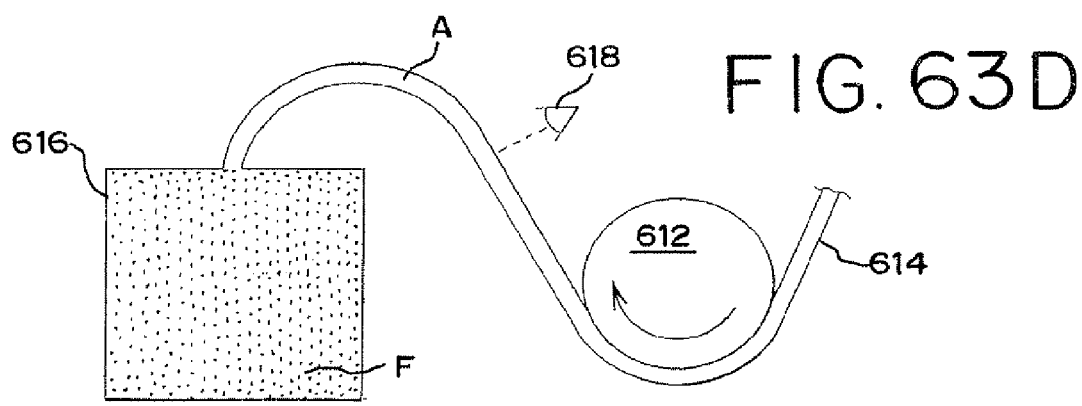

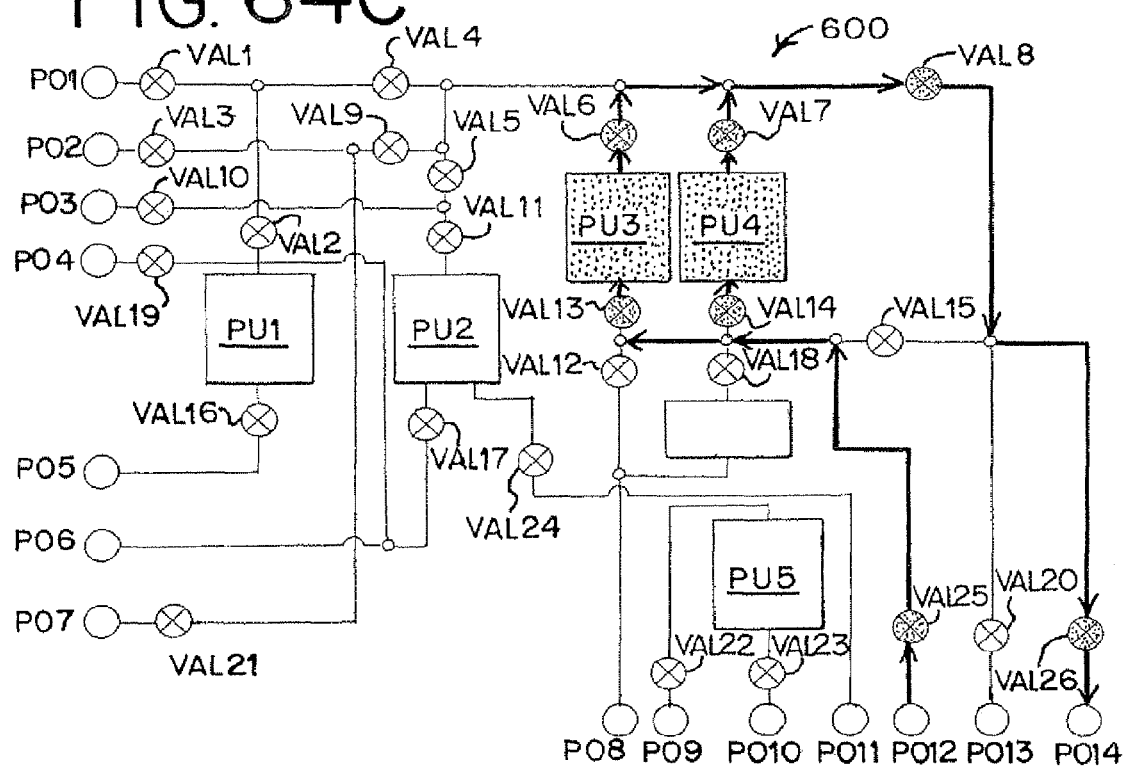

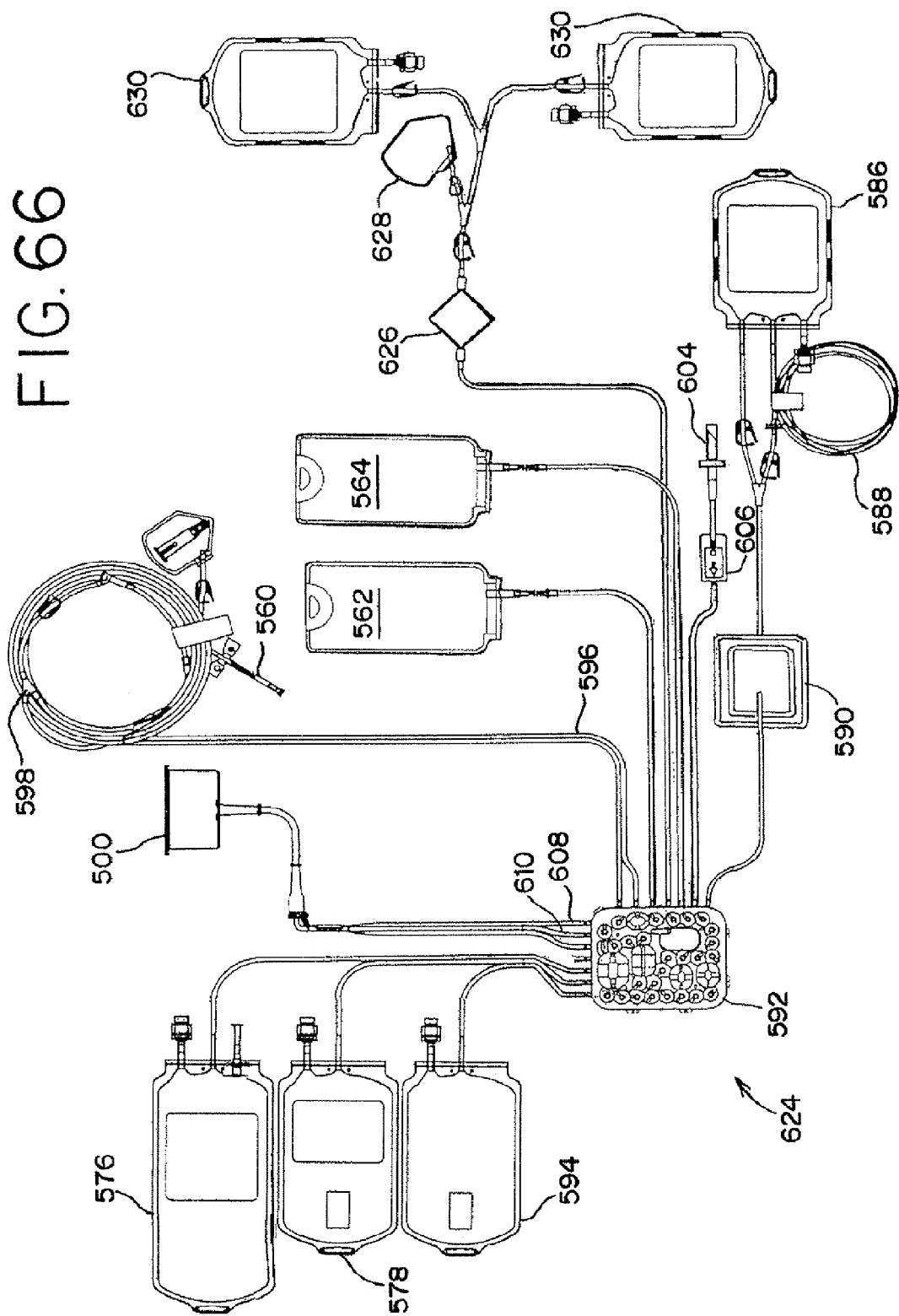

SYSTEMS AND METHODS FOR CONVEYING MULTIPLE BLOOD COMPONENTS TO A RECIPIENT

CROSS REFERENCE TO RELATED APPLICATIONS

This application claims priority from and the benefit of provisional patent application Ser. No. 61/032,003, filed Feb. 27, 2008, which is hereby incorporated herein by reference.

BACKGROUND

1. Field of the Disclosure

The present subject matter relates to systems and methods for processing and collecting blood, blood constituents, or other suspensions of cellular material.

2. Description of Related Art

Today people routinely separate whole blood, usually by centrifugation, into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Many conventional blood centrifuges are of a size that does not permit easy transport between collection sites. Furthermore, loading and unloading operations can sometimes be time consuming and tedious.

In addition, a need exists for further improved systems and methods for collecting blood components in a way that lends itself to use in a variety of applications, particularly, but not exclusively, where the operational and performance demands upon such fluid processing systems become more complex and sophisticated, even as the demand for smaller and more portable systems intensifies. The need therefore exists for automated blood processing controllers that can gather and generate more detailed information and control signals to aid the operator in maximizing processing and separation efficiencies.

The present subject matter described below has particular, but not exclusive application, in portable blood processing systems, such as those described in U.S. Pat. Nos. 6,348,156; 6,875,191; 7,011,761; 7,087,177; and 7,297,272 and U.S. Patent Application Publication No. 2005/0137516, which are hereby incorporated herein by reference, and such as embodied in the ALYX® blood processing systems marketed by Fenwal, Inc. of Lake Zurich, Ill.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately as set forth in the claims appended hereto.

In one aspect, a method for conveying an amount of red blood cells from a red blood cell source and an amount of plasma from a plasma source to a recipient comprises conveying a volume of red blood cells and a volume of plasma to the recipient and repeatedly alternating between conveying the red blood cells and plasma for said amounts of red blood cells and plasma.

In another separate aspect, a blood separation system for conveying an amount of red blood cells and an amount of plasma to a recipient comprises a red blood cell source containing red blood cells, a plasma source containing plasma, and a pump system. The system further includes a controller programmed to actuate the pump system to convey a volume of the red blood cells from the red blood cell source to the recipient and to actuate the pump system to convey a volume of the plasma from the plasma source to the recipient. The controller repeatedly alternates between actuating the pump system to convey the red blood cells and the plasma to the recipient during conveyance of said amounts of red blood cells and plasma.

In yet another separate aspect, a blood separation system for conveying an amount of red blood cells and an amount of plasma to a blood source comprises a separation device adapted to separate blood into a layer containing red blood cells and a layer containing plasma. The system further includes a pump system and a controller programmed to actuate the pump system to convey blood from a blood source into the separation device. The controller is programmed to then actuate the separation device to separate the blood therein into a layer containing red blood cells and a layer containing plasma and to then actuate the pump system to remove separated red blood cells and plasma from the separation device. The controller is programmed to then actuate the pump system to convey volumes of said removed red blood cells and plasma to the blood source and to then repeatedly alternate between actuating the pump system to convey the red blood cells and the plasma to the blood source during conveyance of said amounts of red blood cells and plasma.

BRIEF DESCRIPTION OF THE DRAWINGS

FIG. 16 is a perspective view of a fixture that, when coupled to the plasma and red blood cell collection tubes, holds the tubes in a desired viewing alignment with the in-line sensors, as shown in FIGS. 15A, 15B, and 15C;

FIG. 17 is a perspective view of the fixture shown in FIG. 16, with a plasma cell collection tube, a red blood cell collection tube, and a whole blood inlet tube attached, gathering the tubes in an organized, side-by-side array;

FIG. 18 is a perspective view of the fixture and tubes shown in FIG. 17, as being placed into viewing alignment with the two sensors shown in FIGS. 15A, 15B, and 15C;

FIGS. 38A and 38B are schematic views of the blood processing circuit shown in FIG. 34, showing the programming of the cassette to carry out fluid flow tasks in connection with on-line transfer of an additive solution into red blood cells separated from whole blood;

FIG. 49 is a plane view of the front side of a cassette having fourteen ports;

FIG. 50 is a plane view of the rear side of the cassette of FIG. 49;

FIGS. 55A and 55B are schematic views of the blood processing circuit of FIG. 51, showing the programming of the cassette to carry out different fluid flow tasks in connection with establishing a target hematocrit in the blood processing chamber;

FIGS. 58A and 58B are schematic views of the blood processing circuit of FIG. 51, showing the programming of the cassette to carry out different fluid flow tasks in connection with re-separating the previously recombined blood components;

FIG. 62 is a schematic view of the blood processing circuit of FIG. 51, showing the programming of the cassette to carry out different fluid flow tasks in connection with harvesting red blood cells;

FIGS. 63A-63D are schematic views of an automated burping procedure for removing excess air from a flexible bag containing an amount of a collected blood component;

FIGS. 64A-64C are schematic views of the blood processing circuit of FIG. 51, showing the programming of the cassette to carry out different fluid flow tasks in connection with mixing packed red cells and an additive solution;

FIG. 66 is a plane view of another disposable set, which can be mounted on the device shown in FIG. 1;

DESCRIPTION OF THE ILLUSTRATED EMBODIMENTS

The embodiments disclosed herein are for the purpose of providing the required description of the present subject matter. These embodiments are only exemplary, and may be embodied in various forms. Therefore, specific details disclosed herein are not to be interpreted as limiting the subject matter as defined in the accompanying claims.

Figure 1:
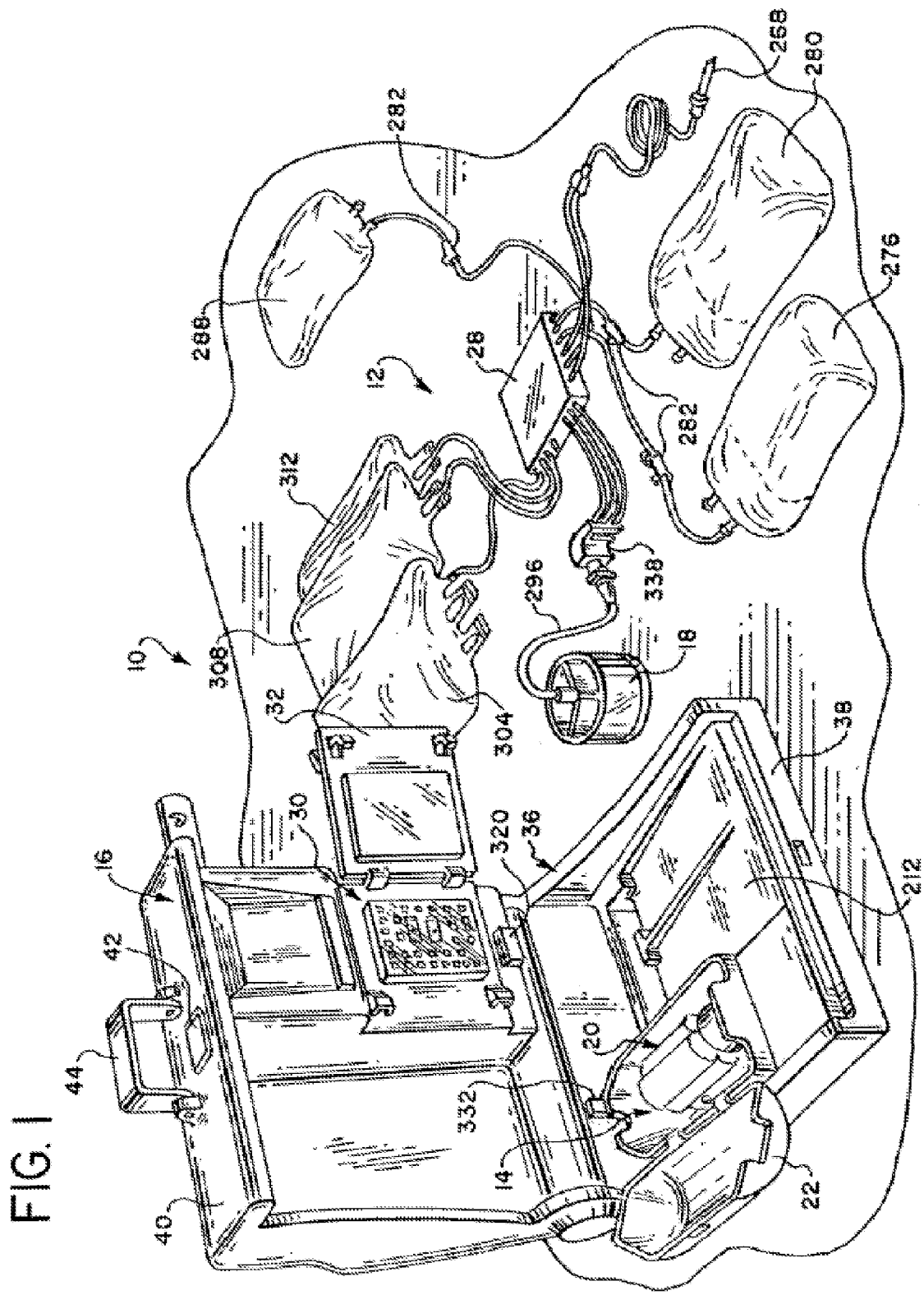
FIG. 1 is a perspective view of a blood or blood component processing system, with the disposable processing set of the system shown out of association with the processing device prior to use.

FIG. 1 shows a fluid processing system 10 that embodies various aspects of the present subject matter. The system 10 can be used for processing various fluids. The system 10 is particularly well suited for processing whole blood and other suspensions of biological cellular materials. Accordingly, the illustrated embodiment shows the system 10 used for this purpose.

I. System Overview

The system 10 includes three principal components. These are (i) a liquid and blood flow set 12; (ii) a blood processing device 14 that interacts with the flow set 12 to cause separation and collection of one or more blood components; and (iii) a controller 16 that governs the interaction to perform a blood processing and collection procedure selected by the operator.

A. The Processing Device and Controller

The blood processing device 14 and controller 16 are intended to be durable items capable of long term use. In the illustrated embodiment, the blood processing device 14 and controller 16 are mounted inside a portable housing or case 36. The case 36 presents a compact footprint, suited for set up and operation upon a table top or other relatively small surface. The case 36 is also intended to be transported easily to a collection site.

Figure 4:
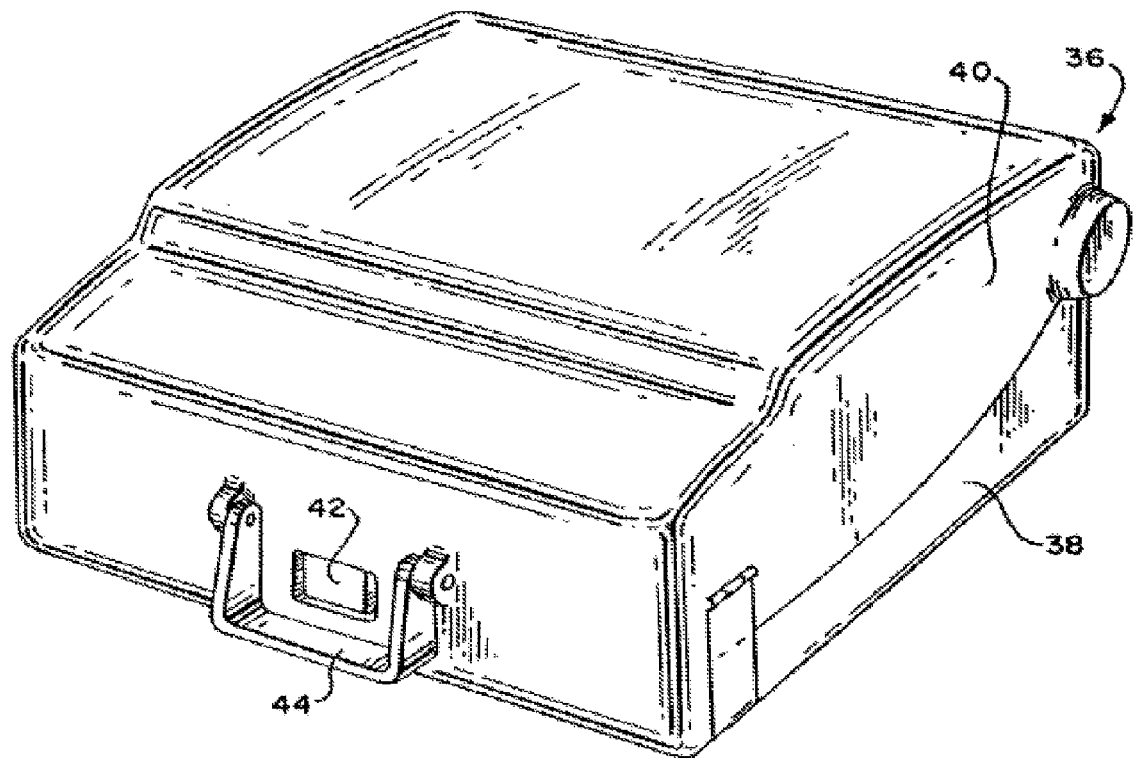
FIG. 4 is a right perspective front view of the case that houses the processing device shown in FIG. 1, with the lid closed for transporting the device.

The case 36 includes a base 38 and a hinged lid 40, which opens (as FIG. 1 shows) and closes (as FIG. 4 shows). The lid 40 includes a latch 42, for releasably locking the lid 40 closed. The lid 40 also includes a handle 44, which the operator can grasp for transporting the case 36 when the lid 40 is closed. In use, the base 38 is intended to rest on a generally horizontal support surface.

The case 36 can be formed into a desired configuration, e.g., by molding. In one embodiment, the case 36 is made from a lightweight, yet durable, plastic material.

B. The Flow Set

Figure 2:
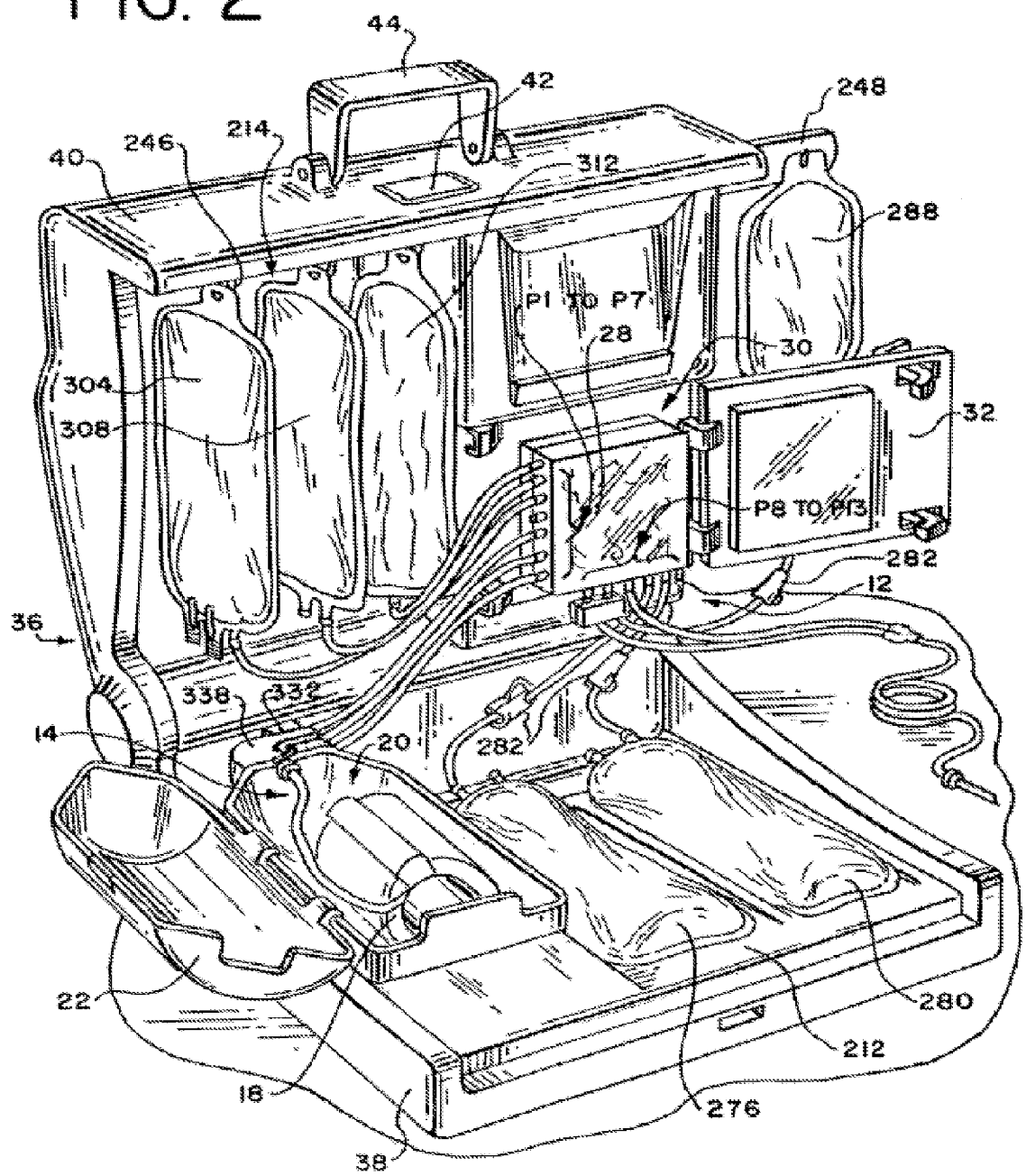
FIG. 2 is a perspective view of the system shown in FIG. 1, with the doors to the centrifuge station and pump and valve station being shown open to accommodate mounting of the processing set.

The flow set 12 is intended to be a sterile, single use, disposable item. As FIG. 2 shows, before beginning a given blood processing and collection procedure, the operator loads various components of the flow set 12 in the case 36 in association with the device 14. The controller 16 implements the procedure based upon preset protocols, taking into account other input from the operator. Upon completing the procedure, the operator removes the flow set 12 from association with the device 14. The portions of the set 12 holding the collected blood component or components are removed from the case 36 and retained for storage, transfusion, or further processing. The remainder of the set 12 is removed from the case 36 and discarded.

Figure 3:
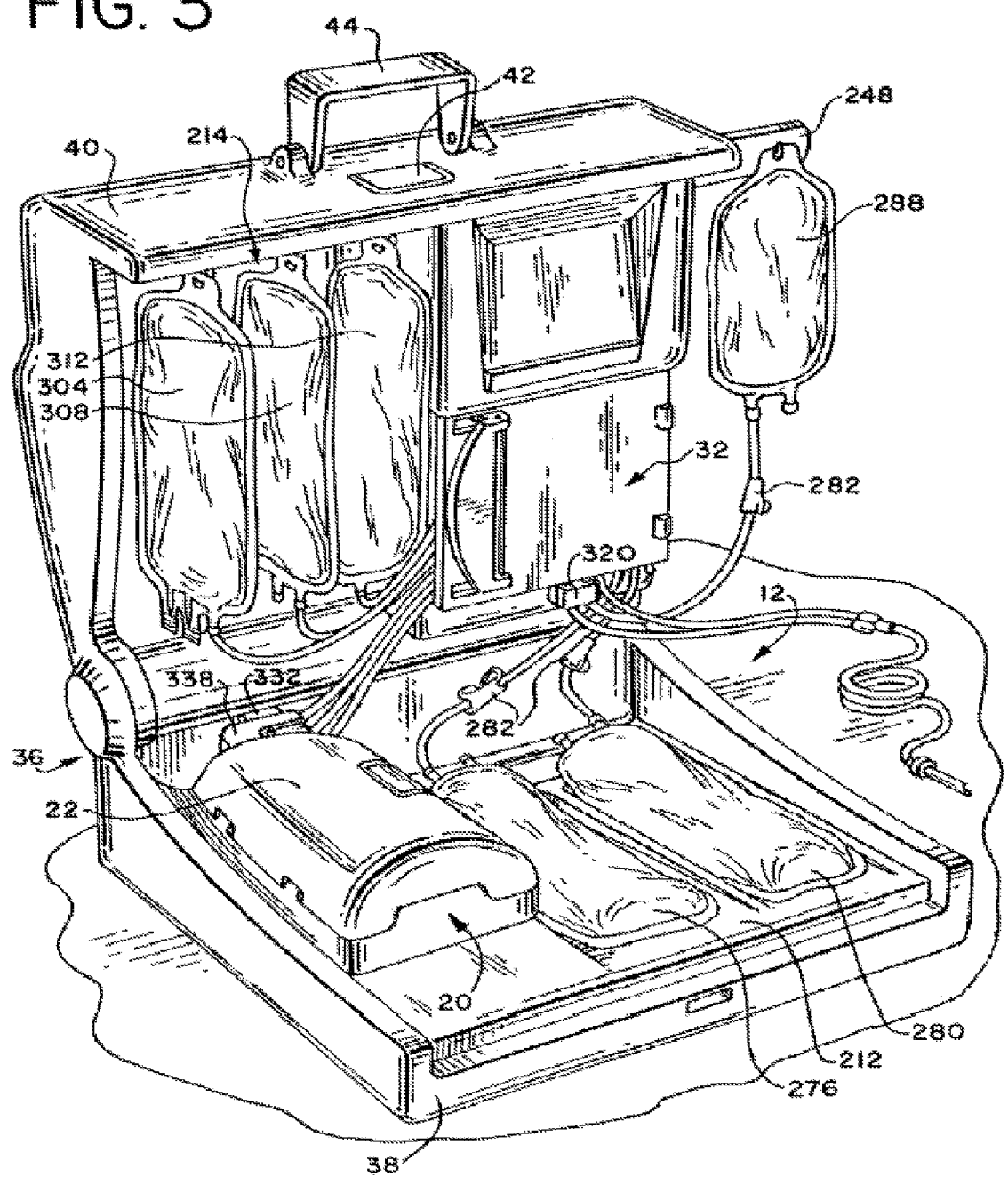
FIG. 3 is a perspective view of the system shown in FIG. 1 with the processing set fully mounted on the processing device and ready for use.

The flow set 12 shown in FIG. 1 includes a blood processing chamber 18 designed for use in association with a centrifuge. Accordingly, as FIG. 2 shows, the processing device 14 includes a centrifuge station 20, which receives the processing chamber 18 for use. As FIGS. 2 and 3 show, the centrifuge station 20 comprises a compartment formed in the base 38. The centrifuge station 20 includes a door 22, which opens and closes the compartment. The door 22 opens to allow loading of the processing chamber 18. The door 22 closes to enclose the processing chamber 18 during operation.

The centrifuge station 20 rotates the processing chamber 18. When rotated, the processing chamber 18 centrifugally separates whole blood received from a donor into component parts, e.g., red blood cells, plasma, and buffy coat comprising platelets and leukocytes.

It should also be appreciated that the system 10 need not separate blood centrifugally. The system 10 can accommodate other types of blood separation devices, e.g., a membrane blood separation device.

II. The Programmable Blood Processing Circuit

Figure 5:
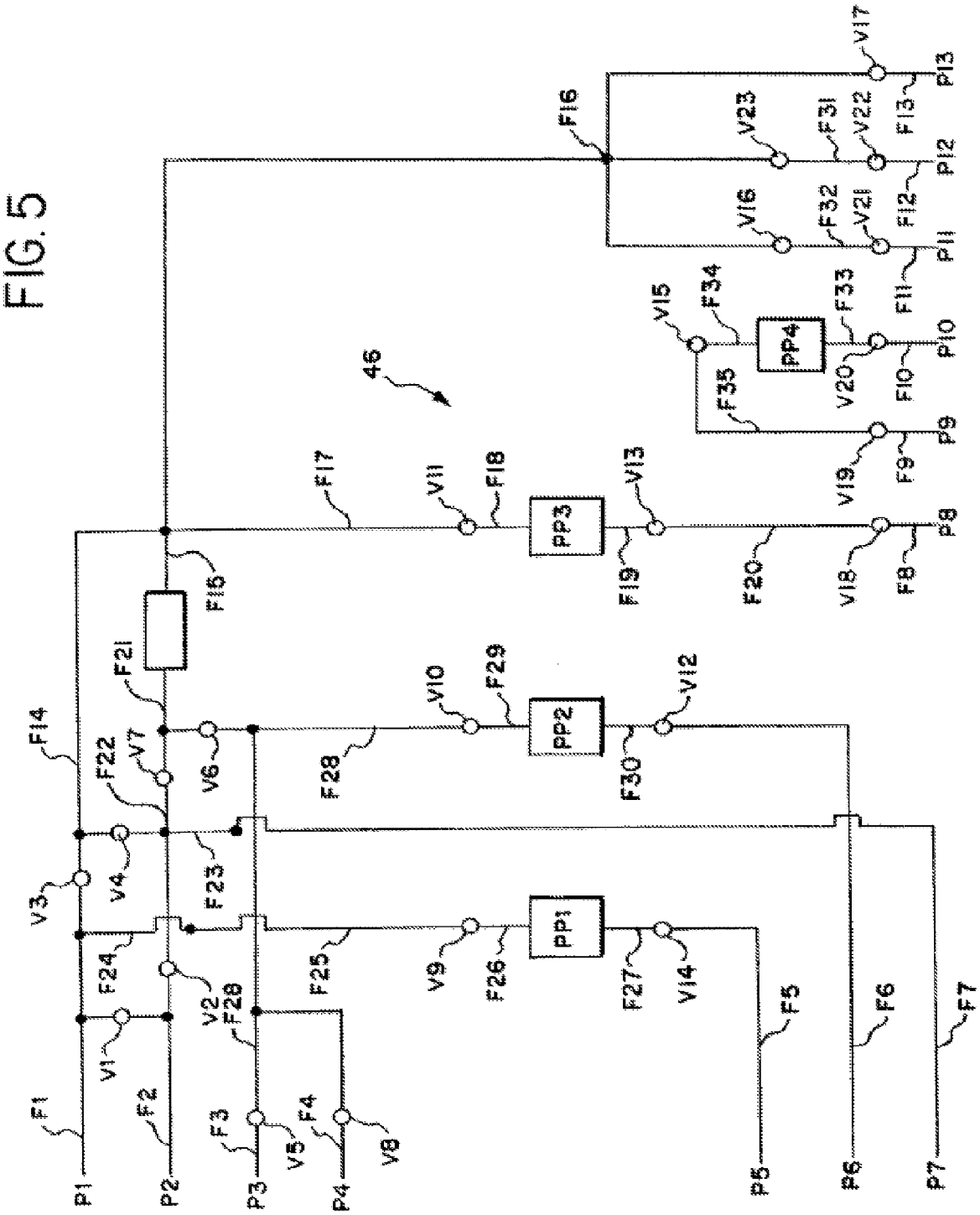
FIG. 5 is a schematic view of a blood processing circuit, which can be programmed to perform a variety of different blood processing procedures in association with the device shown in FIG. 1.
Figure 34:
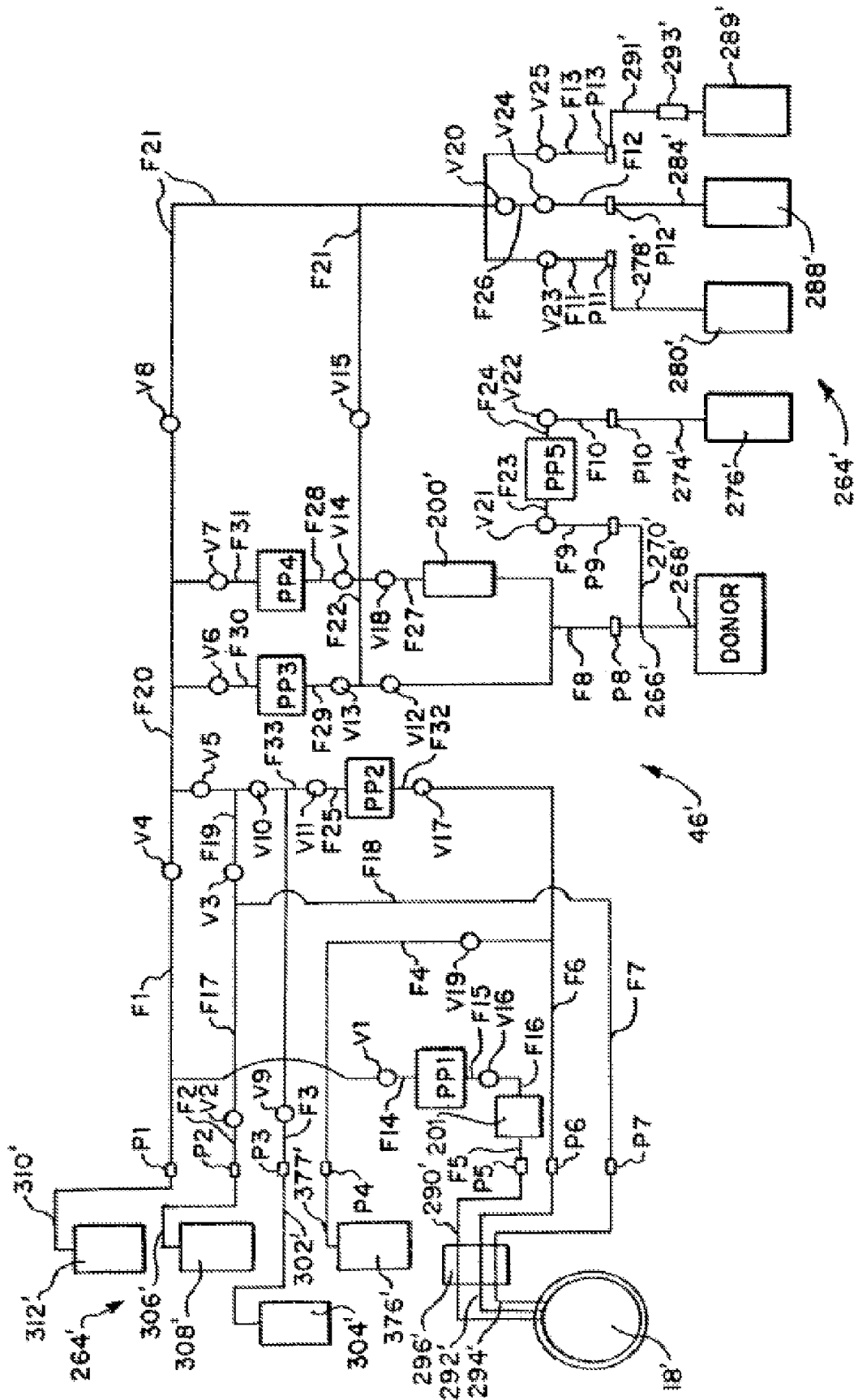
FIG. 34 is a schematic view of another blood processing circuit, which can be programmed to perform a variety of different blood processing procedures in association with the device shown in FIG. 1.

The set 12 defines a programmable blood processing circuit 46. Various configurations are possible. FIG. 5 schematically shows one representative configuration. FIG. 34 schematically shows another representative configuration, which will be described later.

Referring to FIG. 5, the circuit 46 can be programmed to perform a variety of different blood processing procedures in which, e.g., red blood cells are collected, or plasma is collected, or both plasma and red blood cells are collected, or the buffy coat is collected.

The circuit 46 includes several pump stations PP(N), which are interconnected by a pattern of fluid flow paths F(N) through an array of in-line valves V(N). The circuit is coupled to the remainder of the blood processing set by ports P(N).

The circuit 46 includes a programmable network of flow paths, comprising eleven universal ports P1 to P8 and P11 to P13 and three universal pump stations PP1, PP2, and PP3. By selective operation of the in-line valves V1 to V14, V16 to V18, and V21 to 23, any universal port P1 to P8 and P11 to P13 can be placed in flow communication with any universal pump station PP1, PP2, and PP3. By selective operation of the universal valves, fluid flow can be directed through any universal pump station in a forward direction or reverse direction between two valves, or an in-out direction through a single valve.

In the illustrated embodiment, the circuit also includes an isolated flow path comprising two ports P9 and P10 and one pump station PP4. The flow path is termed "isolated," because it cannot be placed into direct flow communication with any other flow path in the circuit 46 without exterior tubing. By selective operation of the in-line valves V15, V19, and V20, fluid flow can be directed through the pump station in a forward direction or reverse direction between two valves, or an in-out direction through a single valve.

The circuit 46 can be programmed to assign dedicated pumping functions to the various pump stations. For example, in one embodiment, the universal pump station PP3 can serve as a general purpose, donor interface pump, regardless of the particular blood procedure performed, to either draw blood from the donor or return blood or other fluid to the donor through the port P8. In this arrangement, the pump station PP4 can serve as a dedicated anticoagulant pump, to draw anticoagulant from a source through the port P10 and to meter anticoagulant into the blood through port P9.

In this arrangement, the universal pump station PP1 can serve, regardless of the particular blood processing procedure performed, as a dedicated in-process whole blood pump, to convey whole blood into the blood separator. This dedicated function frees the donor interface pump PP3 from the added function of supplying whole blood to the blood separator. Thus, the in-process whole blood pump PP1 can maintain a continuous supply of blood to the blood separator, while the donor interface pump PP3 is simultaneously used to draw blood or return fluid to the donor through the single phlebotomy needle. Processing time is thereby minimized.

In this arrangement, the universal pump station PP2 can serve, regardless of the particular blood processing procedure performed, as a plasma pump, to convey plasma from the blood separator. The ability to dedicate separate pumping functions provides a continuous flow of blood and/or fluid into and out of the separator, as well as to and from the donor.

The circuit 46 can be programmed, depending upon the objectives of the particular blood processing procedure, to retain all or some of the plasma for storage or fractionation purposes, or to return all or some of the plasma to the donor. The circuit 46 can be further programmed, depending upon the objectives of the particular blood processing procedure, to retain all or some of the red blood cells for storage, or to return all or some of the red blood cells to the donor. The circuit 46 can also be programmed, depending upon the objectives of the particular blood processing procedure, to retain all or some of the buffy coat for storage, or to return all or some of the buffy coat to the donor.

A. The Cassette

Figure 6:
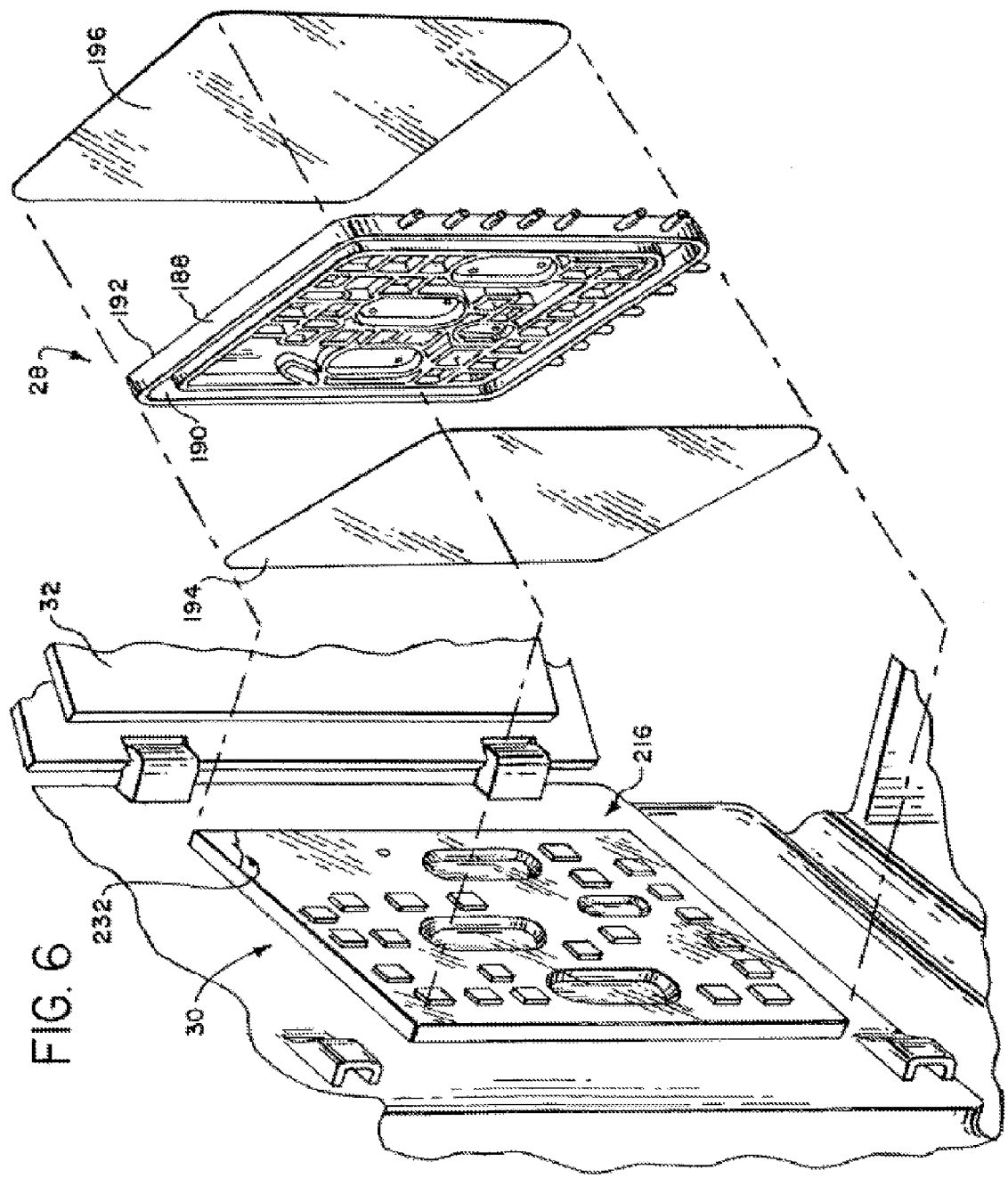
FIG. 6 is an exploded perspective view of a cassette, which contains the programmable blood processing circuit shown in FIG. 5, and the pump and valve station on the processing device shown in FIG. 1, which receives the cassette for use.

In one embodiment, the programmable fluid circuit 46 is implemented by use of a fluid pressure actuated cassette 28 (see FIG. 6). The cassette 28 provides a centralized, programmable, integrated platform for all the pumping and valving functions required for a given blood processing procedure. In the illustrated embodiment, the fluid pressure comprises positive and negative pneumatic pressure. Other types of fluid pressure can be used.

As FIG. 6 shows, the cassette 28 interacts with a pneumatic actuated pump and valve station 30, which is mounted in the lid 40 of the case 36 (see FIG. 1). The cassette 28 is, in use, mounted in the pump and valve station 30. The pump and valve station 30 applies positive and negative pneumatic pressure upon the cassette 28 to direct liquid flow through the circuit. Further details will be provided later.

The cassette 28 can take various forms. As illustrated (see FIG. 6), the cassette 28 comprises an injection molded body 188 having a front side 190 and a back side 192. For the purposes of description, the front side 190 is the side of the cassette 28 that, when the cassette 28 is mounted in the pump and valve station 30, faces away from the operator. Flexible diaphragms 194 and 196 overlay both the front side 190 and the back side 192 of the cassette 28, respectively.

The cassette body 188 is advantageously made of a rigid medical grade plastic material. The diaphragms 194 and 196 are made of a flexible material, for example, sheets of medical grade plastic. The diaphragms 194 and 196 are sealed about their peripheries to the peripheral edges of the front and back sides of the cassette body 188. Interior regions of the diaphragms 194 and 196 can also be sealed to interior regions of the cassette body 188.

Figure 7:
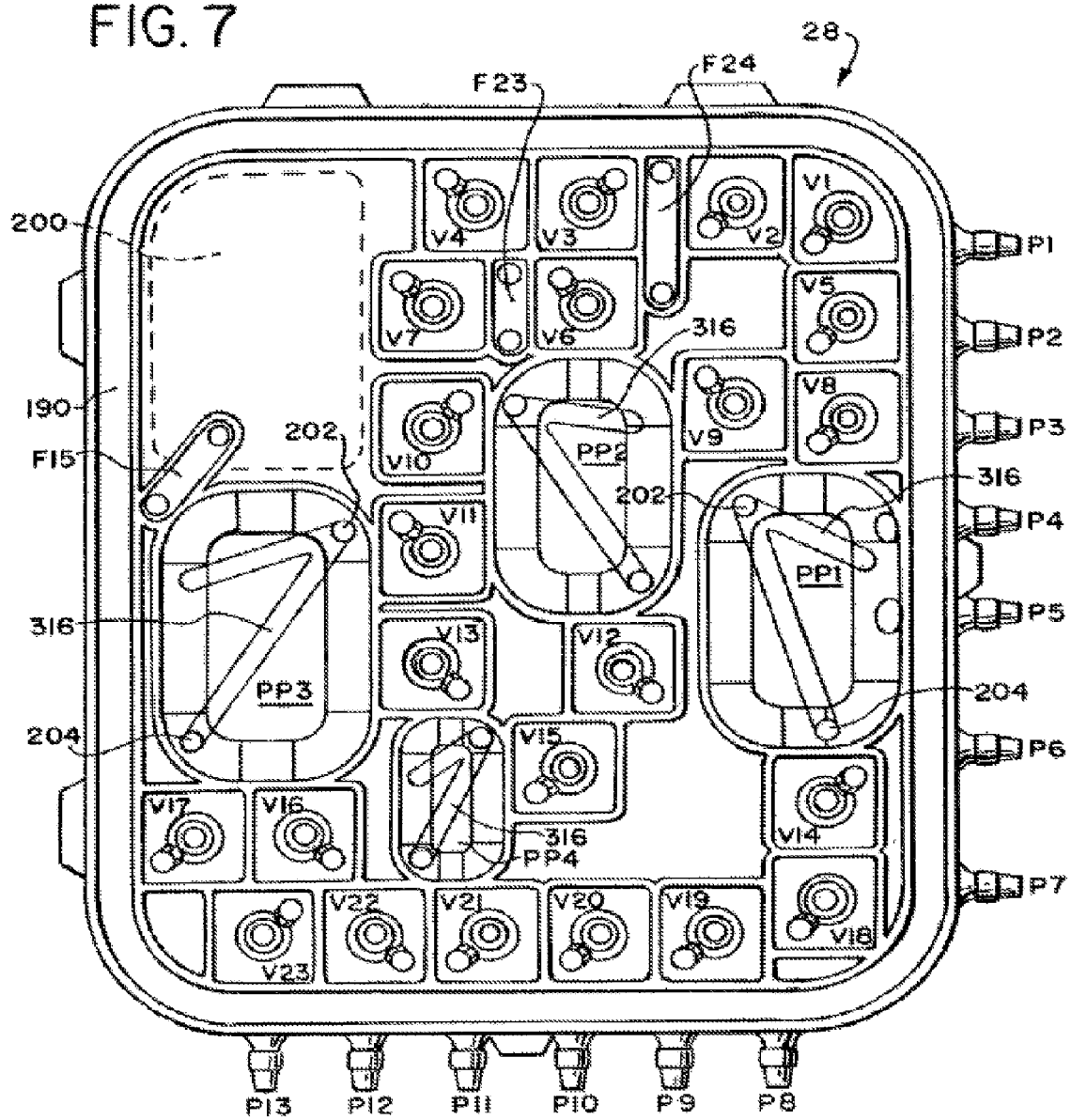
FIG. 7 is a plane view of the front side of the cassette shown in FIG. 6.
Figure 9:
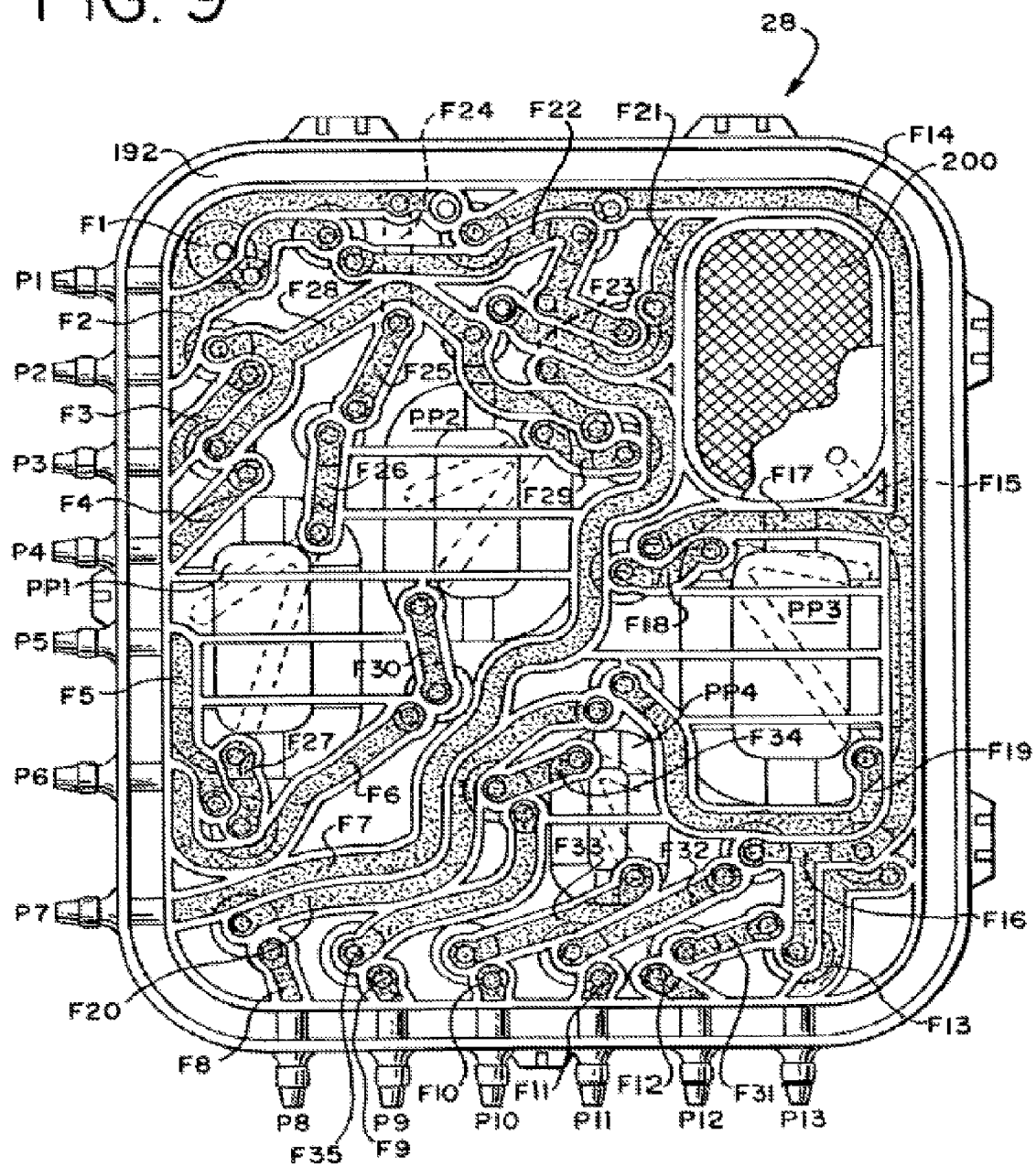
FIG. 9 is a plane view of the back side of the cassette shown in FIG. 6.

The cassette body 188 has an array of interior cavities formed on both the front and back sides 190 and 192 (see FIGS. 7 and 9). The interior cavities define the valve stations and flow paths shown schematically in FIG. 5. An additional interior cavity is provided in the back side of the cassette 28 to form a station that holds a filter material 200. In the illustrated embodiment, the filter material 200 comprises an overmolded mesh filter construction. The filter material 200 is intended, during use, to remove clots and cellular aggregations that can form during blood processing.

The pump stations PP1 to PP4 are formed as wells that are open on the front side 190 of the cassette body 188. Upstanding edges peripherally surround the open wells of the pump stations. The pump wells are closed on the back side 192 of the cassette body 188, except for a spaced pair of through holes or ports 202 and 204 for each pump station. The ports 202 and 204 extend through to the back side 192 of the cassette body 188. As will become apparent either port 202 or 204 can serve its associated pump station as an inlet or an outlet, or both inlet and outlet.

Figure 8:
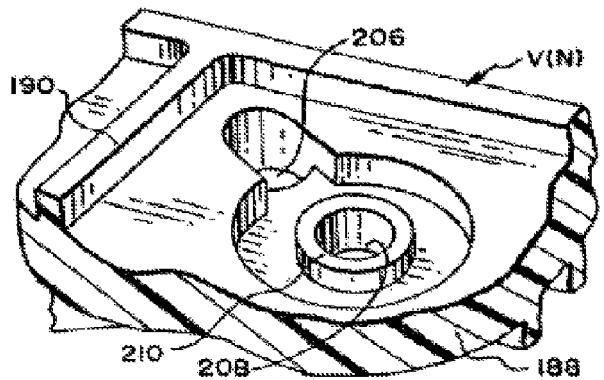
FIG. 8 is an enlarged perspective view of a valve station on the cassette shown in FIG. 6.

The in-line valves V1 to V23 are likewise formed as wells that are open on the front side 190 of the cassette. FIG. 8 shows a typical valve V(N). Upstanding edges peripherally surround the open wells of the valves on the front side 190 of the cassette body 188. The valves are closed on the back side 192 of the cassette 28, except that each valve includes a pair of through holes or ports 206 and 208. One port 206 communicates with a selected liquid path on the back side 192 of the cassette body 188. The other port 208 communicates with another selected liquid path on the back side 192 of the cassette body 188.

In each valve, a valve seat 210 extends about one of the ports 208. The valve seat 210 is recessed below the surface of the recessed valve well, such that the port 208 is essentially flush with the surrounding surface of the recessed valve well, and the valve seat 210 extends below the surface of the valve well.

The flexible diaphragm 194 overlying the front side 190 of the cassette 28 rests against the upstanding peripheral edges surrounding the pump stations and valves. With the application of positive force uniformly against this side of the cassette body 188, the flexible diaphragm 194 seats against the upstanding edges. The positive force forms peripheral seals about the pump stations and valves. This, in turn, isolates the pumps and valves from each other and the rest of the system. The pump and valve station 30 applies positive force to the front side 190 of the cassette body 188 for this purpose.

Further localized application of positive and negative fluid pressures upon the regions of the diaphragm 194 overlying these peripherally sealed areas serve to flex the diaphragm regions in these peripherally sealed areas. These localized applications of positive and negative fluid pressures on these diaphragm regions overlying the pump stations serve to expel liquid out of the pump stations (with application of positive pressure) and draw liquid into the pump stations (with application of negative pressure).

In the illustrated embodiment, the bottom of each pump station PP1 to PP4 includes a recessed race 316 (see FIG. 7). The race 316 extends between the ports 202 and 204, and also includes a dogleg extending at an angle from the top port 202. The race 316 provides better liquid flow continuity between the ports 202 and 204, particularly when the diaphragm region is forced by positive pressure against the bottom of the pump station. The race 316 also prevents the diaphragm region from trapping air within the pump station. Air within the pump station is forced into the race 316, where it can be readily venting through the top port 202 out of the pump station, even if the diaphragm region is bottomed out in the station.

Likewise, localized applications of positive and negative fluid pressure on the diaphragm regions overlying the valves will serve to seat (with application of positive pressure) and unseat (with application of negative pressure) these diaphragm regions against the valve seats, thereby closing and opening the associated valve port. The flexible diaphragm is responsive to an applied negative pressure for flexure out of the valve seat 210 to open the respective port. The flexible diaphragm is responsive to an applied positive pressure for flexure into the valve seat 210 to close and seal the respective port. When so flexed, the flexible diaphragm forms within the recessed valve seat 210 a peripheral seal about the valve port 208.

In operation, the pump and valve station 30 applies localized positive and negative fluid pressures to these regions of the front diaphragm 194 for opening and closing the valve ports.

The liquid paths F1 to F35 are formed as elongated channels that are open on the back side 192 of the cassette body 188, except for the liquid paths F15, F23, and F24 are formed as elongated channels that are open on the front side 190 of the cassette body 188. The liquid paths are shaded in FIG. 9 to facilitate their viewing. Upstanding edges peripherally surround the open channels on the front and back sides 190 and 192 of the cassette body 188.

The liquid paths F1 to F35 (except for liquid paths F15, F23, and F24) are closed on the front side 190 of the cassette body 188, except where the channels cross over valve station ports or pump station ports. Likewise, the liquid paths F15, F23, and F24 are closed on the back side 192 of the cassette body 188, except where the channels cross over in-line ports communicating with certain channels on the back side 192 of the cassette 28.

The flexible diaphragms 194 and 196 overlying the front and back sides 190 and 192 of the cassette body 188 rest against the upstanding peripheral edges surrounding the liquid paths F1 to F35. With the application of positive force uniformly against the front and back sides 190 and 192 of the cassette body 188, the flexible diaphragms 194 and 196 seat against the upstanding edges. This forms peripheral seals along the liquid paths F1 to F35. In operation, the pump and valve station 30 applies positive force to the diaphragms 194 and 196 for this purpose.

The pre-molded ports P1 to P13 extend out along two side edges of the cassette body 188. The cassette 28 is vertically mounted for use in the pump and valve station 30 (see FIG. 2). In this orientation, the ports P8 to P13 face downward, and the ports P1 to P7 are vertically stacked one above the other and face inward.

As FIG. 2 shows, the ports P8 to P13, by facing downward, are oriented with container support trays 212 formed in the base 38, as will be described later. The ports P1 to P7, facing inward, are oriented with the centrifuge station 20 and a container weigh station. 214, as will also be described in greater detail later. The orientation of the ports P5 to P7 (which serve the processing chamber 18) below the ports P1 to P4 keeps air from entering the processing chamber 18.

This ordered orientation of the ports provides a centralized, compact unit aligned with the operative regions of the case 36.

B. The Universal Set

Figure 10:
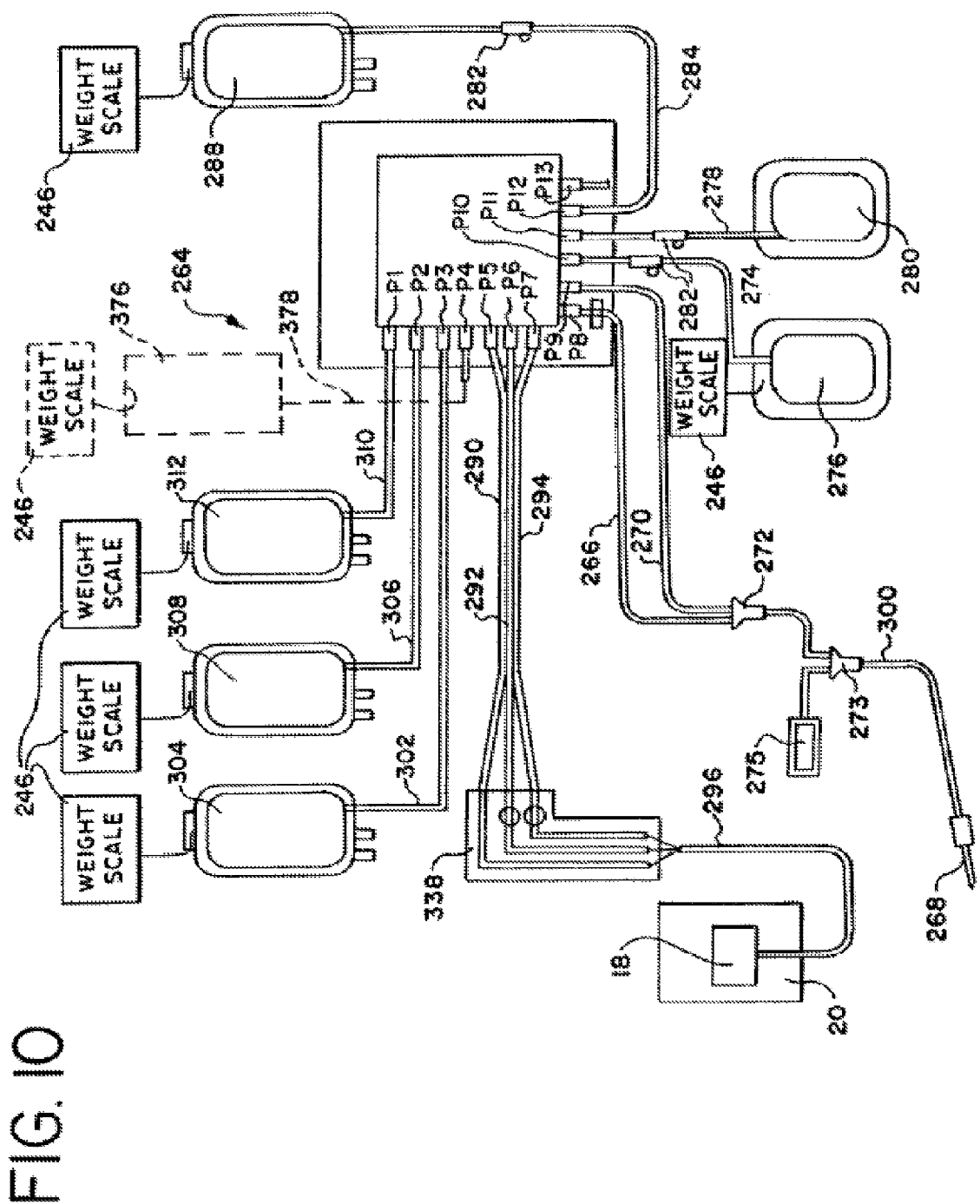
FIG. 10 is a plane view of a universal processing set, which incorporates the cassette shown in FIG. 6, and which can be mounted on the device shown in FIG. 1 as shown in FIGS. 2 and 3.

FIG. 10 schematically shows a universal set 264, which, by selective programming of the blood processing circuit 46 implemented by the cassette 28, is capable of performing several different blood processing procedures.

The universal set 264 includes a donor tube 266, which is attached (through y-connectors 272 and 273) to tubing 300 having an attached phlebotomy needle 268. The donor tube 266 is coupled to the port P8 of the cassette 28.

A container 275 for collecting an in-line sample of blood drawn through the tube 300 is also attached through the y-connector 273.

An anticoagulant tube 270 is coupled to the phlebotomy needle 268 via the y-connector 272. The anticoagulant tube 270 is coupled to cassette port P9. A container 276 holding anticoagulant is coupled via a tube 274 to the cassette port P10. The anticoagulant tube 270 carries an external, manually operated in-line clamp 282 of conventional construction.

A container 280 holding a red blood cell additive solution is coupled via a tube 278 to the cassette port P3. The tube 278 also carries an external, manually operated in-line clamp 282.

A container 288 holding saline is coupled via a tube 284 to the cassette port P12.

FIG. 10 shows the fluid holding containers 276, 280, and 288 as being integrally attached during manufacture of the set 264. Alternatively, all or some of the containers 276, 280, and 288 can be supplied separate from the set 264. The containers 276, 280, and 288 may be coupled by conventional spike connectors, or the set 264 may be configured to accommodate the attachment of the separate container or containers at the time of use through a suitable sterile connection, to thereby maintain a sterile, closed blood processing environment. Alternatively, the tubes 274, 278, and 284 can carry an in-line sterilizing filter and a conventional spike connector for insertion into a container port at time of use, to thereby maintain a sterile, closed blood processing environment.

The set 264 further includes tubes 290, 292, 294, which extend to an umbilicus 296. When installed in the processing station, the umbilicus 296 links the rotating processing chamber 18 with the cassette 28 without need for rotating seals. Further details of this construction will be provided later.

The tubes 290, 292, and 294 are coupled, respectively, to the cassette ports P5, P6, and P7. The tube 290 conveys whole blood into the processing chamber 18. The tube 292 conveys plasma from the processing chamber 18. The tube 294 conveys red blood cells from the processing chamber 18.

A plasma collection container 304 is coupled by a tube 302 to the cassette port P3. The collection container 304 is intended, in use, to serve as a reservoir for plasma during processing.

A red blood cell collection container 308 is coupled by a tube 306 to the cassette port P2. The collection container 308 is intended, in use, to receive a first unit of red blood cells for storage.

A whole blood reservoir 312 is coupled by a tube 310 to the cassette port P1. The collection container 312 is intended, in use, to serve as a reservoir for whole blood during processing. It can also serve to receive a second unit of red blood cells for storage.

As shown in FIG. 10, no tubing is coupled to the utility cassette port P13 and buffy port P4.

C. The Pump and Valve Station

The pump and valve station 30 includes a cassette holder 216. The door 32 is hinged to move with respect to the cassette holder 216 between the opened position, exposing the cassette holder 216 (shown in FIG. 6) and the closed position, covering the cassette holder 216 (shown in FIG. 3). The door 32 also includes an over center latch 218 with a latch handle 220 (shown in FIG. 11). When the door 32 is closed, the latch 218 swings into engagement with the latch pin 222.

Figure 11:
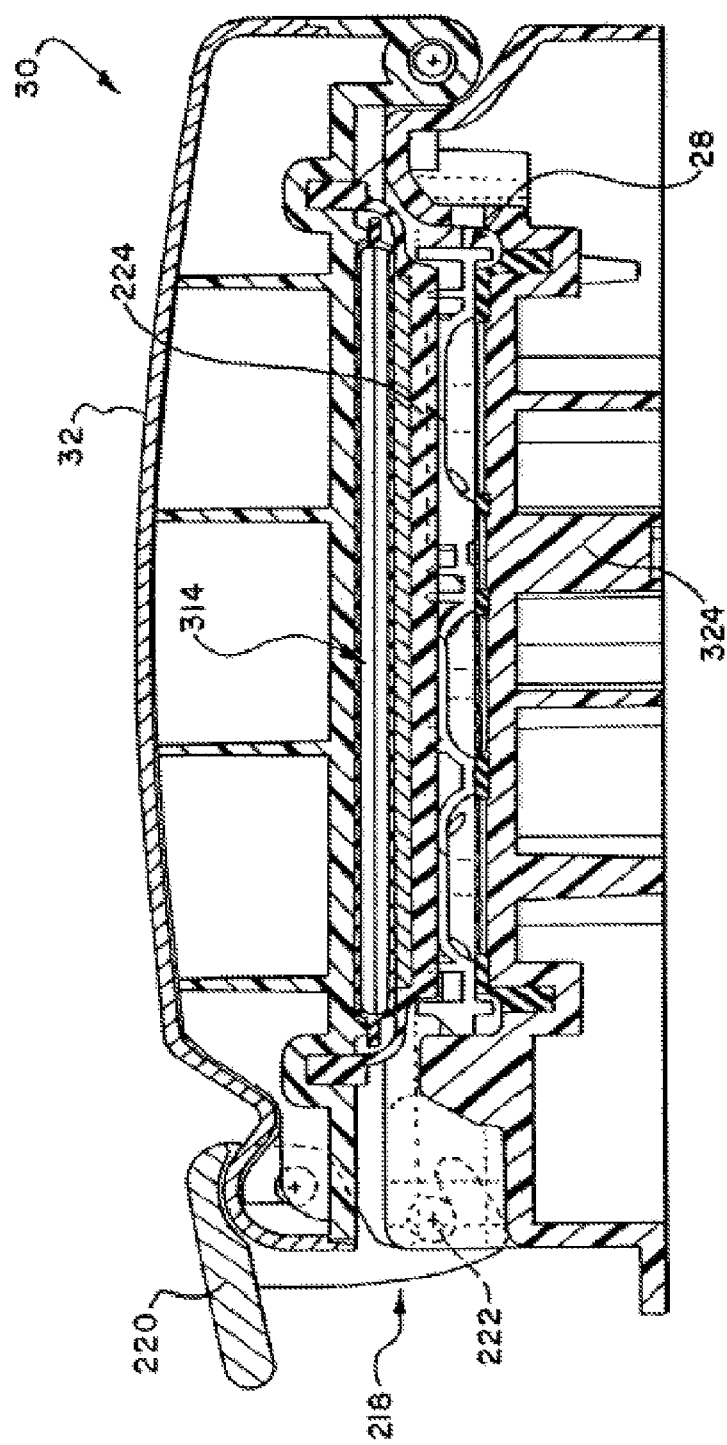
FIG. 11 is a top section view of the pump and valve station in which the cassette as shown in FIG. 6 is carried for use.

As FIG. 11 shows, the inside face of the door 32 carries an elastomeric gasket 224. The gasket 224 contacts the back side 192 of the cassette 28 when the door 32 is closed. An inflatable bladder 314 underlies the gasket 224.

With the door 32 opened (see FIG. 2), the operator can place the cassette 28 into the cassette holder 216. Closing the door 32 and securing the latch 218 brings the gasket 224 into facing contact with the diaphragm 196 on the back side 192 of the cassette 28. Inflating the bladder 314 presses the gasket 224 into intimate, sealing engagement against the diaphragm 196. The cassette 28 is thereby secured in a tight, sealing fit within the cassette holder 216.

The inflation of the bladder 314 also fully loads the over center latch 218 against the latch pin 222 with a force that cannot be overcome by normal manual force against the latch handle 220. The door 32 is securely locked and cannot be opened when the bladder 314 is inflated. In this construction, there is no need for an auxiliary lock-out device or sensor to assure against opening of the door 32 during blood processing.

Figure 12:
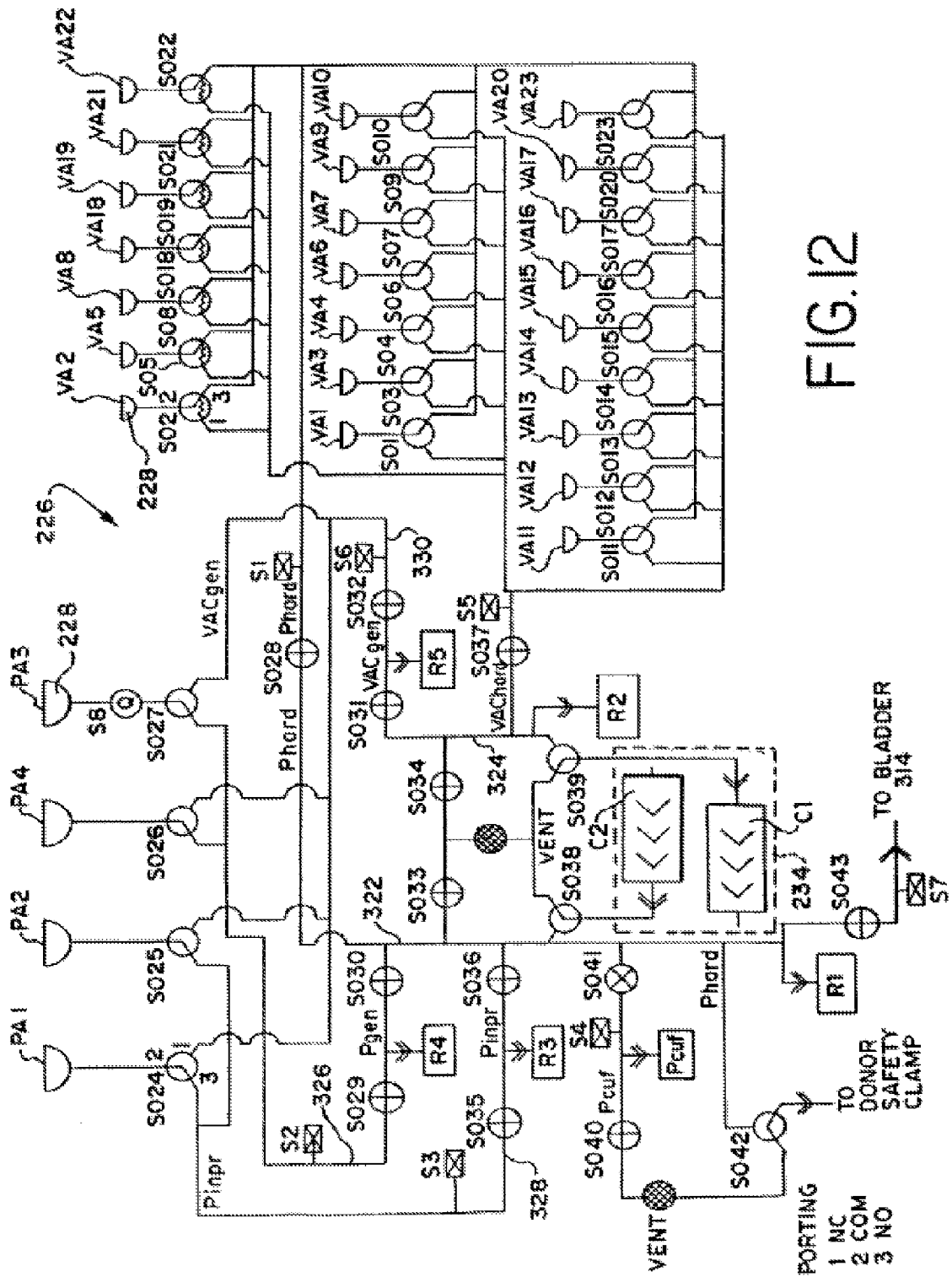
FIG. 12 is a schematic view of a pneumatic manifold assembly, which is part of the pump and valve station shown in FIG. 6, and which supplies positive and negative pneumatic pressures to convey fluid through the cassette shown in FIGS. 7 and 9.

The pump and valve station 30 also includes a manifold assembly 226 located in the cassette holder 216 (FIG. 12). The manifold assembly 226 comprises a molded or machined plastic or metal body. The front side 194 of the diaphragm is held in intimate engagement against the manifold assembly 226 when the door 32 is closed and the bladder 314 inflated.

The manifold assembly 226 is coupled to a pneumatic pressure source 234, which supplies positive and negative air pressure. The pneumatic pressure source 234 is carried inside the lid 40 behind the manifold assembly 226.

In the illustrated embodiment, the pressure source 234 comprises two compressors C1 and C2. However, one or several dual-head compressors could be used as well. As FIG. 12 shows, one compressor C1 supplies negative pressure through the manifold 226 to the cassette 28. The other compressor C2 supplies positive pressure through the manifold 226 to the cassette 28.

As FIG. 12 shows, the manifold 226 contains four pump actuators PA1 to PA4 and twenty-three valve actuators VA1 to VA23. The pump actuators PA1 to PA4 and the valve actuators VA1 to VA23 are mutually oriented to form a mirror image of the pump stations PP1 to PP4 and valve stations V1 to V23 on the front side 190 of the cassette 28.

As FIG. 12 also shows, each actuator PA1 to PA4 and VA1 to VA23 includes a port 228. The ports 228 convey positive or negative pneumatic pressures from the source in a sequence governed by the controller 16. These positive and negative pressure pulses flex the front diaphragm 194 to operate the pump stations PP1 to PP4 and valve stations V1 to V23 in the cassette 28. This, in turn, moves blood and processing liquid through the cassette 28.

In the illustrated embodiment, the cassette holder 216 includes an integral elastomeric membrane 232 (see FIG. 6) stretched across the manifold assembly 226. The membrane 232 serves as the interface between the manifold assembly 226 and the diaphragm 194 of the cassette 28, when fitted into the holder 216. The membrane 232 may include one or more small through holes (not shown) in the regions overlying the pump and valve actuators PA1 to PA4 and V1 to V23. The holes are sized to convey pneumatic fluid pressure from the manifold assembly 226 to the cassette diaphragm 194. Still, the holes are small enough to retard the passage of liquid. The membrane 232 forms a flexible splash guard across the exposed face of the manifold assembly 226.

The splash guard membrane 232 keeps liquid out of the pump and valve actuators PA1 to PA4 and VA1 to VA23, should the cassette diaphragm 194 leak. The splash guard membrane 232 also serves as a filter to keep particulate matter out of the pump and valve actuators of the manifold assembly 226. The splash guard membrane 232 can be periodically wiped clean when cassettes 28 are exchanged.

The manifold assembly 226 includes an array of solenoid actuated pneumatic valves, which are coupled in-line with the pump and valve actuators PA1 to PA4 and VA1 to VA23. The manifold assembly 226, under the control of the controller 16, selectively distributes the different pressure and vacuum levels to the pump and valve actuators PA(N) and VA(N). These levels of pressure and vacuum are systematically applied to the cassette 28, to route blood and processing liquids.

Under the control of a controller 16, the manifold assembly 226 also distributes pressure levels to the door bladder 314 (already described), as well as to a donor pressure cuff (not shown) and to a donor line occluder 320.

As FIG. 1 shows, the donor line occluder 320 is located in the case 36, immediately below the pump and valve station 30, in alignment with the ports P8 and P9 of the cassette 28. The donor line 266, coupled to the port P8, passes through the occluder 320. The anticoagulant line 270, coupled to the port P9, also passes through the occluder 320. The occluder 320 is a spring loaded, normally closed pinch valve, between which the lines 266 and 270 pass. Pneumatic pressure from the manifold assembly 234 is supplied to a bladder (not shown) through a solenoid valve. The bladder, when expanded with pneumatic pressure, opens the pinch valve, to thereby open the lines 266 and 270. In the absence of pneumatic pressure, the solenoid valve closes and the bladder vents to atmosphere. The spring loaded pinch valve of the occluder 320 closes, thereby closing the lines 266 and 270.

The manifold assembly 226 maintains several different pressure and vacuum conditions, under the control of the controller 16. In the illustrated embodiment, the following multiple pressure and vacuum conditions are maintained:

(i) Phard, or Hard Pressure, and Pinpr, or In-Process Pressure are the highest pressures maintained in the manifold assembly 226. Phard is applied for closing cassette valves V1 to V23. Pinpr is applied to drive the expression of liquid from the in-process pump PP1 and the plasma pump PP2. A typical pressure level for Phard and Pinpr in the context of an exemplary embodiment is 500 mmHg.

(ii) Pgen, or General Pressure, is applied to drive the expression of liquid from the donor interface pump PP3 and the anticoagulant pump PP4. A typical pressure level for Pgen in the context of an exemplary embodiment is 150 mmHg.

(iii) Pcuff, or Cuff Pressure, is supplied to the donor pressure cuff. A typical pressure level for Pcuff in the context of an exemplary embodiment is 80 mmHg.

(iv) Vhard, or Hard Vacuum, is the deepest vacuum applied in the manifold assembly 226. Vhard is applied to open cassette valves V1 to V23. A typical vacuum level for Vhard in the context of an exemplary embodiment is −350 mmHg.

(v) Vgen, or General Vacuum, is applied to drive the draw function of each of the four pumps PP1 to PP4. A typical pressure level for Vgen in the context of an exemplary embodiment is −300 mmHg.

(vi) Pdoor, or Door Pressure, is applied to the bladder 314 to seal the cassette 28 into the holder 216. A typical pressure level for Pdoor in the context of an exemplary embodiment is 700 mmHg.

For each pressure and vacuum level, a variation of plus or minus 20 mmHg, for example, is tolerated.

Pinpr is used to operate the in-process pump PP1, to pump blood into the processing chamber 18. The magnitude of Pinpr must be sufficient to overcome the pressure within the processing chamber 18, which may be approximately 300 mmHg.

Similarly, Pinpr is used for the plasma pump PP2, since it must have similar pressure capabilities in the event that plasma needs to be pumped backwards into the processing chamber 18, e.g., during a spill condition, as will be described later.

Pinpr and Phard are operated at the highest pressure to ensure that upstream and downstream valves used in conjunction with pumping are not forced opened by the pressures applied to operate the pumps. The cascaded, interconnectable design of the fluid paths F1 to F35 through the cassette 28 requires Pinpr-Phard to be the highest pressure applied. By the same token, Vgen is required to be less extreme than Vhard, to ensure that pumps PP1 to PP4 do not overwhelm upstream and downstream cassette valves V1 to V23.

Pgen is used to drive the donor interface pump PP3 and can be maintained at a lower pressure, as can the AC pump PP4.

A main hard pressure line 322 and a main vacuum line 324 distribute Phard and Vhard in the manifold assembly 226. The pressure and vacuum sources 234 run continuously to supply Phard to the hard pressure line 322 and Vhard to the hard vacuum line 324.

A pressure sensor S1 monitors Phard in the hard pressure line 322. The sensor S1 controls a solenoid SO38. The solenoid SO38 is normally closed. The sensor S1 opens the solenoid SO38 to build Phard up to its maximum set value. Solenoid SO38 is closed as long as Phard is within its specified pressure range and is opened when Phard falls below its minimum acceptable value.

Similarly, a pressure sensor S5 in the hard vacuum line 324 monitors Vhard. The sensor S5 controls a solenoid SO39. The solenoid SO39 is normally closed. The sensor S5 opens the solenoid SO39 to build Vhard up to its maximum value. Solenoid SO39 is closed as long as Vhard is within its specified pressure range and is opened when Vhard falls outside its specified range.

A general pressure line 326 branches from the hard pressure line 322. A sensor S2 in the general pressure line 326 monitors Pgen. The sensor S2 controls a solenoid SO30. The solenoid SO30 is normally closed. The sensor S2 opens the solenoid SO30 to refresh Pgen from the hard pressure line 322, up to the maximum value of Pgen. Solenoid SO30 is closed as long as Pgen is within its specified pressure range and is opened when Pgen falls outside its specified range.

An in-process pressure line 328 also branches from the hard pressure line 322. A sensor S3 in the in-process pressure line 328 monitors Pinpr. The sensor S3 controls a solenoid SO36. The solenoid SO36 is normally closed. The sensor S3 opens the solenoid SO36 to refresh Pinpr from the hard pressure line 322, up to the maximum value of Pinpr. Solenoid SO36 is closed as long as Pinpr is within its specified pressure range and is opened when Pinpr falls outside its specified range.

A general vacuum line 330 branches from the hard vacuum line 324. A sensor S6 monitors Vgen in the general vacuum line 330. The sensor S6 controls a solenoid SO31. The solenoid SO31 is normally closed. The sensor S6 opens the solenoid SO31 to refresh Vgen from the hard vacuum line 324, up to the maximum value of Vgen. The solenoid SO31 is closed as long as Vgen is within its specified range and is opened when Vgen falls outside its specified range.

In-line reservoirs R1 to R5 are provided in the hard pressure line 322, the in-process pressure line 328, the general pressure line 326, the hard vacuum line 324, and the general vacuum line 330. The reservoirs R1 to R5 assure that the constant pressure and vacuum adjustments as above described are smooth and predictable.

The solenoids SO33 and SO34 provide a vent for the pressures and vacuums, respectively, upon procedure completion. Since pumping and valving will continually consume pressure and vacuum, the solenoids SO33 and SO34 are normally closed. The solenoids SO33 and SO34 are opened to vent the manifold assembly upon the completion of a blood processing procedure.

The solenoids SO28, SO29, SO35, SO37 and SO32 provide the capability to isolate the reservoirs R1 to R5 from the air lines that supply vacuum and pressure to the manifold assembly 226. This provides for much quicker pressure/vacuum decay feedback, so that testing of cassette/manifold assembly seal integrity can be accomplished. These solenoids SO28, SO29, SO35, SO37, and SO32 are normally opened, so that pressure cannot be built in the assembly 226 without a command to close the solenoids SO28, SO29, SO35, SO37, and SO32, and, further, so that the system pressures and vacuums can vent in an error mode or with loss of power.

The solenoids SO1 to SO23 provide Phard or Vhard to drive the valve actuators VA1 to V23. In the unpowered state, these solenoids are normally opened to keep all cassette valves V1 to V23 closed.

The solenoids SO24 and SO25 provide Pinpr and Vgen to drive the in-process and plasma pumps PP1 and PP2. In the unpowered state, these solenoids are opened to keep both pumps PP1 and PP2 closed.

The solenoids SO26 and SO27 provide Pgen and Vgen to drive the donor interface and AC pumps PP3 and PP4. In the unpowered state, these solenoids are opened to keep both pumps PP3 and PP4 closed.

The solenoid SO43 provides isolation of the door bladder 314 from the hard pressure line 322 during the procedure. The solenoid SO43 is normally opened and is closed when Pdoor is reached. A sensor S7 monitors Pdoor and signals when the bladder pressure falls below Pdoor. The solenoid SO43 is opened in the unpowered state to ensure bladder 314 venting, as the cassette 28 cannot be removed from the holder while the door bladder 314 is pressurized.

The solenoid SO42 provides Phard to open the safety occluder valve 320. Any error modes that might endanger the donor will relax (vent) the solenoid SO42 to close the occluder 320 and isolate the donor. Similarly, any loss of power will relax the solenoid SO42 and isolate the donor.

The sensor S4 monitors Pcuff and communicates with solenoid SO41 (for increases in pressure) and solenoid SO40 (for venting) to maintain the donor cuff within its specified ranges during the procedure. The solenoid SO40 is normally open so that the cuff line will vent in the event of system error or loss of power. The solenoid SO41 is normally closed to isolate the donor from any Phard in the event of power loss or system error.

FIG. 12 shows a sensor S8 in the pneumatic line serving the donor interface pump actuator PA3. The sensor S8 is a bidirectional mass air flow sensor, which can monitor air flow to the donor interface pump actuator PA3 to detect occlusions in the donor line. Alternatively, as will be described in greater detail later, electrical field variations can be sensed by an electrode carried within the donor interface pump station PP3, or any or all other pump stations PP1, PP2, or PP4, to detect occlusions, as well as to permit calculation of flow rates and the detection of air.

Various alternative embodiments are possible. For example, the pressure and vacuum available to the four pumping stations could be modified to include more or less distinct levels or different groupings of "shared" pressure and vacuum levels. As another example, Vhard could be removed from access to the solenoids SO2, SO5, SO8, SO18, SO19, SO21, SO22 since the restoring springs will return the cassette valves to a closed position upon removal of a vacuum. Furthermore, the vents shown as grouped together could be isolated or joined in numerous combinations.

It should also be appreciated that any of the solenoids used in "normally open" mode could be re-routed pneumatically to be realized as "normally closed". Similarly, any of the "normally closed" solenoids could be realized as "normally open."

As another example of an alternative embodiment, the hard pressure reservoir RI could be removed if Pdoor and Phard were set to identical magnitudes. In this arrangement, the door bladder 314 could serve as the hard pressure reservoir. The pressure sensor S7 and the solenoid SO43 would also be removed in this arrangement.

III. Other Process Control Components of the System

Figure 13:
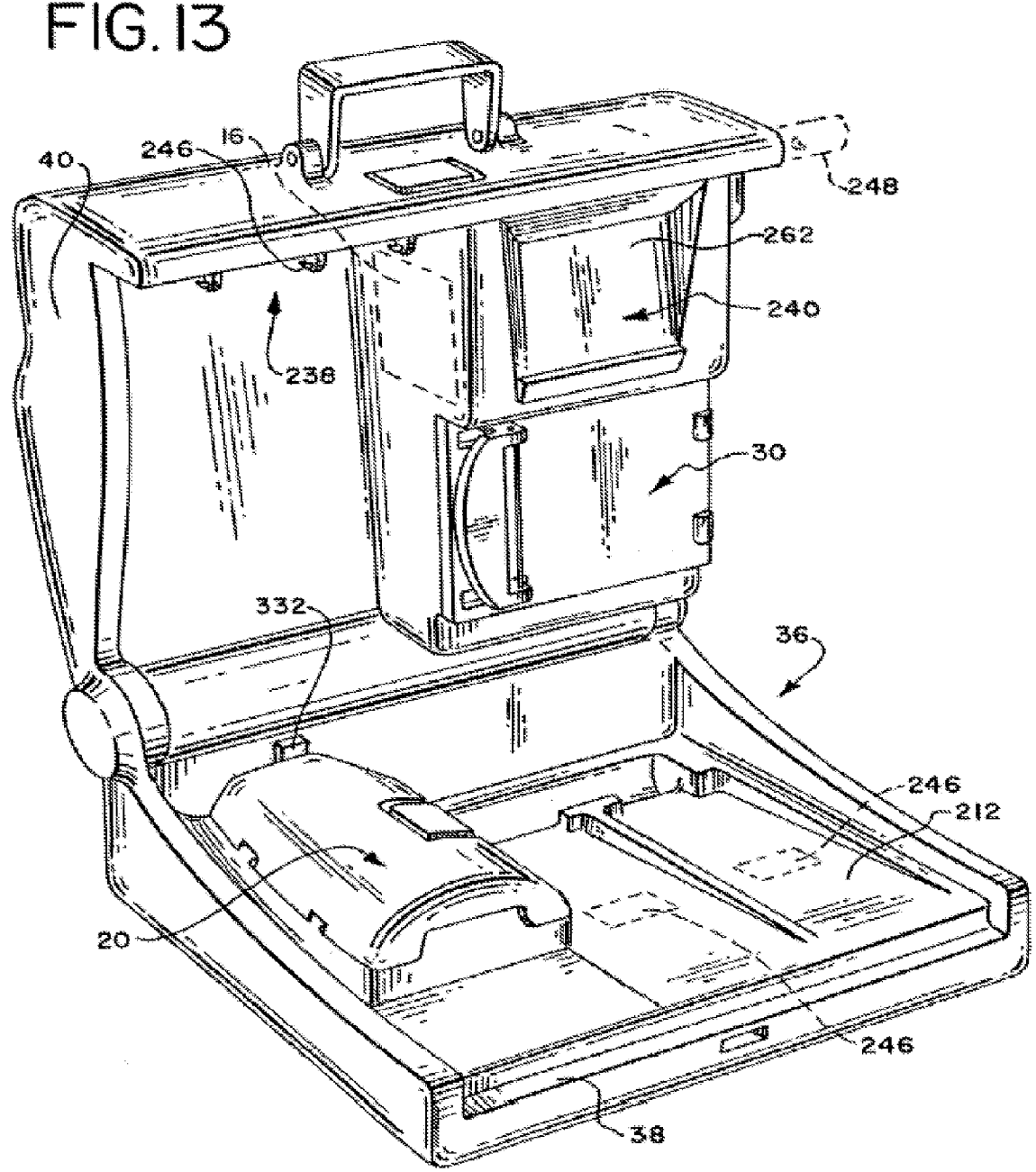
FIG. 13 is a perspective front view of the case that houses the processing device, with the lid open for use of the device, and showing the location of various processing elements housed within the case.

As FIG. 13 best shows, the case 36 contains other components compactly arranged to aid blood processing. In addition to the centrifuge station 20 and pump and valve station 30, already described, the case 36 includes a weigh station 238, an operator interface station 240, and one or more trays 212 or hangers 248 for containers. The arrangement of these components in the case 36 can vary. In the illustrated embodiment, the weigh station 238, the controller 16, and the user interface station 240, like the pump and valve station 30, are located in the lid 40 of the case 36. The holding trays 212 are located in the base 38 of the case 36, adjacent the centrifuge station 20.

A. Container Support Components

The weigh station 238 comprises a series of container hangers/weigh sensors 246 arranged along the top of the lid 40. In use (see FIG. 2), containers 304, 308, 312 are suspended on the hangers/weigh sensors 246.

The containers receive blood components separated during processing, as will be described in greater detail later. The weigh sensors 246 provide output reflecting weight changes over time. This output is conveyed to the controller 16. The controller 16 processes the incremental weight changes to derive fluid processing volumes and flow rates. The controller generates signals to control processing events based, in part, upon the derived processing volumes. Further details of the operation of the controller to control processing events will be provided later.

The holding trays 212 comprise molded recesses in the base 38. The trays 212 accommodate the containers 276 and 280 (see FIG. 2). In the illustrated embodiment, an additional swing-out hanger 248 is also provided on the side of the lid 40. The hanger 248 (see FIG. 2) supports the container 288 during processing. In the illustrated embodiment, the trays 212 and hanger 248 also include weigh sensors 246.

Figure 40:
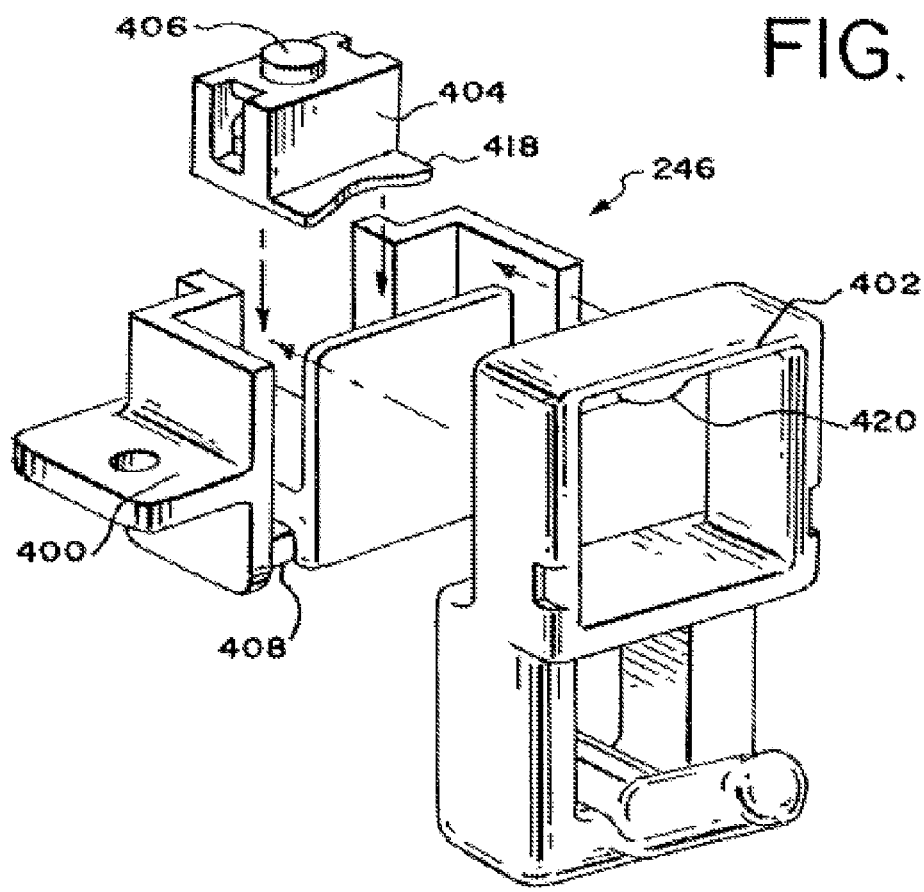
FIG. 40 is a representative embodiment of a weigh scale suited for use in association with the device shown in FIG. 1.

The weigh sensors 246 can be variously constructed. In the embodiment shown in FIG. 40, the scale includes a force sensor 404 incorporated into a housing 400, to which a hanger 402 is attached. The top surface 420 of hanger 402 engages a spring 406 on the sensor 404. Another spring 418 is compressed as a load, carried by the hanger 402, is applied. The spring 418 resists load movement of the hanger 402, until the load exceeds a predetermined weight (e.g., 2 kg.). At that time, the hanger 402 bottoms out on mechanical stops 408 in the housing 400, thereby providing over load protection.

Figure 41:
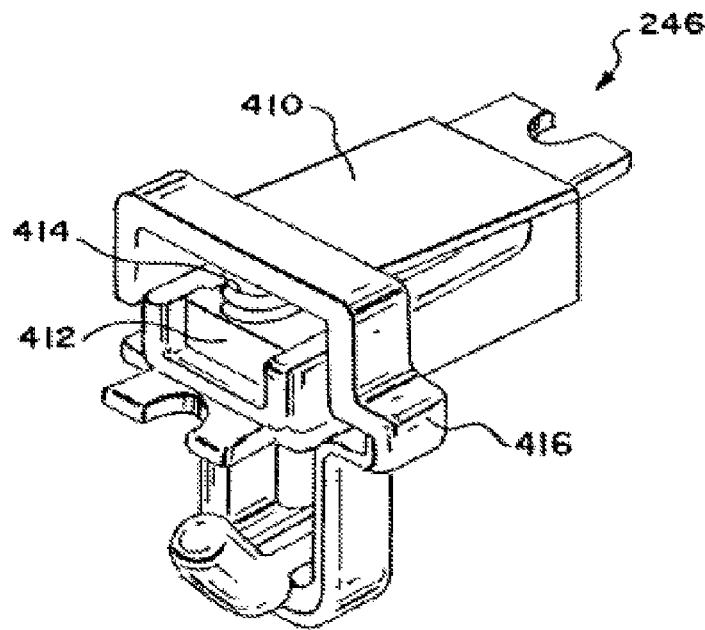
FIG. 41 is a representative embodiment of another weigh scale suited for use in association with the device shown in FIG. 1.

In the embodiment shown in FIG. 41, a supported beam 410 transfers force applied by a hanger 416 to a force sensor 412 through a spring 414. This design virtually eliminates friction from the weight sensing system. The magnitude of the load carried by the beam is linear in behavior, and the weight sensing system can be readily calibrated to ascertain an actual load applied to the hanger 416.

B. The Controller and Operator Interface Station

Figure 14:
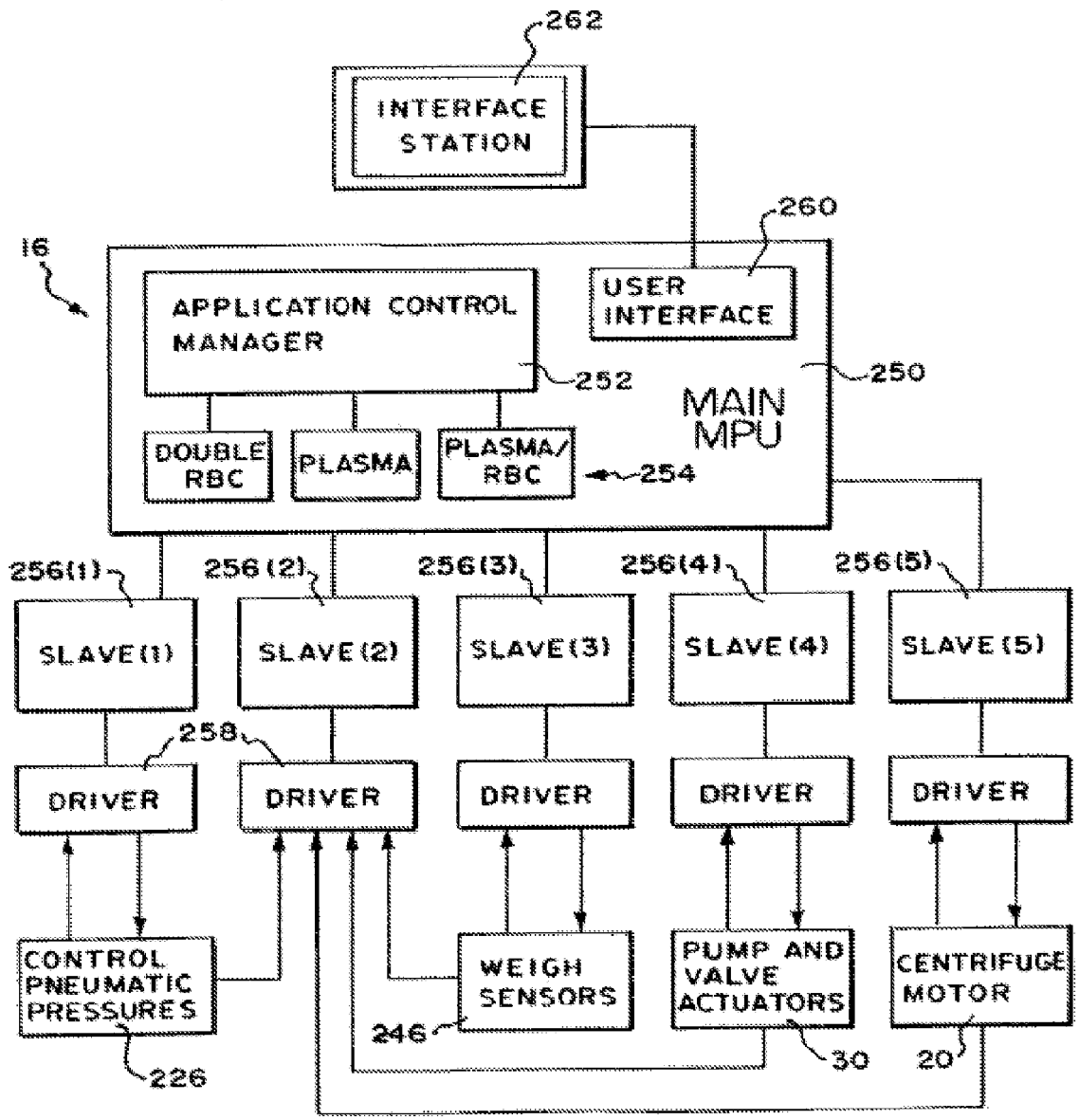
FIG. 14 is a schematic view of the controller that carries out the process control and monitoring functions of the device shown in FIG. 1.

The controller 16 carries out process control and monitoring functions for the system 10. As FIG. 14 shows schematically, the controller 16 comprises a main processing unit (MPU) 250, which can comprise, e.g., a Pentium™ type microprocessor made by Intel Corporation, although other types of conventional microprocessors can be used. The controller 16 is mounted inside the lid 40 of the case 36 (as FIG. 13 shows).

In one embodiment, the MPU 250 employs conventional real time multi-tasking to allocate MPU cycles to processing tasks. A periodic timer interrupt (for example, every 5 milliseconds) preempts the executing task and schedules another that is in a ready state for execution. If a reschedule is requested, the highest priority task in the ready state is scheduled. Otherwise, the next task on the list in the ready state is scheduled.

As FIG. 14 shows, the MPU 250 includes an application control manager 252. The application control manager 252 administers the activation of a library of at least one control application 254. Each control application 254 prescribes procedures for carrying out given functional tasks using the centrifuge station 20 and the pump and valve station 30 in a predetermined way. In the illustrated embodiment, the applications 254 reside as process software in EPROM's in the MPU 250.

The number of applications 254 can vary. In the illustrated embodiment, the applications 254 include at least one clinical procedure application. The procedure application contains the steps to carry out one prescribed clinical processing procedure. For the sake of example, in the illustrated embodiment, the application 254 includes three procedure applications: (1) a double unit red blood cell collection procedure; (2) a plasma collection procedure; and (3) a plasma/red blood cell collection procedure. The details of these procedures will be described later. Of course, additional procedure applications can be included.

As FIG. 14 shows, several slave processing units communicate with the application control manager 252. While the number of slave processing units can vary, the illustrated embodiment shows five units 256(1) to 256(5). The slave processing units 256(1) to 256(5), in turn, communicate with low level peripheral controllers 258 for controlling the pneumatic pressures within the manifold assembly 226, the weigh sensors 246, the pump and valve actuators PA1 to PA4 and VA1 to VA23 in the pump and valve station 30, the motor for the centrifuge station 20, the interface sensing station 332, and other functional hardware of the system.

The MPU 250 contains in EPROM's the commands for the peripheral controllers 258, which are downloaded to the appropriate slave processing unit 256(1) to 256(5) at start-up. The application control manager 252 also downloads to the appropriate slave processing unit 256(1) to 256(5) the operating parameters prescribed by the activated application 254.

With this downloaded information, the slave processing units 256(1) to 256(5) proceed to generate device commands for the peripheral controllers 258, causing the hardware to operate in a specified way to carry out the procedure. The peripheral controllers 258 return current hardware status information to the appropriate slave processing unit 256(1) to 256(5), which, in turn, generates the commands necessary to maintain the operating parameters ordered by the application control manager 252.

In the illustrated embodiment, one slave processing unit 256(2) performs the function of an environmental manager. The unit 256(2) receives redundant current hardware status information and reports to the MPU 250 should a slave unit malfunction and fail to maintain the desired operating conditions.

As FIG. 14 shows, the MPU 250 also includes an interactive user interface 260, which allows the operator to view and comprehend information regarding the operation of the system 10. The interface 260 is coupled to the interface station 240. The interface 260 allows the operator to use the interface station 240 to select applications 254 residing in the application control manager 252, as well as to change certain functions and performance criteria of the system 10.

As FIG. 13 shows, the interface station 240 includes an interface screen 262 carried in the lid 40. The interface screen 262 displays information for viewing by the operator in alpha-numeric format and as graphical images. In the illustrated embodiment, the interface screen 262 also serves as an input device. It receives input from the operator by conventional touch activation.

C. On-Line Monitoring of Pump Flows

1. Gravimetric Monitoring

Using the weigh scales 246, either upstream or downstream of the pumps, the controller 16 can continuously determine the actual volume of fluid that is moved per pump stroke and correct for any deviations from commanded flow. The controller 16 can also diagnose exceptional situations, such as leaks and obstructions in the fluid path. This measure of monitoring and control is desirable in an automated apheresis application, where anticoagulant has to be accurately metered with the whole blood as it is drawn from the donor, and where product quality (e.g., hematocrit, plasma purity) is influenced by the accuracy of the pump flow rates.

The pumps PP1 to PP4 in the cassette 28 each provides a relatively-constant nominal stroke volume, or SV. The flow rate for a given pump can therefore be expressed as follows:

$$Q = \frac{SV}{(T_{Pump} + T_{Fill} + T_{Idle})} \quad (1)$$

where:

Q is the flow rate of the pump.

$T_{Pump}$ is the time the fluid is moved out of the pump station.

$T_{Fill}$ is the time the pump is filled with fluid.

$T_{Idle}$ is the time when the pump is idle, that is, when no fluid movement occurs.

The SV can be affected by the interaction of the pump with attached downstream and upstream fluid circuits. This is analogous, in electrical circuit theory, to the interaction of a non-ideal current source with the input impedance of the load it sees. Because of this, the actual SV can be different than the nominal SV.

The actual fluid flow in volume per unit of time $Q_{Actual}$ can therefore be expressed as follows:

$$Q_{Actual} = k \times \frac{SV_{Ideal}}{T_{Pump} + T_{Fill} + T_{Idle}} \quad (2)$$

where:

$Q_{Actual}$ is the actual fluid flow in volume per unit of time.
$SV_{Ideal}$ is the theoretical stroke volume, based upon the geometry of the pump station. k is a correction factor that accounts for the interactions between the pump and the upstream and downstream pressures.

The actual flow rate can be ascertained gravimetrically, using the upstream or downstream weigh scales 246, based upon the following relationship:

$$Q_{Actual} = \frac{\Delta Wt}{\rho \times \Delta T} \quad (3)$$

where:

ΔWt is the change in weight of fluid as detected by the upstream or downstream weigh scale 246 during the time period ΔT.
ρ is the density of fluid.
ΔT is the time period where the change in weight ΔWt is detected in the weigh scale 246.

The following expression is derived by combining Equations (2) and (3):

$$k = (T_{Pump} + T_{Fill} + T_{Idle}) \times \frac{\Delta Wt}{(SV_{Ideal} \times \rho \times \Delta T)} \quad (4)$$

The controller 16 computes k according to Equation (4) and then adjusts $T_{Idle}$ so that the desired flow rate is achieved, as follows:

$$T_{Idle} = \left(k \times \frac{SV_{Ideal}}{Q_{Desired}}\right) - T_{Pump} - T_{Fill} \quad (5)$$

The controller 16 updates the values for k and $T_{Idle}$ frequently to adjust the flow rates.

Alternatively, the controller 16 can change $T_{Pump}$ and/or $T_{Fill}$ and/or $T_{Idle}$ to adjust the flow rates.

In this arrangement, one or more of the time interval components $T_{pump}$, or $T_{Fill}$, or $T_{Idle}$ is adjusted to a new magnitude to achieve $Q_{Desired}$, according to the following relationship:

$$T_{n(Adjusted)} = k\left(\frac{SV_{Ideal}}{Q_{Desired}}\right) - T_{n(NotAdjusted)}$$

where:

$T_{n(Adjusted)}$ is the magnitude of the time interval component or components after adjustment to achieve the desired flow rate $Q_{Desired}$.

$T_{n(NotAdjusted)}$ is the magnitude of the value of the other time interval component or components of $T_{Stroke}$ that are not adjusted. The adjusted stroke interval after adjustment to achieve the desired flow rate $Q_{Desired}$ is the sum of $T_{n(Adjusted)}$ and $T_{n(NotAdjusted)}$.

The controller 16 also applies the correction factor k as a diagnostics tool to determine abnormal operating conditions. For example, if k differs significantly from its nominal value, the fluid path may have either a leak or an obstruction. Similarly, if the computed value of k is of a polarity different from what was expected, then the direction of the pump may be reversed.

With the weigh scales 246, the controller 16 can perform on-line diagnostics even if the pumps are not moving fluid. For example, if the weigh scales 246 detect changes in weight when no flow is expected, then a leaky valve or a leak in the set 264 may be present.

In computing k and $T_{Idle}$ and/or $T_{Pump}$ and/or $T_{Fill}$, the controller 16 may rely upon multiple measurements of ΔWt and/or ΔT. A variety of averaging or recursive techniques (e.g., recursive least mean squares, Kalman filtering, etc.) may be used to decrease the error associated with the estimation schemes.

The above described monitoring technique is applicable for use for other constant stroke volume pumps, e.g. peristaltic pumps, etc.

2. Electrical Monitoring

Figure 42:
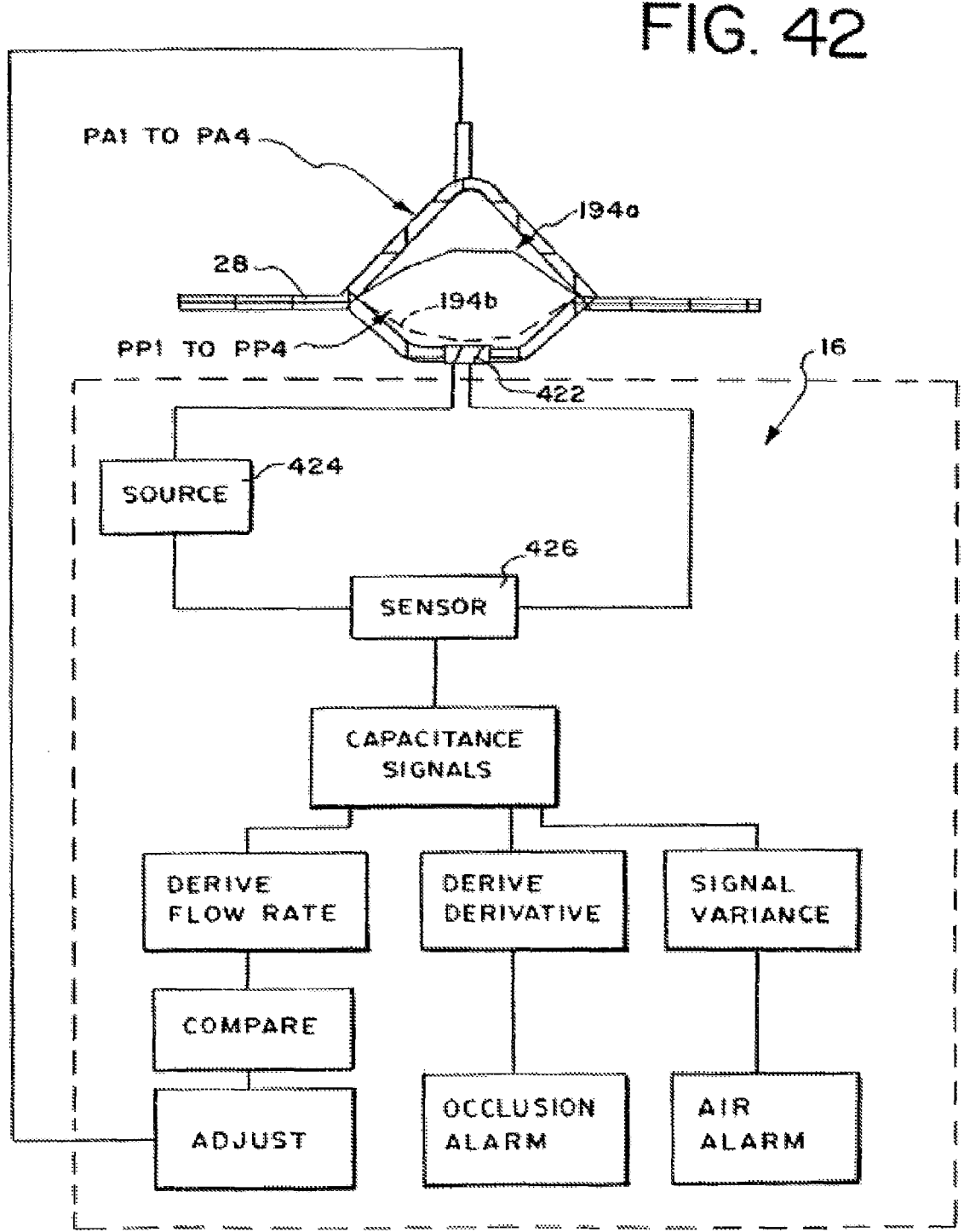
FIG. 42 is a schematic view of a flow rate sensing and control system for a pneumatic pump station employing an electrode to create an electrical field inside the pump station.

In an alternative arrangement (see FIG. 42), the controller 16 includes a metal electrode 422 located in the chamber of each pump station PP1 to PP4 on the cassette 28. The electrodes 422 are coupled to a current source 424. The passage of current through each electrode 422 creates an electrical field within the respective pump station PP1 to PP4.

Cyclic deflection of the diaphragm 194 to draw fluid into and expel fluid from the pump station PP1 to PP4 changes the electrical field, resulting in a change in total capacitance of the circuit through the electrode 422. Capacitance increases as fluid is drawn into the pump station PP1 to PP4, and capacitance decreases as fluid is expelled from the pump station PP1 to PP4.

The controller 16 includes a capacitive sensor 426 (e.g., a QProx™ E2S sensor from Quantum Research Group Ltd. of Hamble, England) coupled to each electrode 422. The capacitive sensor 426 registers changes in capacitance for the electrode 422 in each pump station PP1 to PP4. The capacitance signal for a given electrode 422 has a high signal magnitude when the pump station is filled with liquid (diaphragm position 194*a*), has a low signal magnitude signal when the pump station is empty of fluid (diaphragm position 194*b*), and has a range of intermediate signal magnitudes when the diaphragm occupies positions between positions 194*a* and 194*b*.

At the outset of a blood processing procedure, the controller 16 calibrates the difference between the high and low signal magnitudes for each sensor to the maximum stroke volume SV of the respective pump station. The controller 16 then relates the difference between sensed maximum and minimum signal values during subsequent draw and expel cycles to fluid volume drawn and expelled through the pump station. The controller 16 sums the fluid volumes pumped over a sample time period to yield an actual flow rate.

The controller 16 compares the actual flow rate to a desired flow rate. If a deviance exists, the controller 16 varies pneumatic pressure pulses delivered to the actuator PA1 to PA4, to adjust $T_{Idle}$ and/or $T_{Pump}$ and/or $T_{Fill}$ to minimize the deviance.

The controller 16 also operates to detect abnormal operating conditions based upon the variations in the electric field and to generate an alarm output. In the illustrated embodiment, the controller 16 monitors for an increase in the magnitude of the low signal magnitude over time. The increase in magnitude reflects the presence of air inside a pump station.

In the illustrated embodiment, the controller 16 also generates a derivative of the signal output of the sensor 426. Changes in the derivative, or the absence of a derivative, reflects a partial or complete occlusion of flow through the pump station PP1 to PP4. The derivative itself also varies in a distinct fashion depending upon whether the occlusion occurs at the inlet or outlet of the pump station PP1 to PP4.

IV. The Blood Processing Procedures

A. Double RBC Collection Procedure (No Plasma Collection)

During this procedure, whole blood from a donor is centrifugally processed to yield up to two units (approximately 500 ml) of red blood cells for collection. All plasma constituent is returned to the donor. This procedure will, in shorthand, be called the double red blood cell collection procedure.

Prior to undertaking the double red blood cell collection procedure, as well as any blood collection procedure, the controller 16 operates the manifold assembly 226 to conduct an appropriate integrity check of the cassette 28, to determine whether there are any leaks in the cassette 28. Once the cassette integrity check is complete and no leaks are found, the controller 16 begins the desired blood collection procedure.

The double red blood cell collection procedure includes a pre-collection cycle, a collection cycle, a post-collection cycle, and a storage preparation cycle. During the pre-collection cycle, the set 264 is primed to vent air prior to venipuncture. During the collection cycle, whole blood drawn from the donor is processed to collect two units of red blood cells, while returning plasma to the donor. During the post-collection cycle, excess plasma is returned to the donor, and the set is flushed with saline. During the storage preparation cycle, a red blood cell storage solution is added.

1. The Pre-Collection Cycle a. Anticoagulant Prime 1

In a first phase of the pre-collection cycle (AC Prime 1), tube 300 leading to the phlebotomy needle 268 is clamped closed (see FIG. 10). The blood processing circuit 46 is programmed (through the selective application of pressure to the valves and pump stations of the cassette) to operate the donor interface pump PP3, drawing anticoagulant through the anticoagulant tube 270 and up the donor tube 266 through the y-connector 272 (i.e., in through valve V13 and out through valve V11). The circuit is further programmed to convey air residing in the anticoagulant tube 270, the donor tube 266, and the cassette into the in-process container 312. This phase continues until an air detector 298 along the donor tube 266 detects liquid, confirming the pumping function of the donor interface pump PP3.

b. Anticoagulant Prime 2

In a second phase of the pre-collection cycle (AC Prime 2), the circuit is programmed to operate the anticoagulant pump PP4 to convey anticoagulant into the in-process container 312. Weight changes in the in-process container 312. AC Prime 2 is terminated when the anticoagulant pump PP4 conveys a predetermined volume of anticoagulant (e.g., 10 g) into the in-process container 312, confirming its pumping function.

c. Saline Prime 1

In a third phase of the pre-collection cycle (Saline Prime 1), the processing chamber 18 remains stationary. The circuit is programmed to operate the in-process pump station PP1 to draw saline from the saline container 288 through the in-process pump PP1. This creates a reverse flow of saline through the stationary processing chamber 18 toward the in-process container 312. In this sequence saline is drawn through the processing chamber 18 from the saline container 288 into the in-process pump PP1 through valve V14. The saline is expelled from the pump station PP1 toward the in-process container 312 through valve V9. Weight changes in the saline container 288 are monitored. This phase is terminated upon registering a predetermined weight change in the saline container 288, which indicates conveyance of a saline volume sufficient to initially fill about one half of the processing chamber 18 (e.g., about 60 g).

d. Saline Prime 2

With the processing chamber 18 about half full of priming saline, a fourth phase of the pre-collection cycle begins (Saline Prime 2). The processing chamber 18 is rotated at a low rate (e.g., about 300 RPM), while the circuit continues to operate in the same fashion as in Saline Prime 1. Additional saline is drawn into the pump station PP1 through valve V14 and expelled out of the pump station PP1 through valve V9 and into the in-process container 312. Weight changes in the in-process container 312 are monitored. This phase is terminated upon registering a predetermined weight change in the in-process container 312, which indicates the conveyance of an additional volume of saline sufficient to substantially fill the processing chamber 18 (e.g., about 80 g).

e. Saline Prime 3

In a fifth phase of the pre-collection cycle (Saline Prime 3), the circuit is programmed to first operate the in-process pump station PP1 to convey saline from the in-process container 312 through all outlet ports of the separation device and back into the saline container 288 through the plasma pump station PP2. This completes the priming of the processing chamber 18 and the in-process pump station PP1 (pumping in through valve V9 and out through valve V14), as well as primes the plasma pump station PP2, with the valves V7, V6, V10 and V12 opened to allow passive flow of saline. During this time, the rate at which the processing chamber 18 is rotated is successively ramped between zero and 300 RPM. Weight changes in the in-process container 312 are monitored. When a predetermined initial volume of saline is conveyed in this manner, the circuit is programmed to close valve V7, open valves V9 and V14, and to commence pumping saline to the saline container 288 through the plasma pump PP2, in through valve V12 and out through valve V10, allowing saline to passively flow through the in-process pump PP1. Saline in returned in this manner from the in-process container 312 to the saline container 288 until weight sensing indicated that a preestablished minimum volume of saline occupies the in-process container 312.

f. Vent Donor Line

In a sixth phase of the pre-collection cycle (Vent Donor Line), the circuit is programmed to purge air from the venipuncture needle, prior to venipuncture, by operating the donor interface pump PP3 to pump anticoagulant through anticoagulant pump PP4 and into the in-process container 312 g. Venipuncture

In a seventh phase of the pre-collection cycle (Venipuncture), the circuit is programmed to close all valves V1 to V23, so that venipuncture can be accomplished.

The programming of the circuit during the phases of the pre-collection cycle is summarized in the following table.

TABLE

Programming of Blood Processing Circuit During Pre-Collection Cycle
(Double Red Blood Cell Collection Procedure)

| Phase | AC Prime 1 | AC Prime 2 | Saline Prime 1 | Saline Prime 2 | Saline Prime 3 | Vent Donor Line | Venipuncture |
|---|---|---|---|---|---|---|---|
| V1 | ● | ● | ● | ● | ● | ● | ● |
| V2 | ● | ● | ● | ● | ● | ● | ● |
| V3 | ○ | ○ | ● | ● | ● | ○ | ● |
| V4 | ● | ● | ○ | ○ | ● | ● | ● |
| V5 | ● | ● | ● | ● | ● | ● | ● |
| V6 | ● | ● | ● | ● | ○ | ● | ● |
| V7 | ● | ● | ● | ● | ○ (Stage 1) ● (Stage 2) | ● | ● |
| V8 | ● | ● | ● | ● | ● | ● | ● |
| V9 | ● | ● | ○/● Pump Out | ○/● Pump Out | ○/● Pump In (Stage 1) ○ (Stage 2) | ● | ● |
| V10 | ● | ● | ● | ● | ○ (Stage 1) ○/● Pump Out (Stage 2) | ● | ● |
| V11 | ○/● Pump Out | ○ | ● | ● | ● | ○/● Pump In | ● |
| V12 | ● | ● | ● | ● | ○ (Stage 1) ○/● Pump In (Stage 2) | ● | ● |
| V13 | ○/● Pump In | ○ | ● | ● | ● | ○/● Pump Out | ● |
| V14 | ● | ● | ○/● Pump In | ○/● Pump In | ○/● Pump Out (Stage 1) ○ (Stage 2) | ● | ● |
| V15 | ○ | ○/● Pump Out | ● | ● | ● | ○ | ● |
| V16 | ● | ● | ● | ● | ● | ● | ● |
| V17 | ● | ● | ● | ● | ● | ● | ● |
| V18 | ○ | ○ | ● | ● | ● | ○ | ● |
| V19 | ○ | ○ | ● | ● | ● | ○ | ● |
| V20 | ○ | ○/● Pump In | ● | ● | ● | ○ | ● |
| V21 | ● | ● | ● | ● | ● | ● | ● |
| V22 | ● | ● | ○ | ○ | ○ | ● | ● |
| V23 | ● | ● | ○ | ○ | ○ | ● | ● |
| PP1 | ■ | ■ | □ | □ | □ | ■ | ■ |

TABLE-continued

Programming of Blood Processing Circuit During Pre-Collection Cycle
(Double Red Blood Cell Collection Procedure)

| Phase | AC Prime 1 | AC Prime 2 | Saline Prime 1 | Saline Prime 2 | Saline Prime 3 | Vent Donor Line | Venipuncture |
|---|---|---|---|---|---|---|---|
| PP2 | ■ | ■ | ■ | ■ | (Stage 1) □ (Stage 2) ● | ■ | ■ |
| PP3 | □ | ■ | ■ | ■ | ● | □ | ■ |
| PP4 | ■ | □ | ■ | ■ | ● | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

2. The Collection Cycle a. Blood Prime 1

With venipuncture, tube 300 leading to the phlebotomy needle 268 is opened. In a first phase of the collection cycle (Blood Prime 1), the blood processing circuit 46 is programmed (through the selective application of pressure to the valves and pump stations of the cassette) to operate the donor interface pump PP3 (i.e., in through valve V13 and out through valve V11) and the anticoagulant pump PP4 (i.e., in through valve V20 and out through valve V15) to draw anticoagulated blood through the donor tube 270 into the in-process container 312. This phase continues until an incremental volume of anticoagulated whole blood enters the in-process container 312, as monitored by the weigh sensor.

b. Blood Prime 2

In a next phase (Blood Prime 2), the blood processing circuit 46 is programmed to operate the in-process pump station PP1 to draw anticoagulated blood from the in-process container 312 through the separation device. During this phase, saline displaced by the blood is returned to the donor. This phase primes the separation device with anticoagulated whole blood. This phase continues until an incremental volume of anticoagulated whole blood leaves the in-process container 312, as monitored by the weigh sensor.

c. Blood Separation while Drawing Whole Blood or without Drawing Whole Blood In a next phase of the blood collection cycle (Blood Separation While Drawing Whole Blood), the blood processing circuit 46 is programmed to operate the donor interface pump station PP3 (i.e., in through valve V13 and out through valve V11); the anticoagulant pump PP4 (i.e., in through valve V20 and out through valve V15); the in-process pump PP1 (i.e., in through valve V9 and out through valve V14); and the plasma pump PP2 (i.e., in through valve V12 and out through valve V10). This arrangement draws anticoagulated blood into the in-process container 312, while conveying the blood from the in-process container 312 into the processing chamber for separation. This arrangement also removes plasma from the processing chamber into the plasma container 304, while removing red blood cells from the processing chamber into the red blood cell container 308. This phase continues until an incremental volume of plasma is collected in the plasma collection container 304 (as monitored by the weigh sensor) or until a targeted volume of red blood cells is collected in the red blood cell collection container (as monitored by the weigh sensor).

If the volume of whole blood in the in-process container 312 reaches a predetermined maximum threshold before the targeted volume of either plasma or red blood cells is collected, the circuit is programmed for another phase (Blood Separation Without Drawing Whole Blood), to terminate operation of the donor interface pump station PP3 (while also closing valves V13, V11, V18, and V3) to terminate collection of whole blood in the in-process container 312, while still continuing blood separation. If the volume of whole blood reaches a predetermined minimum threshold in the in-process container 312 during blood separation, but before the targeted volume of either plasma or red blood cells is collected, the circuit is programmed to return to the Blood Separation While Drawing Whole Blood Phase, to thereby allow whole blood to enter the in-process container 312. The circuit is programmed to toggle between the Blood Separation While Drawing Whole Blood Phase and the Blood Separation Without Drawing Whole Blood Phase according to the high and low volume thresholds for the in-process container 312, until the requisite volume of plasma has been collected, or until the target volume of red blood cells has been collected, whichever occurs first.

d. Return Plasma and Saline

If the targeted volume of red blood cells has not been collected, the next phase of the blood collection cycle (Return Plasma With Separation) programs the blood processing circuit 46 to operate the donor interface pump station PP3 (i.e., in through valve V11 and out through valve V13); the in-process pump PP1 (i.e., in through valve V9 and out through valve V14); and the plasma pump PP2 (i.e., in through valve V12 and out through valve V10). This arrangement conveys anticoagulated whole blood from the in-process container 312 into the processing chamber for separation, while removing plasma into the plasma container 304 and red blood cells into the red blood cell container 308. This arrangement also conveys plasma from the plasma container 304 to the donor, while also mixing saline from the container 288 in-line with the returned plasma. The in-line mixing of saline with plasma raises the saline temperature and improves donor comfort.

This phase continues until the plasma container 304 is empty, as monitored by the weigh sensor.

If the volume of whole blood in the in-process container 312 reaches a specified low threshold before the plasma container 304 empties, the circuit is programmed to enter another phase (Return Plasma Without Separation), to terminate operation of the in-process pump station PP1 (while also closing valves V9, V10, V12, and V14) to terminate blood separation. The phase continues until the plasma container 304 empties.

e. Fill Donor Line

Upon emptying the plasma container 304, the circuit is programmed to enter a phase (Fill Donor Line), to operate the donor interface pump station PP3 (i.e., in through valve V11 and out through valve V13) to draw whole blood from the in-process container 312 to fill the donor tube 266, thereby purging plasma (mixed with saline) in preparation for another draw whole blood cycle.

The circuit is then programmed to conduct another Blood Separation While Drawing Whole Blood Phase, to refill the in-process container 312. The circuit is programmed in successive Blood Separation and Return Plasma Phases until the weigh sensor indicates that a desired volume of red blood cells has been collected in the red blood cell collection container 308. When the targeted volume of red blood cells has been collected, the post-collection cycle commences.

The programming of the circuit during the phases of the collection cycle is summarized in the following table.

TABLE

Programming of Blood Processing Circuit During The Collection Cycle
(Double Red Blood Cell Collection Procedure)

| Phase | Blood Prime 1 | Blood Prime 2 | Blood Separation While Drawing Whole Blood (Without Drawing Whole Blood) | Return Plasma/ With Separation (Without Separation) | Fill Donor Line |
|---|---|---|---|---|---|
| V1 | ● | ● | ● | ● | ○ |
| V2 | ● | ● | ○ | ○ (●) | ● |
| V3 | ○ | ● | ○ (●) | ● | ● |
| V4 | ● | ● | ● | ● | ● |
| V5 | ● | ● | ○ | ○ | ● |
| V6 | ● | ● | ● | ○/● Alternates With V23 | ● |
| V7 | ● | ○ | ● | ● | ○ |
| V8 | ● | ● | ● | ● | ● |
| V9 | ● | ○/● Pump In | ○/● Pump In | ○/● Pump In (●) | ● |
| V10 | ● | ● | ○/● Pump Out | ○/● Pump Out (●) | ● |
| V11 | ○/● Pump Out | ○ | ○/● Pump Out (●) | ○/● Pump In | ○/● Pump In |
| V12 | ● | ● | ○/● Pump In | ○/● Pump In (●) | ● |
| V13 | ○/● Pump In | ○ | ○/● Pump In (●) | ○/● Pump Out | ○/● Pump Out |
| V14 | ● | ○/● Pump Out | ○/● Pump Out | ○/● Pump Out (●) | ● |
| V15 | ○/● Pump Out | ● | ○/● Pump Out (●) | ● | ● |
| V16 | ● | ● | ● | ● | ● |
| V17 | ● | ● | ● | ● | ● |
| V18 | ○ | ○ | ○ (●) | ○ | ○ |
| V19 | ○ | ● | ○ (●) | ● | ● |
| V20 | ○/● Pump In | ● | ○/● Pump In (●) | ● | ● |
| V21 | ● | ● | ● | ● | ● |
| V22 | ● | ● | ● | ○ | ● |
| V23 | ● | ● | ● | ○/● Alternates With V6 | ● |
| PP1 | ■ | □ | □ | □ (■) | ■ |
| PP2 | ■ | ■ | □ | □ (■) | ■ |
| PP3 | □ | ■ | □ (■) | □ | □ |
| PP4 | □ | ■ | □ (■) | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

3. The Post-Collection Cycle

Once the targeted volume of red blood cells has been collected (as monitored by the weigh sensor), the circuit is programmed to carry out the phases of the post-collection cycle.

a. Return Excess Plasma

In a first phase of the post-collection cycle (Excess Plasma Return), the circuit is programmed to terminate the supply and removal of blood to and from the processing chamber, while operating the donor interface pump station PP3 (i.e., in through valve V11 and out through valve V13) to convey plasma remaining in the plasma container 304 to the donor. The circuit is also programmed in this phase to mix saline from the container 288 in-line with the returned plasma. This phase continues until the plasma container 304 is empty, as monitored by the weigh sensor.

b. Saline Purge

In the next phase of the post-collection cycle (Saline Purge), the circuit is programmed to operate the in-process pump station PP1 (i.e., in through valve V14 and out through valve V9) to convey saline from the container 288 through the separation device, to displace the blood contents of the separation device into the in-process container 312, in preparation for their return to the donor. This phase reduces the loss of donor blood. This phase continues until a predetermined volume of saline is pumped through the separation device, as monitored by the weigh sensor.

c. Final Return to Donor

In the next phase of the post-collection cycle (Final Return), the circuit is programmed to operate the donor interface pump station PP3 (i.e., in through valve V11 and out through valve V13) to convey the blood contents of the in-process container 312 to the donor. Saline is intermittently mixed with the blood contents. This phase continues until the in-process container 312 is empty, as monitored by the weigh sensor.

d. Fluid Replacement

In the next phase (Fluid Replacement), the circuit is programmed to operate the donor interface pump station PP3 (i.e., in through valve V11 and out through valve V13) to convey the saline to the donor. This phase continues until a prescribed replacement volume amount is infused, as monitored by the weigh sensor.

e. Empty In-Process Container

In the next phase of the post-collection cycle (Empty In-Process Container), the circuit is programmed to operate the donor interface pump station PP3 (i.e., in through valve V11 and out through valve V13) to convey all remaining contents of the in-process container 312 to the donor, in preparation for splitting the contents of the red blood cell container 308 for storage in both containers 308 and 312. This phase continues until a zero volume reading for the in-process container 312 occurs, as monitored by the weigh sensor, and air is detected at the air detector.

At this phase, the circuit is programmed to close all valves and idle all pump stations, so that the phlebotomy needle 268 can be removed from the donor.

The programming of the circuit during the phases of the post-collection cycle is summarized in the following table.

TABLE

Programming of Blood Processing Circuit During The Post-Collection Cycle
(Double Red Blood Cell Collection Procedure)

| Phase | Excess Plasma Return | Saline Purge | Final Return | Fluid Replacement | Empty In-Process Container |
|---|---|---|---|---|---|
| V1 | ● | ● | ○ | ● | ○ |
| V2 | ● | ● | ● | ● | ● |
| V3 | ● | ● | ● | ● | ● |
| V4 | ● | ○ | ● | ● | ● |
| V5 | ○ | ● | ● | ● | ● |
| V6 | ○/● Alternates With V23 | ● | ● | ● | ● |
| V7 | ● | ● | ○/● Alternates With V23 | ● | ○ |
| V8 | ● | ● | ● | ● | ● |
| V9 | ○ | ○/● Pump Out | ● | ● | ● |
| V10 | ● | ● | ● | ● | ● |
| V11 | ○/● Pump In | ● | ○/● Pump In | ○/● Pump In | ○/● Pump In |
| V12 | ● | ● | ● | ● | ● |
| V13 | ○/● Pump Out | ● | ○/● Pump Out | ○/● Pump Out | ○/● Pump Out |
| V14 | ● | ○/● Pump In | ● | ● | ● |
| V15 | ● | ● | ● | ● | ● |
| V16 | ● | ● | ● | ● | ● |
| V17 | ● | ● | ● | ● | ● |
| V18 | ○ | ● | ○ | ○ | ○ |
| V19 | ● | ● | ● | ● | ● |
| V20 | ● | ● | ● | ● | ● |
| V21 | ● | ● | ● | ● | ● |
| V22 | ○ | ○ | ○ | ○ | ● |
| V23 | ○/● Alternates With V6 | ○ | ○/● Alternates With V7 | ○ | ● |
| PP1 | ■ | □ | ■ | ■ | ■ |
| PP2 | ■ | ■ | ■ | ■ | ■ |
| PP3 | □ | ■ | □ | □ | □ |
| PP4 | ■ | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

4. The Storage Preparation Cycle a. Split RBC

In the first phase of the storage preparation cycle (Split RBC), the circuit is programmed to operate the donor interface pump station PP3 to transfer half of the contents of the red blood cell collection container 308 into the in-process container 312. The volume pumped is monitored by the weigh sensors for the containers 308 and 312.

b. Add RBC Preservative

In the next phases of the storage preparation cycle (Add Storage Solution to the In-Process Container and Add Storage Solution to the Red Blood Cell Collection Container), the circuit is programmed to operate the donor interface pump station PP3 to transfer a desired volume of red blood cell storage solution from the container 280 first into the in-process container 312 and then into the red blood cell collection container 308. The transfer of the desired volume is monitored by the weigh scale.

c. End Procedure

In the next and final phase (End Procedure), the circuit is programmed to close all valves and idle all pump stations, so that the red blood cell containers 308 and 312 can be separated and removed for storage. The remainder of the disposable set can now be removed and discarded.

The programming of the circuit during the phases of the storage preparation cycle is summarized in the following table.

TABLE

Programming of Blood Processing Circuit During The Storage Preparation Cycle (Double Red Blood Cell Collection Procedure)

| Phase | Split RBC Between RBC Collection And In-Process Containers | Add Storage Solution To In-Process Container | Add Storage Solution To RBC Collection Container | End Procedure (Remove Venipuncture) |
|---|---|---|---|---|
| V1 | ● | ● | ● | ● |
| V2 | ○ | ● | ○ | ● |
| V3 | ○/● Alternates With V11 And V4 | ○ | ● | ● |
| V4 | ○/● Alternates With V11 And V3 | ● | ○ | ● |
| V5 | ● | ● | ● | ● |
| V6 | ● | ● | ● | ● |
| V7 | ● | ● | ● | ● |
| V8 | ● | ● | ● | ● |
| V9 | ● | ● | ● | ● |
| V10 | ● | ● | ● | ● |
| V11 | ○/● Pump In/Pump Out | ○/● Pump In/Pump Out | ○/● Pump In/Pump Out | ● |
| V12 | ● | ● | ● | ● |
| V13 | ● | ● | ● | ● |
| V14 | ● | ● | ● | ● |
| V15 | ● | ● | ● | ● |
| V16 | ● | ○ | ○ | ● |
| V17 | ● | ● | ● | ● |
| V18 | ● | ● | ● | ● |
| V19 | ● | ● | ● | ● |
| V20 | ● | ● | ● | ● |
| V21 | ● | ○ | ○ | ● |
| V22 | ● | ● | ● | ● |
| V23 | ● | ● | ● | ● |
| PP1 | ■ | ■ | ■ | ■ |
| PP2 | ■ | ■ | ■ | ■ |
| PP3 | □ | □ | □ | ■ |
| PP4 | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

B. Plasma Collection (No Red Blood Cell Collection)

During this procedure, whole blood from a donor is centrifugally processed to yield up to 880 ml of plasma for collection. All red blood cells are returned to the donor. This procedure will, in shorthand, be called the plasma collection procedure.

Programming of the blood processing circuit 46 (through the selective application of pressure to the valves and pump stations of the cassette) makes it possible to use the same universal set 264 as in the double red blood cell collection procedure.

The procedure includes a pre-collection cycle, a collection cycle, and a postcollection cycle.

During the pre-collection cycle, the set 264 is primed to vent air prior to venipuncture. During the collection cycle, whole blood drawn from the donor is processed to collect plasma, while returning red blood cells to the donor. During the post-collection cycle, excess plasma is returned to the donor, and the set is flushed with saline.

1. The Pre-Collection Cycle a. Anticoagulant Prime

In the pre-collection cycle for the plasma collection (no red blood cells) procedure, the cassette is programmed to carry out AC Prime 1 and AC Prime 2 Phases that are identical to the AC Prime 1 and AC Prime 2 Phases of the double red blood cell collection procedure.

b. Saline Prime/Vent Donor Line/Venipuncture

In the pre-collection cycle for the plasma collection (no red blood cell) procedure, the cassette is programmed to carry out Saline Prime 1, Saline Prime 2, Saline Prime 3, Vent Donor Line, and Venipuncture Phases that are identical to the Saline Prime 1, Saline Prime 2, Saline Prime 3; Vent Donor Line, and Venipuncture Phases of the double red blood cell collection procedure.

The programming of the circuit during the phases of the pre-collection cycle is summarized in the following table.

TABLE

Programming of Blood Processing Circuit During Pre-Collection Cycle (Plasma Collection Procedure)

| Phase | AC Prime1 | AC Prime 2 | Saline Prime 1 | Saline Prime 2 | Saline Prime 3 | Vent Donor Line | Venipuncture |
|---|---|---|---|---|---|---|---|
| V1 | ● | ● | ● | ● | ● | ● | ● |
| V2 | ● | ● | ● | ● | ● | ● | ● |
| V3 | ○ | ○ | ● | ● | ● | ○ | ● |
| V4 | ● | ● | ○ | ○ | ● | ● | ● |
| V5 | ● | ● | ● | ● | ● | ● | ● |
| V6 | ● | ● | ● | ● | ○ | ● | ● |
| V7 | ● | ● | ● | ● | ○ (Stage 1) ● (Stage 2) | ● | ● |
| V8 | ● | ● | ● | ● | ● | ● | ● |
| V9 | ● | ● | ○/● Pump Out | ○/● Pump Out | ○/● Pump In (Stage 1) ○ | ● | ● |

TABLE-continued

Programming of Blood Processing Circuit During Pre-Collection Cycle
(Plasma Collection Procedure)

| Phase | AC Prime1 | AC Prime 2 | Saline Prime 1 | Saline Prime 2 | Saline Prime 3 | Vent Donor Line | Venipuncture |
|---|---|---|---|---|---|---|---|
| V10 | ● | ● | ● | ● | (Stage 2) ○ (Stage 1) ○/● Pump Out | ● | ● |
| V11 | ○/● Pump Out | ○ | ● | ● | (Stage 2) ● | ○/● Pump In | ● |
| V12 | ● | ● | ● | ● | ○ (Stage 1) ○/● Pump In (Stage 2) | ● | ● |
| V13 | ○/● Pump In | ○ | ● | ● | ● | ○/● Pump Out | ● |
| V14 | ● | ● | ○/● Pump In | ○/● Pump In | ○/● Pump Out (Stage 1) ○ (Stage 2) | ● | ● |
| V15 | ○ | ○/● Pump Out | ● | ● | ● | ○ | ● |
| V16 | ● | ● | ● | ● | ● | ● | ● |
| V17 | ● | ● | ● | ● | ● | ● | ● |
| V18 | ○ | ○ | ● | ● | ● | ○ | ● |
| V19 | ○ | ○ | ● | ● | ● | ○ | ● |
| V20 | ○ | ○/● Pump In | ● | ● | ● | ○ | ● |
| V21 | ● | ● | ● | ● | ● | ● | ● |
| V22 | ● | ● | ○ | ○ | ○ | ● | ● |
| V23 | ● | ● | ○ | ○ | ○ | ● | ● |
| PP1 | ■ | ■ | □ | □ | □ (Stage 1) ■ (Stage 2) | ■ | ■ |
| PP2 | ■ | ■ | ■ | ■ | ■ | ■ | ■ |
| PP3 | □ | ■ | ■ | ■ | ■ | □ | ■ |
| PP4 | ■ | □ | ■ | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

2. The Collection Cycle a. Blood Prime 1

With venipuncture, the tube 300 leading to the phlebotomy needle 268 is opened. In a first phase of the collection cycle (Blood Prime 1), the blood processing circuit 46 is programmed to operate the donor interface pump PP3 (i.e., in through valve V13 and out through valve V11) and the anticoagulant pump PP4 (i.e., in through valve V20 and out through valve V15) to draw anticoagulated blood through the donor tube 270 into the in-process container 312, in the same fashion as the Blood Prime 1 Phase of the double red blood cell collection procedure, as already described.

b. Blood Prime 2

In a next phase (Blood Prime 2), the blood processing circuit 46 is programmed to operate the in-process pump station PP1 to draw anticoagulated blood from the in-process container 312 through the separation device, in the same fashion as the Blood Prime 2 Phase for the double red blood cell collection procedure, as already described. During this phase, saline displaced by the blood is returned to the donor.

c. Blood Separation while Drawing Whole Blood or without Drawing Whole Blood In a next phase of the blood collection cycle (Blood Separation While Drawing Whole Blood), the blood processing circuit 46 is programmed to operate the donor interface pump station PP3 (i.e., in through valve V13 and out through valve V11), the anticoagulant pump PP4 (i.e., in through valve V20 and out through valve V15); the in-process pump PP1 (i.e., in through valve V9 and out through valve V14); and the plasma pump PP2 (i.e., in through valve V12 and out through valve V10), in the same fashion as the Blood Separation While Drawing Whole Blood Phase for the double red blood cell collection procedure, as already described. This arrangement draws anticoagulated blood into the in-process container 312, while conveying the blood from the in-process container 312 into the processing chamber for separation. This arrangement also removes plasma from the processing chamber into the plasma container 304, while removing red blood cells from the processing chamber into the red blood cell container 308. This phase continues until the targeted volume of plasma is collected in the plasma collection container 304 (as monitored by the weigh sensor) or until a targeted volume of red blood cells is collected in the red blood cell collection container (as monitored by the weigh sensor).

As in the double red blood cell collection procedure, if the volume of whole blood in the in-process container 312 reaches a predetermined maximum threshold before the targeted volume of either plasma or red blood cells is collected, the circuit is programmed to enter another phase (Blood Separation Without Drawing Whole Blood), to terminate operation of the donor interface pump station PP3 (while also closing valves V13, V11, V18, and V3) to terminate collection of whole blood in the in-process container 312, while still continuing blood separation. If the volume of whole blood reaches a predetermined minimum threshold in the in-process container 312 during blood separation, but before the targeted volume of either plasma or red blood cells is collected, the circuit is programmed to return to the Blood Separation While Drawing Whole Blood Phase, to thereby refill the in-process container 312. The circuit is programmed to toggle between the Blood Separation Phases while drawing whole blood and without drawing whole blood, according to the high and low volume thresholds for the in-process container 312, until the requisite volume of plasma has been collected, or until the target volume of red blood cells has been collected, whichever occurs first.

d. Return Red Blood Cells/Saline

If the targeted volume of plasma has not been collected, the next phase of the blood collection cycle (Return Red Blood Cells With Separation) programs the blood processing circuit 46 to operate the donor interface pump station PP3 (i.e., in through valve V11 and out through valve V13); the in-process pump PP1 (i.e., in through valve V9 and out through valve V14); and the plasma pump PP2 (i.e., in through valve V12 and out through valve V10). This arrangement conveys anticoagulated whole blood from the in-process container 312 into the processing chamber for separation, while removing plasma into the plasma container 304 and red blood cells into the red blood cell container 308. This arrangement also conveys red blood cells from the red blood cell container 308 to the donor, while also mixing saline from the container 288 in-line with the returned red blood cells. The in-line mixing of saline with the red blood cells raises the saline temperature and improves donor comfort. The in-line mixing of saline with the red blood cells also lowers the hematocrit of the red blood cells being returned to the donor, thereby allowing a larger gauge (i.e., smaller diameter) phlebotomy needle to be used, to further improve donor comfort. This phase continues until the red blood cell container 308 is empty, as monitored by the weigh sensor.

If the volume of whole blood in the in-process container 312 reaches a specified low threshold before the red blood cell container 308 empties, the circuit is programmed to enter another phase (Red Blood Cell Return Without Separation), to terminate operation of the in-process pump station PP1 (while also closing valves V9, V10, V12, and V14) to terminate blood separation. The phase continues until the red blood cell container 308 empties.

e. Fill Donor Line

Upon emptying the red blood cell container 308, the circuit is programmed to enter another phase (Fill Donor Line), to operate the donor interface pump station PP3 (i.e., in through valve V11 and out through valve V13) to draw whole blood from the in-process container 312 to fill the donor tube 266, thereby purging red blood cells (mixed with saline) in preparation for another draw whole blood cycle.

The circuit is then programmed to conduct another Blood Separation While Drawing Whole Blood Phase, to refill the in-process container 312. The circuit is programmed to conduct successive draw whole blood and return red blood cells/saline cycles, as described, until the weigh sensor indicates that a desired volume of plasma has been collected in the plasma collection container 304. When the targeted volume of plasma has been collected, the post-collection cycle commences.

The programming of the circuit during the phases of the collection cycle is summarized in the following table.

TABLE

Programming of Blood Processing Circuit During The Collection Cycle (Plasma Collection Procedure)

| Phase | Blood Prime1 | Blood Prime 2 | Blood Separation While Drawing Whole Blood (Without Drawing Whole Blood) | Return Red Blood Cells/ Saline With Separation (Without Separation) | Fill Donor Line |
|---|---|---|---|---|---|
| V1 | ● | ● | ● | ● | ○ |
| V2 | ● | ● | ○ | ○ | ● |
| V3 | ○ | ● | ○ (●) | ● | ● |
| V4 | ● | ● | ● | ● | ● |
| V5 | ● | ● | ○ | ○ (●) | ● |
| V6 | ● | ● | ● | ● | ● |
| V7 | ● | ○ | ● | ○/● Alternates With V23 | ○ |
| V8 | ● | ● | ● | ● | ● |
| V9 | ● | ○/● Pump In | ○/● Pump In | ○/● Pump In (●) | ● |
| V10 | ● | ● | ○/● Pump Out | ○/● Pump Out (●) | ● |
| V11 | ○/● Pump Out | ○ | ○/● Pump Out (●) | ○/● Pump In | ○/● Pump In |
| V12 | ● | ● | ○/● Pump In | ○/● Pump In (●) | ● |

TABLE-continued

Programming of Blood Processing Circuit During The Collection Cycle (Plasma Collection Procedure)

| Phase | Blood Prime1 | Blood Prime 2 | Blood Separation While Drawing Whole Blood (Without Drawing Whole Blood) | Return Red Blood Cells/ Saline With Separation (Without Separation) | Fill Donor Line |
|---|---|---|---|---|---|
| V13 | ○/● Pump In | ○ | ○/● Pump In (●) | ○/● Pump Out | ○/● Pump Out |
| V14 | ● | ○/● Pump Out | ○/● Pump Out | ○/● Pump Out (●) | ● |
| V15 | ○/● Pump Out | ● | ○/● Pump Out (●) | ● | ● |
| V16 | ● | ● | ● | ● | ● |
| V17 | ● | ● | ● | ● | ● |
| V18 | ○ | ○ | ○ (●) | ○ | ○ |
| V19 | ○ | ● | ○ (●) | ● | ● |
| V20 | ○/● Pump In | ● | ○/● Pump In (●) | ● | ● |
| V21 | ● | ● | ● | ● | ● |
| V22 | ● | ● | ● | ○ | ● |
| V23 | ● | ● | ● | ○/● Alternates With V7 | ● |
| PP1 | ■ | □ | □ | □ (■) | ■ |
| PP2 | ■ | ■ | □ | □ (■) | ■ |
| PP3 | □ | ■ | □ | □ | □ |
| PP4 | □ | ■ | □ (■) | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

3. The Post-Collection Cycle

Once the targeted volume of plasma has been collected (as monitored by the weigh sensor), the circuit is programmed to carry out the phases of the post-collection cycle.

a. Remove Plasma Collection Container

In a first phase of the post-collection cycle (Remove Plasma Collection Container), the circuit is programmed to close all valves and disable all pump stations to allow separation of the plasma collection container 304 from the set 264.

b. Return Red Blood Cells

In the second phase of the post-collection cycle (Return Red Blood Cells), the circuit is programmed to operate the donor interface pump station PP3 (i.e., in through valve V11 and out through valve V13) to convey red blood cells remaining in the red blood cell collection container 308 to the donor. The circuit is also programmed in this phase to mix saline from the container 288 in-line with the returned red blood cells. This phase continues until the red blood cell container 308 is empty, as monitored by the weigh sensor.

c. Saline Purge

In the next phase of the post-collection cycle (Saline Purge), the circuit is programmed to operate the in-process pump station PP1 (i.e., in through valve V14 and out through valve V9) to convey saline from the container 288 through the separation device, to displace the blood contents of the separation device into the in-process container 312, in preparation for their return to the donor. This phase reduces the loss of donor blood. This phase continues until a predetermined volume of saline is pumped through the separation device, as monitored by the weigh sensor.

d. Final Return to Donor

In the next phase of the post-collection cycle (Final Return), the circuit is programmed to operate the donor interface pump station PP3 (i.e., in through valve V11 and out through valve V13) to convey the blood contents of the in-process container 312 to the donor. Saline is intermittently mixed with the blood contents. This phase continues until the in-process container 312 is empty, as monitored by the weigh sensor.

e. Fluid Replacement

In the next phase (Fluid Replacement), the circuit is programmed to operate the donor interface pump station PP3 (i.e., in through valve V11 and out through valve V13) to convey the saline to the donor. This phase continues until a prescribed replacement volume amount is infused, as monitored by the weigh sensor.

f. End Procedure

In the final phase (End Procedure), the circuit is programmed to close all valves and idle all pump stations, so that venipuncture can be terminated, and the plasma container can be separated and removed for storage. The remaining parts of the disposable set can be removed and discarded.

The programming of the circuit during the phases of the post-collection cycle is summarized in the following table.

TABLE

Programming of Blood Processing Circuit During The Post-Collection Cycle (Plasma Collection Procedure)

| Phase | Remove Plasma Collection Container | Return RBC | Saline Purge | Final Return | Fluid Replacement | End Procedure |
|---|---|---|---|---|---|---|
| V1 | ● | ● | ● | ○ | ● | ● |
| V2 | ● | ○ | ● | ● | ● | ● |
| V3 | ● | ● | ● | ● | ● | ● |
| V4 | ● | ● | ○ | ● | ● | ● |
| V5 | ● | ● | ● | ● | ● | ● |
| V6 | ● | ● | ● | ● | ● | ● |
| V7 | ● | ○/● Alternates With V23 | ● | ○/● Alternates With V23 | ● | ● |
| V8 | ● | ● | ● | ● | ● | ● |
| V9 | ● | ○ | ○/● Pump Out | ● | ● | ● |
| V10 | ● | ● | ● | ● | ● | ● |
| V11 | ● | ○/● Pump In | ● | ○/● Pump In | ○/● Pump In | ● |
| V12 | ● | ● | ● | ● | ● | ● |

TABLE-continued

Programming of Blood Processing Circuit During The Post-Collection Cycle (Plasma Collection Procedure)

| Phase | Remove Plasma Collection Container | Return RBC | Saline Purge | Final Return | Fluid Replacement | End Procedure |
|---|---|---|---|---|---|---|
| V13 | ● | o/● Pump Out | ● | o/● Pump Out | o/● Pump Out | ● |
| V14 | ● | ● | o/● Pump In | ● | ● | ● |
| V15 | ● | ● | ● | ● | ● | ● |
| V16 | ● | ● | ● | ● | ● | ● |
| V17 | ● | ● | ● | ● | ● | ● |
| V18 | o | o | ● | o | o | ● |
| V19 | ● | ● | ● | ● | ● | ● |
| V20 | ● | ● | ● | ● | ● | ● |
| V21 | ● | ● | ● | ● | ● | ● |
| V22 | ● | o | o | o | o | ● |
| V23 | ● | o/● Alternates With V7 | o | o/● Alternates With V7 | o | ● |
| PP1 | ■ | ■ | □ | ■ | ■ | ■ |
| PP2 | ■ | ■ | ■ | ■ | ■ | ■ |
| PP3 | ■ | □ | ■ | □ | □ | ■ |
| PP4 | ■ | ■ | ■ | ■ | ■ | ■ |

Caption:
o denotes an open valve;
● denotes a closed valve;
o/● denotes a valve opening and closing during a pumping sequence;
■ denotes an idle pump station (not in use); and
□ denotes a pump station in use.

C. Red Blood Cell and Plasma Collection

During this procedure, whole blood from a donor is centrifugally processed to collect up to about 550 ml of plasma and up to about 250 ml of red blood cells. This procedure will, in shorthand, be called the red blood cell/plasma collection procedure.

The portion of the red blood cells not retained for collection is periodically returned to the donor during blood separation. Plasma collected in excess of the 550 ml target and red blood cells collected in excess of the 250 ml target are also returned to the donor at the end of the procedure.

Programming of the blood processing circuit 46 (through the selective application of pressure to the valves and pump stations of the cassette) makes it possible to use the same universal set 264 used to carry out the double red blood cell collection or the plasma collection procedure.

The procedure includes a pre-collection cycle, a collection cycle, and a post-collection cycle, and a storage preparation cycle.

During the pre-collection cycle, the set 264 is primed to vent air prior to venipuncture. During the collection cycle, whole blood drawn from the donor is processed to collect plasma and red blood cells, while returning a portion of the red blood cells to the donor. During the post-collection cycle, excess plasma and red blood cells are returned to the donor, and the set is flushed with saline. During the storage preparation cycle, a red blood cell storage solution is added to the collected red blood cells.

1 The Pre-Collection Cycle a. Anticoagulant Prime

In the pre-collection cycle for the red blood cell/plasma collection procedure, the cassette is programmed to carry out AC Prime 1 and AC Prime 2 Phases that are identical to the AC Prime 1 and AC Prime 2 Phases of the double red blood cell collection procedure.

b. Saline Prime/Vent Donor Line/Venipuncture

In the pre-collection cycle for the red blood cell/plasma collection procedure, the cassette is programmed to carry out Saline Prime 1, Saline Prime 2, Saline Prime 3, Vent Donor Line, and Venipuncture Phases that are identical to the Saline Prime 1, Saline Prime 2, Saline Prime 3, Vent Donor Line, and Venipuncture Phases of the double red blood cell collection procedure.

The programming of the circuit during the phases of the pre-collection cycle is summarized in the following table.

TABLE

Programming of Blood Processing Circuit During Pre-Collection Cycle (Red Blood Cell/Plasma Collection Procedure)

| Phase | AC Prime1 | AC Prime 2 | Saline Prime 1 | Saline Prime 2 | Saline Prime 3 | Vent Donor Line | Venipuncture |
|---|---|---|---|---|---|---|---|
| V1 | ● | ● | ● | ● | ● | ● | ● |
| V2 | ● | ● | ● | ● | ● | ● | ● |
| V3 | o | o | ● | ● | ● | o | ● |
| V4 | ● | ● | o | o | ● | ● | ● |
| V5 | ● | ● | ● | ● | ● | ● | ● |
| V6 | ● | ● | ● | ● | o | ● | ● |
| V7 | ● | ● | ● | ● | o (Stage 1) / ● (Stage 2) | ● | ● |
| V8 | ● | ● | ● | ● | ● | ● | ● |
| V9 | ● | ● | o/● Pump Out | o/● Pump Out | o/● Pump In (Stage 1) / o (Stage 2) | ● | ● |

TABLE-continued

Programming of Blood Processing Circuit During Pre-Collection Cycle
(Red Blood Cell/Plasma Collection Procedure)

| Phase | AC Prime1 | AC Prime 2 | Saline Prime 1 | Saline Prime 2 | Saline Prime 3 | Vent Donor Line | Venipuncture |
|---|---|---|---|---|---|---|---|
| V10 | ● | ● | ● | ● | ○ (Stage 1) ○/● Pump Out (Stage 2) | ● | ● |
| V11 | ○/● Pump Out | ○ | ● | ● | ● | ○/● Pump In | ● |
| V12 | ● | ● | ● | ● | ○ (Stage 1) ○/● Pump In (Stage 2) | ● | ● |
| V13 | ○/● Pump In | ○ | ● | ● | ● | ○/● Pump Out | ● |
| V14 | ● | ● | ○/● Pump In | ○/● Pump In | ○/● Pump Out (Stage 1) ○ (Stage 2) | ● | ● |
| V15 | ○ | ○/● Pump Out | ● | ● | ● | ○ | ● |
| V16 | ● | ● | ● | ● | ● | ● | ● |
| V17 | ● | ● | ● | ● | ● | ● | ● |
| V18 | ○ | ○ | ● | ● | ● | ○ | ● |
| V19 | ○ | ○ | ● | ● | ● | ○ | ● |
| V20 | ○ | ○/● Pump In | ● | ● | ● | ○ | ● |
| V21 | ● | ● | ● | ● | ● | ● | ● |
| V22 | ● | ● | ○ | ○ | ○ | ● | ● |
| V23 | ● | ● | ○ | ○ | ○ | ● | ● |
| PP1 | ■ | ■ | □ | □ | □ (Stage 1) | ■ | ■ |
| PP2 | ■ | ■ | ■ | ■ | □ (Stage 2) | ■ | ■ |
| PP3 | □ | ■ | ■ | ■ | ■ | □ | ■ |
| PP4 | ■ | □ | ■ | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

2. The Collection Cycle a. Blood Prime

With venipuncture, tube 300 leading to the phlebotomy needle 268 is opened. The collection cycle of the red blood cell/plasma collection procedure programs the circuit to carry out Blood Prime 1 and Blood Prime 2 Phases that are identical to the Blood Prime 1 and Blood Prime 2 Phases of the Double Red Blood Cell Collection Procedure, already described.

b. Blood Separation while Drawing Whole Blood or without Drawing Whole Blood In the blood collection cycle for the red blood cell/plasma collection procedure, the circuit is programmed to conduct a Blood Separation While Drawing Whole Blood Phase, in the same fashion that the Blood Separation While Drawing Whole Blood Phase is conducted for the double red blood cell collection procedure. This arrangement draws anticoagulated blood into the in-process container 312, while conveying the blood from the in-process container 312 into the processing chamber for separation. This arrangement also removes plasma from the processing chamber into the plasma container 304, while removing red blood cells from the processing chamber into the red blood cell container 308. This phase continues until the desired maximum volumes of plasma and red blood cells have been collected in the plasma and red blood cell collection containers 304 and 308 (as monitored by the weigh sensor).

As in the double red blood cell collection procedure and the plasma collection procedure, if the volume of whole blood in the in-process container 312 reaches a predetermined maximum threshold before the targeted volume of either plasma or red blood cells is collected, the circuit is programmed to enter a phase (Blood Separation Without Whole Blood Draw) to terminate operation of the donor interface pump station PP3 (while also closing valves V13, V11, V18, and V3) to terminate collection of whole blood in the in-process container 312, while still continuing blood separation. If the volume of whole blood reaches a predetermined minimum threshold in the in-process container 312 during blood separation, but before the targeted volume of either plasma or red blood cells is collected, the circuit is programmed to return to the Blood Separation With Whole Blood Draw, to thereby refill the in-process container 312. The circuit is programmed to toggle between the Blood Separation cycle with whole blood draw and without whole blood draw according to the high and low volume thresholds for the in-process container 312, until the requisite maximum volumes of plasma and red blood cells have been collected.

c. Return Red Blood Cells and Saline

If the targeted volume of plasma has not been collected, and red blood cells collected in the red blood cell container 308 exceed a predetermined maximum threshold, the next phase of the blood collection cycle (Return Red Blood Cells With Separation) programs the blood processing circuit 46 to operate the donor interface pump station PP3 (i.e., in through valve V11 and out through valve V13); the in-process pump PP1 (i.e., in through valve V9 and out through valve V14); and the plasma pump PP2 (i.e., in through valve V12 and out through valve V10). This arrangement continues to convey anticoagulated whole blood from the in-process container 312 into the processing chamber for separation, while removing plasma into the plasma container 304 and red blood cells into the red blood cell container 308. This arrangement also conveys all or a portion of the red blood cells collected in the red blood cell container 308 to the donor. This arrangement also mixes saline from the container 288 in-line with the returned red blood cells. The in-line mixing of saline with the red blood cells raises the saline temperature and improves donor comfort. The in-line mixing of saline with the red blood cells also lowers the hematocrit of the red blood cells being returned to the donor, thereby allowing a larger gauge (i.e., smaller diameter) phlebotomy needle to be used, to further improve donor comfort.

This phase can continue until the red blood cell container 308 is empty, as monitored by the weigh sensor, thereby corresponding to the Return Red Blood Cells With Separation Phase of the plasma collection procedure. More advantageously, however, the processor determines how much additional plasma needs to be collected to meet the plasma target volume. From this, the processor derives the incremental red blood cell volume associated with the incremental plasma volume. In this arrangement, the processor returns a partial volume of red blood cells to the donor, so that, upon collection of the next incremental red blood cell volume, the total volume of red blood cells in the container 308 will be at or slightly over the targeted red blood cell collection volume.

If the volume of whole blood in the in-process container 312 reaches a specified low threshold before return of the desired volume of red blood cells, the circuit is programmed to enter a phase (Return Red Blood Cells Without Separation), to terminate operation of the in-process pump station PP1 (while also closing valves V9, V10, V12, and V14) to terminate blood separation. This phase corresponds to the Return Red Blood Cells Without Separation Phase of the plasma collection procedure.

d. Fill Donor Line

Upon returning the desired volume of red blood cells from the container 308, the circuit is programmed to enter a phase (Fill Donor Line), to operate the donor interface pump station PP3 (i.e., in through valve V11 and out through valve V13) to draw whole blood from the in-process container 312 to fill the donor tube 266, thereby purging red blood cells (mixed with saline) in preparation for another draw whole blood cycle.

The circuit is then programmed to conduct another Blood Separation While Drawing Whole Blood Phase, to refill the in-process container 312. If required, the circuit is capable of performing successive draw whole blood and return red blood cells cycles, until the weigh sensors indicate that volumes of red blood cells and plasma collected in the containers 304 and 308 are at or somewhat greater than the targeted values. The post-collection cycle then commences.

The programming of the circuit during the phases of the collection cycle is summarized in the following table.

TABLE

Programming of Blood Processing Circuit During The Collection Cycle
(Red Blood Cell/Plasma Collection Procedure)

| Phase | Blood Prime 1 | Blood Prime 2 | Blood Separation While Drawing Whole Blood | Return Red Blood Cells/ Saline With Separation (Without Separation) | Fill Donor Line |
|---|---|---|---|---|---|
| V1 | ● | ● | ● | ● | ○ |
| V2 | ● | ● | ○ | ○ | ● |
| V3 | ○ | ● | ○ (●) | ● | ● |
| V4 | ● | ● | ● | ● | ● |
| V5 | ● | ● | ○ | ○ (●) | ● |
| V6 | ● | ● | ● | ● | ● |
| V7 | ● | ○ | ● | ○/● Alternates With V23 | ○ |
| V8 | ● | ● | ● | ● | ● |
| V9 | ● | ○/● Pump In | ○/● Pump In | ○/● Pump In (●) | ● |
| V10 | ● | ● | ○/● Pump Out | ○/● Pump Out (●) | ● |
| V11 | ○/● Pump Out | ○ | ○/● Pump Out (●) | ○/● Pump In | ○/● Pump In |
| V12 | ● | ● | ○/● Pump In | ○/● Pump In (●) | ● |
| V13 | ○/● Pump In | ○ | ○/● Pump In (●) | ○/● Pump Out | ○/● Pump Out |
| V14 | ● | ○/● Pump Out | ○/● Pump Out | ○/● Pump Out (●) | ● |

TABLE-continued

Programming of Blood Processing Circuit During The Collection Cycle
(Red Blood Cell/Plasma Collection Procedure)

| Phase | Blood Prime 1 | Blood Prime 2 | Blood Separation While Drawing Whole Blood (Without Drawing Whole Blood) | Return Red Blood Cells/ Saline With Separation (Without Separation) | Fill Donor Line |
|---|---|---|---|---|---|
| V15 | o/● Pump Out | ● | o/● Pump Out (●) | ● | ● |
| V16 | ● | ● | ● | ● | ● |
| V17 | ● | ● | ● | ● | ● |
| V18 | o | o | o (●) | o | o |
| V19 | o | ● | o (●) | ● | ● |
| V20 | o/● Pump In | ● | o/● Pump In (●) | ● | ● |
| V21 | ● | ● | ● | ● | ● |
| V22 | ● | ● | ● | o | ● |
| V23 | ● | ● | ● | o/● Alternates With V7 | ● |
| PP1 | ■ | □ | □ | □ (■) | ■ |
| PP2 | ■ | ■ | □ | □ (■) | ■ |
| PP3 | □ | ■ | □ (■) | □ | □ |
| PP4 | □ | ■ | □ (■) | ■ | ■ |

Caption:
o denotes an open valve;
● denotes a closed valve;
o/● denotes a valve opening and closing during a pumping sequence;
■ denotes an idle pump station (not in use); and
□ denotes a pump station in use.

3. The Post-Collection Cycle

Once the targeted maximum volumes of plasma and red blood cells have been collected (as monitored by the weigh sensor), the circuit is programmed to carry out the phases of the post-collection cycle.

a. Return Excess Plasma

If the volume of plasma collected in the plasma collection container 304 is over the targeted volume, a phase of the post-collection cycle (Excess Plasma Return) is entered, during which the circuit is programmed to terminate the supply and removal of blood to and from the processing chamber, while operating the donor interface pump station PP3 (i.e., in through valve V11 and out through valve V13) to convey plasma in the plasma container 304 to the donor. The circuit is also programmed in this phase to mix saline from the container 288 in-line with the returned plasma. This phase continues until the volume of plasma in the plasma collection container 304 is at the targeted value, as monitored by the weigh sensor.

b. Return Excess Red Blood Cells

If the volume of red blood cells collected in the red blood cell collection container 308 is also over the targeted volume, a phase of the post-collection cycle (Excess RBC Return) is entered, during which the circuit is programmed to operate the donor interface pump station PP3 (i.e., in through valve V11 and out through valve V13) to convey red blood cells remaining in the red blood cell collection container 308 to the donor. The circuit is also programmed in this phase to mix saline from the container 288 in-line with the returned red blood cells. This phase continues until the volume of red blood cells in the container 308 equals the targeted value, as monitored by the weigh sensor.

c. Saline Purge

When the volumes of red blood cells and plasma collected in the containers 308 and 304 equal the targeted values, the next phase of the post-collection cycle (Saline Purge) is entered, during which the circuit is programmed to operate the in-process pump station PP1 (i.e., in through valve V14 and out through valve V9) to convey saline from the container 288 through the separation device, to displace the blood contents of the separation device into the in-process container 312, in preparation for their return to the donor. This phase reduces the loss of donor blood. This phase continues until a predetermined volume of saline is pumped through the separation device, as monitored by the weigh sensor.

d. Final Return to Donor

In the next phase of the post-collection cycle (Final Return), the circuit is programmed to operate the donor interface pump station PP3 (i.e., in through valve V11 and out through valve V13) to convey the blood contents of the in-process container 312 to the donor. Saline is intermittently mixed with the blood contents. This phase continues until the in-process container 312 is empty, as monitored by the weigh sensor.

e. Fluid Replacement

In the next phase (Fluid Replacement), the circuit is programmed to operate the donor interface pump station PP3 (i.e., in through valve V11 and out through valve V13) to convey the saline to the donor. This phase continues until a prescribed replacement volume amount is infused, as monitored by the weigh sensor.

f. End Venipuncture

In the next phase (End Venipuncture), the circuit is programmed to close all valves and idle all pump stations, so that venipuncture can be terminated.

The programming of the circuit during the phases of the post-collection cycle is summarized in the following table.

TABLE

Programming of Blood Processing Circuit During The Post-Collection Cycle (Red Blood Cell/Plasma Collection Procedure)

| Phase | Excess Plasma Return | Excess RBC Return | Saline Purge | Final Return | Fluid Replacement | End Venipuncture |
|---|---|---|---|---|---|---|
| V1 | ● | ● | ● | o | ● | ● |
| V2 | ● | o | ● | ● | ● | ● |
| V3 | ● | ● | ● | ● | ● | ● |
| V4 | ● | ● | o | ● | ● | ● |
| V5 | o | ● | ● | ● | ● | ● |
| V6 | o/● Alternates With V23 | ● | ● | ● | ● | ● |
| V7 | ● | o/● Alternates With V23 | ● | o/● Alternates With V23 | ● | ● |
| V8 | ● | ● | ● | ● | ● | ● |
| V9 | o | o | o/● Pump Out | ● | ● | ● |
| V10 | ● | ● | ● | ● | ● | ● |
| V11 | o/● Pump In | o/● Pump In | ● | o/● Pump In | o/● Pump In | ● |
| V12 | ● | ● | ● | ● | ● | ● |
| V13 | o/● Pump Out | o/● Pump Out | ● | o/● Pump Out | o/● Pump Out | ● |
| V14 | ● | ● | o/● Pump In | ● | ● | ● |
| V15 | ● | ● | ● | ● | ● | ● |
| V16 | ● | ● | ● | ● | ● | ● |
| V17 | ● | ● | ● | ● | ● | ● |
| V18 | o | o | ● | o | o | ● |
| V19 | ● | ● | ● | ● | ● | ● |
| V20 | ● | ● | ● | ● | ● | ● |
| V21 | ● | ● | ● | ● | ● | ● |
| V22 | o | o | o | o | o | ● |
| V23 | o/● Alternates With V6 | o/● Alternates With V7 | o | o/● Alternates With V7 | o | ● |
| PP1 | ■ | ■ | □ | ■ | ■ | ■ |
| PP2 | ■ | ■ | ■ | ■ | ■ | ■ |
| PP3 | □ | □ | ■ | □ | □ | ■ |
| PP4 | ■ | ■ | ■ | ■ | ■ | ■ |

Caption:
o denotes an open valve;
● denotes a closed valve;
o/● denotes a valve opening and closing during a pumping sequence;
■ denotes an idle pump station (not in use); and
□ denotes a pump station in use.

4. The Storage Preparation Cycle a. RBC Preservative Prime

In the first phase of the storage preparation cycle (Prime Storage Solution), the circuit is programmed to operate the donor interface pump station PP3 to transfer a desired volume of red blood cell storage solution from the container 280 into the in-process container 312. The transfer of the desired volume is monitored by the weigh scale.

b. Transfer Storage Solution

In the next phase (Transfer Storage Solution), the circuit is programmed to operate the donor interface pump station PP3 to transfer a desired volume of red blood cell storage solution from the in-process container 312 into the red blood cell collection container 308. The transfer of the desired volume is monitored by the weigh scale.

c. End Procedure

In the next and final phase (End Procedure), the circuit is programmed to close all valves and idle all pump stations, so that the plasma and red blood cell storage containers 304 and 308 can be separated and removed for storage. The remainder of the disposable set can now be removed and discarded.

The programming of the circuit during the phases of the storage preparation cycle is summarized in the following table.

TABLE

Programming of Blood Processing Circuit During The Storage Preparation Cycle (Red Blood Cell/Plasma Collection Procedure)

| Phase | Prime Storage Solution | Transfer Storage Solution | End Procedure |
|---|---|---|---|
| V1 | ● | ● | ● |
| V2 | ● | o | ● |
| V3 | o | ● | ● |
| V4 | ● | o | ● |

TABLE-continued

Programming of Blood Processing Circuit During The Storage
Preparation Cycle (Red Blood Cell/Plasma Collection Procedure)

| Phase | Prime Storage Solution | Transfer Storage Solution | End Procedure |
|---|---|---|---|
| V5 | ● | ● | ● |
| V6 | ● | ● | ● |
| V7 | ● | ● | ● |
| V8 | ● | ● | ● |
| V9 | ● | ● | ● |
| V10 | ● | ● | ● |
| V11 | ○/● | ○/● | ● |
|  | Pump In/ | Pump In/ |  |
|  | Pump Out | Pump Out |  |
| V12 | ● | ● | ● |
| V13 | ● | ● | ● |
| V14 | ● | ● | ● |
| V15 | ● | ● | ● |
| V16 | ○ | ○ | ● |
| V17 | ● | ● | ● |
| V18 | ● | ● | ● |
| V19 | ● | ● | ● |
| V20 | ● | ● | ● |
| V21 | ○ | ○ | ● |
| V22 | ● | ● | ● |
| V23 | ● | ● | ● |
| PP1 | ■ | ■ | ■ |
| PP2 | ■ | ■ | ■ |
| PP3 | □ | □ | ■ |
| PP4 | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

V. Interface Control

A. Underspill and Overspill Detection

Figure 15A:
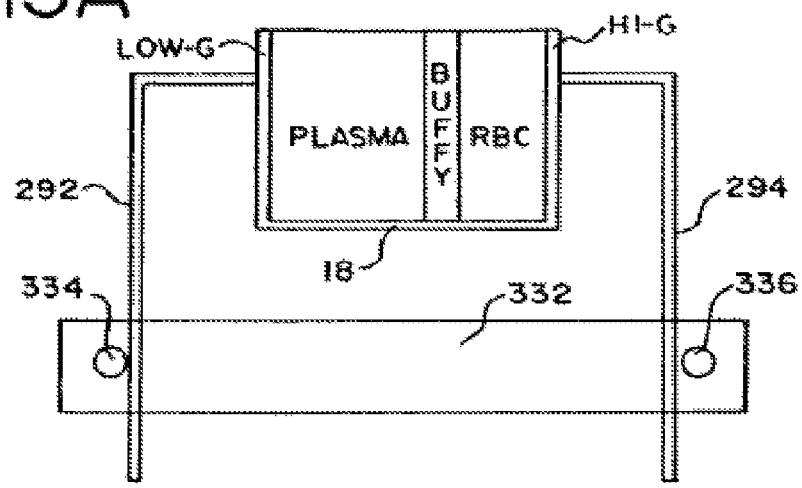
FIGS. 15A, 15B, and 15C are schematic side views of the blood separation chamber that the device shown in FIG. 1 incorporates, showing the plasma and red blood cell collection tubes and the associated two in-line sensors, which detect a normal operating condition (FIG. 15A), an overspill condition (FIG. 15B), and an underspill condition (FIG. 15C)

In any of the above-described procedures, the centrifugal forces present within the processing chamber 18 separate whole blood into a region of packed red blood cells and a region of plasma (see FIG. 15A). The centrifugal forces cause the region of packed red blood cells to congregate along the outside or high-G wall of the chamber, while the region of plasma is transported to the inside or low-G wall of the chamber.

An intermediate region forms an interface between the red blood cell region and the plasma region. Intermediate density cellular blood species like platelets and leukocytes populate the interface, arranged according to density, with the platelets closer to the plasma layer than the leukocytes. The interface is also called the "buffy coat," because of its cloudy color, compared to the straw color of the plasma region and the red color of the red blood cell region.

It is desirable to monitor the location of the buffy coat, either to keep the buffy coat materials out of the plasma or out of the red blood cells, depending on the procedure, or to collect the cellular contents of the buffy coat. The system includes a sensing station 332 comprising two optical sensors 334 and 336 for this purpose.

In the illustrated embodiment of FIG. 13, the sensing station 332 is located a short distance outside the centrifuge station 20. This arrangement minimizes the fluid volume of components leaving the chamber before monitoring by the sensing station 332.

The first sensor 334 in the station 332 optically monitors the passage of blood components through the plasma collection tube 292. The second sensor 336 in the station 332 optically monitors the passage of blood components through the red blood cell collection tube 294.

The tubes 292 and 294 are made from plastic (e.g. polyvinylchloride) material that is transparent to the optical energy used for sensing, at least in the region where the tubes 292 and 294 are to be placed into association with the sensing station 332.

In the illustrated embodiment, the set 264 includes a fixture 338 (see FIGS. 16 to 18) to hold the tubes 292 and 294 in viewing alignment with their respective sensor 334 and 336. The fixture 338 gathers the tubes 292 and 294 in a compact, organized, side-by-side array, to be placed and removed as a group in association with the sensors 334 and 336, which are also arranged in a compact, side-by-side relationship within the station 332.

In the illustrated embodiment, the fixture 338 also holds the tube 290, which conveys whole blood into the centrifuge station 20, even though no associated sensor is provided. The fixture 338 serves to gather and hold all tubes 290, 292, and 294 that are coupled to the umbilicus 296 in a compact and easily handled bundle.

The fixture 338 can be an integral part of the umbilicus 296, formed, e.g., by over molding. Alternatively, the fixture 338 can be a separately fabricated part, which snap fits about the tubes 290, 292, and 294 for use.

In the illustrated embodiment (as FIG. 2 shows), the containers 304, 308, and 312 coupled to the cassette 28 are suspended during use above the centrifugation station 20. In this arrangement, the fixture 338 directs the tubes 290, 292, and 294 through an abrupt, ninety degree bend immediately beyond the end of the umbilicus 296 to the cassette 28. The bend imposed by the fixture 338 directs the tubes 290, 292, and 294 in tandem away from the area immediately beneath the containers 304, 308, and 312, thereby preventing clutter in this area. The presence of the fixture 338 to support and guide the tubes 290, 292, and 294 through the bend also reduces the risk of kinking or entanglement.

The first sensor 334 is capable of detecting the presence of optically targeted cellular species or components in the plasma collection tube 292. The components that are optically targeted for detection vary depending upon the procedure.

For a plasma collection procedure, the first sensor 334 detects the presence of platelets in the plasma collection tube 292, so that control measures can be initiated to move the interface between the plasma and platelet cell layer back into the processing chamber. This provides a plasma product that can be essentially platelet-free or at least in which the number of platelets is minimized.

For a red blood cell-only collection procedure, the first sensor 334 detects the interface between the buffy coat and the red blood cell layer, so that control measures can be initiated to move this interface back into the processing chamber. This maximizes the red blood cell yield.

For a buffy coat collection procedure (which will be described later), the first sensor 334 detects when the leading edge of the buffy coat (i.e., the plasma/platelet interface) begins to exit the processing chamber, as well as detects when the trailing edge of the buffy coat (i.e., the buffy coat/red blood cell interface) has completely exited the processing chamber.

Figure 15B:
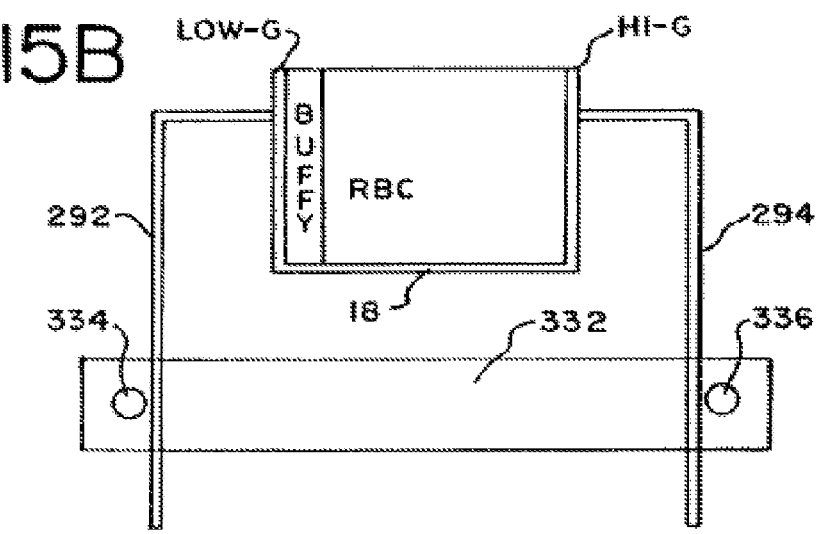

The presence of these cellular components in the plasma, as detected by the first sensor 334, indicates that the interface is close enough to the low-G wall of the processing chamber to allow all or some of these components to be swept into the plasma collection line (see FIG. 15B). This condition will also be called an "overspill."

Figure 15C:
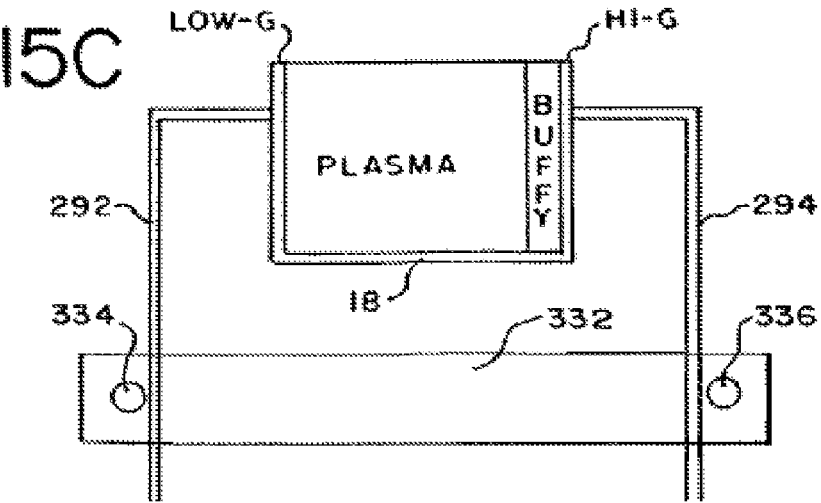

The second sensor 336 is capable of detecting the hematocrit of the red blood cells in the red blood cell collection tube 294. The decrease of red blood hematocrit below a set minimum level during processing indicates that the interface is close enough to the high-G wall of the processing chamber to allow plasma and/or buffy coat materials to enter the red blood cell collection tube 294 (see FIG. 15C). This condition will also be called an "underspill."

B. The Sensing Circuit

Figure 19:
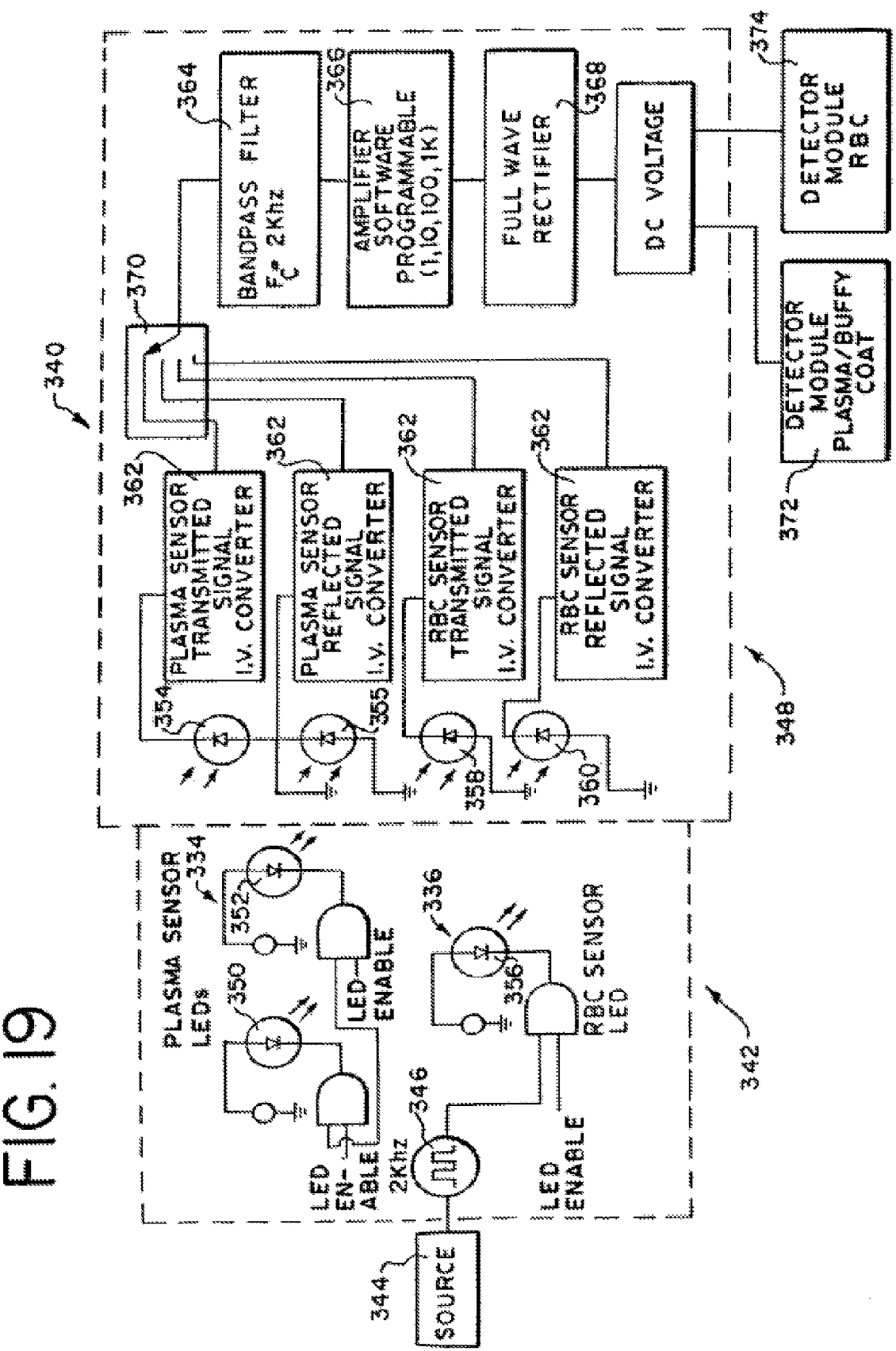
FIG. 19 is a schematic view of the sensing station, of which the first and second sensors shown in FIGS. 15A, 15B, and 15C form a part.

The sensing station 332 includes a sensing circuit 340 (see FIG. 19), of which the first sensor 334 and second sensor 336 form a part.

The first sensor 334 includes one green light emitting diode (LED) 350, one red LED 352, and two photodiodes 354 and 355. The photodiode 354 measures transmitted light and the photodiode 355 measures reflected light.

The second sensor 336 includes one red LED 356 and two photodiodes 358 and 360. The photodiode 358 measures transmitted light and the photodiode 360 measures reflected light.

The sensing circuit 340 further includes an LED driver component 342. The driver component 342 includes a constant current source 344, coupled to the LED's 350, 352, and 356 of the sensors 334 and 336. The constant current source 344 supplies a constant current to each LED 350, 352, and 356, independent of temperature and the power supply voltage levels. The constant current source 344 thereby provides a constant output intensity for each LED 350, 352, and 356.

The LED drive component 342 includes a modulator 346. The modulator 346 modulates the constant current at a prescribed frequency. The modulator 346 removes the effects of ambient light and electromagnetic interference (EMI) from the optically sensed reading, as will be described in greater detail later.

The sensing circuit 340 also includes a receiver circuit 348 coupled to the photodiodes 354, 355, 358, and 360. The receiver circuit 348 includes, for each photodiode 354, 355, 358, and 360, a dedicated current-to-voltage (I-V) converter 362. The remainder of the receiver circuit 348 includes a bandpass filter 364, a programmable amplifier 366, and a full wave rectifier 368. These components 364, 366, and 368 are shared, e.g., using a multiplexer.

Ambient light typically contains frequency components less than 1000 Hz, and EMI typically contains frequency components above 2 kHz. With this in mind, the modulator 346 modulates the current at a frequency below the EMI frequency components, e.g., at about 2 kHz. The bandpass filter 364 has a center frequency of about the same value, i.e., about 2 kHz. The sensing circuit 340 eliminates frequency components above and below the ambient light source and EMI components from the sensed measurement. In this way, the sensing circuit 340 is not sensitive to ambient lighting conditions and EMI.

More particularly, transmitted or reflected light from the tube 292 or 294 containing the fluid to be measured is incident on photodiodes 354 and 355 (for the tube 292) or photodiodes 358 and 360 (for tube 294). Each photodiode produces a photocurrent proportional to the received light intensity. This current is converted to a voltage. The voltage is fed, via the multiplexer 370, to the bandpass filter 364. The bandpass filter 364 has a center frequency at the carrier frequency of the modulated source light (i.e., 2 kHz in the illustrated embodiment).

The sinusoidal output of the bandpass filter 364 is sent to the variable gain amplifier 366. The gain of the amplifier is preprogrammed in preestablished steps, e.g., X1, X10, X100, and X1000. This provides the amplifier with the capability to respond to a large dynamic range.

The sinusoidal output of the amplifier 366 is sent to the full wave rectifier 368, which transforms the sinusoidal output to a DC output voltage proportional to the transmitted light energy.

The controller 16 generates timing pulses for the sensing circuit 340. The timing pulses comprise, for each LED, (i) a modulation square wave at the desired modulation frequency (i.e., 2 kHz in the illustrated embodiment), (ii) an enable signal, (iii) two sensor select bits (which select the sensor output to feed to the bandpass filter 364), and (iv) two bits for the receiver circuit gain selection (for the amplifier 366).

The controller 16 conditions the driver circuit 342 to operate each LED in an ON state and an OFF state.

In the ON state, the LED enable is set HIGH, and the LED is illuminated for a set time interval, e.g., 100 ms. During the first 83.3 ms of the ON state, the finite rise time for the incident photodiode and receiver circuit 348 are allowed to stabilize. During the final 16.7 ms of the ON state, the output of the circuit 340 is sampled at twice the modulation rate (i.e., 4 kHz in the illustrated embodiment). The sampling interval is selected to comprise one complete cycle of 60 Hz, allowing the main frequency to be filtered from the measurement. The 4 kHz sampling frequency allows the 2 kHz ripple to be captured for later removal from the measurement.

During the OFF state, the LED is left dark for 100 ms. The LED baseline due to ambient light and electromagnetic interference is recorded during the final 16.7 ms.

1. The First Sensor: Platelet/RBC Differentiation

In general, cell free ("free") plasma has a straw color. As the concentration of platelets in the plasma increases, the clarity of the plasma decreases. The plasma looks "cloudy." As the concentration of red blood cells in the plasma increases, the plasma color turns from straw to red.

The sensing circuit 340 includes a detection/differentiation module 372, which analyzes sensed attenuations of light at two different wavelengths from the first sensor 334 (using the transmitted light sensing photodiode 354). The different wavelengths are selected to possess generally the same optical attenuation for platelets, but significantly different optical attenuations for red blood cells.

In the illustrated embodiment, the first sensor 334 includes an emitter 350 of light at a first wavelength ($\lambda_1$), which, in the illustrated embodiment, is green light (570 nm and 571 nm). The first sensor 334 also includes an emitter 352 of light at a second wavelength ($\lambda_2$), which, in the illustrated embodiment, is red light (645 nm to 660 nm).

The optical attenuation for platelets at the first wavelength ($\epsilon_{platelets}^{\lambda_1}$) and the optical attenuation for platelets at the second wavelength ($\epsilon_{platelets}^{\lambda_2}$) are generally the same. Thus, changes in attenuation over time, as affected by increases or decreases in platelet concentration, will be similar.

However, the optical attenuation for hemoglobin at the first wavelength ($\epsilon_{Hb}^{\lambda_1}$) is about ten times greater than the optical attenuation for hemoglobin at the second wavelength ($\epsilon_{Hb}^{\lambda_2}$). Thus, changes in attenuation over time, as affected by the presence of red blood cells, will not be similar.

The tube 292, through which plasma is to be sensed, is transparent to light at the first and second wavelengths. The tube 292 conveys the plasma flow past the first and second emitters 350 and 352.

The light detector 354 receives light emitted by the first and second emitters 350 and 352 through the tube 292. The detector 354 generates signals proportional to intensities of received light. The intensities vary with optical attenuation caused by the presence of platelets and/or red blood cells.

The module 372 is coupled to the light detector 354 to analyze the signals to derive intensities of the received light at the first and second wavelengths. The module 372 compares changes of the intensities of the first and second wavelengths over time. When the intensities of the first and second wavelengths change over time in substantially the same manner, the module 372 generates an output representing presence of platelets in the plasma flow. When the intensities of the first and second wavelengths change over time in a substantially different manner, the module 372 generates an output representing presence of red blood cells in the plasma flow. The outputs therefore differentiate between changes in intensity attributable to changes in platelet concentration in the plasma flow and changes in intensity attributable to changes in red blood cell concentration in the plasma flow.

There are various ways to implement the module 372. In one embodiment, the detection/differentiation module 372 considers that the attenuation of a beam of monochromatic light of wavelength λ by a plasma solution can be described by the modified Lambert-Beer law, as follows:

$$I = I_o e^{-[(\epsilon_{Hb}^\lambda c_{Hb} H + \epsilon_{platelets}^\lambda c_{platelets})d + G_{platelets}^\lambda + G_{RBC}^\lambda]} \quad (1)$$

where:
I is transmitted light intensity.
I-hd O is incident light intensity.
$\epsilon_{Hb}^\lambda$ is the optical attenuation of hemoglobin (Hb) (gm/dl) at the applied wavelength.
$\epsilon_{platelets}^\lambda$ is the optical attenuation of platelets at the applied wavelength.
$C_{Hb}$ is the concentration of hemoglobin in a red blood cell, taken to be 34 gm/dl.
$C_{platelets}$ is the concentration of platelets in the sample.
d is the thickness of the plasma stream through the tube 294.
$G^\lambda$ is the path length factor at the applied wavelength, which accounts for additional photon path length in the plasma sample due to light scattering.
H is whole blood hematocrit, which is percentage of red blood cells in the sample.
$G_{RBC}^\lambda$ and $G_{platelets}^\lambda$ are a function of the concentration and scattering coefficients oft respectively, red blood cells and platelets at the applied wavelengths, as well as the measurement geometry.

For wavelengths in the visible and near infrared spectrum, $\epsilon_{platelets}^\lambda \approx 0$, therefore:

$$Ln\left(\frac{I^\lambda}{I_o^\lambda}\right) = Ln(T^\lambda) \approx -[(\epsilon_{Hb}^\lambda C_{Hb} H)d + G_{platelets}^\lambda + G_{RBC}^\lambda] \quad (2)$$

In an overspill condition (shown in FIG. 15B), the first cellular component to be detected by the first sensor 334 in the plasma collection line 292 will be platelets. Therefore, for the detection of platelets, $Ln(T^\lambda) \approx G_{platelets}^\lambda$.

To detect the buffy coat interface between the platelet layer and the red blood cell layer, the two wavelengths ($\lambda_1$ and $\lambda_2$) are chosen based upon the criteria that (i) $\lambda_1$ and $\lambda_2$ have approximately the same path length factor ($G^\lambda$), and (ii) one wavelength $\lambda_1$ or $\lambda_2$ has a much greater optical attenuation for hemoglobin than the other wavelength.

Assuming the wavelengths $\lambda_1$ and $\lambda_2$ have the same $G^\lambda$, Equation (2) reduces to:

$$Ln(T^{\lambda_1}) - Ln(T^{\lambda_2}) \approx Hdc_{Hb}(\epsilon_{Hb}^{\lambda_2} - \epsilon_{Hb}^{\lambda_1}) \quad (3)$$

In one embodiment, $\lambda_1 = 660$ nm (green) and $\lambda_2 = 571$ nm (red). The path length factor ($G^\lambda$) for 571 nm light is greater than for 660 nm light. Therefore the path length factors have to be modified by coefficients α and β, as follows:

$$G_{RBC}^{\lambda_1} = \alpha G_{RBC}^{\lambda_1}$$

$$G_{platelets}^{\lambda_1} = \beta G_{platelets}^{\lambda_2}$$

Therefore, Equation (3) can be reexpressed as follows:

$$Ln(T^{\lambda_1}) - Ln(T^{\lambda_2}) \approx Hdc_{Hb}(\epsilon_{Hb}^{\lambda_1} - \epsilon_{Hb}^{\lambda_2}) + (\alpha-1)G_{RBC}^\lambda + (\beta-1)G_{platelets}^\lambda \quad (4)$$

In the absence of red blood cells, Equation (3) causes a false red blood cell detect with increasing platelet concentrations, as Equation (5) demonstrates:

$$Ln(T^{\lambda_1}) - Ln(T^{\lambda_2}) = (\beta-1)G_{platelets}^{\lambda_2} \quad (5)$$

For the detection of platelets and the interface between the platelet/red blood cell layers, Equation (4) provides a better resolution. The module 372 therefore applies Equation (4). The coefficient (β−1) can be determined by empirically measuring $G_{platelets}^{\lambda_1}$ and $G_{platelets}^{\lambda_2}$ in the desired measurement geometry for different known concentrations of platelets in prepared platelet-spiked plasma.

The detection/differentiation module 372 also differentiates between intensity changes due to the presence of red blood cells in the plasma or the presence of free hemoglobin in the plasma due to hemolysis. Both circumstances will cause a decrease in the output of the transmitted light sensing photodiode 354. However, the output of the reflected light sensing photodiode 355 increases in the presence of red blood cells and decreases in the presence of free hemoglobin. The detection/differentiation module 372 thus senses the undesired occurrence of hemolysis during blood processing, so that the operator can be alerted and corrective action can be taken.

2. The Second Sensor: Packed Red Blood Cell Measurement

In an underspill condition (shown in FIG. 15C), the hematocrit of red blood cells exiting the processing chamber 18 will dramatically decrease, e.g., from a targeted hematocrit of about 80 to a hematocrit of about 50, as plasma (and the buffy coat) mixes with the red blood cells. An underspill condition is desirable during a plasma collection procedure, as it allows the return of the buffy coat to the donor with the red blood cells. An underspill condition is not desired during a red blood cell-only collection procedure, as it jeopardizes the yield and quality of red blood cells that are collected for storage.

In either situation, the ability to sense when an underspill condition exists is desirable.

Photon wavelengths in the near infrared spectrum (NIR) (approximately 540 nm to 1000 nm) are suitable for sensing red blood cells, as their intensity can be measured after transmission through many millimeters of blood.

The sensing circuit 340 includes a red blood cell detection module 374. The detection module 374 analyzes sensed optical transmissions of the second sensor 336 to discern the hematocrit and changes in the hematocrit of red blood cells exiting the processing chamber 18.

The detection module 374 considers that the attenuation of a beam of monochromatic light of wavelength λ by blood may be described by the modified Lambert-Beer law, as follows:

$$I = I_o e^{-[(\epsilon_{Hb}^\lambda c_{Hb} H)d + G_{RBC}^\lambda]} \quad (6)$$

where:
I is transmitted light intensity.
$I_O$ is incident light intensity.

$\epsilon_{Hb}^\lambda$ is the extinction coefficient of hemoglobin (Hb) (gm/dl) at the applied wavelength.

$C_{Hb}$ is the concentration of hemoglobin in a red blood cell, taken to be 34 gm/dl.

d is the distance between the light source and light detector.

$G^\lambda$ is the path length factor at the applied wavelength, which accounts for additional photon path length in the media due to light scattering H is whole blood hematocrit, which is percentage of red blood cells in the sample.

$G_{RBC}^\lambda$ is a function of the hematocrit and scattering coefficients of red blood cells at the applied wavelengths, as well as the measurement geometry.

Given Equation (6), the optical density O.D. of the sample can be expressed as follows:

$$\operatorname{Ln}\left(\frac{I^\lambda}{I_0^\lambda}\right) = O.D. \approx -[(\varepsilon_{Hb}^\lambda C_{Hb} H)d + G_{RBC}^\lambda] \quad (7)$$

The optical density of the sample can further be expressed as follows:

$$O.D. = O.D._{Absorption} + O.D._{Scattering} \quad (8)$$

where:

$O.D._{Absorption}$ is the optical density due to absorption by red blood cells, expressed as follows:

$$O.D._{Absorption} = -(\epsilon_{Hb}^\lambda C_{Hb} H)d \quad (9)$$

$O.D._{Scattering}$ is the optical density due to scattering of red blood cells, expressed as follows:

$$O.D._{Scattering} = -G_{RBC}^\lambda \quad (10)$$

From Equation (9), $O.D._{Absorption}$ increases linearly with hematocrit (H). For transmittance measurements in the red and NIR spectrum, $G_{RBC}^\lambda$ is generally parabolic, reaching a maximum at a hematocrit of between 50 and 75 (depending on illumination wavelength and measurement geometry) and is zero at hematocrits of 0 and 100 (see, e.g., Steinke et al., "Diffusion Model of the Optical Absorbance of Whole Blood," J. Opt. Soc. Am., Vol 5, No. 6, June 1988). Therefore, for light transmission measurements, the measured optical density is a nonlinear function of hematocrit.

Nevertheless, it has been discovered that $G_{RBC}^\lambda$ for reflected light measured at a predetermined radial distance from the incident light source is observed to remain linear for the hematocrit range of at least 10 to 90. Thus, with the second sensor 336 so configured, the detection module can treat the optical density of the sample for the reflected light to be a linear function of hematocrit. The same relationship exists for the first sensor 334 with respect to the detection of red blood cells in plasma.

This arrangement relies upon maintaining straightforward measurement geometries. No mirrors or focusing lenses are required. The LED or photodiode need not be positioned at an exact angle with respect to the blood flow tube. No special optical cuvettes are required. The second sensor 336 can interface directly with the transparent plastic tubing 294. Similarly, the first sensor 334 can interface directly with the transparent tubing 292.

In the illustrated embodiment, the wavelength 805 nm is selected, as it is an isosbestic wavelength for red blood cells, meaning that light absorption by the red blood cells at this wavelength is independent of oxygen saturation. Still, other wavelengths can be selected within the NIR spectrum.

In the illustrated embodiment, for a wavelength of 805 nm, the set distance may be 7.5 mm from the light source. The fixture 338, above described (see FIG. 18), facilitates the placement of the tube 294 in the desired relation to the light source and the reflected light detector of the second sensor 336. The fixture 338 also facilitates the placement of the tube 292 in the desired relation to the light source and the reflected light detector of the first sensor 334.

Measurements at a distance greater than 7.5 mm can be made and will show a greater sensitivity to changes in the red blood cell hematocrit. However a lower signal to noise ratio will be encountered at these greater distances. Likewise, measurements at a distance closer to the light source will show a greater signal to noise ratio, but will be less sensitive to changes in the red blood cell hematocrit. The optimal distance for a given wavelength in which a linear relationship between hematocrit and sensed intensity exists for a given hematocrit range can be empirically determined.

Figure 20:
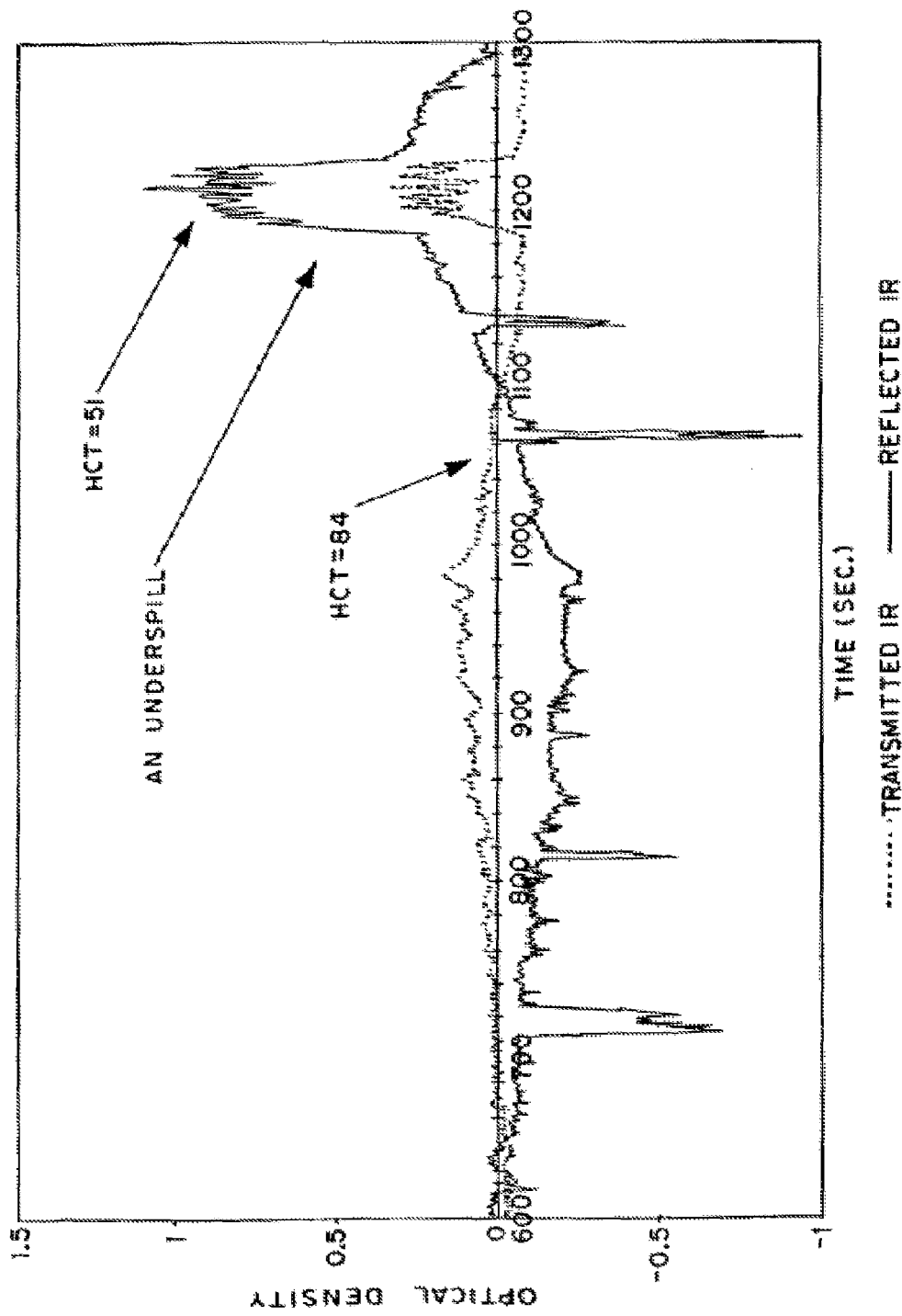
FIG. 20 is a graph of optical densities as sensed by the first and second sensors plotted over time, showing an underspill condition.

The second sensor 336 detects absolute differences in the mean transmitted light intensity of the signal transmitted through the red blood cells in the red blood cell collection line. The detection module analyzes these measured absolute differences in intensities, along with increases in the standard deviation of the measured intensities, to reliably signal an underspill condition, as FIG. 20 shows.

At a given absolute hematocrit, $G_{RBC}^\lambda$ varies slightly from donor to donor, due to variations in the mean red blood cell volume and/or the refractive index difference between the plasma and red blood cells. Still, by measuring the reflected light from a sample of a given donor's blood having a known hematocrit, $G_{RBC}^\lambda$ may be calibrated to yield, for that donor, an absolute measurement of the hematocrit of red blood cells exiting the processing chamber.

C. Pre-Processing Calibration of the Sensors

The first and second sensors 334 and 336 are calibrated during the saline and blood prime phases of a given blood collection procedure, the details of which have already been described.

During the saline prime stage, saline is conveyed into the blood processing chamber 18 and out through the plasma collection line 292. During this time, the blood processing chamber 18 is rotated in cycles between 0 RPM and 200 RPM, until air is purged from the chamber 18. The speed of rotation of the processing chamber 18 is then increased to full operational speed.

The blood prime stage follows, during which whole blood is introduced into the processing chamber 18 at the desired whole blood flow rate ($Q_{WB}$). The flow rate of plasma from the processing chamber through the plasma collection line 292 is set at a fraction (e.g., 80%) of the desired plasma flow rate ($Q_P$) from the processing chamber 18, to purge saline from the chamber 18. The purge of saline continues under these conditions until the first sensor 334 optically senses the presence of saline in the plasma collection line 292.

1. For Plasma Collection Procedures (Induced Underspill)

If the procedure to be performed collects plasma for storage (e.g., the Plasma Collection Procedure or the Red Blood Cell/Plasma Collection Procedure), an underspill condition is induced during calibration. The underspill condition is created by decreasing or stopping the flow of plasma through the plasma collection line 292. This forces the buffy coat away from the low-G side of the chamber 18 (as FIG. 15C) to assure that a flow of "clean" plasma exists in the plasma collection line 292, free or essentially free of platelets and leukocytes.

The induced underspill allows the first sensor 334 to be calibrated and normalized with respect to the physiologic color of the donor's plasma, taking into account the donor's background lipid level, but without the presence of platelets or leukocytes. The first sensor 334 thereby possesses maximum sensitivity to changes brought about by the presence of platelets or leukocytes in the buffy coat, should an overspill subsequently occur during processing.

Forcing an underspill condition also positions the interface close to the high-G wall at the outset of blood processing. This creates an initial offset condition on the high-G side of the chamber, to prolong the ultimate development of an overspill condition as blood processing proceeds.

2. Red Blood Cell Collection Procedures

If a procedure is to be performed in which no plasma is to be collected (e.g., the Double Unit Red Blood Cell Collection Procedure), an underspill condition is not induced during the blood purge phase. This is because, in a red blood cell only collection procedure, the first sensor 334 need only detect, during an overspill, the presence of red blood cells in the plasma. The first sensor 334 does not need to be further sensitized to detect platelets. Furthermore, in a red blood cell only collection procedure, it may be desirable to keep the interface as near the low-G wall as possible. The desired condition allows the buffy coat to be returned to the donor with the plasma and maximizes the hematocrit of the red blood cells collected.

D. Blood Cell Collection

1. Plasma Collection Procedures

In procedures where plasma is collected (e.g., the Plasma Collection Procedure or the Red Blood Cell/Plasma Collection Procedure), $Q_P$ is set at $Q_{P(Ideal)}$, which is an empirically determined plasma flow rate that allows the system to maintain a steady state collection condition, with no underspills and no overspills.

$Q_{P(Ideal)}$ (in grams/ml) is a function of the anticoagulated whole blood inlet flow rate $Q_{WB}$, the anticoagulant whole blood inlet hematocrit $HCT_{WB}$, and the red blood cell exit hematocrit $HCT_{RBC}$ (as estimated or measured), expressed as follows:

$$Q_{P(Ideal)} = \left( \rho_{Plasma} Q_{WB} * \frac{(1 - HCT_{WB}) - \left[\frac{\rho_{WB}}{\rho_{RBC}}(1 - HCT_{RBC})\right]}{\left(1 - \frac{\rho_{Plasma}}{\rho_{RBC}} X1 - HCT_{RBC}\right)} \right)$$

where:
$\rho_{plasma}$ is the density of plasma (in g/ml)=1.03
$\rho_{WB}$ is the density of whole blood (in g/ml)=1.05
$\rho_{RBC}$ is the density of red blood cells=1.08
$Q_{WB}$ is set to the desired whole blood inlet flow rate for plasma collection, which, for a plasma only collection procedure, is generally about 70 ml/min. For a red blood cell/plasma collection procedure, $Q_{WB}$ is set at about 50 ml/min, thereby providing packed red blood cells with a higher hematocrit than in a traditional plasma collection procedure.

The system controller 16 maintains the pump settings until the desired plasma collection volume is achieved, unless an underspill condition or an overspill condition is detected.

If set $Q_P$ is too high for the actual blood separation conditions, or, if due to the physiology of the donor, the buffy coat volume is larger (i.e., "thicker") than expected, the first sensor 334 will detect the presence of platelets or leukocytes, or both in the plasma, indicating an overspill condition.

In response to an overspill condition caused by a high $Q_P$, the system controller 16 terminates operation of the plasma collection pump PP2, while keeping set $Q_{WB}$ unchanged. In response to an overspill condition caused by a high volume buffy coat, the system controller 16 terminates operation of the plasma collection pump PP2, until an underspill condition is detected by the red blood cell sensor 336. This serves to expel the buffy coat layer from the separation chamber through the red blood cell tube 294.

To carry out the overspill response, the blood processing circuit 46 is programmed to operate the in-process pump PP1 (i.e., drawing in through the valve V9 and expelling out of the valve V14), to draw whole blood from the in-process container 312 into the processing chamber 18 at the set $Q_{WB}$. Red blood cells exit the chamber 18 through the tube 294 for collection in the collection container 308. The flow rate of red blood cells directly depends upon the magnitude of $Q_{WB}$. During this time, the blood processing circuit 46 is also programmed to cease operation of the plasma pump PP2 for a preestablished time period (e.g., 20 seconds). This forces the interface back toward the middle of the separation chamber. After the preestablished time period, the operation of the plasma pump PP2 is resumed, but at a low flow rate (e.g., 10 ml/min) for a short time period (e.g., 10 seconds). If the spill has been corrected, clean plasma will be detected by the first sensor 334, and normal operation of the blood processing circuit 46 is resumed. If clean plasma is not sensed, indicating that the overspill has not been corrected, the blood processing circuit 46 repeats the above-described sequence.

The programming of the circuit to relieve an overspill condition is summarized in the following table.

TABLE

Programming of Blood Processing Circuit To Relieve An Overspill Condition (Plasma Collection Procedures)

| | |
|---|---|
| V1 | ● |
| V2 | ○ |
| V3 | ● |
| V4 | ● |
| V5 | ○ |
| V6 | ● |
| V7 | ● |
| V8 | ● |
| V9 | ○/● Pump In |
| V10 | ● |
| V11 | ● |
| V12 | ● |
| V13 | ● |
| V14 | ○/● Pump Out |
| V15 | ● |
| V16 | ● |
| V17 | ● |
| V18 | ● |
| V19 | ● |
| V20 | ● |
| V21 | ● |
| V22 | ● |
| V23 | ● |
| PP1 | □ |
| PP2 | ■ |
| PP3 | ■ |
| PP4 | ■ |

Caption:
○ denotes an open valve;
● denotes a closed valve;
○/● denotes a valve opening and closing during a pumping sequence;
■ denotes an idle pump station (not in use); and
□ denotes a pump station in use.

Upon correction of an overspill condition, the controller 16 returns the blood processing circuit 46 to resume normal blood processing, but applies a percent reduction factor (% RF) to the $Q_P$ set at the time the overspill condition was initially sensed. The reduction factor (% RF) is a function of the time between overspills, i.e., % RF increases as the frequency of overspills increases, and vice versa.

If set $Q_P$ is too low, the second sensor 336 will detect a decrease in the red blood cell hematocrit below a set level, which indicates an underspill condition.

In response to an underspill condition, the system controller 16 resets $Q_P$ close to the set $Q_{WB}$. As processing continues, the interface will, in time, move back toward the low-G wall. The controller 16 maintains these settings until the second sensor 336 detects a red blood cell hematocrit above the desired set level. At this time, the controller 16 applies a percent enlargement factor (% EF) to the $Q_P$ set at the time the underspill condition was initially sensed. The enlargement factor (% EF) is a function of the time between underspills, i.e., % EF increases as the frequency of underspills increases.

Should the controller 16 be unable to correct a given underor overspill condition after multiple attempts (e.g., three attempts), an alarm is commanded.

2. Red Blood Cell only Collection Procedures

In procedures where only red blood cells and no plasma is collected (e.g., the Double Unit Red Blood Cell Collection Procedure), $Q_P$ is set to no greater than $Q_{P(Ideal)}$, and $Q_{WB}$ is set to the desired whole blood inlet flow rate into the processing chamber 18 for the procedure, which is generally about 50 ml/min for a double unit red blood cell collection procedure.

It may be desired during a double unit red blood cell collection procedure that overspills occur frequently. This maximizes the hematocrit of the red blood cells for collection and returns the buffy coat to the donor with the plasma. $Q_P$ is increased over time if overspills occur at less than a set frequency. Likewise, $Q_P$ is decreased over time if overspills occur above the set frequency. However, to avoid an undesirably high hematocrit, it may be just as desirable to operate at $Q_{P(Ideal)}$.

The system controller 16 controls the pump settings in this way until the desired red blood cell collection volume is achieved, taking care of underspills or overspills as they occur.

The first sensor 334 detects an overspill by the presence of red blood cells in the plasma. In response to an overspill condition, the system controller 16 terminates operation of the plasma collection pump to draw plasma from the processing chamber, while keeping the set $Q_{WB}$ unchanged.

To implement the overspill response, the blood processing circuit 46 is programmed (through the selective application of pressure to the valves and pump stations) to operate the plasma pump PP2 and in-process pump PP1 in the manner set forth in the immediately preceding Table. The red blood cells detected in the tube 292 are thereby returned to the processing chamber 18, and are thereby prevented from entering the plasma collection container 304.

The interface will, in time, move back toward the high-G wall. The controller 16 maintains these settings until the second sensor 336 detects a decrease in the red blood cell hematocrit below a set level, which indicates an underspill condition.

In response to an underspill condition, the system controller 16 increases $Q_P$ until the second sensor 336 detects a red blood cell hematocrit above the desired set level. At this time, the controller 16 resets $Q_P$ to the value at the time the most recent overspill condition was sensed.

3. Buffy Coat Collection

If desired, an overspill condition can be periodically induced during a given plasma collection procedure to collect the buffy coat in a buffy coat collection container 376 (see FIG. 10). As FIG. 10 shows, in the illustrated embodiment, the buffy coat collection container 376 is coupled by tubing 378 to the buffy port P4 of the cassette 28. The buffy coat collection container 376 is suspended on a weigh scale 246, which provides output reflecting weight changes over time, from which the controller 16 derives the volume of buffy coat collected.

In this arrangement, when the induced overspill condition is detected, the blood processing circuit 46 is programmed (through the selective application of pressure to the valves and pump stations) to operate the plasma pump PP2 (i.e., drawing in through valve V12 and expelling out through valve V10), to draw plasma from the processing chamber 18 through the tube 378, while valves V4 and V6 are closed and valve V8 is opened. The buffy coat in the tube 378 is conveyed into the buffy coat collection container 376. The blood processing circuit 46 is also programmed during this time to operate the in-process pump PP1 (i.e., drawing in through the valve V9 and expelling out of the valve V14), to draw whole blood from the in-process container 312 into the processing chamber 18 at the set $Q_{WB}$. Red blood cells exit the chamber 18 through the tube 294 for collection in the collection container 308.

The programming of the circuit to relieve an overspill condition by collecting the buffy coat in the buffy coat collection container 376 is summarized in the following table.

TABLE

Programming of Blood Processing Circuit To Relieve An Overspill Condition by Collecting the Buffy Coat (Plasma Collection Procedures)

| | | |
|---|---|---|
| V1 | ● | |
| V2 | ● | |
| V3 | ● | |
| V4 | ● | |
| V5 | ● | |
| V6 | ● | |
| V7 | ● | |
| V8 | ○ | |
| V9 | ○/● | Pump In |
| V10 | ○/● | Pump Out |
| V11 | ● | |
| V12 | ○/● | Pump In |
| V13 | ● | |
| V14 | ○/● | Pump Out |
| V15 | ● | |
| V16 | ● | |
| V17 | ● | |
| V18 | ● | |
| V19 | ● | |
| V20 | ● | |
| V21 | ● | |
| V22 | ● | |
| V23 | ● | |
| PP1 | ☐ | |
| PP2 | ☐ | |
| PP3 | ■ | |
| PP4 | ■ | |

Caption:
○ denotes an open valve;
● denotes a closed valve;
○/● denotes a valve opening and closing during a pumping sequence;
■ denotes an idle pump station (not in use); and
☐ denotes a pump station in use.

After a prescribed volume of buffy coat is conveyed into the buffy coat collection container 376 (as monitored by the weigh scale 246), normal blood processing conditions are resumed. Overspill conditions causing the movement of the buffy coat into the tube 378 can be induced at prescribed intervals during the process period, until a desired buffy coat volume is collected in the buffy coat collection container.

VI. Another Programmable Blood Processing Circuit

A. Circuit Schematic

As previously mentioned, various configurations for the programmable blood processing circuit 46 are possible. FIG. 5 schematically shows one representative configuration 46, the programmable features of which have been described. FIG. 34 shows another representative configuration of a blood processing circuit 46' having comparable programmable features.

Like the circuit 46, the circuit 46' includes several pump stations PP(N), which are interconnected by a pattern of fluid flow paths F(N) through an array of in-line valves V(N). The circuit is coupled to the remainder of the blood processing set by ports P(N).

The circuit 46' includes a programmable network of flow paths F1 to F33. The circuit 46' includes eleven universal ports P1 to P8 and P11 to P13 and four universal pump stations PP1, PP2, PP3, and PP4. By selective operation of the in-line valves V1 to V21 and V23 to V25, any universal port P1 to P8 and P11 to P13 can be placed in flow communication with any universal pump station PP1, PP2, PP3, and PP4. By selective operation of the universal valves, fluid flow can be directed through any universal pump station in a forward direction or reverse direction between two valves, or an in-out direction through a single valve.

In the illustrated embodiment, the circuit 46' also includes an isolated flow path (comprising flow paths F9, F23, F24, and F10) with two ports P9 and P10 and one in-line pump station PP5. The flow path is termed "isolated," because it cannot be placed into direct flow communication with any other flow path in the circuit 46' without exterior tubing. By selective operation of the in-line valves V21 and V22, fluid flow can be directed through the pump station PP5 in a forward direction or reverse direction between two valves, or an in-out direction through a single valve.

Like circuit 46, the circuit 46' can be programmed to assign dedicated pumping functions to the various pump stations. In one embodiment, the universal pump stations PP3 and PP4 in tandem serve as a general purpose, donor interface pump, regardless of the particular blood procedure performed. The dual donor interface pump stations PP3 and PP4 in the circuit 46' work in parallel. One pump station draws fluid into its pump chamber, while the other pump station expels fluid from its pump chamber. The pump station PP3 and PP4 alternate draw and expel functions.

In one arrangement, the draw cycle for the drawing pump station is timed to be longer than the expel cycle for the expelling pump station. This provides a continuous flow of fluid on the inlet side of the pump stations and a pulsatile flow in the outlet side of the pump stations. In one representative embodiment, the draw cycle is ten seconds, and the expel cycle is one second. The expelling pump station performs its one second cycle at the beginning of the draw cycle of the drawing pump, and then rests for the remaining nine seconds of the draw cycle. The pump stations then switch draw and expel functions. This creates a continuous inlet flow and a pulsatile outlet flow. The provision of two alternating pump stations PP3 and PP4 serves to reduce overall processing time, as fluid is continuously conducted into a drawing pump station throughout the procedure.

In this arrangement, the isolated pump station PP5 of the circuit 46' serves as a dedicated anticoagulant pump, like pump station PP4 in the circuit 46, to draw anticoagulant from a source through the port P10 and to meter anticoagulant into the blood through port P9.

In this arrangement, as in the circuit 46, the universal pump station PP1 serves, regardless of the particular blood processing procedure performed, as a dedicated in-process whole blood pump, to convey whole blood into the blood separator. As in the circuit 46, the dedicated function of the pump station PP1 frees the donor interface pumps PP3 and PP4 from the added function of supplying whole blood to the blood separator. Thus, the in-process whole blood pump PP1 can maintain a continuous supply of blood to the blood separator, while the donor interface pumps PP3 and PP4 operate in tandem to simultaneously draw and return blood to the donor through the single phlebotomy needle. The circuit 46' thus minimizes processing time.

In this arrangement, as in circuit 46, the universal pump station PP2 of the circuit 46' serves, regardless of the particular blood processing procedure performed, as a plasma pump, to convey plasma from the blood separator. As in the circuit 46, the ability to dedicate separate pumping functions in the circuit 46' provides a continuous flow of blood into and out of the separator, as well as to and from the donor.

The circuit 46' can be programmed to perform all the different procedures described above for the circuit 46. Depending upon the objectives of the particular blood processing procedure, the circuit 46' can be programmed to retain all or some of the plasma for storage or fractionation purposes, or to return all or some of the plasma to the donor. The circuit 46' can be further programmed, depending upon the objectives of the particular blood processing procedure, to retain all or some of the red blood cells for storage, or to return all or some of the red blood cells to the donor. The circuit 46' can also be programmed, depending upon the objectives of the particular blood processing procedure, to retain all or some of the buffy coat for storage, or to return all or some of the buffy coat to the donor.

In the embodiment illustrated in FIG. 34, the circuit 46' forms a part of a universal set 264', which is coupled to the ports P1 to P13.

More particularly, a donor tube 266', with attached phlebotomy needle 268' is coupled to the port P8 of the circuit 46'. An anticoagulant tube 270', coupled to the phlebotomy needle 268' is coupled to port P9. A container 276' holding anticoagulant is coupled via a tube 274' to the port P10.

A container 280' holding a red blood cell additive solution is coupled via a tube 278' to the port P11. A container 288' holding saline is coupled via a tube 284' to the port P12. A storage container 289' is coupled via a tube 291' to the port P13. An in-line leukocyte depletion filter 293' is carried by the tube 291' between the port P13 and the storage container 289'. The containers 276', 280', 288', and 289' can be integrally attached to the ports or can be attached at the time of use through a suitable sterile connection, to thereby maintain a sterile, closed blood processing environment.

Tubes 290', 292', and 294' extend to an umbilicus 296' which is coupled to the processing chamber 18'. The tubes 290', 292', and 294 are coupled, respectively, to the ports P5, P6, and P7. The tube 290' conveys whole blood into the processing chamber 18 under the operation of the in-process pump station PP1. The tube 292' conveys plasma from the processing chamber 18' under the operation of the plasma pump station PP2. The tube 294' conveys red blood cells from processing chamber 18'.

A plasma collection container 304' is coupled by a tube 302' to the port P3. The collection container 304' is intended, in use, to serve as a reservoir for plasma during processing.

A red blood cell collection container 308' is coupled by a tube 306' to the port P2. The collection container 308' is intended, in use, to receive a unit of red blood cells for storage.

A buffy coat collection container 376' is coupled by a tube 377' to the port P4. The container 376' is intended, in use, to receive a volume of buffy coat for storage.

A whole blood reservoir 312' is coupled by a tube 310' to the port P1. The collection container 312' is intended, in use, to receive whole blood during operation of the donor interface pumps PP3 and PP4, to serve as a reservoir for whole blood during processing. It can also serve to receive a second unit of red blood cells for storage.

B. The Cassette

Figure 35:
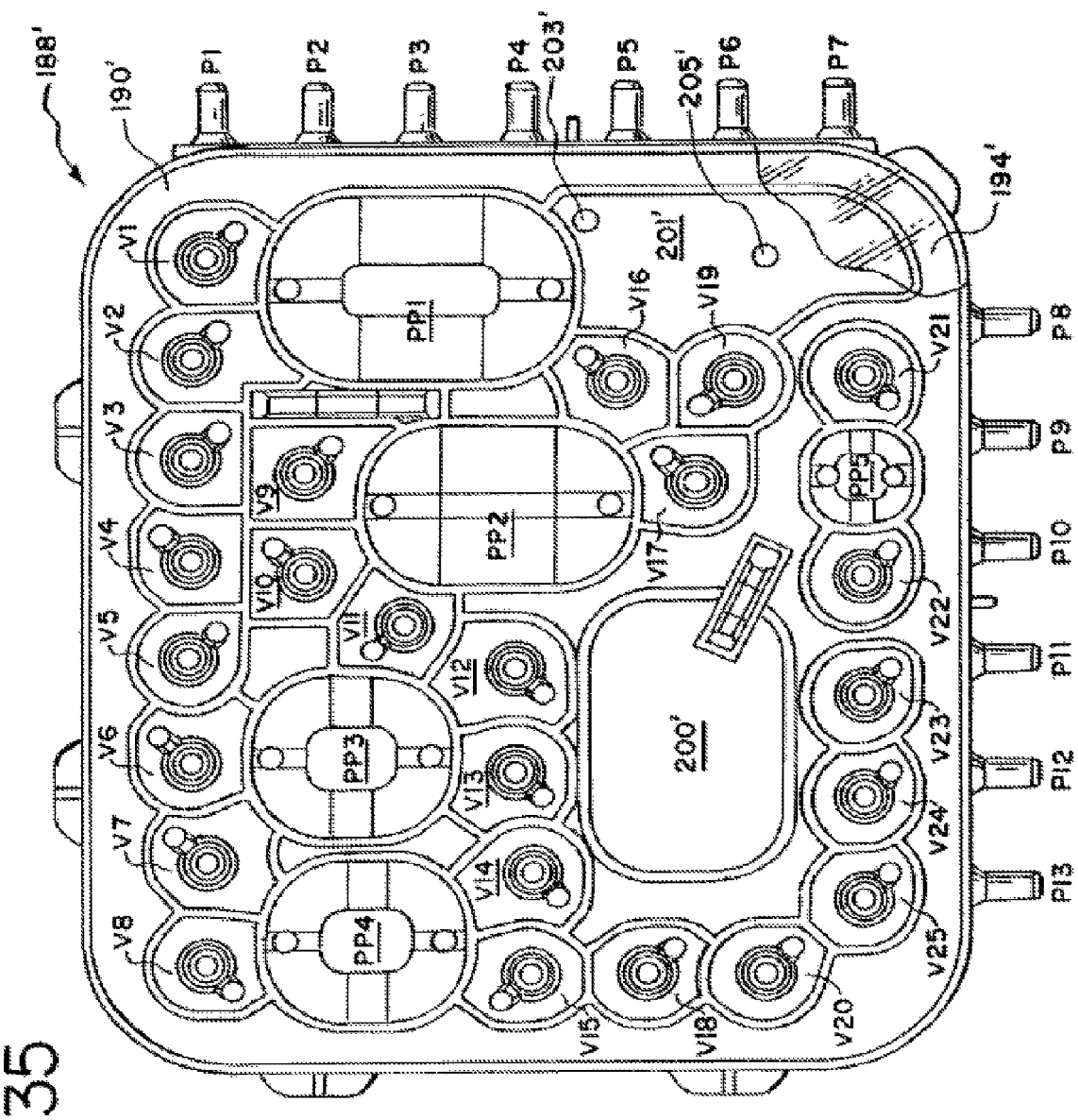
FIG. 35 is a plane view of the front side of a cassette, which contains the programmable blood processing circuit shown in FIG. 34.
Figure 36:
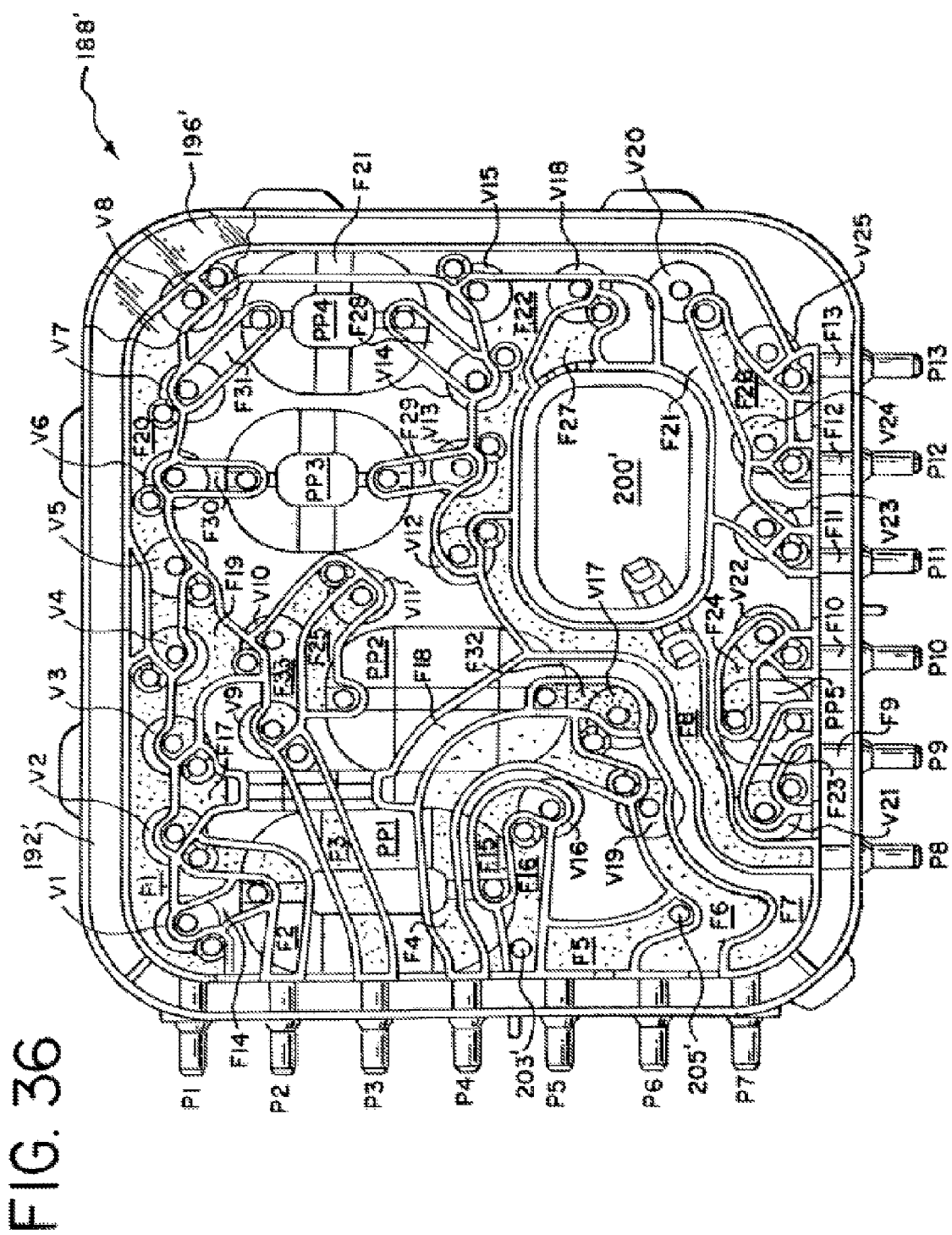
FIG. 36 is a plane view of the back side of the cassette shown in FIG. 35.

As FIGS. 35 and 36 show, the programmable fluid circuit 46' can be implemented as an injection molded, pneumatically controlled cassette 28'. The cassette 28' interacts with the pneumatic pump and valve station 30, as previously described, to provide the same centralized, programmable, integrated platform as the cassette 28.

FIGS. 35 and 36 show the cassette 28' in which the fluid circuit 46' (schematically shown in FIG. 34) is implemented. As previously described for the cassette 28, an array of interior wells, cavities, and channels are formed on both the front and back sides 190' and 192' of the cassette body 188', to define the pump stations PP1 to PP5, valve stations V1 to V25, and flow paths F1 to F33 shown schematically in FIG. 34. In FIG. 36, the flow paths F1 to F33 are shaded to facilitate their viewing. Flexible diaphragms 194' and 196' overlay the front and back sides 190' and 192' of the cassette body 188', resting against the upstanding peripheral edges surrounding the pump stations PP1 to PP5, valves V1 to V25, and flow paths F1 to F33. The pre-molded ports P1 to P13 extend out along two side edges of the cassette body 188'.

The cassette 28' is vertically mounted for use in the pump and valve station 30 in the same fashion shown in FIG. 2. In this orientation (which FIG. 36 shows), the side 192' faces outward, ports P8 to P13 face downward, and the ports P1 to P7 are vertically stacked one above the other and face inward.

As previously described, localized application by the pump and valve station 30 of positive and negative fluid pressures upon the diaphragm 194' serves to flex the diaphragm to close and open the valve stations V1 to V25 or to expel and draw liquid out of the pump stations PP1 to PP5.

An additional interior cavity 200' is provided in the back side 192' of the cassette body 188'. The cavity 200' forms a station that holds a blood filter material to remove clots and cellular aggregations that can form during blood processing. As shown schematically in FIG. 34, the cavity 200' is placed in the circuit 46' between the port P8 and the donor interface pump stations PP3 and PP4, so that blood returned to the donor passes through the filter. Return blood flow enters the cavity 200' through flow path F27 and exits the cavity 200' through flow path F8. The cavity 200' also serves to trap air in the flow path to and from the donor.

Another interior cavity 201' (see FIG. 35) is also provided in the back side 192' of the cassette body 188'. The cavity 201' is placed in the circuit 46' between the port P5 and the valve V16 of the in-process pumping station PP1. Blood enters the cavity 201' from flow path F16 through opening 203' and exits the cavity 201' into flow path F5 through opening 205'. The cavity 201' serves as another air trap within the cassette body 188' in the flow path serving the separation chamber 18'. The cavity 201' also serves as a capacitor to dampen the pulsatile pump strokes of the in-process pump PP1 serving the separation chamber.

C. Associated Pneumatic Manifold Assembly

Figure 43:
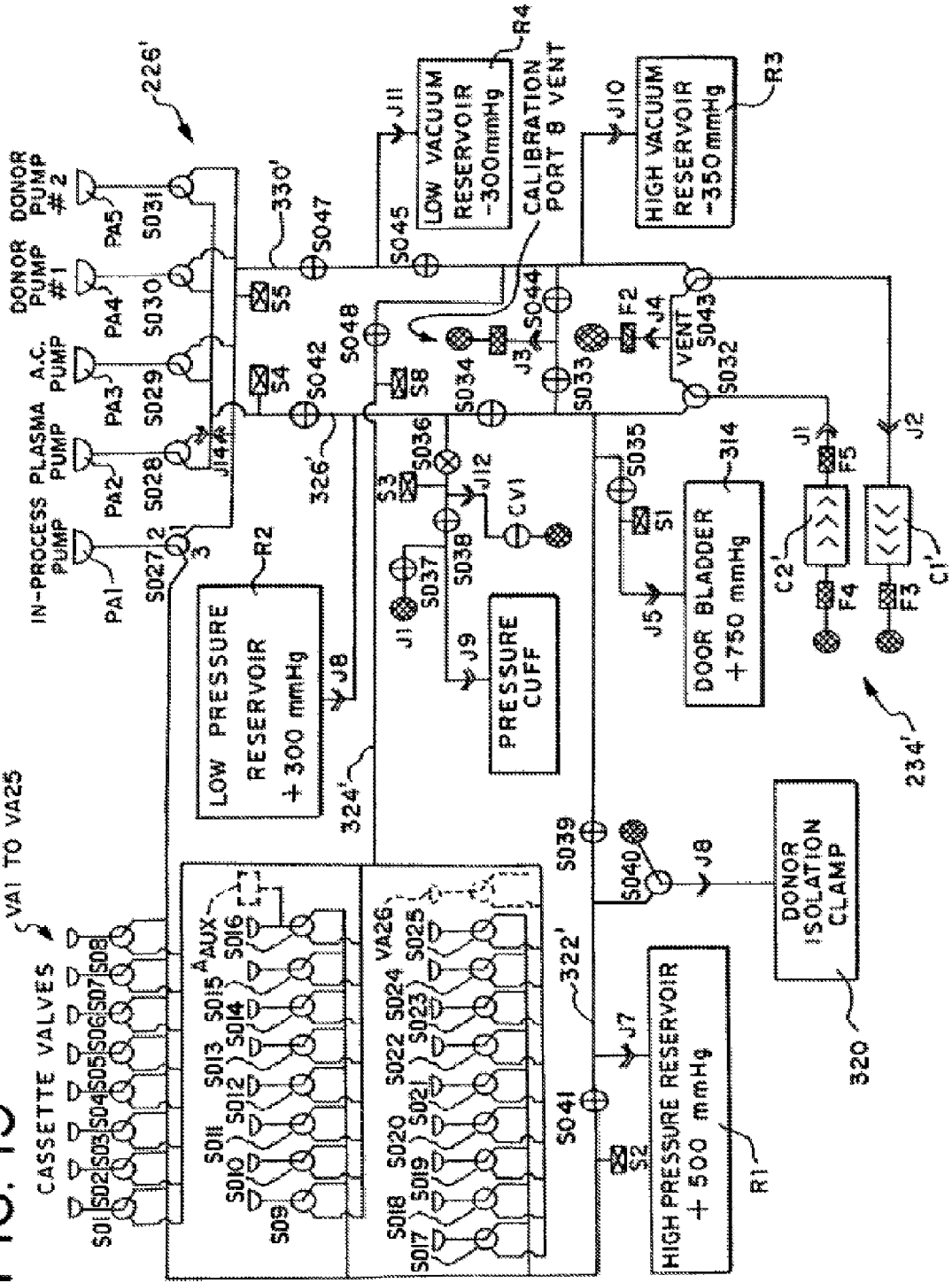
FIG. 43 is a schematic view of a pneumatic manifold assembly, which is part of the pump and valve station shown in FIG. 6, and which supplies positive and negative pneumatic pressures to convey fluid through the cassette shown in FIGS. 35 and 36.

FIG. 43 shows a pneumatic manifold assembly 226' that can be used in association with the cassette 28', to supply positive and negative pneumatic pressures to convey fluid through the cassette 28'. The front side 194' of the diaphragm is held in intimate engagement against the manifold assembly 226' when the door 32 of the centrifuge station 20 is closed and the bladder 314 inflated. The manifold assembly 226', under the control of the controller 16, selectively distributes the different pressure and vacuum levels to the pump and valve actuators PA(N) and VA(N) of the cassette 28'. These levels of pressure and vacuum are systematically applied to the cassette 28', to route blood and processing liquids. Under the control of a controller 16, the manifold assembly 226' also distributes pressure levels to the door bladder 314 (already described), as well as to a donor pressure cuff (also already described) and to a donor line occluder 320 (also already described). The manifold assembly 226' for the cassette 28' shown in FIG. 43 shares many attributes with the manifold assembly 226 previously described for the cassette 28, as shown in FIG. 12.

Like the manifold assembly 226, the manifold assembly 226' is coupled to a pneumatic pressure source 234', which is carried inside the lid 40 behind the manifold assembly 226'. As in the manifold assembly 226, the pressure source 234' for the manifold assembly 226' comprises two compressors C1' and C2', although one or several dual-head compressors could be used as well Compressor C1' supplies negative pressure through the manifold 226' to the cassette 28'. The other compressor C2' supplies positive pressure through the manifold 226' to the cassette 28'.

As FIG. 43 shows, the manifold 226' contains five pump actuators PA1 to PA5 and twenty-five valve actuators VA1 to VA25. The pump actuators PA1 to PA5 and the valve actuators VA1 to VA25 are mutually oriented to form a mirror image of the pump stations PP1 to PP5 and valve stations V1 to V25 on the front side 190' of the cassette 28'.

Like the manifold assembly 226, the manifold assembly 226' shown in FIG. 43 includes an array of solenoid actuated pneumatic valves, which are coupled in-line with the pump and valve actuators PA1 to PA5 and VA1 to VA25.

Like the manifold assembly 226, the manifold assembly 226' maintains several different pressure and vacuum conditions, under the control of the controller 16.

As previously described in connection with the manifold assembly 226, Phard, or Hard Pressure, and Pinpr, or In-Process Pressure are high positive pressures (e.g., +500 mmHg) maintained by the manifold assembly 226' for closing the cassette valves V1 to V25 and to drive the expression of liquid from the in-process pump PP1 and the plasma pump PP2. As before explained, the magnitude of Pinpr must be sufficient to overcome a minimum pressure of approximately 300 mm Hg, which is typically present within the processing chamber 18'. Pinpr and Phard are operated at the highest pressure to ensure that upstream and downstream valves used in conjunction with pumping are not forced open by the pressures applied to operate the pumps.

Pgen, or General Pressure (+300 mmHg), is applied to drive the expression of liquid from the donor interface pumps PP3 and PP4 and the anticoagulant pump PP5.

Vhard, or Hard Vacuum (−350 mmHg), is the deepest vacuum applied in the manifold assembly 226' to open cassette valves V1 to V25. Vgen, or General Vacuum (−300 mmHg), is applied to drive the draw function of each of the pumps PP1 to PP5. Vgen is required to be less extreme than Vhard, to ensure that pumps PP1 to PP5 do not overwhelm upstream and downstream cassette valves V1 to V25.

A main hard pressure line 322' and a main vacuum line 324' distribute Phard and Vhard in the manifold assembly 226'. The pressure and vacuum sources 234' run continuously to supply Phard to the hard pressure line 322' and Vhard to the hard vacuum line 324'. A pressure sensor S2 monitors Phard in the hard pressure line 322'. The sensor S2 opens and closes the solenoid SO32 to build Phard up to its maximum set value.

Similarly, a pressure sensor S8 in the hard vacuum line 324' monitors Vhard. The sensor S8 controls a solenoid SO43 to maintain Vhard as its maximum value.

A general pressure line 326' branches from the hard pressure line 322'. A sensor S4 in the general pressure line 326' monitors Pgen. The sensor S4 controls a solenoid SO34 to maintain Pgen within its specified pressure range.

A general vacuum line 330' branches from the hard vacuum line 324'. A sensor S5 monitors Vgen in the general vacuum line 330'. The sensor S5 controls a solenoid SO45 to keep Vgen within its specified vacuum range.

In-line reservoirs R1 to R4 are provided in the hard pressure line 322', the general pressure line 326', the hard vacuum line 324', and the general vacuum line 330'. The reservoirs R1 to R4 assure that the constant pressure and vacuum adjustments as above described are smooth and predictable.

The solenoids SO32 and SO43 provide a vent for the pressures and vacuums, respectively, upon procedure completion.

The solenoids SO41, SO42, SO47, and SO48 provide the capability to isolate the reservoirs R1 to R4 from the air lines that supply vacuum and pressure to the pump and valve actuators. This provides for much quicker pressure/vacuum decay feedback, so that testing of cassette/manifold assembly seal integrity can be accomplished.

The solenoids SO1 to SO25 provide Phard or Vhard to drive the valve actuators VA1 to V25. The solenoids SO27 and SO28 provide Pinpr and Vgen to drive the in-process and plasma pumps PP1 and PP2. The solenoids SO30 and SO31 provide Pgen and Vgen to drive the donor interface pumps PP3 and PP4. The solenoid SO29 provides Pgen and Vgen to drive the AC pump PP5

The solenoid SO35 provides isolation of the door bladder 314 from the hard pressure line 322' during the procedure. A sensor S1 monitors Pdoor and control the solenoid SO35 to keep the pressure within its specified range.

The solenoid SO40 provides Phard to open the safety occluder valve 320. Any error modes that might endanger the donor will relax (vent) the solenoid SO40 to close the occluder 320 and isolate the donor. Similarly, any loss of power will relax the solenoid SO40 and isolate the donor.

The sensor S3 monitors Pcuff and communicates with solenoid SO36 (for increases in pressure) and solenoid SO37 (for venting) to maintain the donor cuff within its specified ranges during the procedure.

As before explained, any solenoid can be operated in "normally open" mode or can be re-routed pneumatically to be operated in a "normally closed" mode, and vice versa.

D. Exemplary Pumping Functions

Based upon the foregoing description of the programming of the fluid circuit 46 implemented by the cassette 28, one can likewise program the fluid circuit 46' implemented by the cassette 28' to perform all the various blood process functions already described. Certain pumping functions for the fluid circuit 46', common to various blood processing procedures, will be described by way of example.

1. Whole Blood Flow to the In-Process Container

In a first phase of a given blood collection cycle, the blood processing circuit 46' is programmed (through the selective application of pressure to the valves and pump stations of the cassette 28') to jointly operate the donor interface pumps PP3 and PP4 to transfer anticoagulated whole blood into the in-process container 312' prior to separation.

Figure 37A:
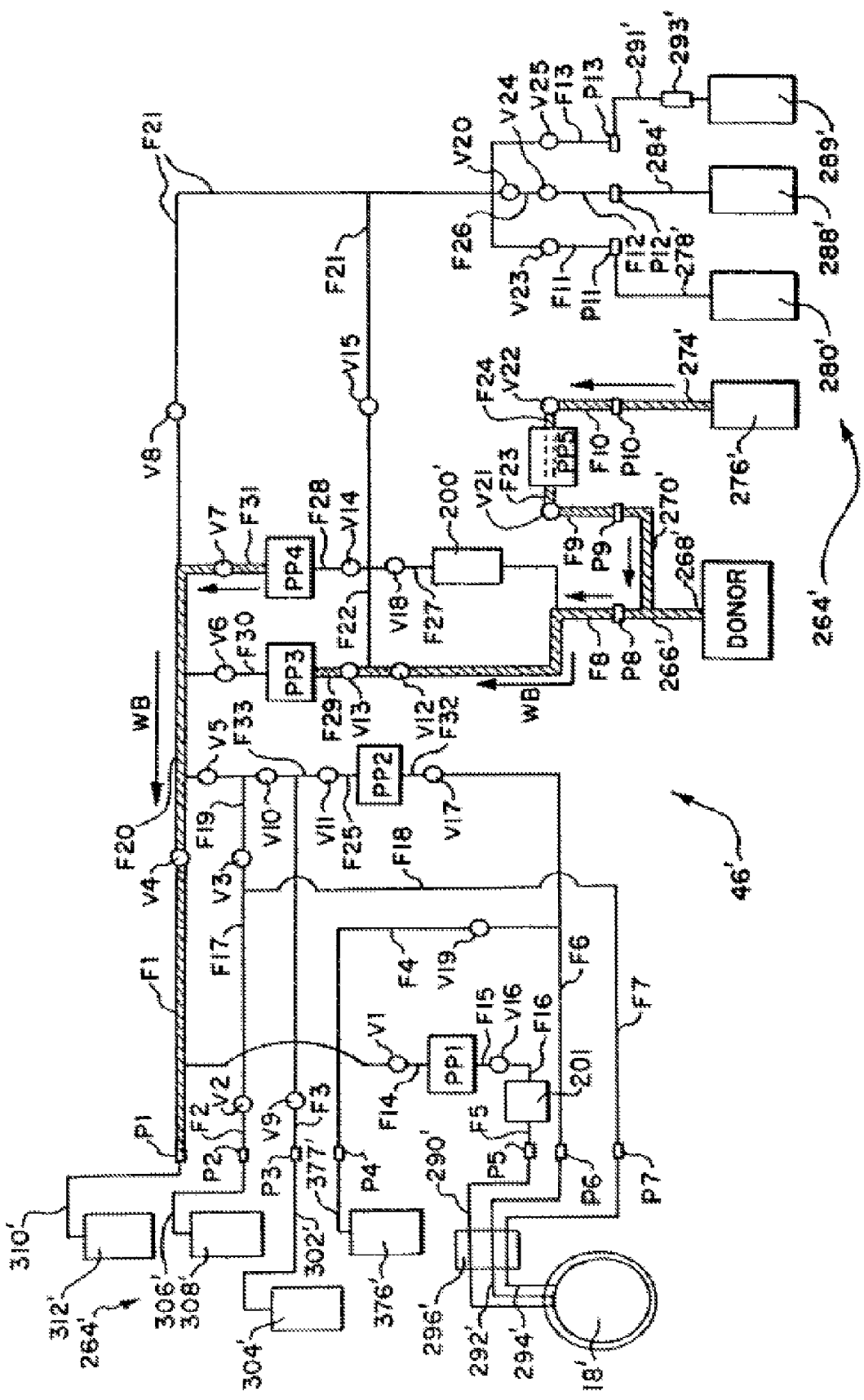
FIGS. 37A to 37E are schematic views of the blood processing circuit shown in FIG. 34, showing the programming of the cassette to carry out different fluid flow tasks in connection with processing whole blood into plasma and red blood cells.

In a first phase (see FIG. 37A), the pump PP3 is operated in a ten second draw cycle (i.e., in through valves V12 and V13, with valves V6, V14, V18, and V15 closed) in tandem with the anticoagulant pump PP5 (i.e., in through valve V22 and out through valve V21) to draw anticoagulated blood through the donor tube 270' into the pump PP3. At the same time, the donor interface pump PP4 is operated in a one second expel cycle to expel (out through valve V7) anticoagulated blood from its chamber into the in-process container 312' through flow paths F20 and F1 (through opened valve V4).

Figure 37B:
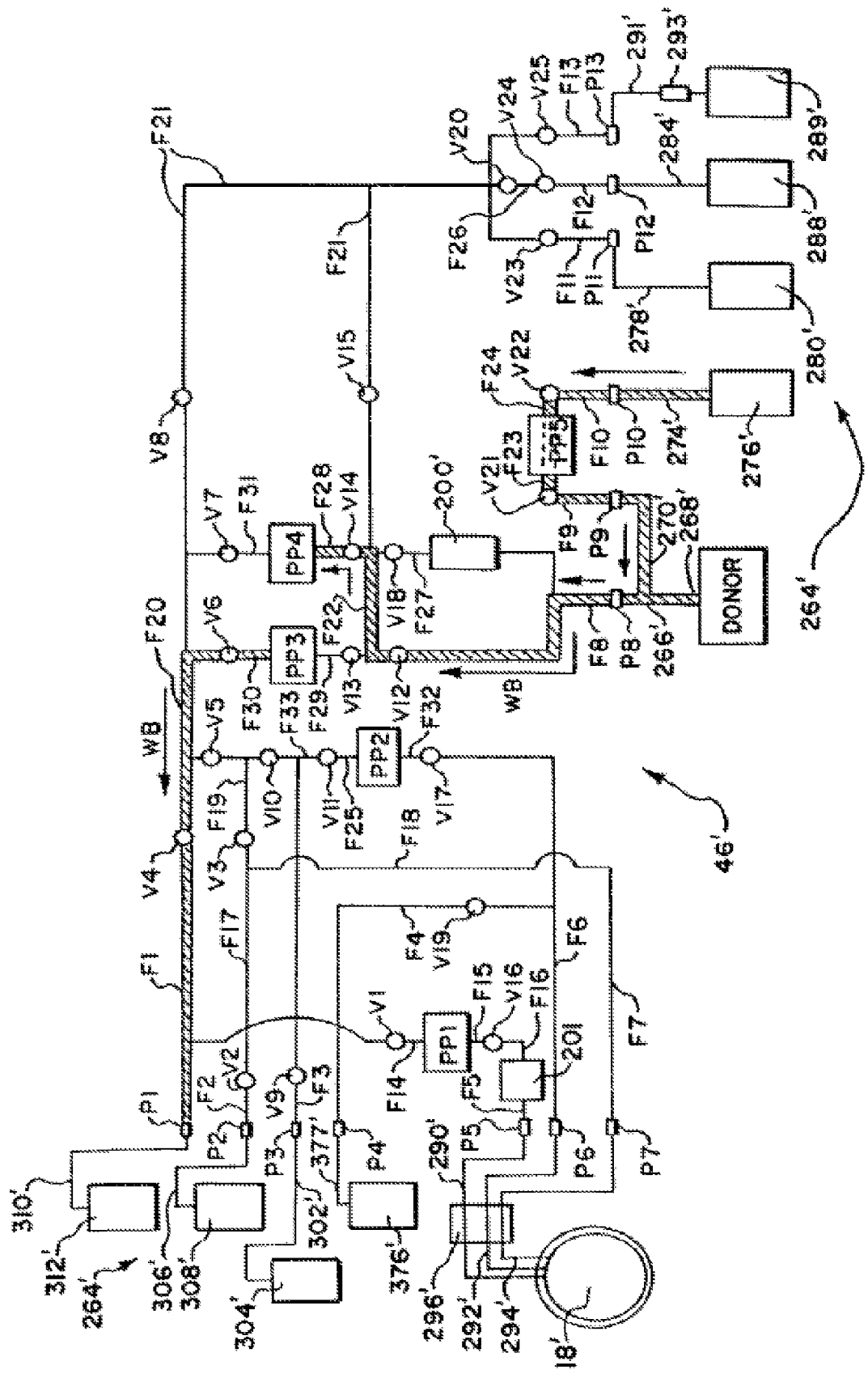

At the end of the draw cycle for pump PP3 (see FIG. 37B), the blood processing circuit 46' is programmed to operate the donor interface pump PP4 in a ten second draw cycle (i.e., in through valves V12 and V14, with valves V13 and V18 closed) in tandem with the anticoagulant pump PP5 to draw anticoagulated blood through the donor tube 270' into the pump PP4. At the same time, the donor interface pump PP3 is operated in a one second expel cycle to expel (out through valve V6) anticoagulated blood from its chamber into the in-process container 312' through the flow paths F20 and F1 (through opened valve V4).

Figure 37C:
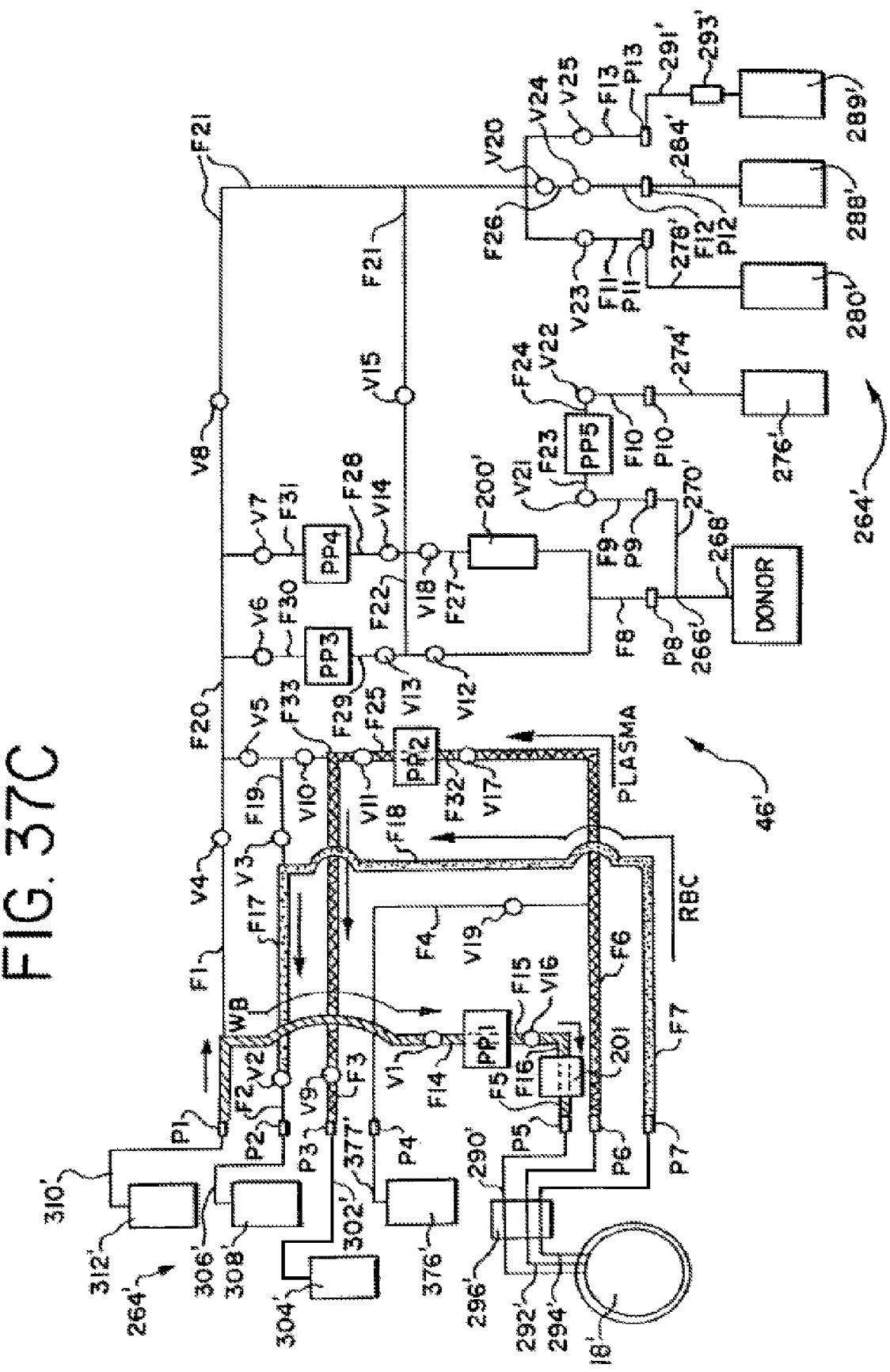

These alternating cycles continue until an incremental volume of anticoagulated whole blood enters the in-process container 312', as monitored by a weigh sensor. As FIG. 37C shows, the blood processing circuit 46' is programmed to operate the in-process pump station PP1 (i.e., in through valve V1 and out through valve V16) and the plasma pump PP2 (i.e., in through valve V17 and out through valve V11, with valve V9 opened and valve V10 closed) to convey anticoagulated whole blood from the in-process container 312' into the processing chamber 18' for separation, while removing plasma into the plasma container 304' (through opened valve V9) and red blood cells into the red blood cell container 308' (through open valve V2), in the manner previously described with respect to the circuit 46. This phase continues until an incremental volume of plasma is collected in the plasma collection container 304' (as monitored by the weigh sensor) or until a targeted volume of red blood cells is collected in the red blood cell collection container (as monitored by the weigh sensor). The donor interface pumps PP3 and PP4 toggle to perform alternating draw and expel cycles as necessary to keep the volume of anticoagulated whole blood in the in-process container 312' between prescribed minimum and maximum levels, as blood processing proceeds.

2. Red Blood Cell Return with In-Line Addition of Saline

Figure 37D:
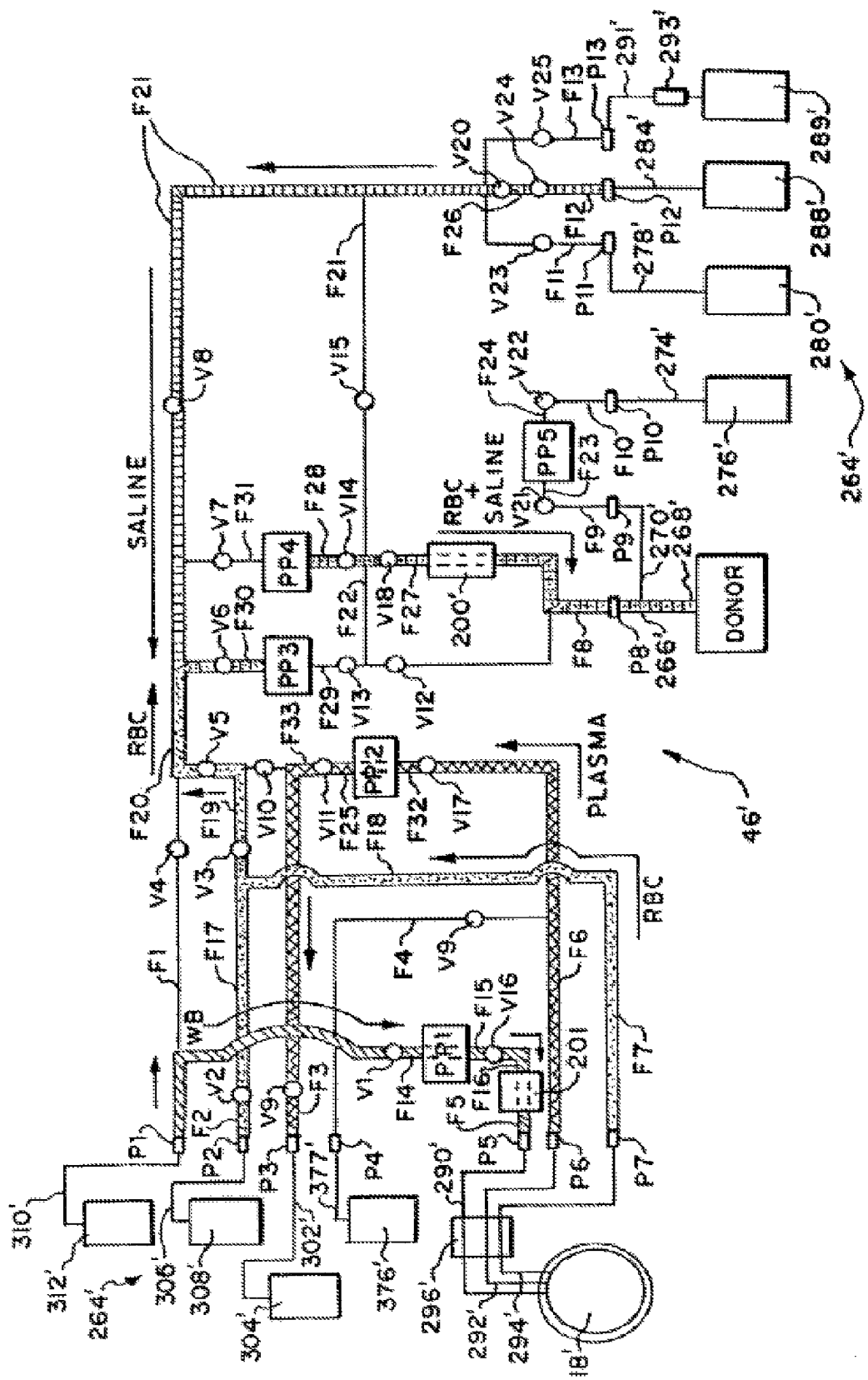

When it is desired to return red blood cells to the donor (see FIG. 37D), the blood processing circuit 46' is programmed to operate the donor interface pump station PP3 in a ten second draw cycle (i.e., in through valve V6, with valves V13 and V7 closed) to draw red blood cells from the red blood cell container 308' into the pump PP3 (through open valves V2, V3, and V5, valve V10 being closed). At the same time, the donor interface pump PP4 is operated in a one second expel cycle to expel (out through valves V14 and V18, with valves V12 and V21 closed) red blood cells from its chamber to the donor through the filter cavity 200'.

Figure 37E:
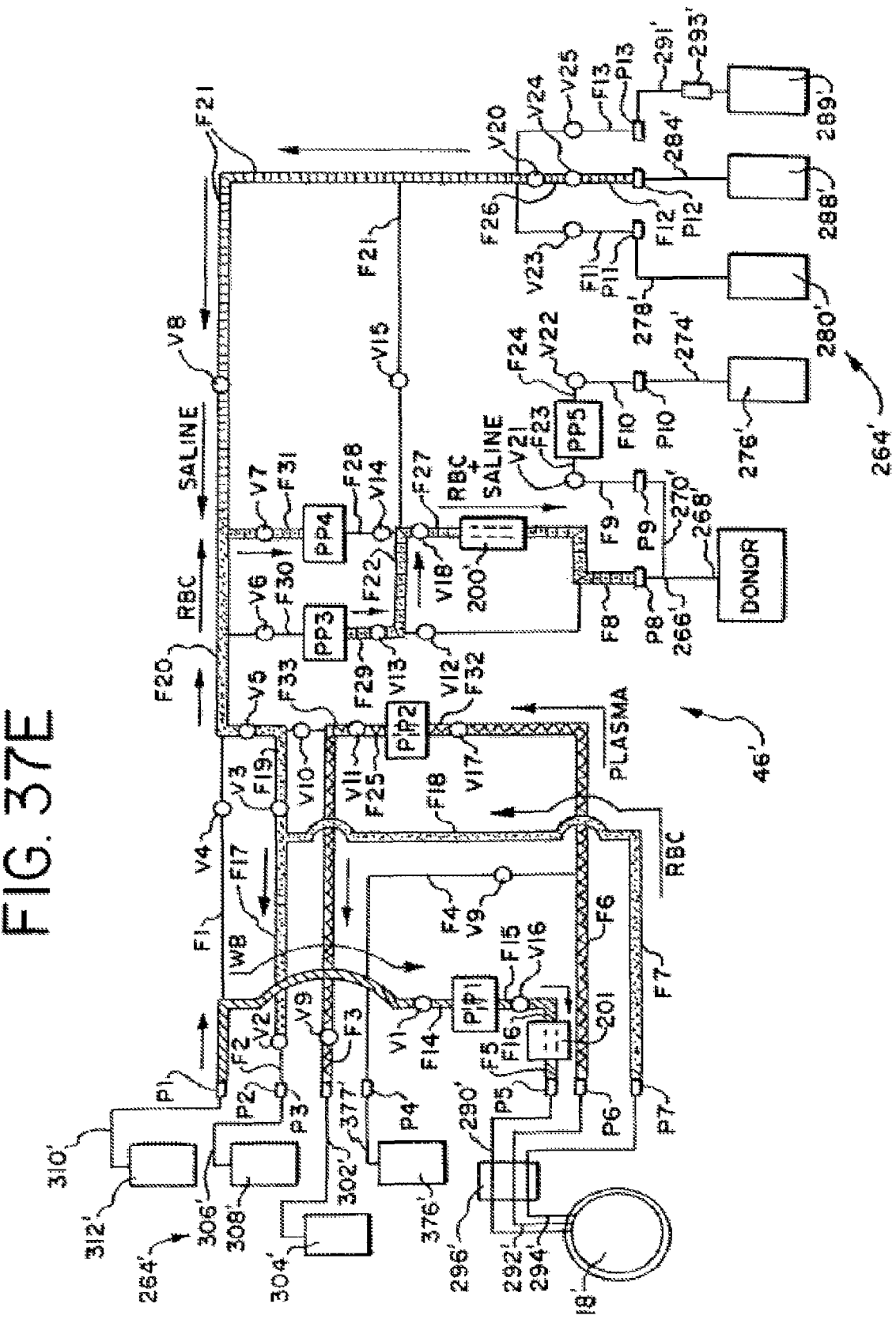

At the end of the draw cycle for pump PP3 (see FIG. 37E), the blood processing circuit 46' is programmed to operate the donor interface pump PP4 in a ten second draw cycle (i.e., in through valve V7, with valves V6 and V14 closed) to draw red blood cells from the red blood cell container 308' into the pump PP4. At the same time, the donor interface pump PP3 is operated in a one second expel cycle to expel (out through valves V13 and V18, with valve V12 closed) red blood cells from its chamber to the donor through the filter chamber 200'. These alternating cycles continue until a desired volume of red blood cells is returned to the donor.

Simultaneously, valves V24, V20, and V8 are opened, so that the drawing pump station PP3 or PP4 also draws saline from the saline container 288' for mixing with red blood cells drawn into the chamber. As before explained, the in-line mixing of saline with the red blood cells raises the saline temperature and improves donor comfort, while also lowering the hematocrit of the red blood cells.

Simultaneously, the in-process pump PP1 is operated (i.e., in through valve V1 and out through valve V16) and the plasma pump PP2 (i.e., in through valve V17 and out through valve V11, with valve V9 open) to convey anticoagulated whole blood from the in-process container 312' into the processing chamber for separation, while removing plasma into the plasma container 304', in the manner previously described with respect to the fluid circuit 46.

3. In-Line Addition of Red Blood Cell Additive Solution

Figure 38A:
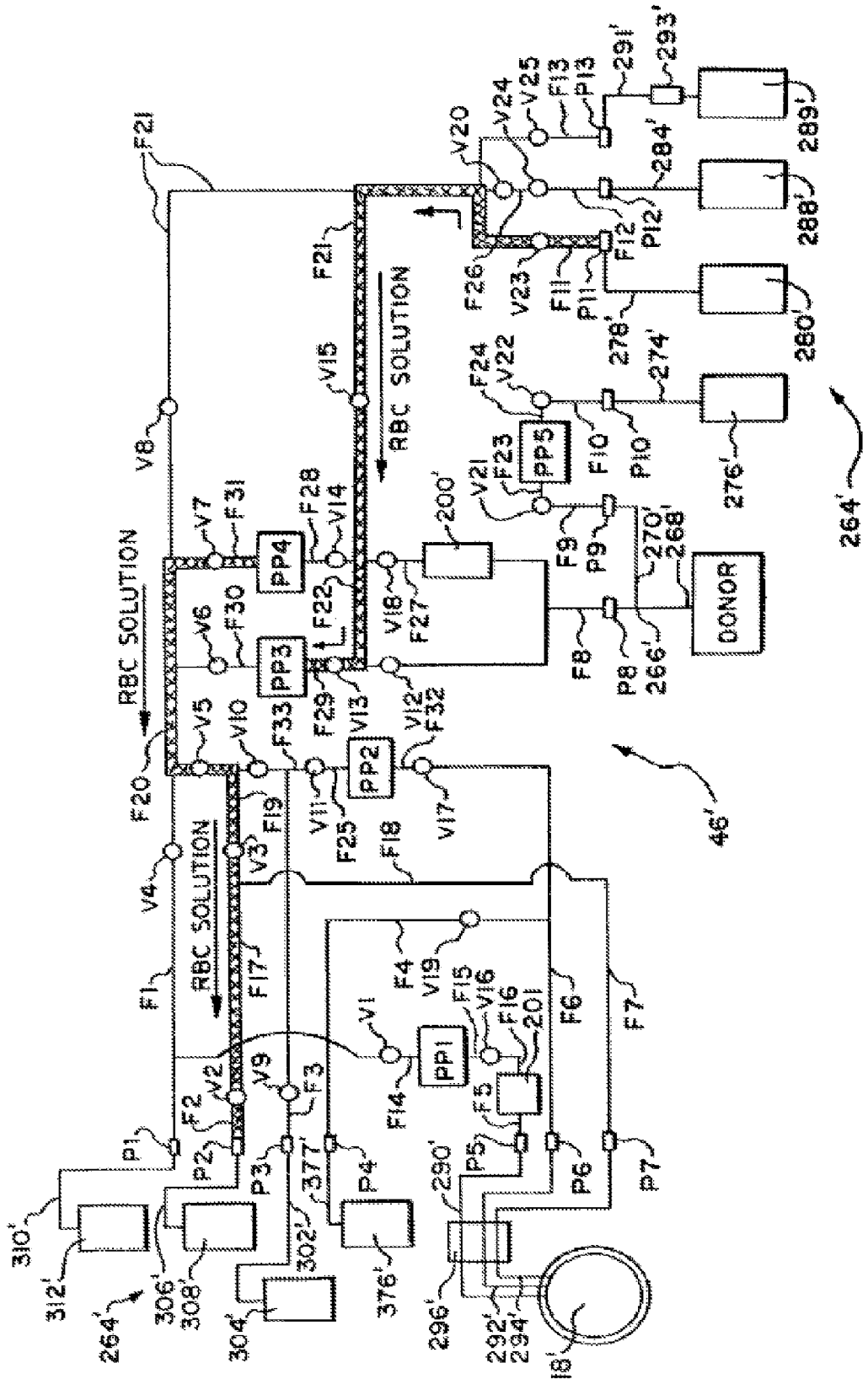

In a blood processing procedure where red blood cells are collected for storage (e.g., the Double Red Blood Cell Collection Procedure or the Red Blood Cell and Plasma Collection Procedure) the circuit 46' is programmed to operate the donor interface pump station PP3 in a ten second draw cycle (in through valves V15 and V13, with valve V23 opened and valves V8, V12 and V18 closed) to draw red blood cell storage solution from the container 280' into the pump PP3 (see FIG. 38A). Simultaneously, the circuit 46' is programmed to operate the donor interface pump station PP4 in a one second expel cycle (out through valve V7, with valves V14 and V18 closed) to expel red blood cell storage solution to the container(s) where red blood cells reside (e.g., the in-process container 312' (through open valve V4) or the red blood cell collection container 308' (through open valves V5, V3, and V2, with valve V10 closed)).

At the end of the draw cycle for pump PP3 (see FIG. 38B), the blood processing circuit 46' is programmed to operate the donor interface pump PP4 in a ten second draw cycle (i.e., in through valve V14, with valves V7, V18, V12, and V13 closed) to draw red blood cell storage solution from the container 280' into the pump PP4. At the same time, the donor interface pump PP3 is operated in a one second expel cycle to expel (out through valve V6, with valves V13 and V12 closed) red blood cell storage solution to the container(s) where red blood cells reside. These alternating cycles continue until a desired volume of red blood cell storage solution is added to the red blood cells.

4. In-Line Leukocyte Depletion

Figure 39A:
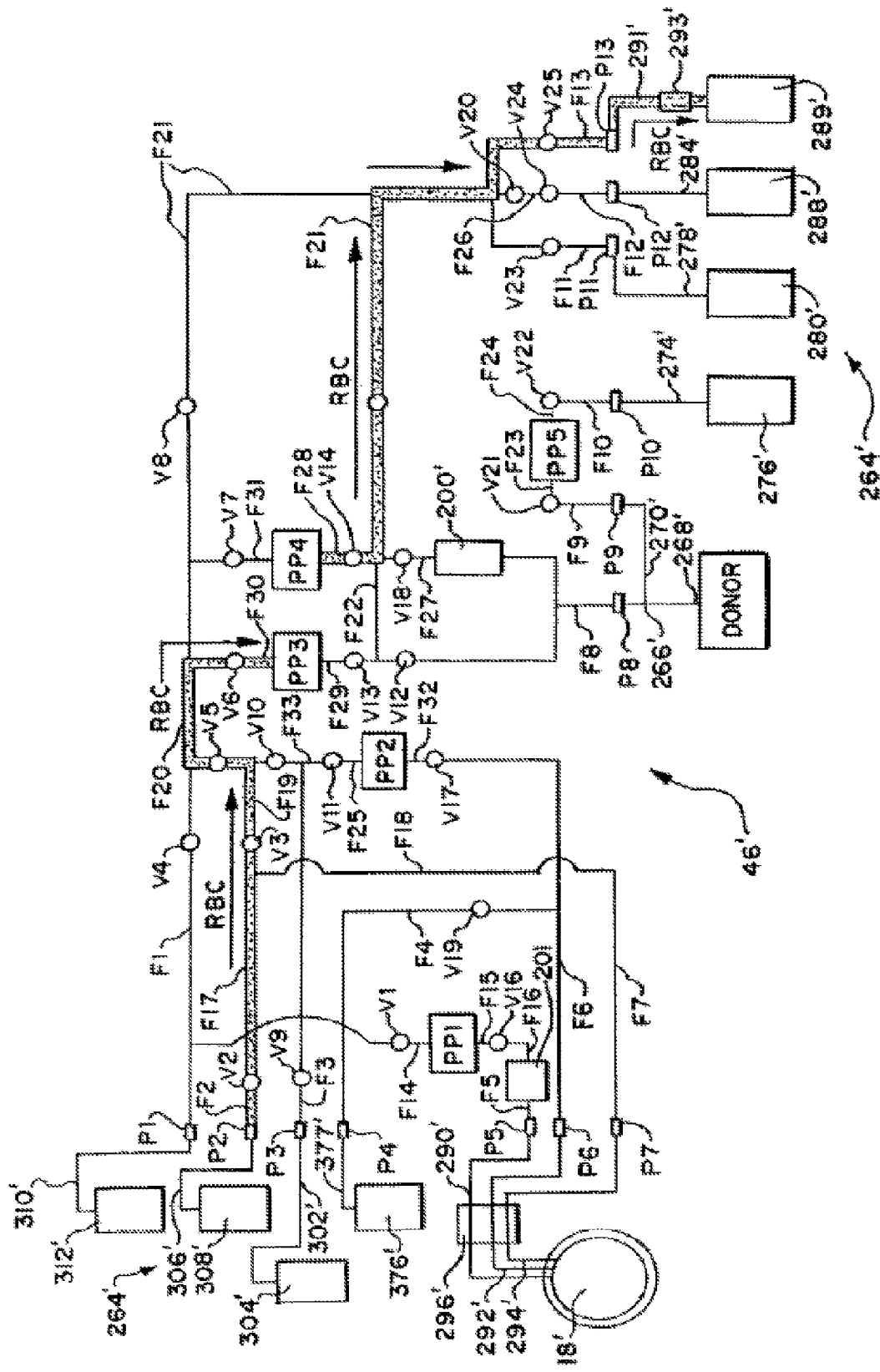
FIGS. 39A and 39B are schematic views of the blood processing circuit shown in FIG. 34, showing the programming of the cassette to carry out fluid flow tasks in connection with on-line transfer of red blood cells separated from whole blood through a filter to remove leukocytes.

Circuit 46' provides the capability to conduct on-line depletion of leukocytes from collected red blood cells. In this mode (see FIG. 39A), the circuit 46' is programmed to operate the donor interface pump station PP3 in a ten second draw cycle (in through valve V6, with valves V13 and V12 closed) to draw red blood cells from the container(s) where red blood cells reside (e.g., the in-process container 312' (through open valve V4) or the red blood cell collection container 308' (through open valves V5, V3, and V2, with valve V10 closed)) into the pump PP3. Simultaneously, the circuit 46' is programmed to operate the donor interface pump station PP4 in a one second expel cycle (out through valve V14, with valves V18 and V8 closed and valves V15 and V25 opened) to expel red blood cells through tube 291' through the in-line leukocyte depletion filter 293' to the leukocyte-depleted red blood cell storage container 289'.

Figure 39B:
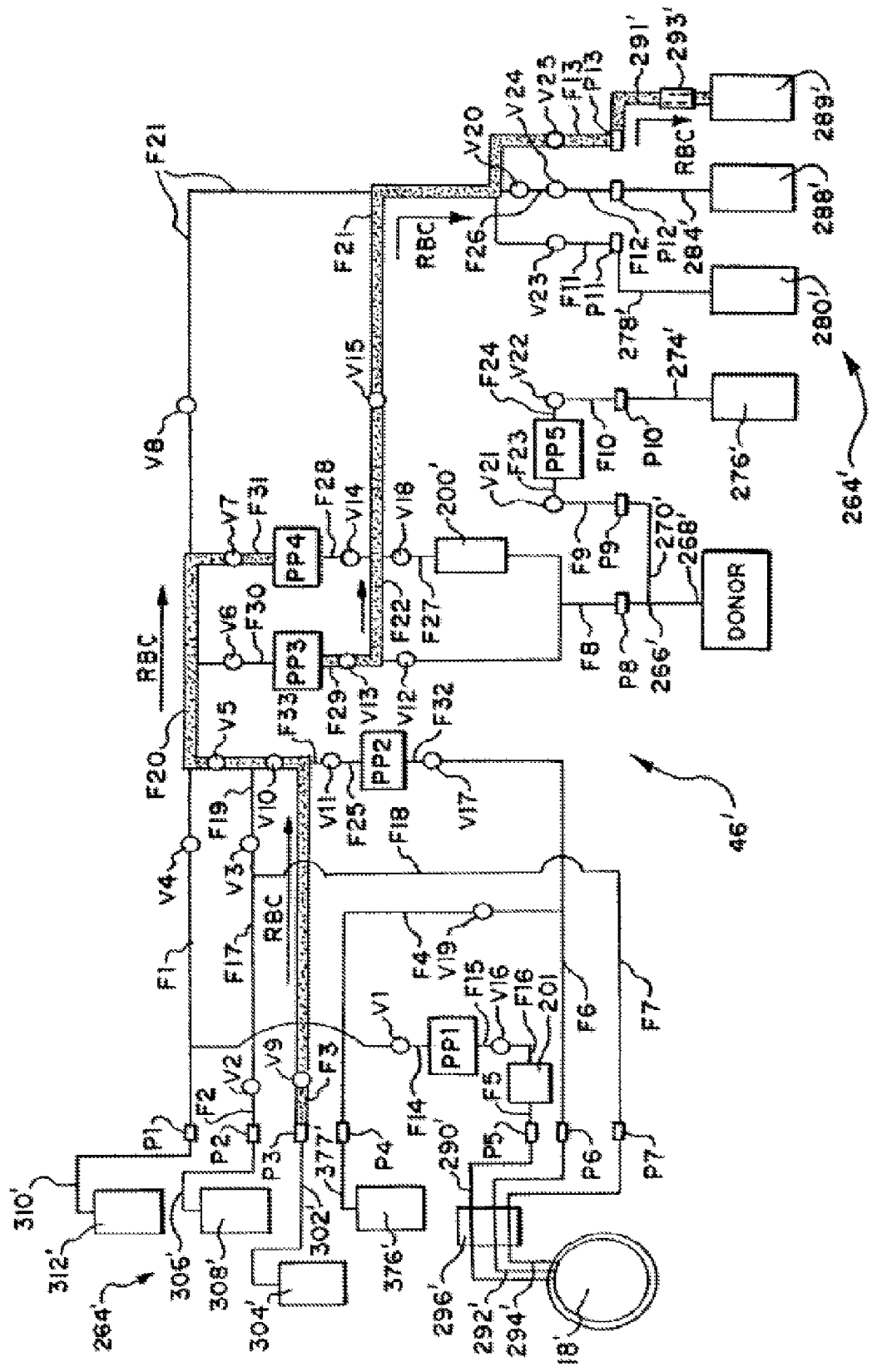

At the end of the draw cycle for pump PP3 (see FIG. 39B), the blood processing circuit 46' is programmed to operate the donor interface pump PP4 in a ten second draw cycle (i.e., in through valve V7, with valves V14 and V18 closed) to draw red blood cells from the container 312' or 308' into the pump PP4. At the same time, the donor interface pump PP3 is operated in a one second expel cycle to expel (out through valve V13, with valve V12 closed and valves V15 and V25 opened) red blood cells through tube 291' through the in-line leukocyte depletion filter 293' to the leukocyte-depleted red blood cell storage container 289'. These alternating cycles continue until a desired volume of red blood cells is transferred through the filter 293' into the container 289'.

5. Staged Buffy Coat Harvesting

In circuit 46 (see FIG. 5), buffy coat is collected through port P4, which is served by flow line F4, which branches from flow line F28, which conveys plasma from the plasma pump station PP2 to the plasma collection container 304 (also see FIG. 10). In the circuit 46' (see FIG. 34), the buffy coat is collected through the port P4 from the flow path F6 as controlled by valve V19. The buffy coat collection path bypasses the plasma pump station PP2, keeping the plasma pump station PP2 free of exposure to the buffy coat, thereby keeping the collected plasma free of contamination by the buffy coat components.

During separation, the system controller (already described) maintains the buffy coat layer within the separation chamber 18' at a distance spaced from the low-G wall, away from the plasma collection line 292 (see FIG. 15A). This allows the buffy coat component to accumulate during processing as plasma is conveyed by operation of the plasma pump PP2 from the chamber into the plasma collection container 304'.

To collect the accumulated buffy coat component, the controller opens the buffy coat collection valve V19, and closes the inlet valve V17 of the plasma pump station PP2 and the red blood cell collection valve V2. The in-process pump PP1 continues to operate, bringing whole blood into the chamber 18'. The flow of whole blood into the chamber 18' moves the buffy coat to the low-G wall, inducing an overspill condition (see FIG. 15B). The buffy coat component enters the plasma collection line 292' and enters flow path F6 through the port P6. The circuit 46' conveys the buffy coat component in F6 through the opened valve V19 directly into path F4 for passage through the port P4 into the collection container 376'.

The valve V19 is closed when the sensing station 332 senses the presence of red blood cells. The plasma pumping station PP2 can be temporarily operated in a reverse flow direction (in through the valve V11 and out through the valve V17, with valve V9 opened) to flow plasma from the collection container 304' through the tube 292' toward the separation chamber, to flush resident red blood from the tube 292' back into the separation chamber. The controller can resume normal plasma and red blood cell collection, by opening the red blood cell collection valve V2 and operating the plasma pumping station PP2 (in through valve V17 and out through valve V11) to resume the conveyance of plasma from the separation chamber to the collection container 304'.

Overspill conditions causing the movement of the buffy coat for collection can be induced at prescribed intervals during the process period, until a desired buffy coat volume is collected in the buffy coat collection container.

6. Miscellaneous

As FIG. 43 shows in phantom lines, the manifold assembly 226' can include an auxiliary pneumatic actuator $A_{AUX}$ to selectively apply $P_{HARD}$ to the region of the flexible diaphragm that overlies the interior cavity 201' (see FIG. 35). As previously described, whole blood expelled by the pumping station PP1 (by application of $P_{HARD}$ by actuator PA1), enters flow path F5 through openings 203' and 205' into the processing chamber 18'. During the next subsequent stroke of the pumping station PP1, to draw whole blood into the pumping station PP1 by application of $V_{GEN}$ by actuator PA1, residual whole blood residing in the cavity 201' is expelled into flow path F5 through opening 205', and into the processing chamber 18' by application of $P_{HARD}$ by $A_{AUX}$. The cavity 201' also serves as a capacitor to dampen the pulsatile pump strokes of the in-process pump PP1 serving the separation chamber 18'.

It is desirable to conduct seal integrity testing of the cassette 28' shown in FIGS. 35 and 36 prior to use. The integrity test determines that the pump and valve stations within the cassette 28' function without leaking. In this situation, it is desirable to isolate the cassette 28' from the separation chamber 18'. Valves V16 and V17 (see FIG. 34) in circuit 264' provide isolation for the whole blood inlet and plasma lines 290' and 292' of the chamber 18'. To provide the capability of also isolating the red blood cell line 294', an extra valve fluid actuated station V26 can be added in fluid flow path F7 serving port P7. As further shown in phantom lines in FIG. 43, an addition valve actuator VA26 can be added to the manifold assembly 226', to apply positive pressure to the valve V26, to close the valve V26 when isolation is required, and to apply negative pressure to the valve V26, to open the valve when isolation is not required.

VII. Blood Separation Elements

A. Molded Processing Chamber

Figure 21:
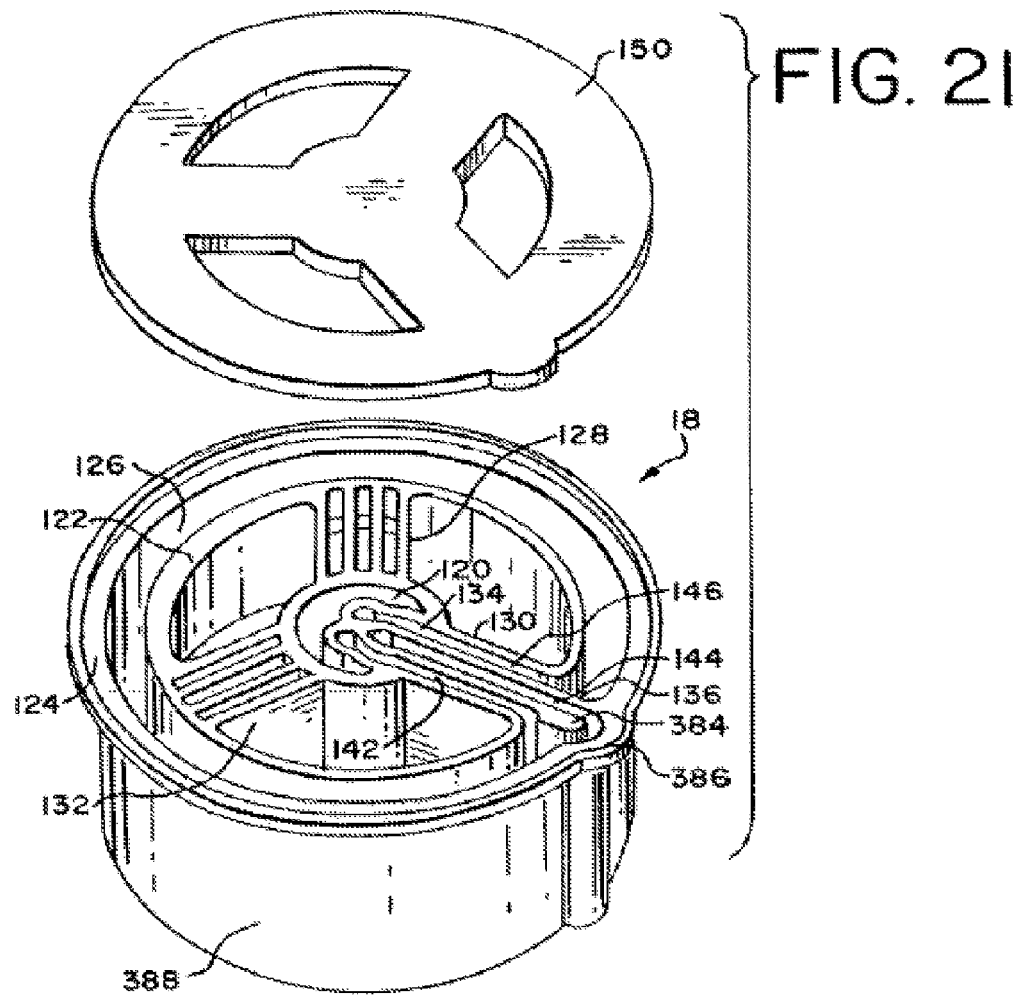
FIG. 21 is an exploded top perspective view of a molded centrifugal blood processing container, which can be used in association with the device shown in FIG. 1.
Figure 22:
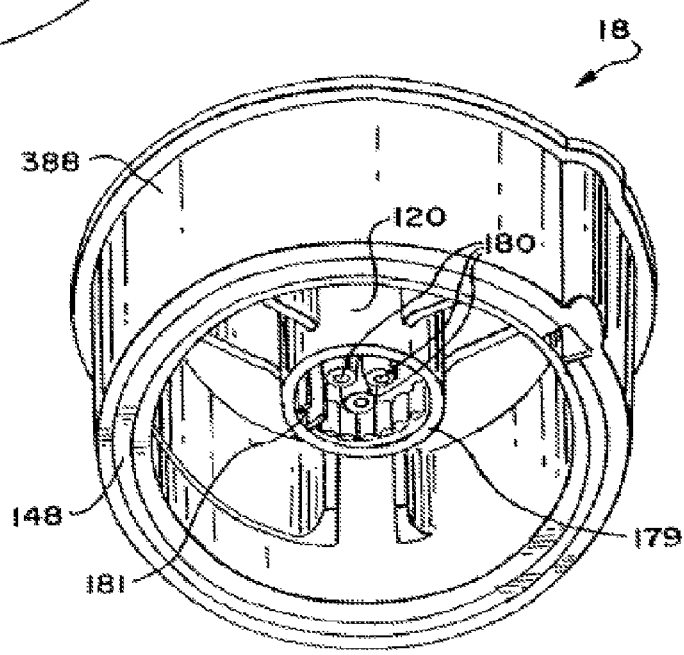
FIG. 22 is a bottom perspective view of the molded processing container shown in FIG. 21.
Figure 23:
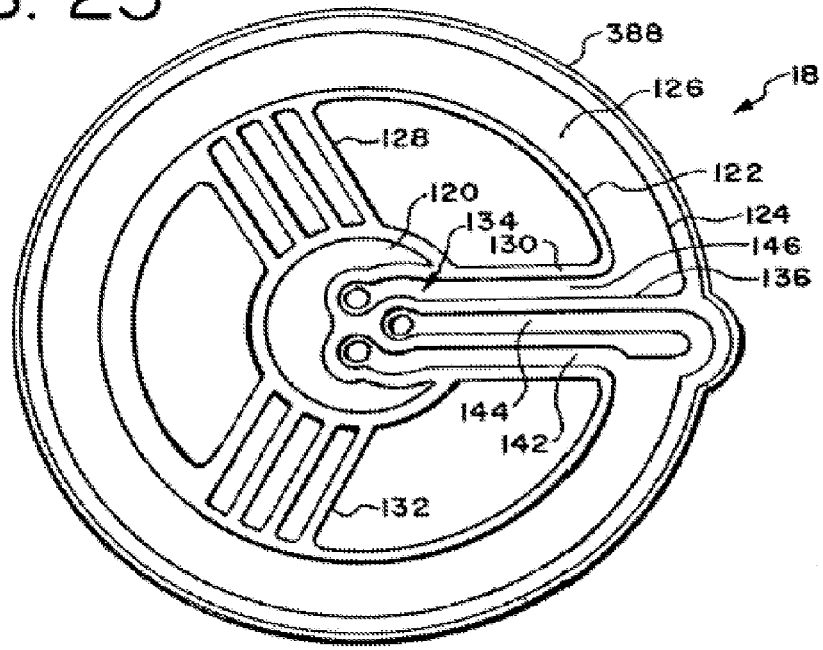
FIG. 23 is a top view of the molded processing container shown in FIG. 21.

FIGS. 21 to 23 show an embodiment of the centrifugal processing chamber 18, which can be used in association with the system 10 shown in FIG. 1.

In the illustrated embodiment, the processing chamber 18 is preformed in a desired shape and configuration, e.g., by injection molding, from a rigid, biocompatible plastic material, such as a non-plasticized medical grade acrylonitrile-butadiene-styrene (ABS).

The preformed configuration of the chamber 18 includes a unitary, molded base 388. The base 388 includes a center hub 120. The hub 120 is surrounded radially by inside and outside annular walls 122 and 124 (see FIGS. 21 and 23). Between them, the inside and outside annular walls 122 and 124 define a circumferential blood separation channel 126. A molded annular wall 148 closes the bottom of the channel 126 (see FIG. 22).

The top of the channel 126 is closed by a separately molded, flat lid 150 (which is shown separated in FIG. 21 for the purpose of illustration). During assembly, the lid 150 is secured to the top of the chamber 18, e.g., by use of a cylindrical sonic welding horn.

All contours, ports, channels, and walls that affect the blood separation process are preformed in the base 388 in a single, injection molded operation. Alternatively, the base 388 can be formed by separate molded parts, either by nesting cup shaped subassemblies or two symmetric halves.

The lid 150 comprises a simple flat part that can be easily welded to the base 388. Because all features that affect the separation process are incorporated into one injection molded component, any tolerance differences between the base 388 and the lid 150 will not affect the separation efficiencies of the chamber 18.

The contours, ports, channels, and walls that are preformed in the base 388 can vary. In the embodiment shown in FIGS. 21 to 23, circumferentially spaced pairs of stiffening walls 128, 130, and 132 emanate from the hub 120 to the inside annular wall 122. The stiffening walls 128, 130, 132 provide rigidity to the chamber 18.

As seen in FIG. 23, the inside annular wall 122 is open between one pair 130 of the stiffening walls. The opposing stiffening walls form an open interior region 134 in the hub 120, which communicates with the channel 126. Blood and fluids are introduced from the umbilicus 296 into and out of the separation channel 126 through this region 134.

In this embodiment (as FIG. 23 shows), a molded interior wall 136 formed inside the region 134 extends entirely across the channel 126, joining the outside annular wall 124. The wall 136 forms a terminus in the separation channel 126, which interrupts flow circumferentially along the channel 126 during separation.

Additional molded interior walls divide the region 134 into three passages 142, 144, and 146. The passages 142, 144, and 146 extend from the hub 120 and communicate with the channel 126 on opposite sides of the terminus wall 136. Blood and other fluids are directed from the hub 120 into and out of the channel 126 through these passages 142, 144, and 146. As will be explained in greater detail later, the passages 142, 144, and 146 can direct blood components into and out of the channel 126 in various flow patterns.

The underside of the base 388 (see FIG. 22) includes a shaped receptacle 179. Three preformed nipples 180 occupy the receptacle 179. Each nipple 180 leads to one of the passages 142, 144, 146 on the opposite side of the base 388.

Figure 24:
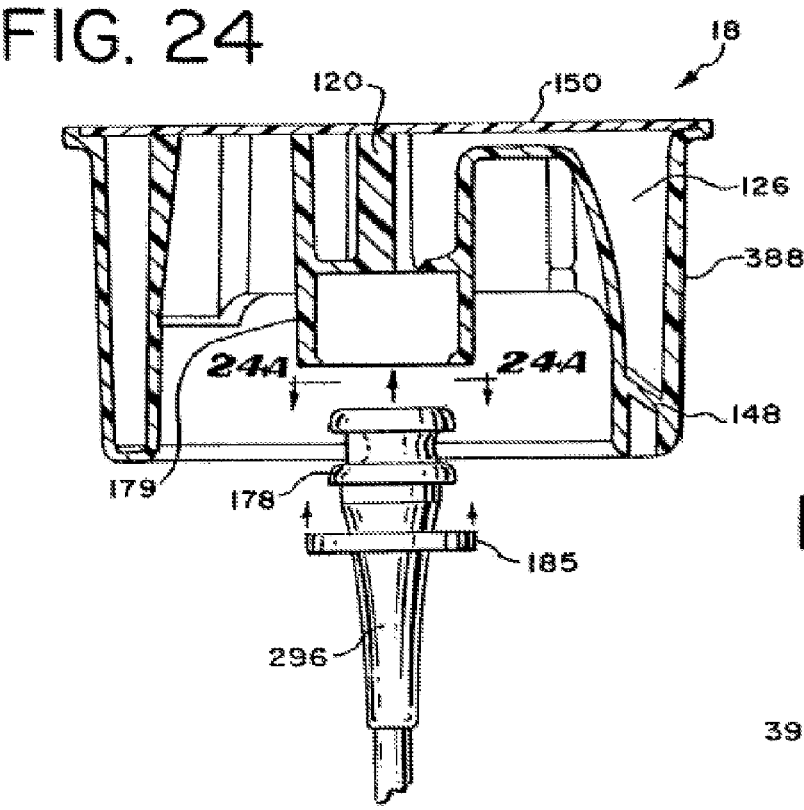
FIG. 24 is a side section view of the molded processing container shown in FIG. 21, showing an umbilicus to be connected to the container.
Figure 24A:
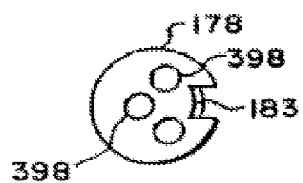
FIG. 24A is a top view of the connector that connects the umbilicus to the molded processing container in the manner shown in FIG. 24, taken generally along line 24A-24A in FIG. 24.
Figure 25:
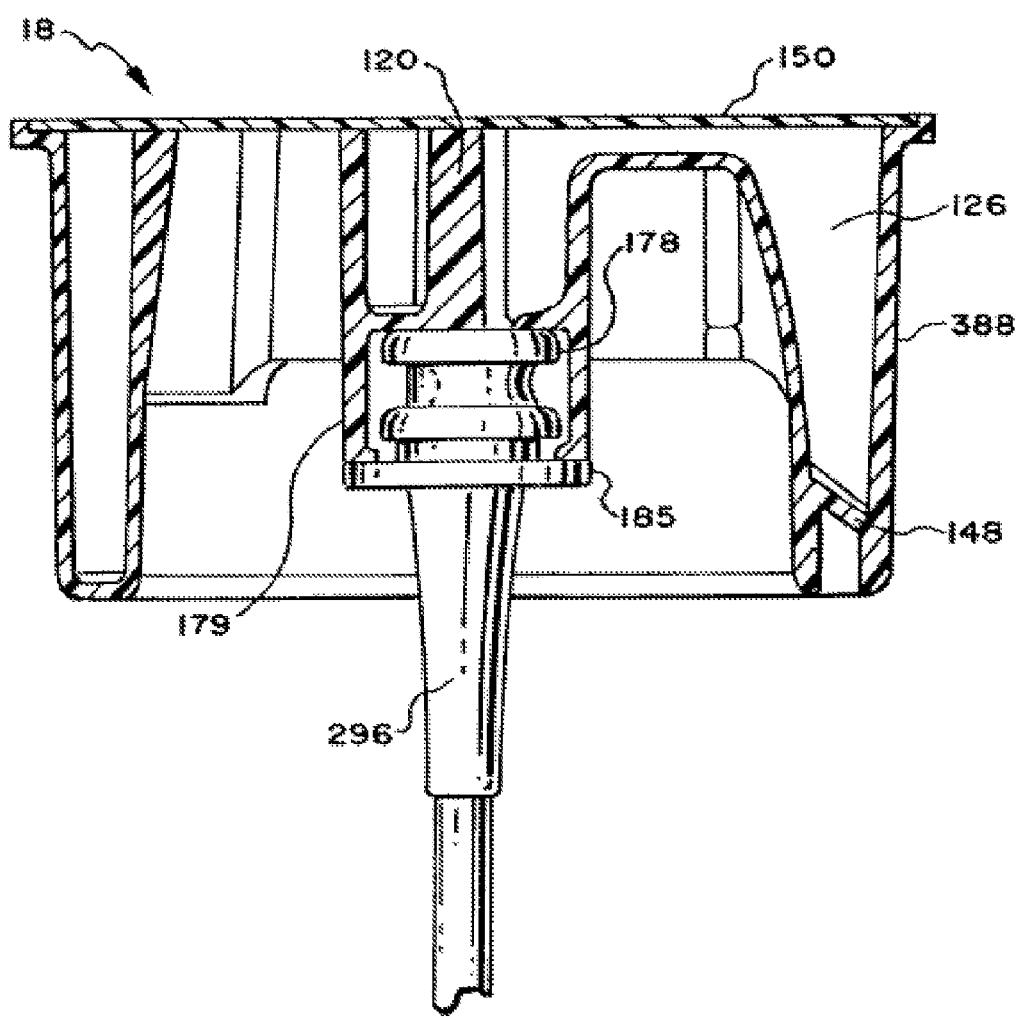
FIG. 25 is a side section view of the molded processing container shown in FIG. 24, after connection of the umbilicus to the container.

The far end of the umbilicus 296 includes a shaped mount 178 (see FIGS. 24 and 24A). The mount 178 is shaped to correspond to the shape of the receptacle 179. The mount 178 can thus be plugged into the receptacle 179 (as FIG. 25 shows). The mount 178 includes interior lumens 398 (see FIG. 24A), which slide over the nipples 180 in the hub 120, to couple the umbilicus 296 in fluid communication with the channel 126.

Ribs 181 within the receptacle 179 (see FIG. 22) uniquely fit within a key way 183 formed on the mount 178 (see FIG. 24A). The unique fit between the ribs 181 and the key way 183 is arranged to require a particular orientation for plugging the shaped mount 178 into the shaped receptacle 179. In this way, a desired flow orientation among the umbilicus 296 and the passages 142, 144, and 146 is assured.

In the illustrated embodiment, the umbilicus 296 and mount 178 are formed from a material or materials that withstand the considerable flexing and twisting forces, to which the umbilicus 296 is subjected during use. For example, a Hytrel® polyester material can be used.

This material, while well suited for the umbilicus 296, is not compatible with the ABS plastic material of the base 388, which is selected to provide a rigid, molded blood processing environment. The mount 178 thus cannot be attached by conventional solvent bonding or ultrasonic welding techniques to the receptacle 179.

In this arrangement (see FIGS. 24 and 25), the dimensions of the shaped receptacle 179 and the shaped mount 178 may be selected to provide a tight, dry press fit. In addition, a capturing piece 185, formed of ABS material (or another material compatible with the material of the base 388), may be placed about the umbilicus 296 outside the receptacle in contact with the peripheral edges of the receptacle 179. The capturing piece 185 is secured to the peripheral edges of the receptacle 179, e.g., by swaging or ultrasonic welding techniques. The capturing piece 185 prevents inadvertent separation of the mount 178 from the receptacle 179. In this way, the umbilicus 296 can be integrally connected to the base 388 of the chamber 18, even though incompatible plastic materials are used.

Figure 26:
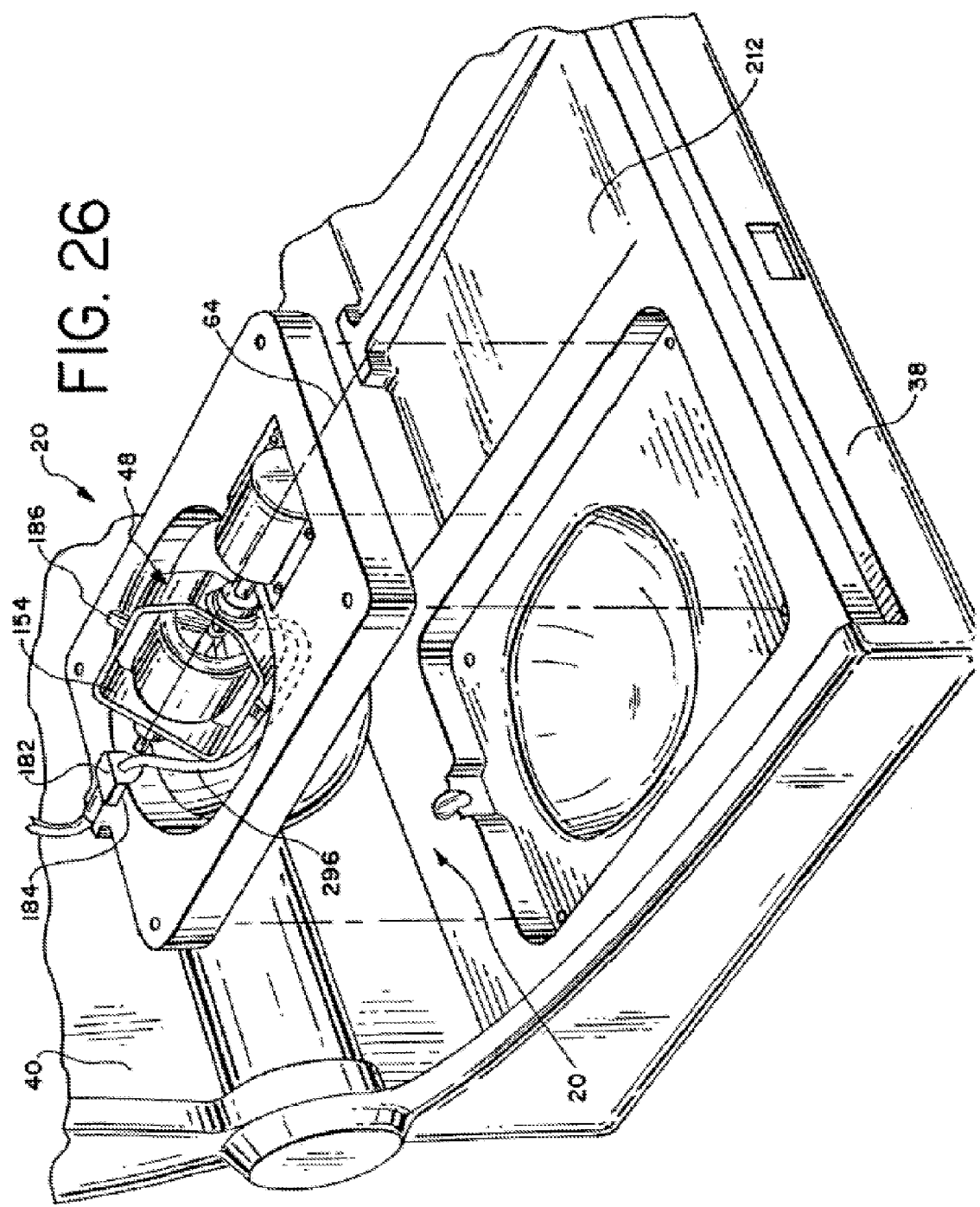
FIG. 26 is an exploded, perspective view of the centrifuge station of the processing device shown in FIG. 1, with the processing container mounted for use.
Figure 27:
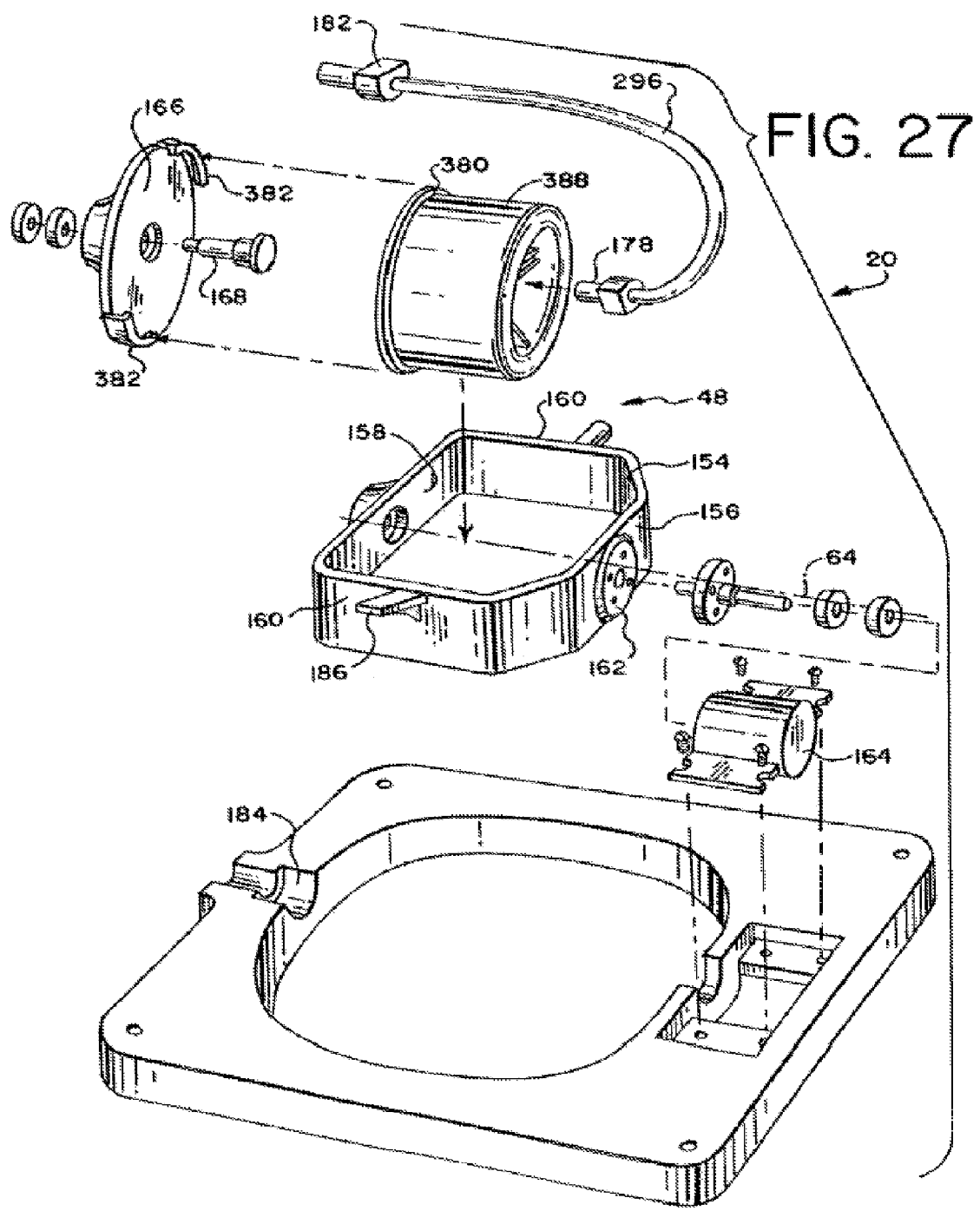
FIG. 27 is a further exploded, perspective view of the centrifuge station and processing container shown in FIG. 26.

The centrifuge station 20 (see FIGS. 26 to 28) includes a centrifuge assembly 48. The centrifuge assembly 48 is constructed to receive and support the molded processing chamber 18 for use.

As illustrated, the centrifuge assembly 48 includes a yoke 154 having bottom top, and side walls 156, 158, 160. The yoke 154 spins on a bearing element 162 attached to the bottom wall 156. An electric drive motor 164 is coupled via an axle to the bottom wall 156 of the yoke 154, to rotate the yoke 154 about an axis 64. In the illustrated embodiment, the axis 64 is tilted about fifteen degrees above the horizontal plane of the base 38, although other angular orientations can be used.

A rotor plate 166 spins within the yoke 154 about its own bearing element 168, which is attached to the top wall 158 of the yoke 154. The rotor plate 166 spins about an axis that is generally aligned with the axis of rotation 64 of the yoke 154.

The top of the processing chamber 18 includes an annular lip 380, to which the lid 150 is secured. Gripping tabs 382 carried on the periphery of the rotor plate 166 make snap-fit engagement with the lip 380, to secure the processing chamber 18 on the rotor plate 166 for rotation.

A sheath 182 on the near end of the umbilicus 296 fits into a bracket 184 in the centrifuge station 20. The bracket 184 holds the near end of the umbilicus 296 in a non-rotating stationary position aligned with the mutually aligned rotational axes 64 of the yoke 154 and rotor plate 166.

An arm 186 protruding from either or both side walls 160 of the yoke 154 contacts the mid portion of the umbilicus 296 during rotation of the yoke 154. Constrained by the bracket 184 at its near end and the chamber 18 at its far end (where the mount 178 is secured inside the receptacle 179), the umbilicus 296 twists about its own axis as it rotates about the yoke axis 64. The twirling of the umbilicus 296 about its axis as it rotates at one omega with the yoke 154 imparts a two omega rotation to the rotor plate 166, and thus to the processing chamber 18 itself.

The relative rotation of the yoke 154 at a one omega rotational speed and the rotor plate 166 at a two omega rotational speed, keeps the umbilicus 296 untwisted, avoiding the need for rotating seals. The illustrated arrangement also allows a single drive motor 164 to impart rotation, through the umbilicus 296, to the mutually rotating yoke 154 and rotor plate 166. Further details of this arrangement are disclosed in Brown et al U.S. Pat. No. 4,120,449, which is hereby incorporated herein by reference.

Blood is introduced into and separated within the processing chamber 18 as it rotates.

Figure 29:
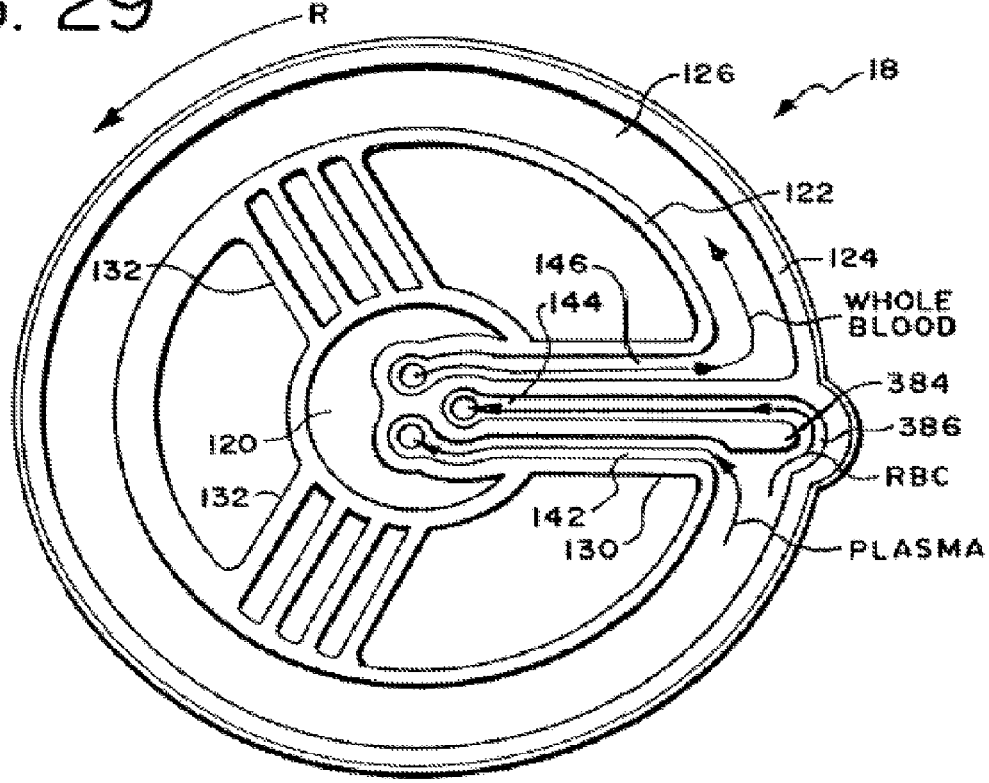
FIG. 29 is a top view of a molded centrifugal blood processing container as shown in FIGS. 21 to 23, showing a flow path arrangement for separating whole blood into plasma and red blood cells.

In one flow arrangement (see FIG. 29), as the processing chamber 18 rotates (arrow R in FIG. 29), the umbilicus 296 conveys whole blood into the channel 126 through the passage 146. The whole blood flows in the channel 126 in the same direction as rotation (which is counterclockwise in FIG. 29). Alternatively, the chamber 18 can be rotated in a direction opposite to the circumferential flow of whole blood, i.e., clockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, a dam 384 projects into the channel 126 toward the high-G wall 124. The dam 384 prevents passage of plasma, while allowing passage of red blood cells into a channel 386 recessed in the high-G wall 124. The channel 386 directs the red blood cells into the umbilicus 296 through the radial passage 144. The plasma constituent is conveyed from the channel 126 through the radial passage 142 into umbilicus 296.

Because the red blood cell exit channel 386 extends outside the high-g wall 124, being spaced further from the rotational axis than the high-g wall, the red blood cell exit channel 386 allows the positioning of the interface between the red blood cells and the buffy coat very close to the high-g wall 124 during blood processing, without spilling the buffy coat into the red blood cell collection passage 144 (creating an underspill condition). The recessed exit channel 386 thereby permits red blood cell yields to be maximized (in a red blood cell collection procedure) or an essentially platelet-free plasma to be collected (in a plasma collection procedure).

Figure 30:
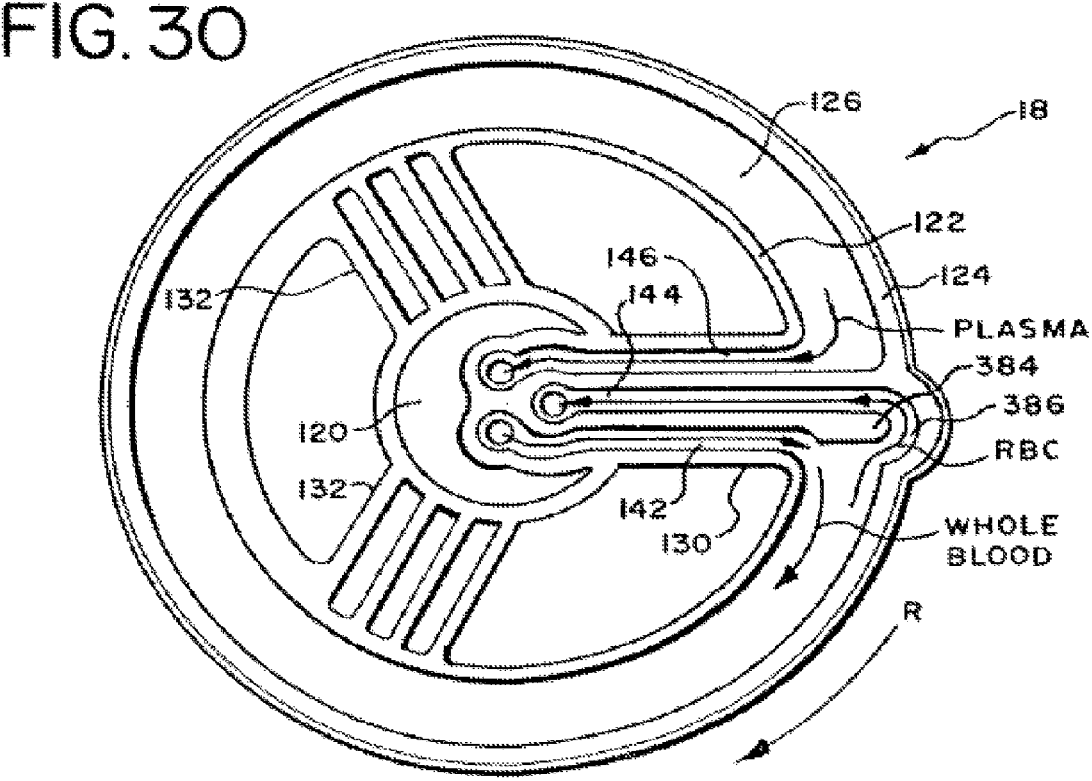
FIGS. 30 to 33 are top views of molded centrifugal blood processing containers as shown in FIGS. 21 to 23, showing other flow path arrangements for separating whole blood into plasma and red blood cells.

In an alternative flow arrangement (see FIG. 30), the umbilicus 296 conveys whole blood into the channel 126 through the passage 142. The processing chamber 18 rotates (arrow R in FIG. 30) in the same direction as whole blood flow (which is clockwise in FIG. 30). Alternatively, the chamber 18 can be rotated in a direction opposite to the circumferential flow of whole blood, i.e., clockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, the dam 384 (previously described) prevents passage of plasma, while allowing passage of red blood cells into the recessed channel 386. The channel 386 directs the red blood cells into the umbilicus 296 through the radial passage 144. The plasma constituent is conveyed from the opposite end of the channel 126 through the radial passage 146 into umbilicus 296.

Figure 31:
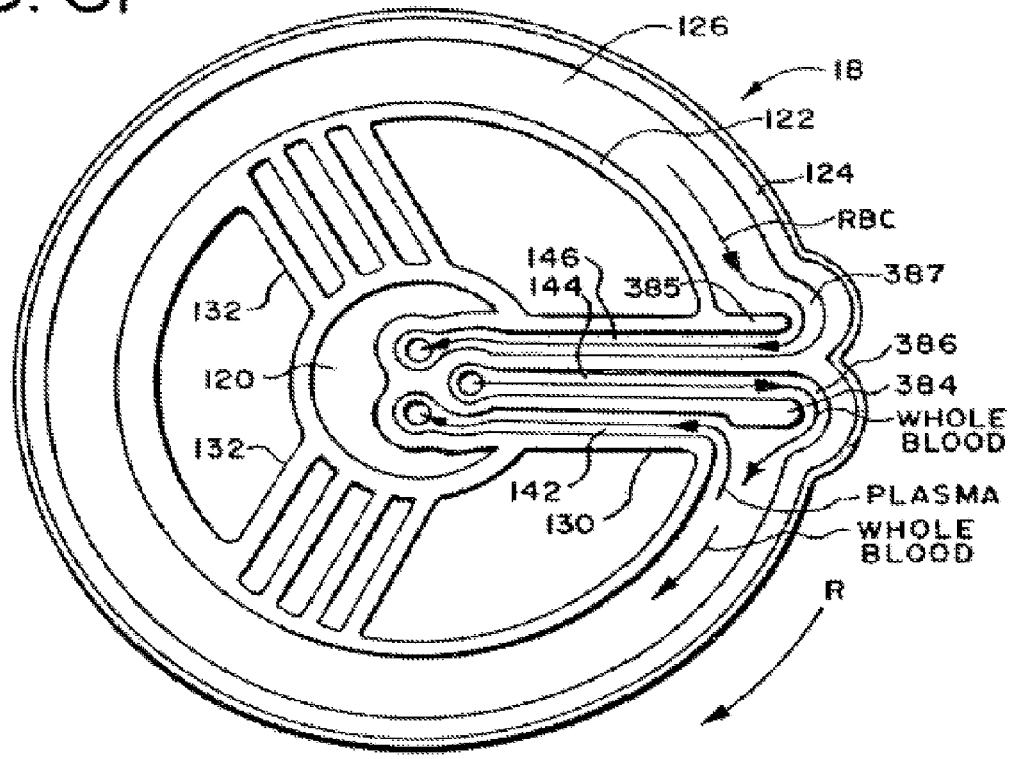

In another alternative flow arrangement (see FIG. 31), the umbilicus 296 conveys whole blood into the channel 126 through the passage 144. The processing chamber 18 is rotated (arrow R in FIG. 31) in the same direction as blood flow (which is clockwise in FIG. 31). Alternatively, the chamber 18 can be rotated in a direction opposite to the circumferential flow of whole blood, i.e., counterclockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, a dam 385 at the opposite end of the channel 126 prevents passage of plasma, while allowing passage of red blood cells into a recessed channel 387. The channel 387 directs the red blood cells into the umbilicus 296 through the radial passage 146. The plasma constituent is conveyed from the other end of the channel 126 through the radial passage 142 into umbilicus 296. In this arrangement, the presence of the dam 384 and the recessed passage 386

(previously described) separates incoming whole blood flow (in passageway 144) from outgoing plasma flow (in passageway 142). This flow arrangement makes possible the collection of platelet-rich plasma, if desired.

Figure 32:
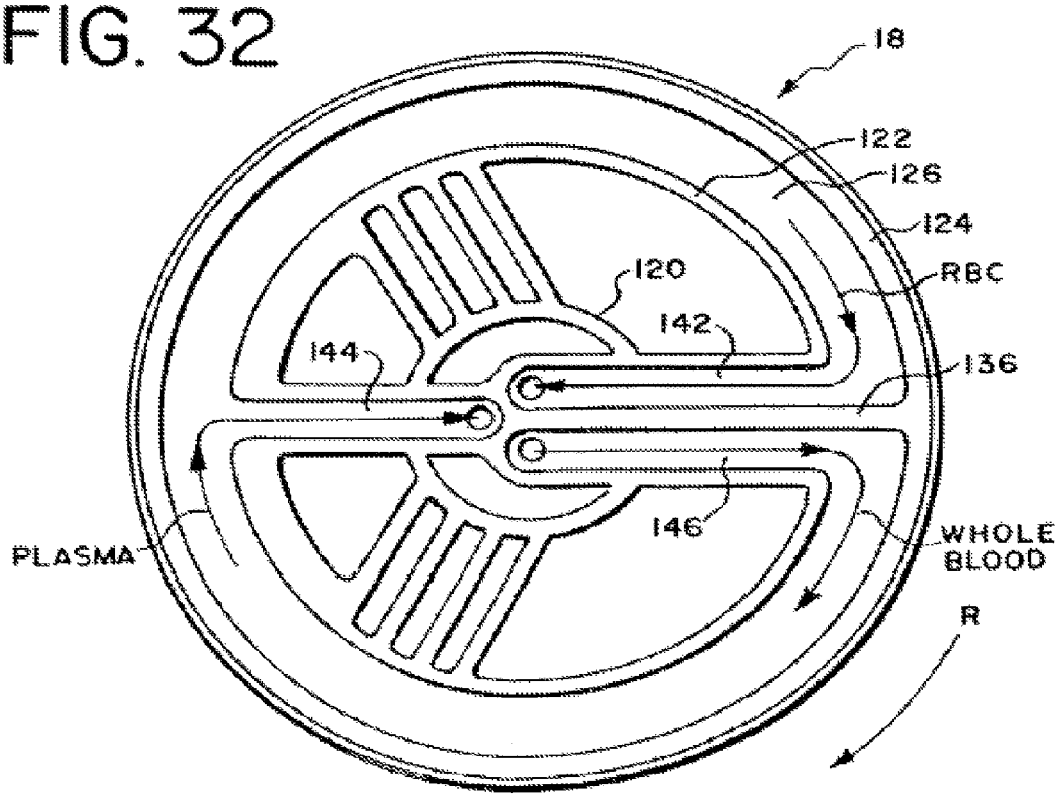

In another alternative flow arrangement (see FIG. 32), the passage 144 extends from the hub 120 into the channel 126 in a direction different than the passages 142 and 146. In this arrangement, the terminus wall 136 separates the passages 142 and 146, and the passage 144 communicates with the channel 126 at a location that lays between the passages 142 and 146. In this arrangement, the umbilicus 296 conveys whole blood into the channel 126 through the passage 146. The processing chamber 18 is rotated (arrow R in FIG. 32) in the same direction as blood flow (which is clockwise in FIG. 32). Alternatively, the chamber 18 can be rotated in a direction opposite to the circumferential flow of whole blood, i.e., counterclockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, the passage 144 conveys plasma from the channel 126, while the passage 142 conveys red blood cells from the channel 126.

As previously mentioned, in any of the flow patterns shown in FIGS. 28 to 32, the chamber 18 can be rotated in the same direction or in an opposite direction to circumferential flow of whole blood in the channel 126. Blood separation as described will occur in either circumstance. Nevertheless, it has been discovered that, rotating the chamber 18 in the same direction as the flow of whole blood in the channel 126 during separation, appears to minimize disturbances, e.g., Coriolis effects, resulting in increased separation efficiencies.

EXAMPLE

Figure 28:
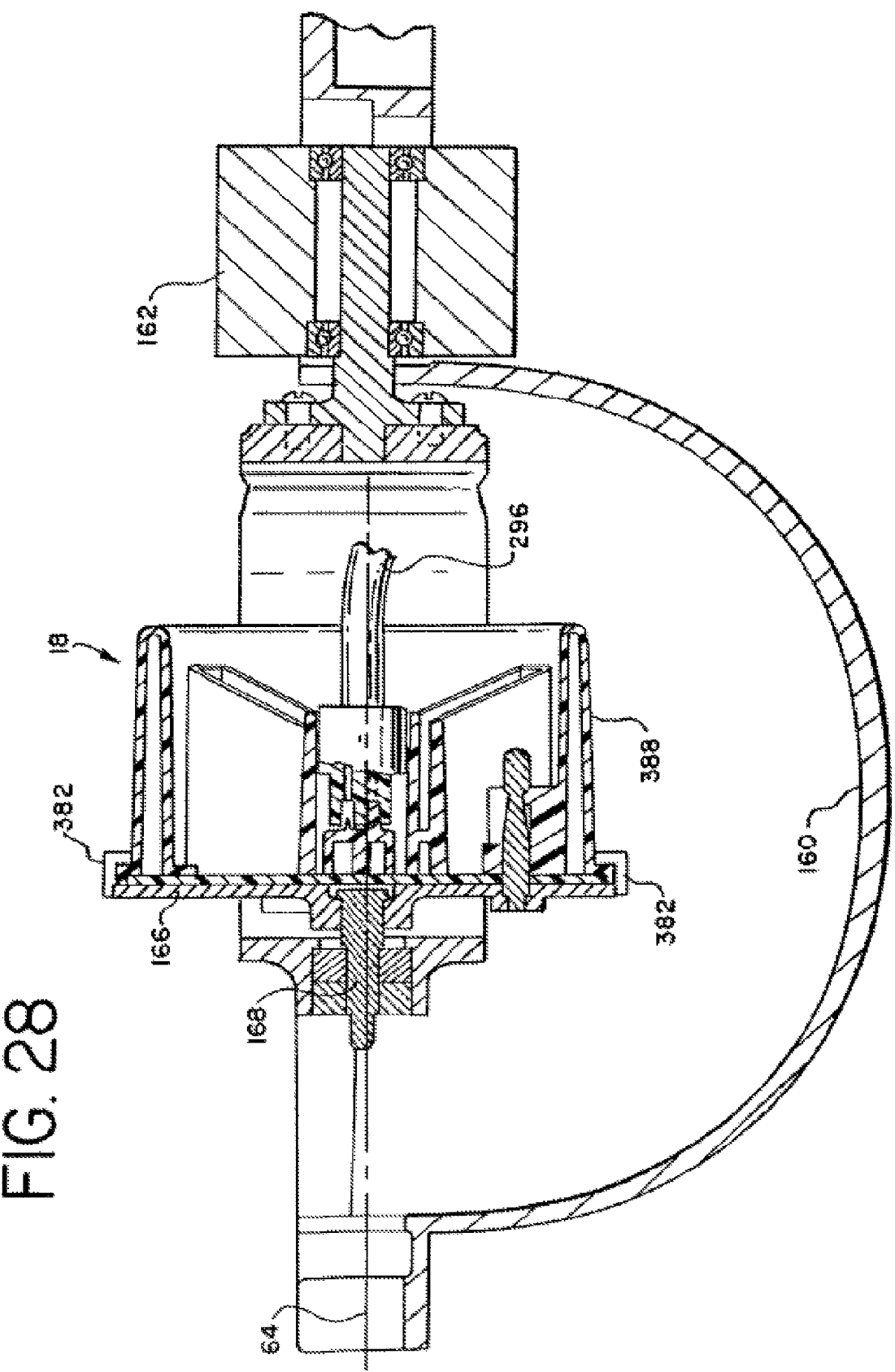
FIG. 28 is a side section view of the centrifuge station of the processing device shown in FIG. 26, with the processing container mounted for use.

Whole blood was separated during various experiments into red blood cells and plasma in processing chambers 18 like that shown in FIG. 28. In one chamber (which will be called Chamber 1), whole blood circumferentially flowed in the channel 126 in the same direction as the chamber 18 was rotated (i.e., the chamber 18 was rotated in a counterclockwise direction). In the other chamber 18 (which will be called Chamber 2), whole blood circumferentially flowed in the channel 126 in a direction opposite to chamber rotation (i.e., the chamber 18 was rotated in a clockwise direction). The average hematocrit for red blood cells collected were measured for various blood volume samples, processed at different combinations of whole blood inlet flow rates and plasma outlet flow rates. The following Tables summarize the results for the various experiments.

TABLE 1

(Flow in the Same Direction as Rotation)

| Number of Blood Samples Processed | Average Whole Blood Hematocrit (%) | Average Hematocrit of Red Blood Cells Collected |
|---|---|---|
| 7 | 45.4 | 74.8 |
| 4 | 40 | 78.8 |

TABLE 2

(Flow in the Opposite Direction as Rotation)

| Number of Blood Samples Processed | Average Whole Blood Hematocrit (%) | Average Hematocrit of Red Blood Cells Collected |
|---|---|---|
| 3 | 43.5 | 55.5 |
| 2 | 42.25 | 58.25 |

Tables 1 and 2 show that, when blood flow in the chamber is in the same direction as rotation, the hematocrit of red blood cells is greater than when blood flow is in the opposite direction. A greater yield of red blood cells also means a greater yield of plasma during the procedure.

B. Alternative Molded Processing Chamber

Figure 33:
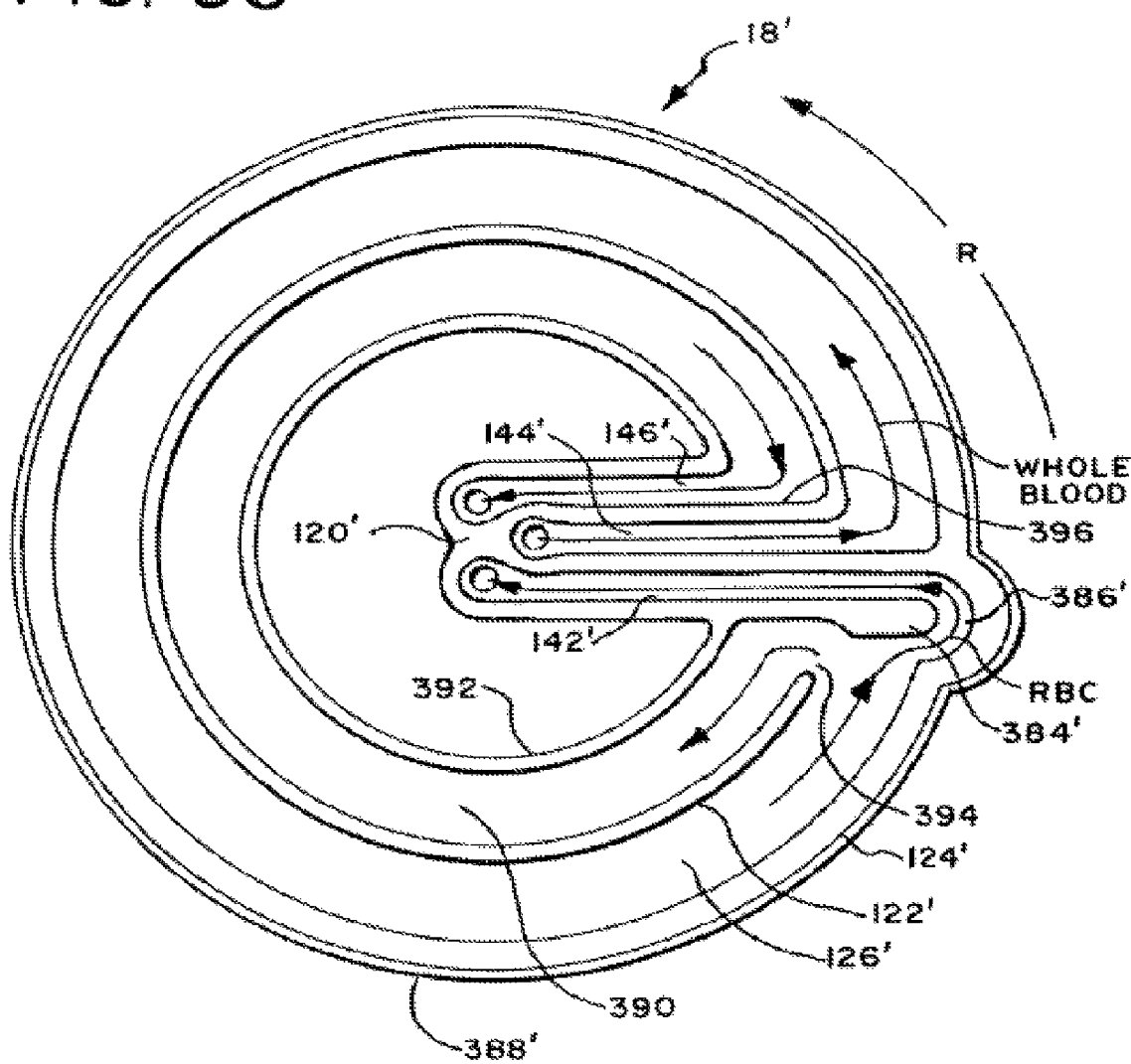

FIG. 33 shows a chamber 18' having a unitary molded base 388' like that shown in FIGS. 21 to 23, but in which two flow paths 126' and 390 are formed. The flow paths 126' and 390 are shown to be concentric, but they need not be. The chamber 18' shares many other structural features in common with the chamber 18 shown in FIG. 23. Common structural features are identified by the same reference number marked with an apostrophe.

The base 388' includes a center hub 120' which is surrounded radially by the inside and outside annular walls 122' and 124', defining between them the circumferential blood separation channel 126'. In this embodiment, a second inside annular wall 392 radially surrounds the hub 120'. The second circumferential blood separation channel 390 is defined between the inside annular walls 122' and 392. This construction forms the concentric outside and inside separation channels 126' and 390.

An interruption 394 in the annular wail 122' adjacent to the dam 384' establishes flow communication between the outside channel 126' and the inside channel 390. An interior wall 396 blocks flow communication between the channels 126' and 390 at their opposite ends.

As the processing chamber 18' rotates (arrow R in FIG. 33), the umbilicus 296 conveys whole blood into the outside channel 126' through the passage 144'. The whole blood flows in the channel 126' in the same direction as rotation (which is counterclockwise in FIG. 33). Alternatively, the chamber 18' can be rotated in a direction opposite to the circumferential flow of whole blood, i.e., clockwise. The whole blood separates in the outside channel 126' as a result of centrifugal forces in the manner shown in FIG. 15A. Red blood cells are driven toward the high-G wall 124', while lighter plasma constituent is displaced toward the low-G wall 122'.

As previously described, the dam 384' prevents passage of plasma, while allowing passage of red blood cells into a channel 386' recessed in the high-G wall 124'. The channel 386' directs the red blood cells into the umbilicus 296 through the radial passage 142'. The plasma constituent is conveyed from the channel 126' through the interruption 394 into the inside separation channel 390.

The plasma flows circumferentially through the inside channel 390 in a direction opposite to the whole blood in the outside channel 126'. Platelets remaining in the plasma migrate in response to centrifugal forces against the annular wall 124'. The channel 390 directs the plasma constituent to the same end of the chamber 18' where whole blood is initially introduced. The plasma constituent is conveyed from the channel 390 by the passage 146'.

C. Another Alternative Molded Processing Chamber

Figure 44:
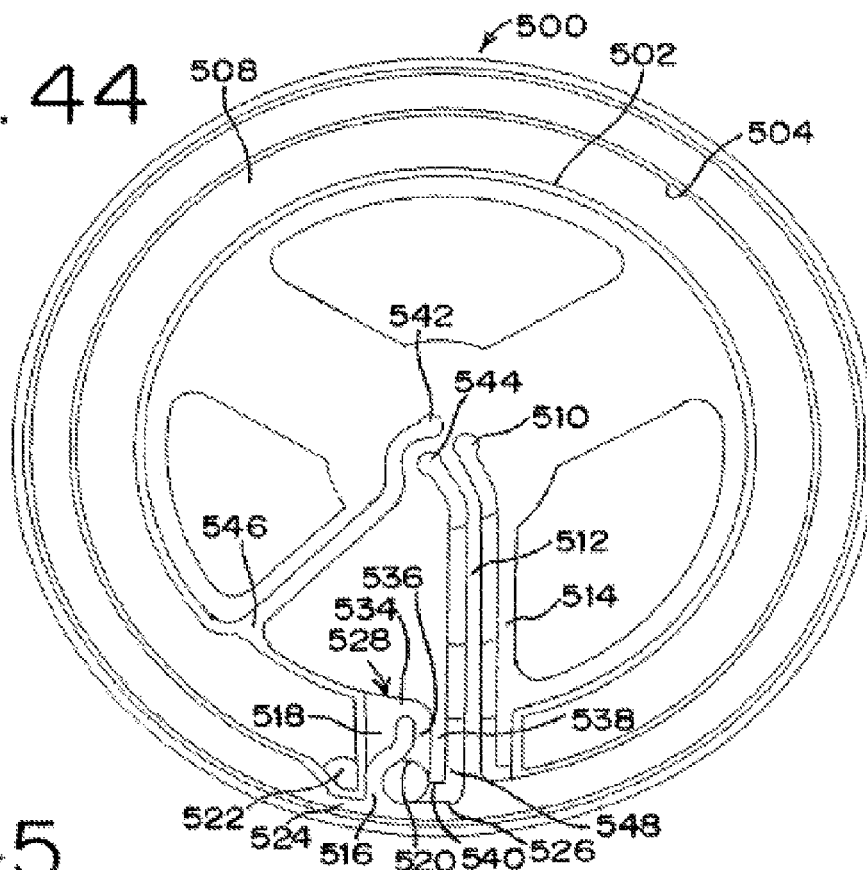
FIG. 44 is a top plan view of another embodiment of a blood processing chamber suitable for use with the blood processing systems and methods of the present disclosure.
Figure 45:
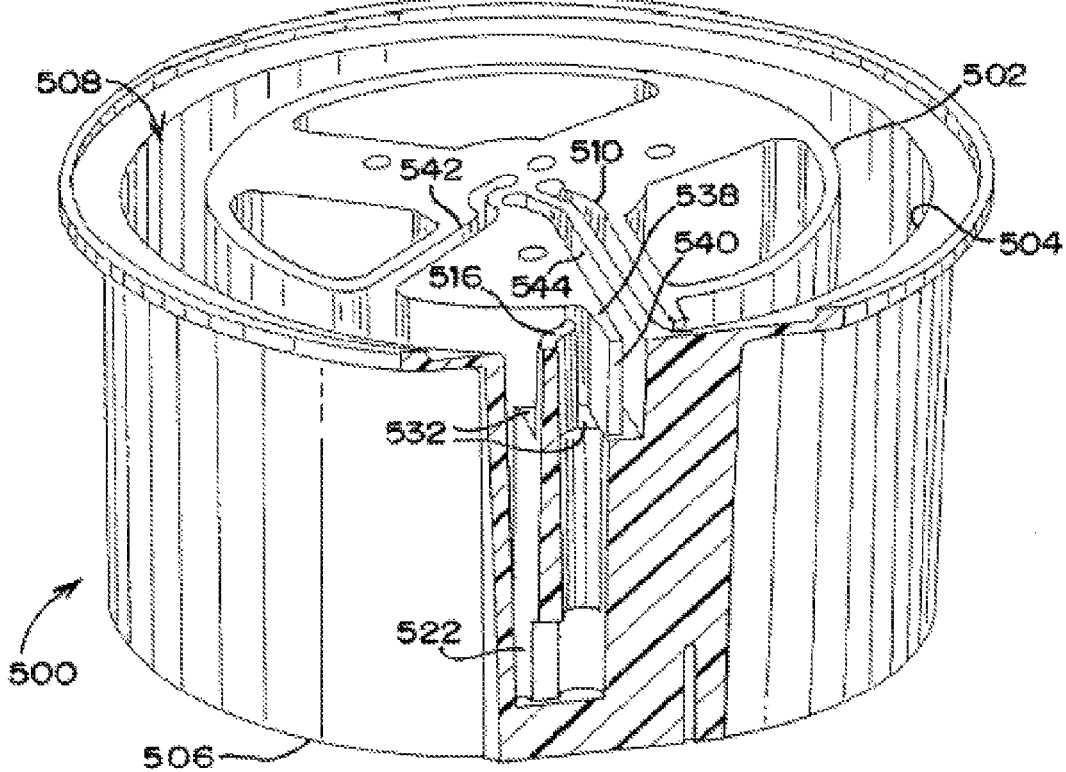
FIG. 45 is front perspective view of the blood processing chamber of FIG. 44, with a portion thereof cut away for illustrative purposes.
Figure 46:
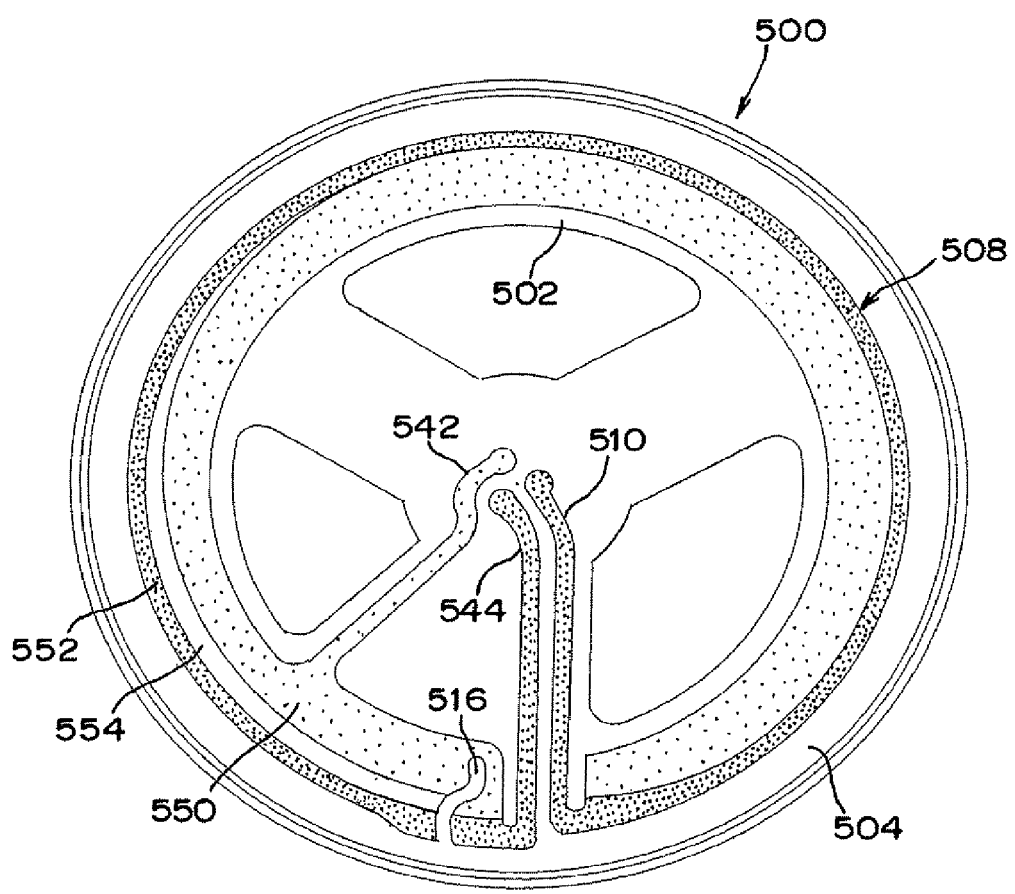
FIG. 46 is a top plan view of the blood processing chamber of FIG. 44, illustrating the relative positions of separated blood components during an exemplary blood component collection procedure.

FIGS. 44-46 illustrate a further embodiment of a chamber, which is generally indicated at 500 having radially spaced apart inner (low-g) and outer (high-g) side wall portions 502 and 504, respectively, a bottom or first end wall portion 506, and a cover or second end wall portion (not illustrated). The wall portions 502 and 504, the bottom 506, and the cover together define an enclosed, generally annular channel 508.

A (whole blood) inlet 510 communicating with the channel 508 is defined between opposing interior radial walls 512 and 514. One of the interior walls 512 joins the outer (high-g) wall portion and separates the upstream and downstream ends of the channel 508. The interior walls 512 and 514 define the inlet passageway 510 of the chamber 500 which, in one flow configuration, allows fluid to enter the upstream end of the channel 508 at a location which is adjacent the outer or high-g side wall portion 504.

A dam or barrier 516 is formed at a downstream end of the channel 508 and has upstream and downstream sides 518 and 520 (FIG. 44). The barrier 516 extends from the outer side wall portion 504 radially inward to a location which is spaced from the inner side wall portion 502. The barrier 516 will be described in further detail below.

In the embodiment of FIG. 45, the barrier 516 extends for the entire axial height of the channel 508, except for an underpass 522 located at an intermediate axial position spaced below the top of the channel and above, but adjacent to, the bottom 506 of the chamber 500. The underpass 522 is positioned in the channel 508 and defines an opening or passageway through or below the barrier 516, thereby allowing for communication between the upstream and the downstream sides 518 and 520 of the barrier 516. The underpass 522, and particularly the underpass inlet and outlet openings, are preferably located near or in the proximity of the high-g side wall portion 504, where higher density cell components, such as red cells, may accumulate under centrifugal force. More specifically, the high-g side wall portion 504 has a radially outward indent or recess on either side of the barrier 516. As seen in FIG. 44, sections 524 and 526 of the outer side wall portion 504 just upstream and downstream of the barrier 516 extend radially outward from (i.e., are located at a greater radial distance than) a more upstream section of the outer side wall portion 504. An outer radial surface of the underpass 522 may be formed in part by one or more of these radially outward sections 524 and 526 of the outer side wall portion 504 (which sections 524 and 526 are shown removed in FIG. 45). An opposed inner radial surface of the underpass 522 (visible in FIG. 45 beneath the barrier 116) may be formed at a radial location which is approximate to that of the outer or high-G wall portion 504.

A second flow path, referred to herein as a low-g flow path and generally indicated at 528, also communicates between the upstream and downstream sides 518 and 520 of the barrier 516. As shown in FIG. 44, the low-g flow path 528 is distinguishable from the underpass 522 for a number of reasons. For one, the low-g flow path 528 is defined between the barrier 516 and the inner side wall portion 502, allowing for fluid flow around, rather than through or below the barrier 516. It will be seen that the low-g flow path 528 is positioned at a more radially inward location than the underpass 522, making the low-g flow path 528 suitable for accommodating flow of a less dense fluid component, such as plasma, that may accumulate along the inner side wall portion 502, as will be described in greater detail herein. Further, the illustrated low-g flow path 528 is positioned adjacent to the top of the channel 508, with a bottom or lower axial surface of the low-g flow path 528 being defined by an intermediate end wall portion 532, in contrast to the underpass 522, which is positioned adjacent to the bottom 506 of the chamber 500 (FIG. 45).

As shown in FIG. 44, the low-g flow path 528 may include both non-radial and radial portions or legs 534 and 536, respectively, giving the low-g flow path 528 a generally L-shaped configuration. In the illustrated embodiment, the non-radial or annular portion or leg 534 is defined by the space between the inner side wall portion 502 and a radially inward surface of the barrier 516. The illustrated radial portion or leg 536 is defined by the downstream side 520 of the barrier 516 and an interior radial wall extension 538. The interior radial wall extension 538 of FIGS. 44 and 45 terminates at an outer edge 540 which is located at an intermediate radial location between the inner and outer side wall portions 502 and 504.

The chamber 500 further includes first and second outlets 542 and 544, respectively, which may be defined by opposing surfaces of interior radial walls. The first (plasma) outlet 542 communicates with the channel 508 upstream of the barrier 516. The second (red blood cell) outlet 544 communicates with the channel 508 downstream of the barrier 516. Both the first and second outlets 542 and 544 extend radially inward from the channel 508. The first outlet 542 extends radially inward from an opening 546 which, in the illustrated embodiment, is located at the inner side wall portion 502. The second outlet 544 extends radially inward from an opening 548 that communicates with the downstream side of the barrier 516. In one embodiment, the opening 546 of the first outlet 542 is disposed at approximately a 45 degree angle relative to the opening 548 of the second outlet 544, although other angles and orientations are also possible.

FIG. 46 shows the relative positions of a radially innermost layer 550, a radially outermost layer 552, and a radially intermediate or interface layer 554 during a typical procedure when the chamber 500 is used to fractionate an amount of blood. The radially innermost layer 550 is positioned adjacent to the inner (low-g) wall portion 502 and, in one embodiment, will be substantially comprised of plasma. The radially outermost layer 552 is positioned adjacent to the outer (high-g) wall portion 504 and, in one embodiment, will be substantially comprised of red blood cells. The interface layer 554 is located radially intermediate the other layers 550 and 552 and, in one embodiment, will be substantially comprised of white blood cells and platelets.

The constitution of the various layers illustrated in FIG. 46 may vary according to the particular procedure. For example, when the chamber 500 is spun at a relatively high speed the radially innermost layer 550 will comprise substantially cell-free plasma, whereas the innermost layer 550 will instead comprise a mixture of plasma and platelets (referred to herein as a "plasma/platelet layer") when a slower spin speed is employed. In other procedures, the radially innermost layer 550 may also contain an amount of anticoagulant, white blood cells, and/or a non-plasma platelet storage solution.

Regardless of the exact composition of the various layers, the radially outermost layer 552 will flow through the underpass 522 (FIG. 45) to the downstream side 520 of the barrier 516 and into the opening 548 of the second outlet 544, where it exits the channel 508 (FIG. 46). A portion of the radially innermost layer 550 will enter the opening 546 of the first outlet 542 and exit the channel 508 therethrough, upstream (approximately 40-45°) of the barrier 516. Another portion of the radially innermost layer 550 will flow past the opening 546 and into the low-g flow path 528, but is prevented from flowing into the opening 548 of the second outlet 544 by the presence of the denser outermost layer 552 on the downstream side 520 of the barrier 516. As for the interface layer 554, it will engage against the upstream side of the barrier 516 and accumulate without exiting the channel 508.

VIII. Red Blood Cell/Platelet/Plasma Collection

The processing chamber 500 of FIGS. 44-46 is particularly well-suited for use in a procedure for collecting red blood cells, platelets, and plasma individually or in combination with other components from a blood source, and reference will be made thereto for illustrative purposes, however the procedure which follows is not limited to any particular processing chamber.

Disposable sets 556 and 558 (FIGS. 47 and 48) may be used in the red blood cell/platelet/plasma collection procedure which follows. Except where noted otherwise, the individual components of the disposable sets are well-known to those having skill in the art and are essentially as described above with regard to the processing set of FIG. 10.

In one embodiment, the disposable set 556 includes a vascular access member 560, such as a needle, an anticoagulant container 562, a red blood cell additive solution container 564, and a saline container 566. The disposable set 556 further includes tubing 568 leading to a connection device 570 (e.g., a spike in FIG. 47 or a luer connector in FIG. 48) for connection to a platelet storage solution container (not illustrated), if platelet storage solution is to be used. The illustrated tubing 568 includes an in-line sterility filter 572 of the type employed in a sub-micron filter, such as a 0.22 μm pore membrane filter, to prevent the passage of viruses or larger microbes, thereby preventing contamination and maintaining an effectively closed system. The disposable set 556 also includes a platelet collection container 574, a plasma collection container 576, and a red blood cell collection container 578 for collecting the blood components that are separated by the chamber 500. The platelet collection container 574 is illustrated with an associated in-line leukoreduction filter 580, a gas exhaust or air burp bag 582 for removing an amount of gas from the collected platelets (as will be described in greater detail herein), and a sampling pack 584 for segregating an amount of the separated platelets for subsequent testing and/or tracking purposes according to known practice. A red blood cell storage container 586, including segmented tubing 588 (for segregating an amount of the separated red blood cells for subsequent testing and/or tracking purposes) and an in-line leukoreduction filter 590, is also included for post-separation storage of the red blood cells, as will be described in greater detail herein.

The various components of the disposable set 556 are connected via tubing to a cassette 592, which is shown in greater detail in FIGS. 49 and 50. It will be seen that the illustrated cassette 592 has fourteen ports PO1-PO14, in contrast to the 13-port cassettes 28 and 28' illustrated in FIGS. 6-9 and 35-36 (respectively) and described with reference to the foregoing blood component collection procedures. The 14-port cassette 592 operates generally according to the foregoing description of the 13-port cassettes 28 and 28', except that it includes a total of twenty-six valves VAL1-VAL26 to allow for an additional port PO14 to communicate with other ports. To accommodate the twenty-six valves, the corresponding manifold assembly (not illustrated) includes twenty-six valve actuators, similar to the manifold assembly 226' of FIG. 43 and works generally according to the foregoing description of the manifold assembly 226'.

More particularly, the cassette 592 includes ports PO1-PO14, each associated with a component of the disposable set via a length of tubing. Those having skill in the art will appreciate that each port may be associated with a variety of components and tasks, but in the illustrated embodiment, the first port PO1 is associated with the in-process container 594. The second port PO2 is associated with the red blood cell collection container 578. The third port PO3 is associated with the plasma collection container 576. The fourth port PO4 is associated with the platelet collection container 574. The fifth port PO5 is associated with the (whole blood) inlet 510 of the chamber 500. The sixth port PO6 is associated with the first (plasma) outlet 542 of the chamber 500. The seventh port PO7 is associated with the second (red blood cell) outlet 544 of the chamber 500. The eighth port PO8 is associated with the vascular access member 560. The ninth port PO9 is associated with the tubing 596 leading to a y-connector 598 for adding anticoagulant to whole blood from the blood source. The tenth port PO10 is associated with the anticoagulant container 562. The eleventh port PO11 is associated with the platelet additive solution container (not illustrated). The twelfth port PO12 is associated with the red blood cell additive solution container 564. The thirteenth port PO13 is associated with the saline container 566. The fourteenth port PO14 is associated with the red blood cell storage container 586.

Figure 51:
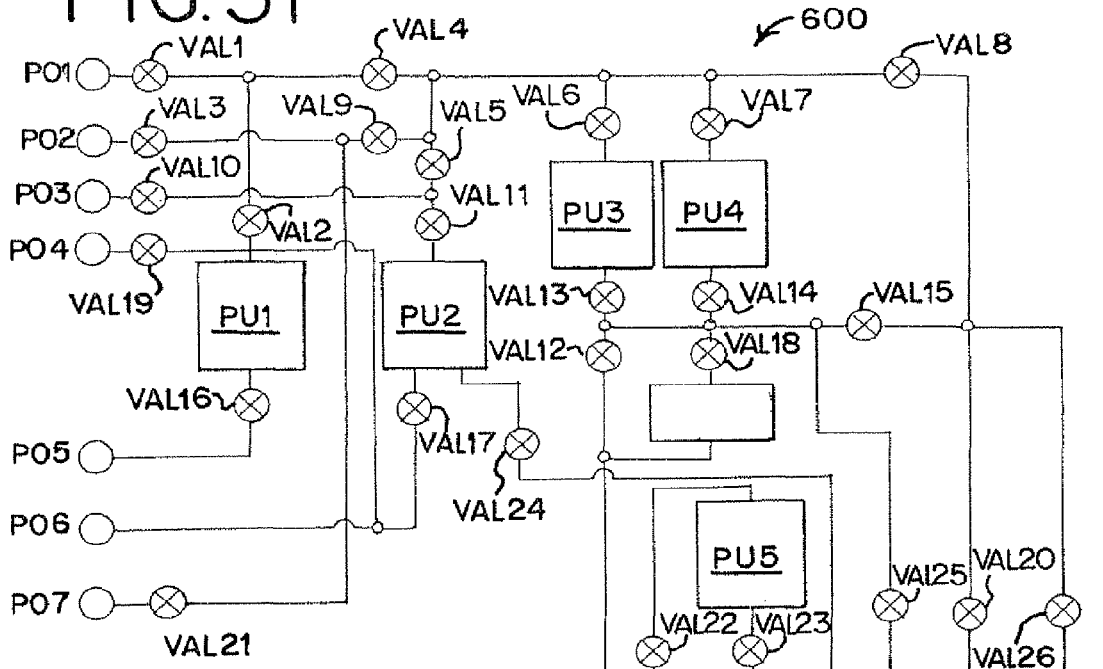
FIG. 51 is a schematic view of a blood processing circuit defined by the cassette of FIGS. 49 and 50, which can be programmed to perform a variety of different blood processing procedures in association with the device shown in FIG. 1.

The various ports are fluidly connected to each other by flow paths defined by the cassette 592, which flow paths are regulated by valves VAL1-VAL26. The flow paths and other cavities defined by the raised cassette walls are shown with stippling in FIG. 50 to distinguish them from the walls. The location of the valves within the cassette 592 is best illustrated in FIG. 49, while the function of each valve can be understood with reference to FIG. 51, which is a schematic view of the blood processing circuit 600 defined by the flow paths of the cassette 592.

In addition to defining a plurality of flow paths and valves, the cassette 592 further defines a plurality of pumps PU1-PU5 and a filter cavity 602. The pumps and filter cavity correspond generally to those described above with regard to the cassette 28' of FIGS. 35-36. More particularly, the first pump PU1 is an in-process pump, the second pump PU2 is a plasma pump, the third and fourth pumps PU3 and PU4 are donor pumps, and the fifth pump PU5 is an anticoagulant pump. The filter cavity 602 forms a station that may hold a blood filter material to remove clots and cellular aggregations that can form during blood processing.

Figure 47:
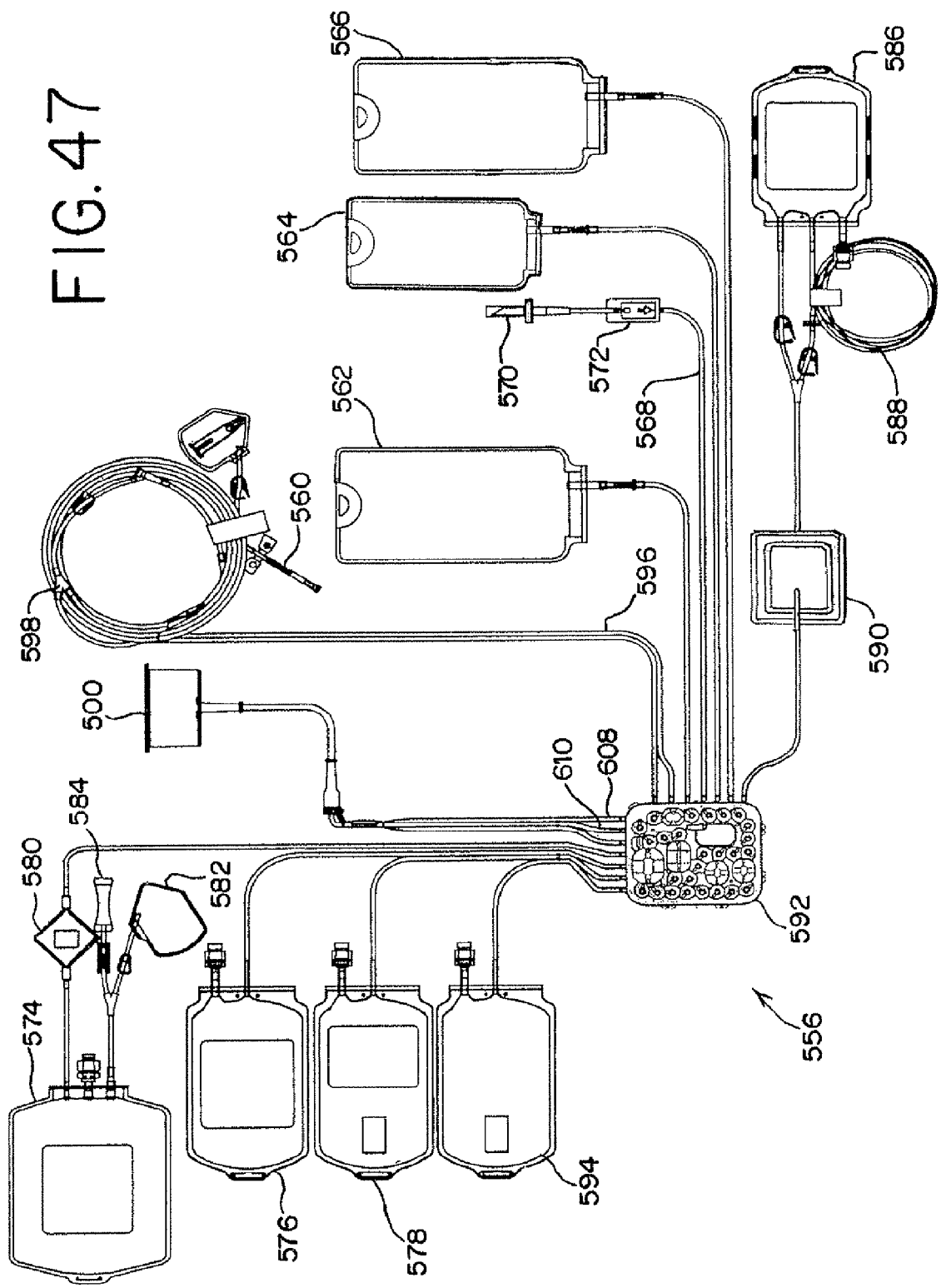
FIG. 47 is a plane view of a disposable set, which can be mounted on the device shown in FIG. 1.
Figure 48:
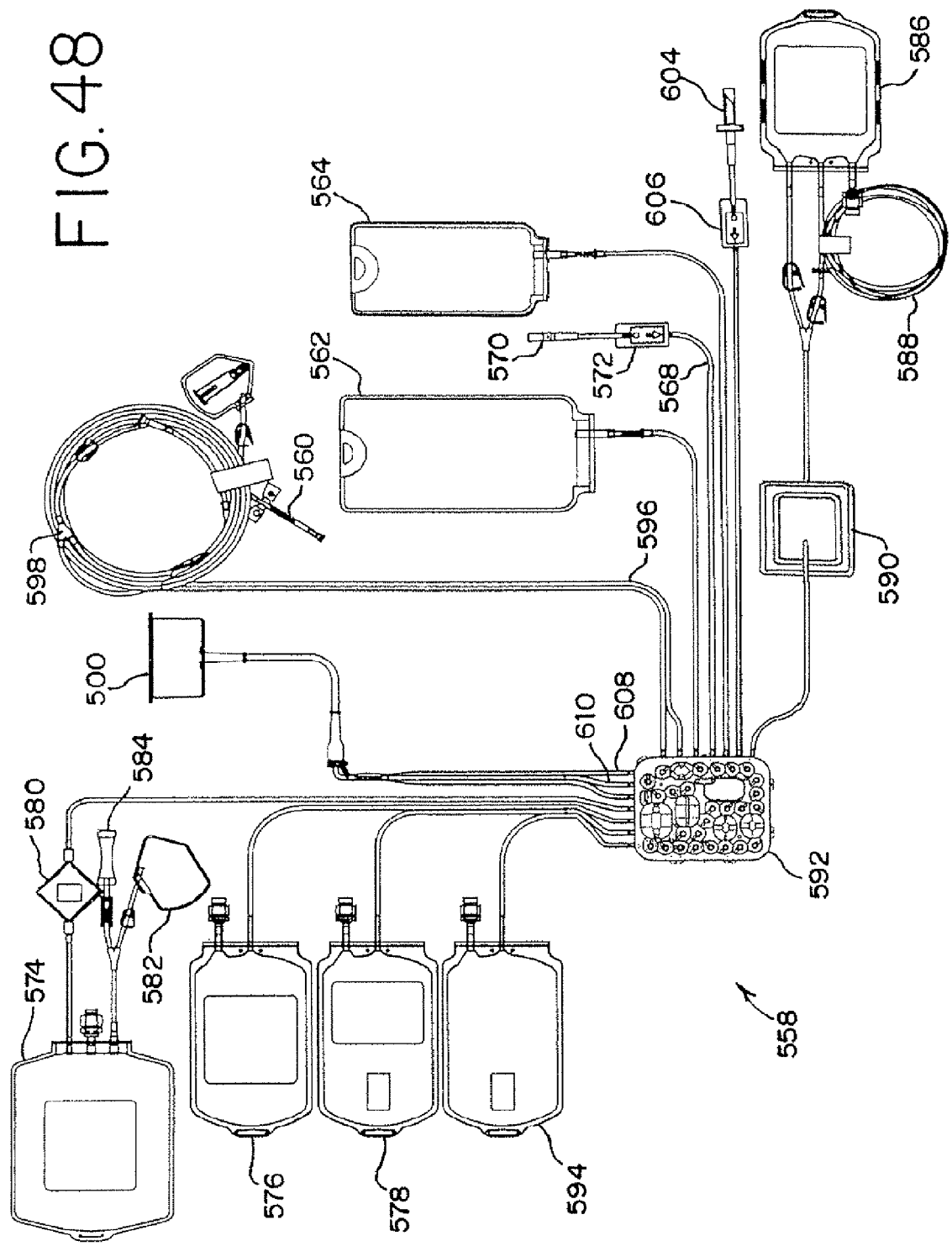
FIG. 48 is a plane view of another disposable set, which can be mounted on the device shown in FIG. 1.

As for the disposable set 558 of FIG. 48, it is similar to the disposable set 556 of FIG. 47, with the exception that the saline container is omitted and replaced by a container access member, such as the illustrated spike 604 and an in-line sterility filter 606. The spike 604 may be provided according to known design, being generally hollow with a sharpened tip suited for piercing a port or membrane of a separate saline container to fluidly connect the container to the disposable set 558. As for the filter 606, it may be of the type employed in a sub-micron filter to prevent the passage of viruses or larger microbes, thereby preventing contamination and maintaining an effectively closed system during association of a saline container with the disposable set 558. Other disposable sets may also be employed without departing from the scope of the present disclosure.

A. Pre-Processing

Prior to processing, an operator selects the "RBC/Platelet/Plasma" protocol from a touch screen display or other user interface system. If the blood source is a donor, the operator then proceeds to enter various parameters, such as the donor gender/height/weight. In one embodiment, the operator also enters the target yield for the various blood components. In an exemplary procedure, the pre-selected yields are one unit each of single dose platelets, packed red cells, and platelet poor plasma. As will be described in greater detail herein, an amount of plasma may be used to harvest platelets and packed red cells from the chamber and act as a platelet storage fluid, so it may be advantageous to specify an additional amount of plasma (e.g., approximately 335 ml extra-300 ml to harvest and store the platelets and 35 ml to harvest the packed red cells) to ensure that one unit remains in the plasma collection container after the platelets and packed red cells have been harvested.

E The operator also selects the collection control system, which may be based on, for example: (1) the amount of whole blood to process, (2) a donor platelet pre-count (i.e., the amount of platelets in a pre-donation sample of the donor's blood) and the target platelet yield, or (3) the target platelet yield. The third option is used when a donor platelet pre-count is not available and implicates use of an online estimator, whereby a volume of whole blood is processed and optical measurements are taken to estimate the platelet pre-count and/or the amount of whole blood that must be processed to achieve the target platelet yield. The online estimator will be described in greater detail herein.

Further, before processing begins, any separate containers (e.g., a platelet storage solution container) are connected to the disposable set, the disposable set is secured to the blood processing system (e.g., a blood processing system according to the foregoing description of system 10), an integrity check of the disposable set is performed to ensure the various components are properly connected and functioning, the blood source is connected to the disposable set (e.g., by phlebotomizing a donor), and the chamber 500 is primed by saline pumped from the saline container 564 by operation of one or more pumps of the cassette 592.

B. Draw Stage

Figure 52A:
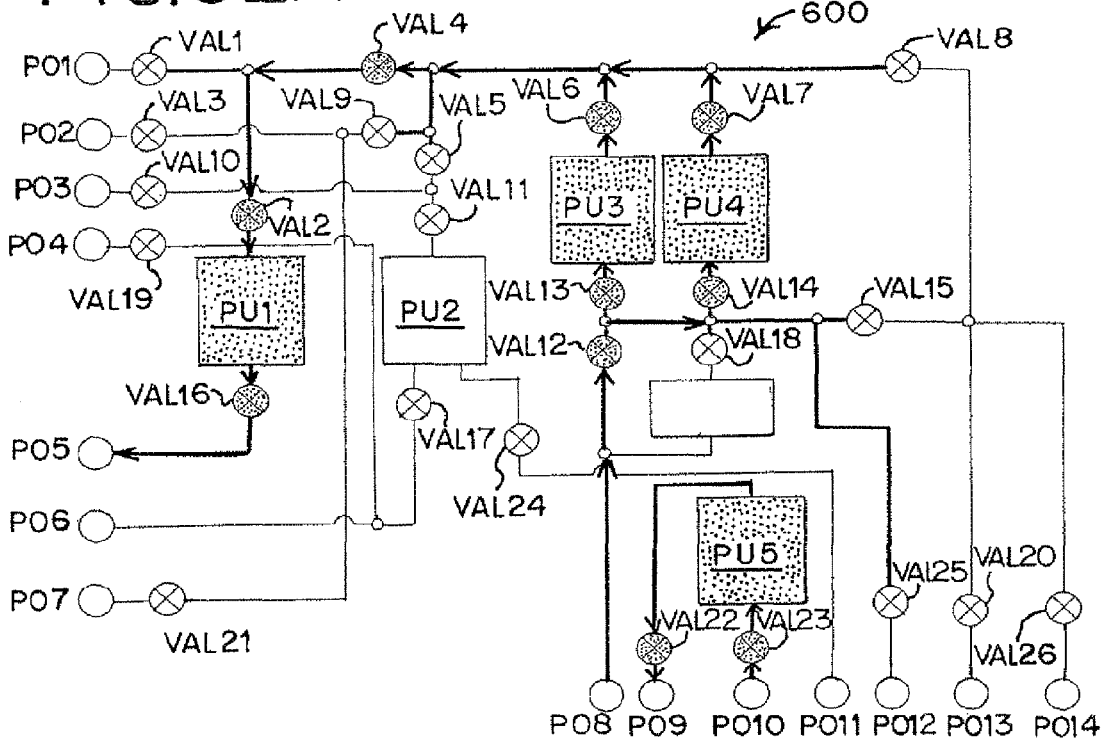
FIGS. 52A and 52B are schematic views of the blood processing circuit of FIG. 51, showing the programming of the cassette to carry out different fluid flow tasks in connection with drawing whole blood from a blood source.
Figure 52B:
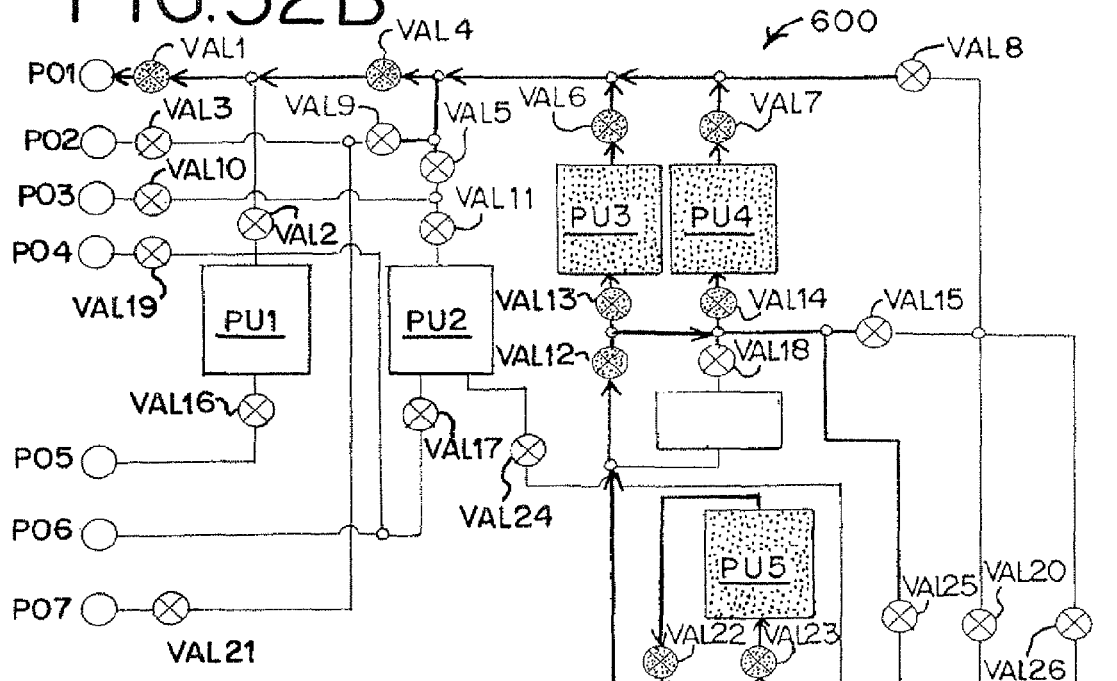

Blood is drawn from a blood source and into the disposable set by a two-phase process that is illustrated in FIGS. 52A and 52B. Before the blood enters the cassette 592 in either of the phases, an amount of anticoagulant is added to it. Anticoagulant is pumped from the anticoagulant container 562 (which is connected via tubing to port PO10 of the cassette 592), through the cassette flow circuit 600, and out port PO9 of the cassette 592 by operation of the anticoagulant pump PU5. The anticoagulant travels through the tubing 596 connected to the port PO9 and exits through the y-connector 598, where it mixes with blood flowing from the blood source into the cassette 592 via port PO8.

FIG. 52A schematically illustrates the path through the cassette 592 taken by anticoagulated whole blood being pumped from the blood source (which is connected via tubing to port PO8 of the cassette 592), through the cassette flow circuit 600, and directly into the chamber 500 (which is connected via tubing to port PO5 of the cassette 592). The donor pumps PU3/PU3 cooperate with the in-process pump PU1 to flow the blood through the cassette flow circuit 600 in this first phase.

In the phase illustrated in FIG. 52B, anticoagulated blood is pumped from the blood source, through the cassette flow circuit from port PO8 to port PO1, and to the in-process container 594 instead of flowing directly into the chamber 500 via port PO5. In contrast to the first phase, the operation of just the donor pumps PU3/PU4 is sufficient for flowing the blood into the in-process container 594 in the phase of FIG. 52B. The blood pumped into the in-process container 594 is temporarily stored therein before it is eventually pumped into the chamber 500, as will be described in greater detail herein.

In one embodiment, blood is drawn from the source by one of the donor pumps PU3/PU4 while the other donor pump PU3/PU4 expels the blood to the chamber 500 or the in-process container 594. This allows for simultaneous blood draw and pumping to the chamber 500 or the in-process container 594.

The blood may be alternately pumped to the chamber 500 (FIG. 52A) and then to the in-process container 594 (FIG. 52B) at a particular ratio (e.g., 9:1) to fill both at the same time.

C. Separation Stage

Within the chamber 500, separation of the fluid components occurs based on density, as shown in FIG. 46, while the chamber spins at a "hard spin" rate of, for example, approximately 4500 RPM. It is noted that the angular velocities used herein conventionally are "two omega" (i.e., the spin speed of the chamber itself) although "one omega" (i.e., the speed at which the umbilicus is orbited around the chamber) may also be used, as well as some combination thereof. Further detail of this separation is set forth in Brown, "The Physics of Continuous Flow Centrifugal Sell Separation," Artificial Organ, 13(1)-420 (1989). A higher density component such as red blood cells is forced towards the outer or high-side wall portion in an outermost layer 552 and a lower density component such as platelet poor plasma is forced towards an inner or low-g side wall portion in an innermost layer 550. The interface layer 554 between the red blood cells and the plasma contains a buffy coat layer which includes at least a portion of platelets and white blood cells, although the components of the interface will vary based on the particular procedure employed.

Figure 53:
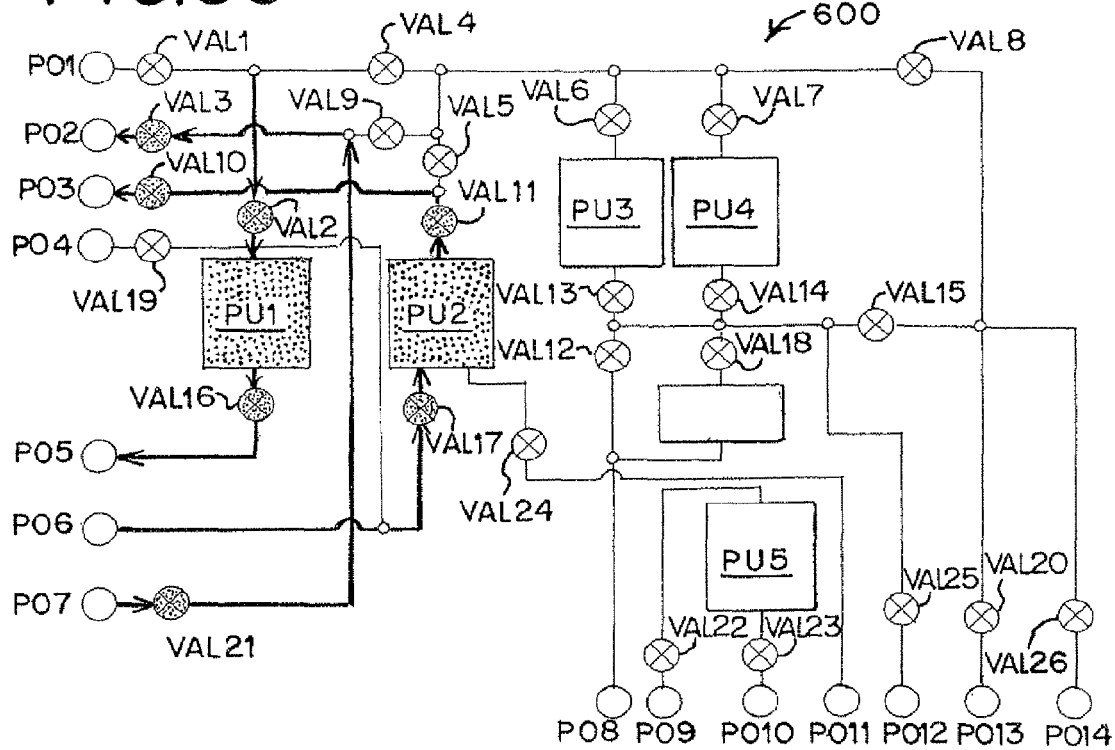
FIG. 53 is a schematic view of the blood processing circuit of FIG. 51, showing the programming of the cassette to carry out different fluid flow tasks in connection with separating whole blood into constituent layers.

As the interface is pooling upstream of the barrier 516, fluid may be collected separately from either side of the interface—or both sides thereof—through the respective outlet 542 or 544 depending on the requirements of the procedure. For example, FIG. 53 schematically illustrates the path of whole blood out of port PO5 of the cassette 592 and into the chamber 500, with the blood separating into its constituent parts and some platelet poor plasma exiting the chamber 500 through the plasma outlet 542 (per FIG. 46). The plasma exiting the plasma outlet 542 flows through tubing and into the cassette 592 via port PO6 of the cassette 592. When the plasma enters the cassette fluid circuit 600, the plasma pump PU2 cooperates with the various valves to convey the plasma to port PO3 of the cassette 592. The plasma exiting port PO3 travels through tubing and into the plasma collection container 576.

Simultaneously, some red blood cells are collected radially outward of the interface, exiting the chamber 500 through the red blood cell outlet 544 (per FIG. 46). The red blood cells exiting the red blood cell outlet 544 flow through tubing and into the cassette 592 via port PO7 of the cassette 592. When the red blood cells enter the cassette fluid circuit 600, they are directed to port PO2 of the cassette 592. The red blood cells exiting the port PO2 travel through tubing and into the red blood cell collection container 578.

While the plasma and red blood cells are being separated and removed from the chamber 500, the barrier 516 allows for accumulation of platelets (which are contained in the buffy coat/interface layer 554) in the channel 508, substantially without the platelets exiting the chamber 500 (per FIG. 46).

In one embodiment, the stages of drawing whole blood into the chamber and collecting platelet poor plasma and red blood cells (while retaining buffy coat in a pool upstream of the barrier 516) are repeated until a predetermined amount of platelets is present in the pooled buffy coat. The amount of platelets that may be pooled in the chamber without causing an overspill or underspill condition depends, in part, upon the distance between the low-g and high-g walls. In one embodiment, the low-g and high-g walls are sufficiently spaced from each other to allow for at least one therapeutic unit of single dose platelets or $6 \times 10^{11}$ platelets to be pooled upstream of the barrier without causing an overspill or underspill condition. In another embodiment, the low-g and high-g walls are sufficiently spaced from each other to allow for at least approximately $7 \times 10^{11}$ platelets to be pooled upstream of the barrier without causing an overspill or underspill condition. As an additional benefit of such a channel configuration, the interface will be farther spaced from the plasma outlet 542, resulting in less white blood cell contamination of the collected platelets.

D. Return Stage

Typically, the amount of blood that must be processed to collect one therapeutic unit of single dose platelets results in a surplus of separated platelet poor plasma and red blood cells. Accordingly, periodically during the platelet pooling process, an amount of the collected platelet poor plasma and red blood cells may be returned to the blood source or otherwise conveyed to a recipient.

Figure 54A:
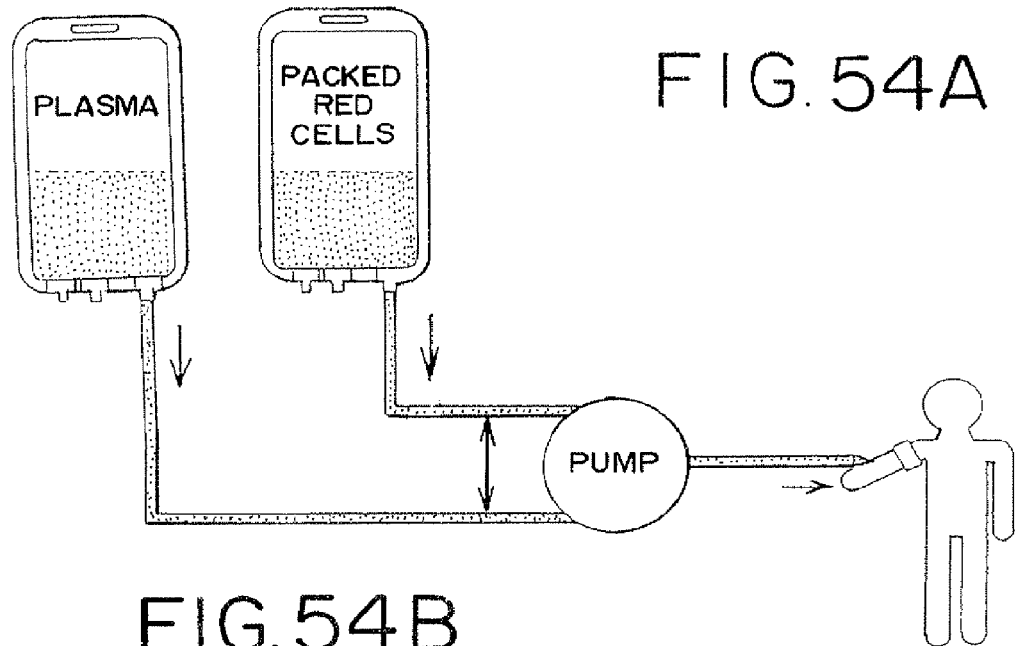
FIGS. 54A-54C are schematic views of an interleaving process for returning excess red blood cells and plasma to the blood source.
Figure 54B:
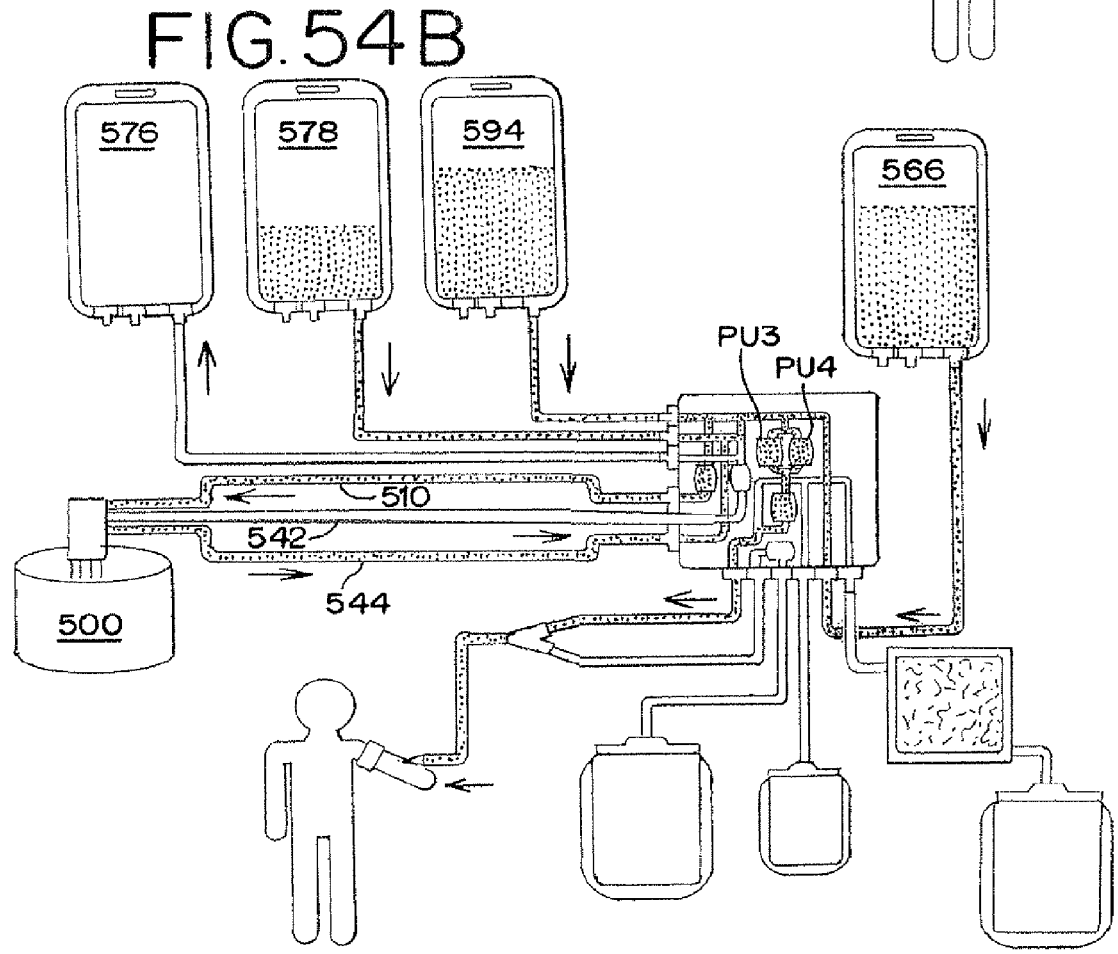
Figure 54C:
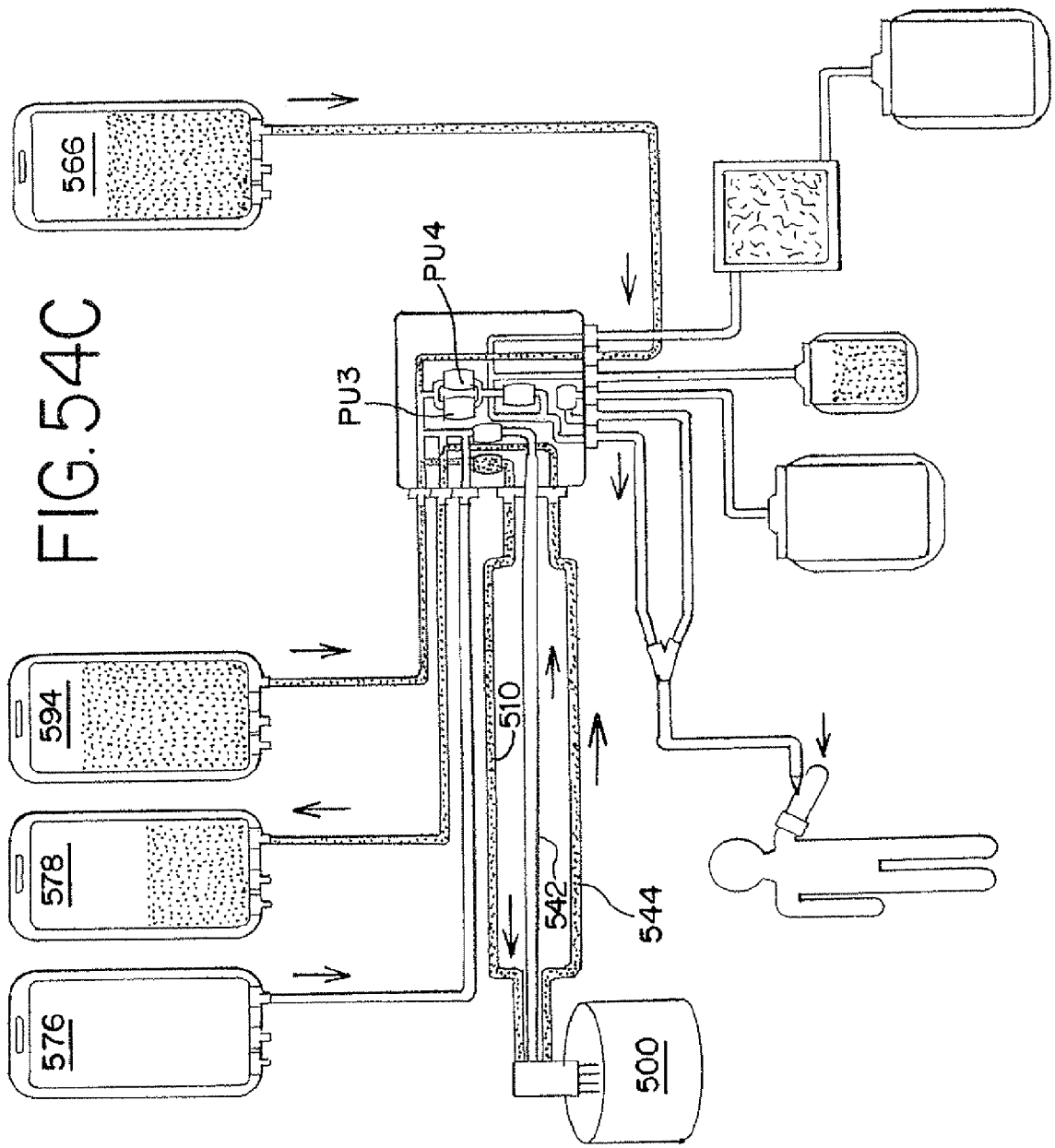

This may be achieved according to conventional methods, i.e., conveying the plasma and red blood cells separately with saline or, more advantageously, the returning volumes of plasma and red blood cells may be interleaved as they are being conveyed to the recipient. An illustrative interleaving process is shown in FIGS. 54A-54C.

In one phase of the interleaving process (FIG. 54B), a volume of separated red blood cells from the red blood cell collection container 578 is conveyed to the recipient by operation of the donor pumps PU3 and PU4 of the cassette during a red blood cell pumping interval. As illustrated, red blood cells from the red blood cell outlet 544 of the chamber 500 and/or saline from the saline container 566 may also be conveyed to the recipient at this time. This phase operates for a selected number of pump strokes to convey a particular volume of red blood cells to the recipient while separated platelet poor plasma from the chamber 500 is directed into the plasma collection container 576 by operation of the cassette.

Once the foregoing phase has been completed, a second phase (illustrated in FIG. 54C) is initiated In this phase, a volume of separated plasma from the plasma collection container 576 is conveyed to the recipient by operation of the donor pumps PU3 and PU4 of the cassette during a plasma pumping interval. As illustrated, plasma from the plasma outlet 542 of the chamber 500 and/or saline from the saline container 566 may also be conveyed to the recipient at this time. This phase operates for a selected number of pump strokes to convey a particular volume of plasma to the recipient while separated red blood cells from the chamber 500 are directed into the red blood cell collection container 578 by operation of the cassette.

These two phases are alternated repeatedly to convey any excess amounts of collected plasma and red blood cells to the recipient. The duration of each pumping interval (i.e., the number of pump cycles) and, hence, the volume of plasma or red blood cells conveyed to the recipient during a particular phase, depends on the ratio of red blood cells vs. plasma to be returned to the recipient (the "interleaving ratio"), taking into account any other relevant factors as well. For example, if the amount of red blood cells to convey to the recipient is twice the amount of plasma to convey to the recipient, the system controller will calculate that the volume of red blood cells to be conveyed in a given phase is twice the volume of plasma to be conveyed in a given phase. With this information, the controller can calculate a 2:1 interleaving ratio and then actuate the pump system to carry out such interleaving ratio. If the efficiency of pumping red blood cells is approximately equal to the efficiency of pumping plasma, the duration of the red blood cell pumping interval should be approximately twice as long as the duration of the plasma pumping interval. On the other hand, if the efficiencies are different, then the relative durations of the pumping intervals will be adjusted to some other ratio so as to carry out the calculated interleaving ratio.

It will be appreciated that the interleaved fluid conveyed to the recipient will be similar to anticoagulated blood, having a lower citrate concentration than plasma, thereby improving donor comfort (if the recipient is a human donor), and a lower viscosity than concentrated red blood cells, thereby decreasing the return time. Further, the return time will also be shorter than known procedures whereby saline is interleaved with the fluid, as no time is spent returning excess saline volume.

Regardless of the manner in which plasma and/or red blood cells are returned to the donor, it will be appreciated that, in a one needle system, blood cannot simultaneously be withdrawn from a donor while returning fluids to the donor. As such, the direct donor-to-chamber draw phase illustrated in FIG. 52A cannot be employed to supply the chamber 500 with additional blood during the return stage. Accordingly, while the plasma and/or red blood cells are being returned to the donor, the whole blood previously supplied to the in-process container 594 (during the draw phase illustrated in FIG. 52B) may be pumped into the chamber 500, as shown in FIGS. 54B and 54C, allowing for non-stop processing.

E. Red Blood Cell/Platelet Flush Stage

At the end of the platelet pooling process and when it has been determined that the required amounts of plasma, red blood cells, and platelets are present in the system, it may be advantageous for an underspill condition to be imposed upon the fluid components. The operation of the cassette 592 to cause an underspill condition is shown in FIG. 55A. The underspill condition may be forced by stopping the in-process pump PU1 of the cassette 592 and reversing the plasma pump PU2, thereby causing plasma to be pulled from the plasma collection container 576 (which is connected via tubing to port PO3 of the cassette 592) and into the cassette flow circuit 600. The continued reverse operation of the plasma pump PU2 directs the plasma through the cassette flow circuit 600 and out the cassette port PO6, causing it to return to the chamber 500 through the plasma outlet 542. The plasma entering the chamber 500 pushes the fluid components in the channel 508 toward the high-g wall 504, thereby displacing red blood cells and buffy coat into the red blood cell outlet 544 (which is connected via tubing 608 to port PO7 of the cassette 592). As described previously, the presence of buffy coat materials in the red blood cell outlet 544 constitutes an underspill condition.

An optical sensor (such as the sensor 336 described above) associated with the tubing 608 connecting the red blood cell outlet 544 to port PO7 of the cassette 592 detects that a portion of the interface/buffy coat layer is exiting the outlet, which usually has red blood cells exiting therethrough. Such underspill condition is empirically determined based on the optical transmissivity of light through the components in the outlet tubing 608. The optical sensor data is converted to a hematocrit. A decrease in hematocrit of the fluid moving through the outlet tubing 608 registers as an underspill condition.

Forcing an underspill condition allows the interface to be forced radially outward as compared to the radial location of the interface during normal collection operation. The underspill condition allows removal of red blood cells into the red blood cell collection container 578 (which is connected via tubing to port PO2 of the cassette 592) until the resulting fluid in the chamber 500 has a hematocrit in a target range of, for example, approximately 20 to 40 percent.

The forced underspill may be followed by an "add RBC" phase to return a controlled amount of packed red cells from the red blood cell collection container 578 to the chamber 500, thereby ensuring that the optimal amount of red blood cells is present in the chamber 500. FIG. 55B illustrates the operation of the cassette 592 during an "add RBC" phase. Such a procedure may be achieved by returning the plasma pump PU2 to its forward pumping direction, causing platelet poor plasma to flow out of the plasma outlet 542 of the chamber 500 (which is connected via tubing to port PO6 of the cassette 592) and into the cassette flow circuit 600. The plasma is directed through the cassette flow circuit 600, out cassette port PO3, and into the plasma collection container 576. Simultaneously, flow into the chamber 500 via the whole blood inlet 510 is stopped which, when combined with the plasma being removed from the chamber 500 via the plasma outlet 542, has the effect of drawing the last-exiting fluid from the cassette 592 via port PO7, through the red blood cell outlet 544, and back into the chamber 500.

Once a desired hematocrit level is achieved in the chamber 500, the fluid in the chamber 500 is advantageously kept within the desired hematocrit range. For example, the flow of separated plasma out of the chamber 500 via the plasma outlet 542 may be stopped and/or the flow of separated red blood cells from the chamber 500 via the red blood cell outlet 544 may also be stopped. Such flow may be stopped by operation of the cassette valves and/or by stopping operation of one or more cassette pumps, such as the plasma pump PU2. The in-process pump PU1 may continue to operate, although it may be advantageous for it to be operated at a lower flow rate.

At this time, the excess collected red blood cells and plasma may be conveyed to a recipient (as described above), followed by the recipient/donor being disconnected from the system. An additional amount of red blood cells may be conveyed to the recipient, with the understanding that the red blood cell harvesting stage (which will be described in greater detail herein) will ultimately bring the amount of collected red blood cells up to the target yield.

F. Recombination Stage

Figure 56A:
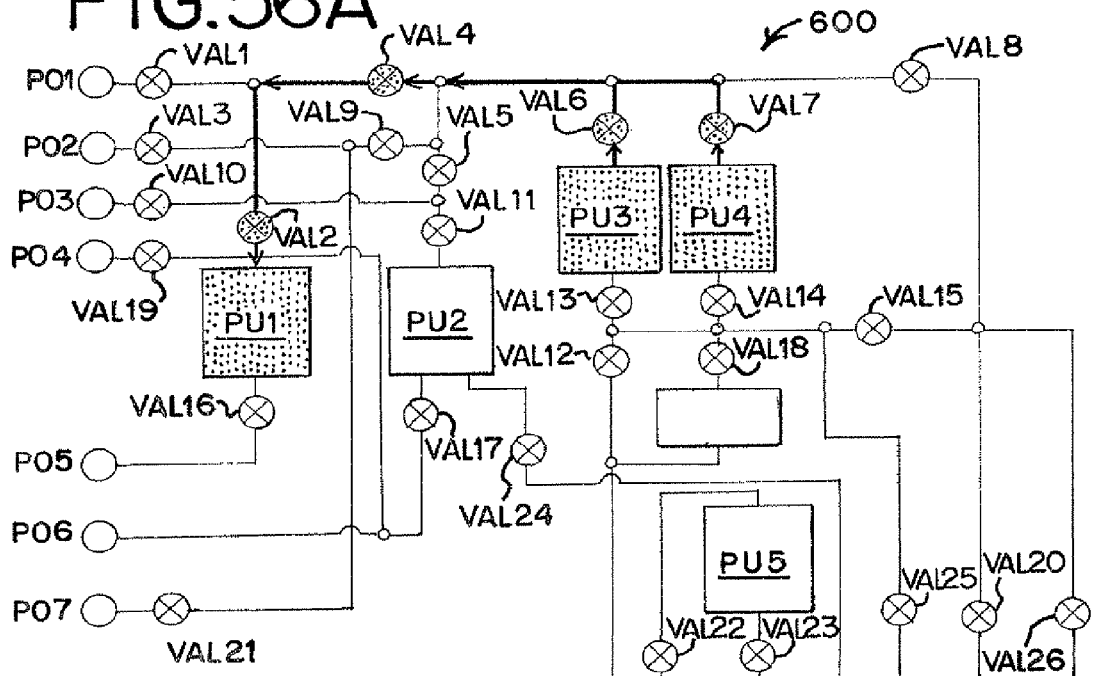
FIGS. 56A and 56B are schematic views of the blood processing circuit of FIG. 51, showing the programming of the cassette to carry out different fluid flow tasks in connection with recombining the previously separated blood components.
Figure 56B:
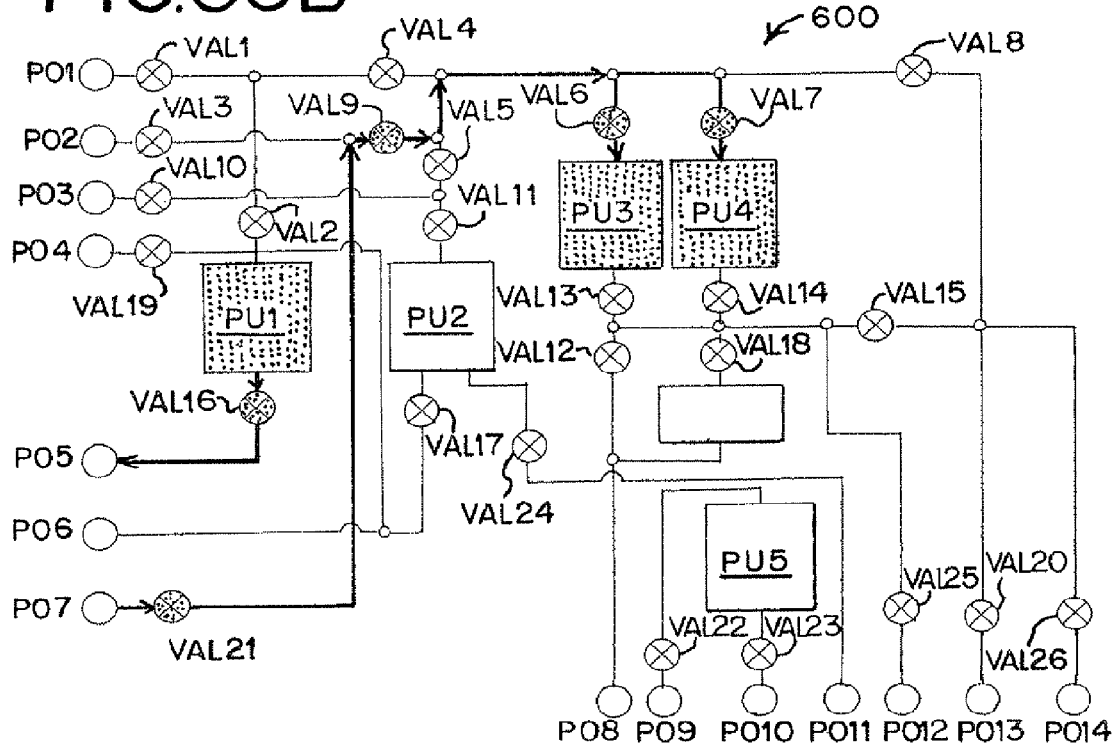

The exemplary method further includes the recombination of the separated fluid components within the chamber. FIGS. 56A and 56B illustrate the operation of the cassette 592 during the recombination stage. In one embodiment, recombination is performed by rotation of the chamber 500 in both clockwise and counterclockwise directions, whereby the chamber 500 is rotated alternately in clockwise and counterclockwise directions one or more times. During this recombination stage, the valves VAL17 and VAL19 associated with the plasma outlet 542 (which is connected via tubing to port PO6 of the cassette 592) are closed. With the plasma outlet 542 effectively closed, the contents of the chamber 500 are forced to exit or enter the chamber 500 via the whole blood inlet 510 and/or the red blood cell outlet 544. The donor pumps PU3 and PU4 and the in-process pump PU1 of the cassette 592 are operated to cycle the blood components into and out of the chamber 500, as generally illustrated in the two-phase process of FIGS. 56A and 56B.

In the phase illustrated in FIG. 56A, the blood components present in the donor pumps PU3 and PU4 are pumped through the cassette flow circuit 600 to the in-process pump PU1. In the phase illustrated in FIG. 56B, the blood components present in the in-process pump PU1 are pumped through the chamber 500 (in through the whole blood inlet 510 via cassette port PO5 and out the red blood cell outlet 544 via cassette port PO7) and into the donor pumps PU3 and PU4. These phases alternate as the chamber 500 is rotated alternately in clockwise and counterclockwise directions.

The recombination stage results in a uniform blood-like mixture which includes plasma, red blood cells, platelets, and white blood cells having an approximate chamber hematocrit as previously described. The recombination stage may last approximately one to three minutes, although this time period may vary. The rotation of the chamber in either direction may be at a rate much lower than the rate of rotation during initial separation of the components and may be, for example, in the range of approximately 300 to 600 RPM, although other rates of rotation are possible.

G. Platelet Storage Solution Prime Stage

Figure 57:
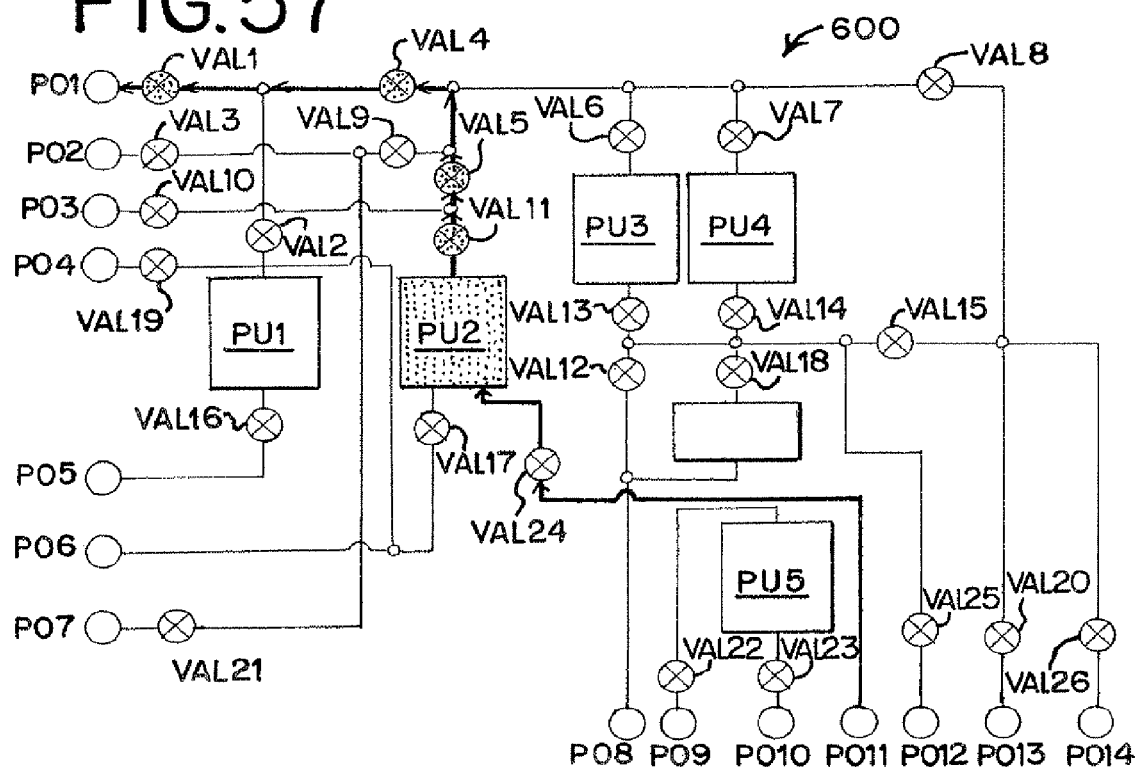
FIG. 57 is a schematic view of the blood processing circuit of FIG. 51, showing the programming of the cassette to carry out different fluid flow tasks in connection with priming the tubing leading to a platelet storage solution container.

If a platelet storage fluid other than plasma (e.g., PAS III) is to be used for storing the separated platelets, as will be described in greater detail herein, it may be advantageous to initiate a "platelet storage solution prime" stage after the recombination stage. The operation of the cassette 592 during such a stage is illustrated in FIG. 57. In such a stage, an amount of (non-plasma) platelet storage solution is pumped from a platelet storage solution container (which is connected via tubing to port PO11 of the cassette 592), through the cassette flow circuit 600, and to the in-process container 594 (which is connected via tubing to port PO1 of the cassette 592) by the plasma pump PU2. This moves any air from the platelet storage solution container into the in-process container 594, ensuring that it will not remain in the flow path during the processing steps which follow.

An amount of (non-plasma) platelet storage solution may be pumped into the chamber to displace some of the plasma out of the plasma outlet 542, through the cassette flow circuit 600, and into the plasma collection container 576. This may be advantageous if it is desired for the resulting platelet storage solution to have a higher non-plasma platelet storage solution to plasma ratio than what is typically achieved by the present procedure.

H. Recirculation Stage

1. Recirculation Phase 1

After a sufficient recombination period, the rotor is then restarted to rotate the chamber in a uniform direction, with the flow within the chamber being generally directed from the inlet 510 to the first and second outlets 542 and 544 (although fluid is still prevented from exiting the chamber via the plasma outlet 542). The specific speed of the rotor may vary, but may be a "slow spin" of approximately 2500-2700 RPM, which separates a red blood cell layer from a layer containing plasma and platelets. During this time, the valves VAL17 and VAL19 associated with cassette port PO6 are closed, effectively closing the plasma outlet 542 and forcing the fluid in the chamber 500 to exit via the red blood cell outlet 544 (which is connected via tubing to port PO7 of the cassette 592) and flow into the donor pumps PU3 and PU4, identical to the second phase of the recombination stage shown in FIG. 56B. The donor pumps PU3 and PU4 pump the fluid through the cassette flow circuit 600 to the in-process pump PU1 (identical to the first phase of the recombination stage shown in FIG. 56A). Finally, the in-process pump PU1 pumps the fluid out of port PO5, through the whole blood inlet 510, and back into the chamber inlet 510. This phase of the recirculation stage continues for a sufficient time to allow the red blood cell layer to settle within the chamber.

2. Recirculation Phase 2

After the red blood cell layer has settled within the chamber, VAL 17 is opened, as shown in FIG. 58A, allowing flow through cassette port PO6 and effectively re-opening plasma outlet 542 (which is connected via tubing to port PO6). During this phase, the red blood cell layer continues exiting the chamber via the red blood cell outlet 544, flowing into the cassette flow circuit 600 via port PO7, and being directed to one of the donor pumps PO3. With the plasma outlet 542 re-opened, the layer including plasma and platelets (and any non-plasma platelet storage solution) is allowed to exit the chamber therethrough and enter the cassette flow circuit 600 via port PO6. The plasma/platelet layer is directed from port PO6 to the plasma pump PU2, as shown in FIG. 58A.

Thereafter, the contents of the donor pump PU3 (i.e., the red blood cell layer) and the plasma pump PU2 (i.e., the plasma/platelet layer) are pumped through the cassette flow circuit 600 and into the in-process pump PU1 (FIG. 58B), where they are recombined. The in-process pump PU1 subsequently pumps the combined fluids out of the cassette 592 via port PO5 and back to the chamber 500 (FIG. 58A). These sub-phases alternate, thereby creating a recirculation loop into and out of the chamber.

During recirculation, no plasma, platelets, or red blood cells are collected. The platelet concentration in the plasma/platelet layer generally increases during this phase, with platelets from the interface becoming suspended in the plasma.

Recirculation of the components continues until an optical sensor (such as the sensor 334 described above) associated with the tubing 610 connecting the plasma outlet 542 and cassette port PO6 detects a plasma/platelet layer which has a desired concentration of platelets and which is visually low in red blood cells. As discussed above, the hematocrit of the recirculated mixture is approximately between 20-40 percent. Recirculation may also be modified so as to recirculate only one of the components, either plasma or red blood cells, as desired.

Figure 59A:
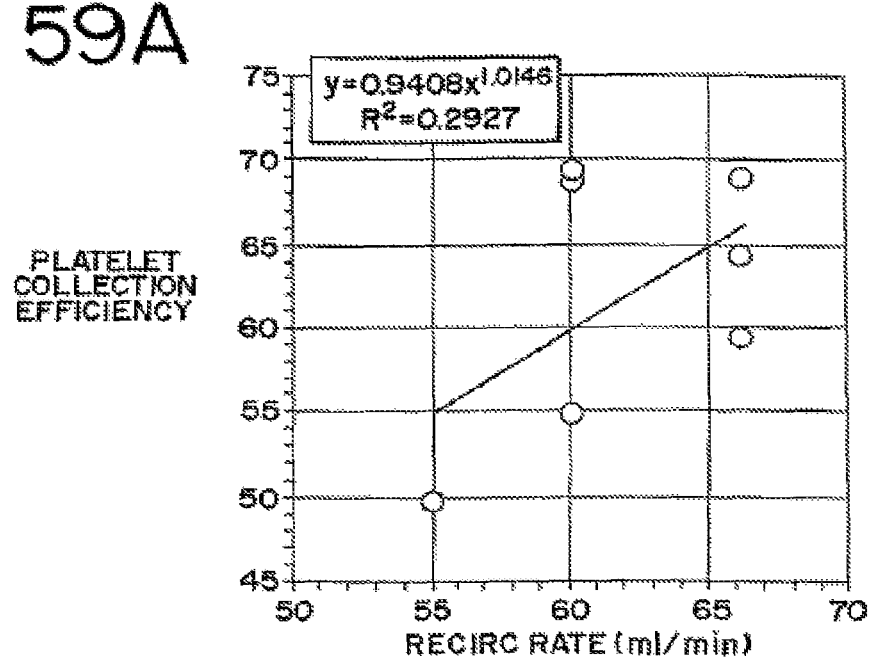
FIG. 59A is a graphical representation of the recirculation rate (in ml/min) versus the platelet concentration in a sample collected radially inward of the red blood cell and plasma interface which has been collected after a predetermined period of recirculation.
Figure 59B:
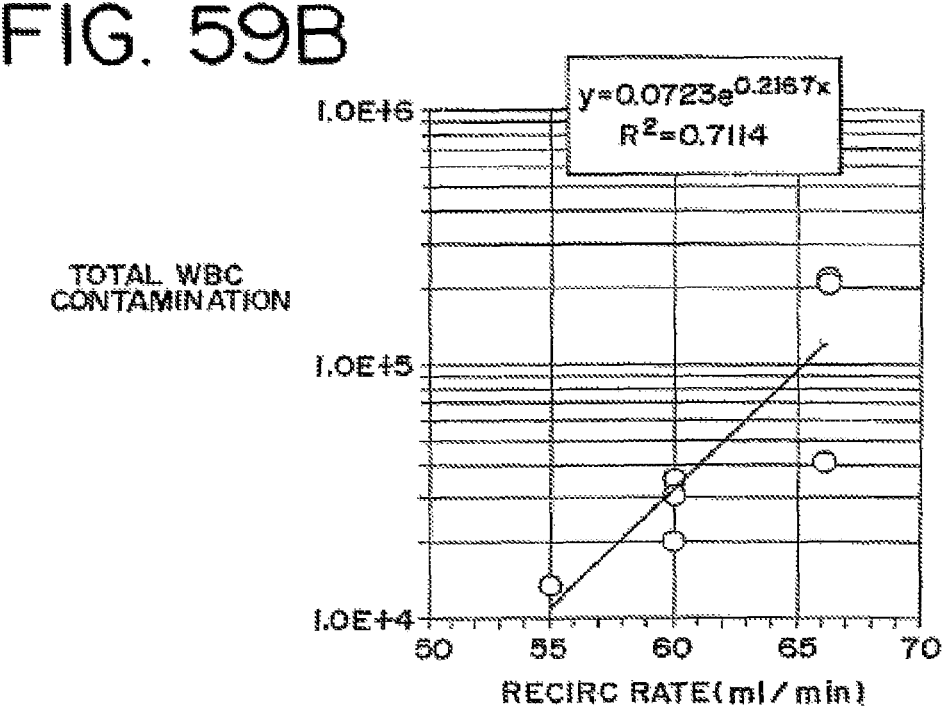
FIG. 59B is a graphical representation of the recirculation rate (in ml/min) versus the white blood cell count in a sample collected radially inward of the red blood cell and plasma interface which has been collected after a predetermined period of recirculation.

During the recirculation stage, an illustrative pump flow rate ratio of the in-process pump PU1 and plasma pump PU2 is 60/40, although other pump rates may be used depending on the particular conditions of the system. Recirculation may also allow an increasing concentration of white blood cells to settle to the interface between the plasma/platelet layer and the red blood cells. Such pump ratio has also been found to have a direct influence on the number of white blood cells that contaminate the plasma/platelet layer and the overall platelet concentration collection efficiency. By way of example and not limitation, FIGS. 59A and 59B show a collected fluid having a higher concentration of platelets (FIG. 59A) and a lower concentration of white blood cells (FIG. 59B). In FIGS. 59A and 59B, such fluid was collected from a chamber having approximately 120 cm$^2$ surface area, which was operated at a speed of approximately 2500 RPM with a chamber hematocrit of approximately 25%. Other collection efficiencies may be developed for different chamber surface areas, centrifugal speeds and chamber hematocrits.

Recirculation of the plasma/platelet layer may continue for several minutes (approximately two to four minutes in one embodiment), which duration may vary depending upon the particular procedure. During this time, the content of the plasma/platelet layer in the tubing 610 associated with the plasma outlet 542 may be monitored by the aforementioned optical sensor. For best results, this monitoring is typically delayed until the plasma/platelet layer is substantially uniform. The sensor can detect the presence of platelets in the plasma, and the data collected by the sensor can be used during recirculation to calculate a number of quantities. Those having skill in the art will appreciate that the plasma/platelet layer will have a higher platelet concentration than typical "platelet rich plasma" (i.e., a plasma/platelet layer that is formed by subjecting whole blood to a "soft spin" without the prior removal of an amount of platelet poor plasma), so the signal will be stronger and the resulting data will tend to be more reliable than data collected by observing typical "platelet rich plasma."

Among the various quantities that can be calculated, the data collected by the optical sensor can be used to estimate the current platelet yield. The difference between a baseline optical density (i.e., the optical density of plasma substantially free of cellular components) and the detected optical density of the plasma/platelet layer is indicative of the platelet concentration of the plasma/platelet layer, so a "snapshot" of the platelet content can be estimated by comparing the two values over a period of time and then integrating the area therebetween during that time. The integrated value can be extrapolated to the total volume of blood processed to estimate the current platelet yield.

When the current platelet yield is known, the platelet precount of the donor can be estimated. This may be estimated, for example, by considering the amount of detected platelets and the volume of blood that has been processed (i.e., the current platelet yield), then comparing those values (along with any other necessary information, such as donor hematocrit, weight, and gender, for example) to empirical data indexing such values with known platelet pre-counts. These calculations may be performed by the software of the system controller or the data may be transmitted to an external integrator before the results are returned to the system as a platelet pre-count.

This information may be used to calculate a number of other values, for example, the volume of blood to be processed to collect a target amount of platelets. In one embodiment, this is calculated by feeding the calculated platelet pre-count, the target platelet yield, and any other necessary information (such as donor hematocrit, weight, and gender) into a predictor that calculates the volume of blood to be processed. If the calculated volume is greater than the volume of blood in the system, then the process may be modified to include additional draw stages to draw additional blood from the donor or the system may give the operator the option to collect less platelets than the target amount.

This information may also be used to calculate the processing time required to collect a target amount of platelets using, for example, a calculation process similar to that described previously with regard to the volume of blood to be processed to collect a target amount of platelets. If the calculated processing time exceeds a selected "maximum" processing time (due, for example, to a donor having a below-average platelet pre-count), the system may present the operator with a number of options. For example, in one embodiment, the expected products are one unit of single dose platelets, one unit of red blood cells, and one unit of plasma. In this case, the operator can be given the option of collecting only the red blood cells and plasma (while returning the platelets to the donor) or collecting the full amounts of red blood cells and plasma and a partial dose of platelets. Alternatively, the choice to modify the expected products during the procedure may be made by the system controller rather than by the operator.

Other adjustments may also be made to the collection procedure during processing for optimal performance. For example, in one embodiment, the target range for collected platelets is between $3.0 \times 10^{11}$ (the industry requirement) and $4.7 \times 10^{11}$ (the maximum platelet capacity of an exemplary platelet collection container). If it is determined that the platelet yield will exceed the target value or range, the spin speed of the chamber may be increased to sediment some of the platelets out of the plasma/platelet layer. As an additional benefit, increasing the spin speed will also cause some white blood cells in the plasma/platelet layer to sediment out of the layer, thereby reducing the white blood cell content of the plasma/platelet layer. Alternatively, if it is determined that the platelet yield will fall below a targeted value or range, the spin speed of the chamber may be decreased to pull more platelets from the interface into the plasma/platelet layer.

Yet another option is to use the calculated platelet yield to calculate the optimal amount of platelet storage fluid (e.g., platelet poor plasma or non-plasma storage solution or a combination thereof to use for storing the platelets.

Those having skill in the art will appreciate that other quantities can also be calculated by measuring the amount of platelets in the outlet tubing 610 during this recirculation stage.

1. Platelet Harvesting Stage

After the recirculation stage and any additional blood processing stages (if it is determined during the recirculation stage that additional blood collection and processing are required to collect the target amount of platelets), a platelet harvesting stage is initiated. In the platelet harvesting stage, the plasma/platelet layer is pumped out of the chamber 500 via the plasma outlet 542 and into the platelet collection container 574. This is achieved by continuing the immediately preceding recirculation stage, but adding a platelet storage fluid (platelet poor plasma from the plasma collection container 576 and/or non-plasma storage solution from the platelet storage solution container) to the circulating fluid. The additional fluid replaces the fluid volume lost within the chamber 500 due to collection of the plasma/platelet layer.

Figure 60A:
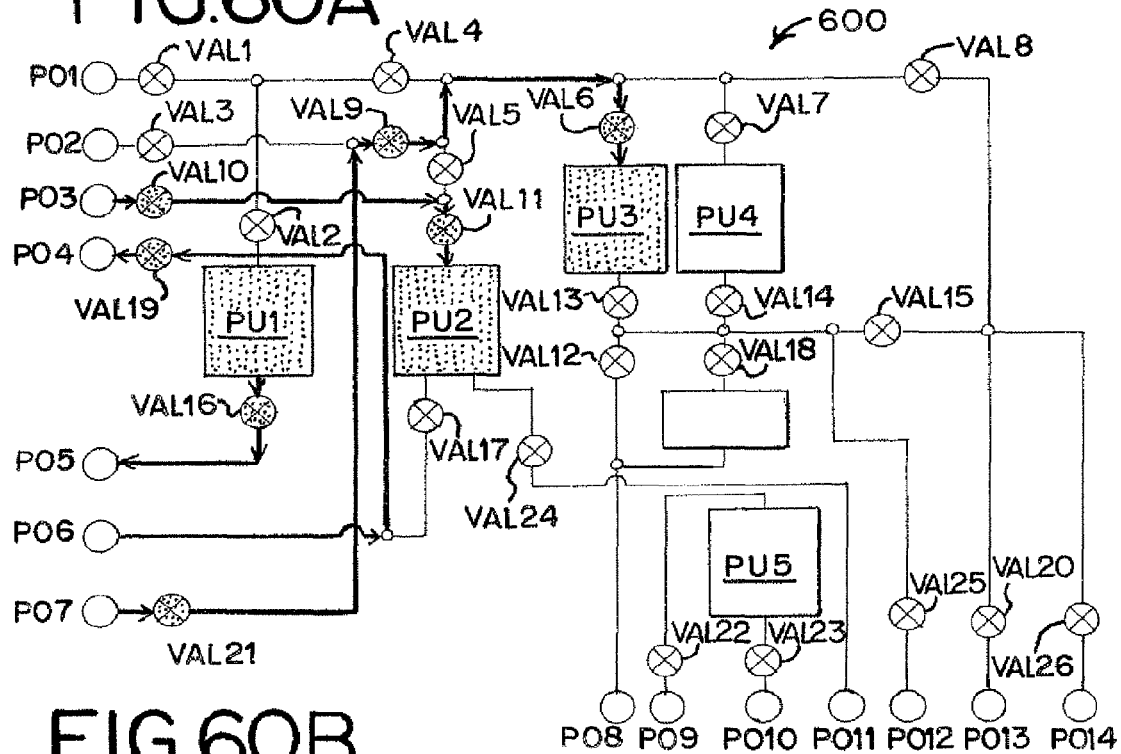
FIG. 60A is a schematic view of the blood processing circuit of FIG. 51, showing the programming of the cassette to carry out different fluid flow tasks in connection with harvesting platelets using platelet poor plasma.

In particular, as shown in FIG. 58B, the contents of the plasma pump PU2 (i.e., the plasma/platelet layer) and the contents of the donor pump PU3 (i.e., the red blood cell layer) flow to the in-process pump PU1. The mixed contents of the in-process pump PU1 are then pumped out of cassette port PO5 and into the chamber 500, as packed red cells exit the chamber 500 via the red blood cell outlet 544 and are pumped through cassette port PO7 into the donor pump PU3 (FIGS. 60A/60B). Simultaneously, the plasma/platelet layer exits the chamber 500 via the plasma outlet 542 and is pumped through cassette port PO6, through the cassette flow circuit 600, and out port PO4 to the platelet collection container 574 (FIGS. 60A/60B). Rather than being filled with the plasma/platelet layer (as in the recirculation stage), the plasma pump PU2 is filled with a platelet storage fluid. In one embodiment, illustrated in FIG. 60A, the plasma pump PU2 is filled with plasma from the plasma collection container 576 (which is connected via tubing to port PO3 of the cassette 592). In another embodiment, illustrated in FIG. 60B, the plasma pump PU2 is instead filled with non-plasma storage solution from the platelet storage solution container (which is connected via tubing to port PO11 of the cassette 592).

With this additional fluid in the plasma pump PU2, the contents thereof and the contents of the donor pump PU3 again flow into the in-process pump PU1 (FIG. 58B). Finally, the in-process pump PU1 is emptied into the chamber 500 through the whole blood inlet 510 (which is connected via tubing to port PO5 of the cassette 592), with the plasma/platelet layer being displaced out of the plasma outlet 542 and into the cassette flow circuit 600 via port PO6 (alternatively illustrated in FIGS. 60A and 60B). Once in the cassette 592, the plasma/platelet layer is pumped from port PO6 to port PO4 and to the platelet collection container 574. Simultaneously, the packed red cells flow from the red blood cell outlet 544, into the cassette flow circuit 600 via port PO7, and through the cassette flow circuit 600 to the donor pump PU3 (alternatively illustrated in FIGS. 60A and 60B). These sub-phases alternate (i.e., between the sub-phase illustrated in FIG. 58B and the sub-phase illustrated in FIGS. 60A/60B), thereby creating a recirculation loop into and out of the chamber, with an amount of the plasma/platelet layer being collected during each iteration of the loop.

Figure 60B:
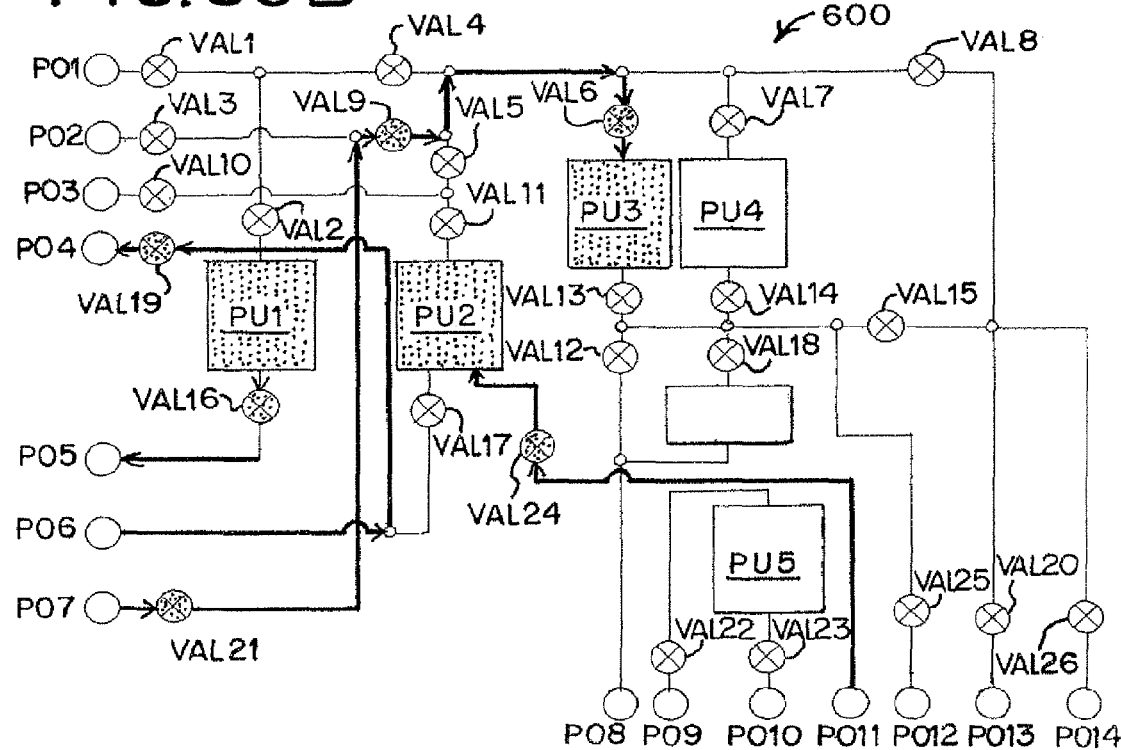
FIG. 60B is a schematic view of the blood processing circuit of FIG. 51, showing the programming of the cassette to carry out different fluid flow tasks in connection with harvesting platelets using a (non-plasma) platelet storage solution.

The sub-phases illustrated in FIGS. 60A and 60B may be practiced independently (e.g., employing only the sub-phase of FIG. 60A in combination with the sub-phase of FIG. 58B to harvest and store platelets in platelet poor plasma) or combined during a given procedure. For example, the platelet harvesting stage may following a repeating loop from the sub-phase illustrated in FIG. 58B, to the sub-phase illustrated in FIG. 60A, to the sub-phase illustrated in FIG. 58B, to the sub-phase illustrated in FIG. 60B, and finally back to the beginning of the loop. Such a harvesting loop may be modified depending on the particular process, for example, by employing a loop initiating two FIG. 60A sub-phases for every FIG. 60B sub-phase that is initiated. In yet another embodiment, non-plasma storage solution is used to displace and store platelets (i.e., the FIGS. 58B and 60B sub-phases are alternated) until a target amount of storage solution has been used, at which time platelet poor plasma is used to displace and store the platelets (i.e., the FIGS. 58B and 60A sub-phases are alternated) until the target platelet yield is achieved.

Figure 61A:
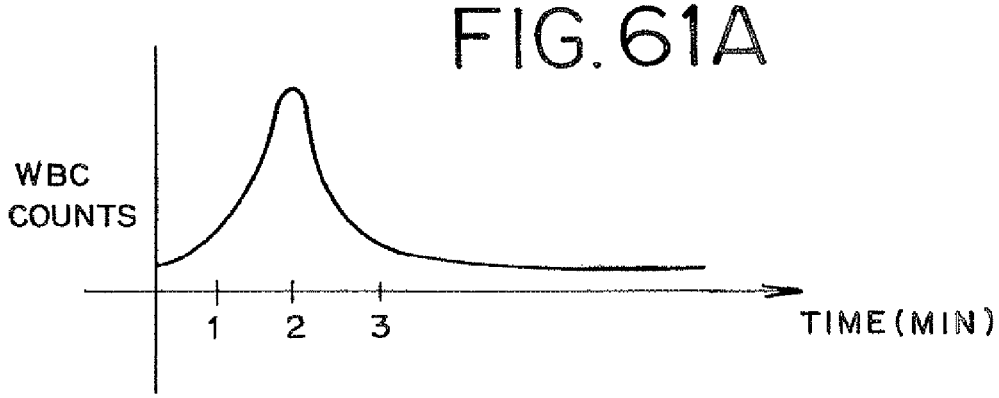
FIG. 61A is a graphical representation of white blood cell contamination of a collected platelet product during a platelet harvesting stage.

One phenomenon that has been observed is the plasma/platelet layer becoming contaminated by white blood cells during the platelet harvesting stage. Rather than a uniform or continuous contamination, the white blood cells typically spill into the plasma/platelet layer in a single "burst" shortly after the harvesting stage begins. A diagram of the white blood cell contamination is shown in FIG. 61A. Typically, this "burst" is detected approximately one minute after the beginning of the harvesting stage, which has led to the belief that the "burst" is caused by non-plasma storage solution reaching the chamber. The non-plasma storage solution is less dense than the plasma/platelet layer, and this slight difference in physical properties may disturb the interface, causing white blood cells to spill through the plasma outlet 542. Typically, around the two-minute mark of the harvesting stage, the white blood cell concentration (as detected by the optical sensor associated with the outlet tubing 610) will begin to decrease and, around the three-minute mark, the white blood cell concentration will be at or below the level at the beginning of the platelet harvesting stage.

Figure 61B:
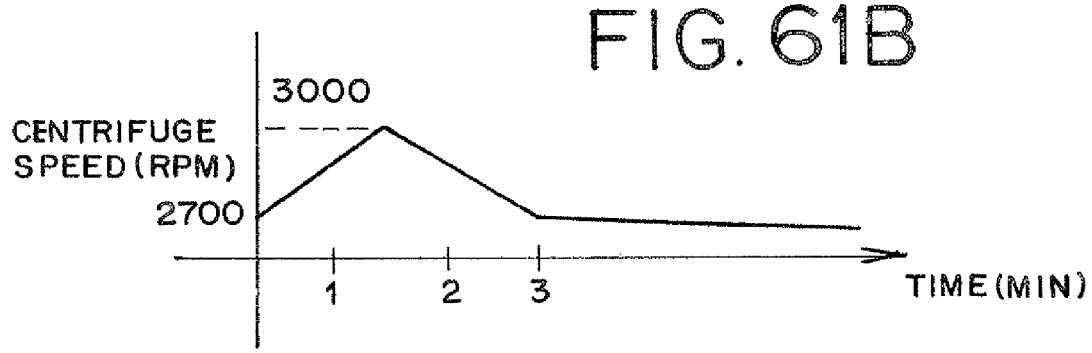
FIGS. 61B-61D are graphical representations of processing chamber spin speed profiles adapted to minimize the white blood cell contamination illustrated in FIG. 61A.
Figure 61C:
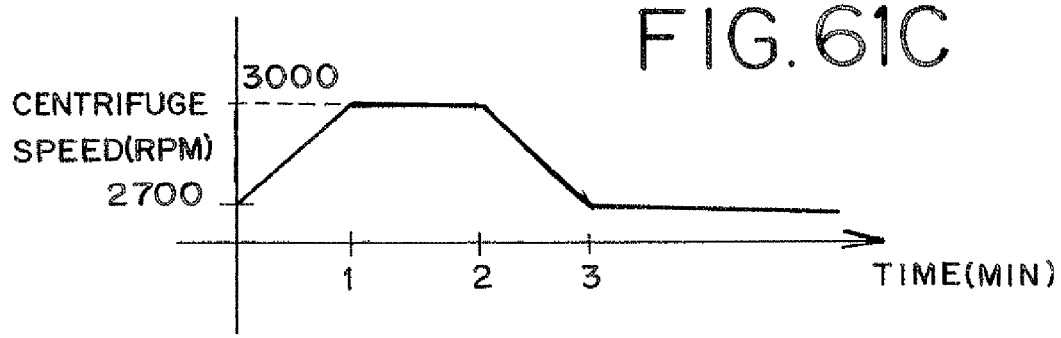
Figure 61D:
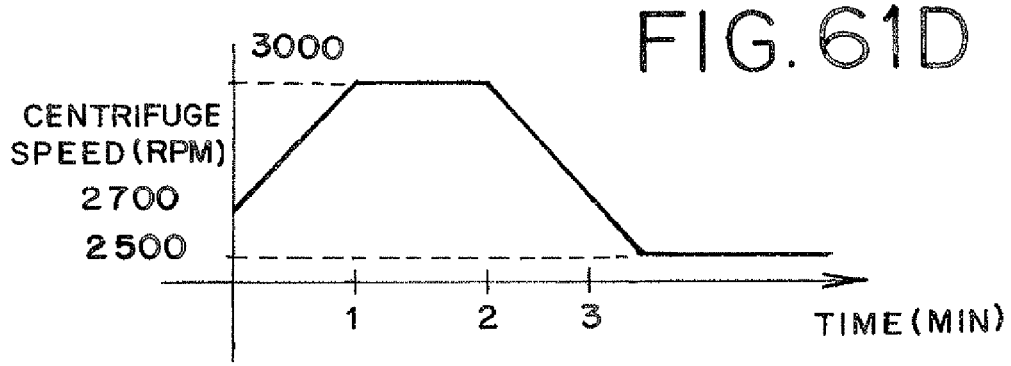

It is known that increasing the spin speed of the chamber 500 will force more white blood cells to sediment from the plasma/platelet layer into the interface, so the "burst" may be combated by spinning the chamber 500 at a higher speed during the harvesting stage. However, increasing the spin speed also degrades the platelet recovery, as some of the platelets will be sedimented into the interface with the white blood cells. Accordingly, it may be advantageous to operate the chamber at an elevated spin speed only during the beginning of the platelet harvesting stage (i.e., during the time of the "burst") and decrease the speed during the remainder of the stage, as is shown in FIGS. 61B-61D. In an exemplary embodiment, the recirculation stage is carried out at a spin speed of approximately 2700 RPM, which may be gradually or incrementally increased to an elevated speed (around 3000 RPM in one embodiment) before being decreased to the original spin speed.

FIGS. 61B and 61C illustrate two different spin speed profiles for combating the "burst." In the embodiment of FIG. 61B, the spin speed is gradually increased at a rate of approximately 200 RPM/min to a maximum spin speed of approximately 3000 RPM at approximately one and a half minutes after the beginning of the harvesting stage. Thereafter, the spin speed is gradually decreased at a rate of approximately 200 RPM/min to return to the original spin speed of approximately 2700 RPM by the three-minute mark of the harvesting stage. The spin speed remains at approximately 2700 RPM for the rest of the harvesting stage.

In the embodiment of FIG. 61C, the spin speed is increased at a rate of approximately 300 RPM/min, such that the chamber will be spinning at approximately 3000 RPM at the time that the "burst" typically occurs. The spin speed remains at 3000 RPM for approximately one minute and then, at the two-minute mark, the spin speed is ramped down at, for example, 300 RPM/min to the original spin speed, where it remains for the rest of the harvesting stage.

FIG. 61D illustrates yet another possible spin speed profile. This profile is similar to that of FIG. 61C, but the spin speed is ultimately ramped down to a speed below the spin speed at the beginning of the harvesting stage, for example 2500 RPM. This may be advantageous to compensate for the decreased collection efficiency during the elevated spin speed and may be employed without risking additional contamination, as it has been observed that the white blood cell concentration detected by the optical sensor is relatively low after the three-minute mark of the harvesting stage. These illustrated spin speed profiles are merely illustrative, and other "burst"-combating spin speed profiles may also be employed without departing from the scope of the present disclosure. This principle may also be employed to combat other contamination profiles, such as those characterized by multiple "bursts" or the like.

In yet another embodiment, the platelet harvesting stage may be modified by incrementally decreasing the spin speed of the chamber while the plasma/platelet layer is being collected. So decreasing the spin speed will move the interface closer to the low-g wall 502, thereby pushing the platelets toward the plasma outlet 542 and increasing the efficiency of the system. This embodiment is best employed when only platelet poor plasma is used to collect and store the platelets, as the use of platelet poor plasma alone will typically avoid the aforementioned "burst" of white blood cells.

Regardless of the particular chamber spin speed profile that is employed during the platelet harvesting stage, it may be advantageous to continue monitoring the platelet concentration of the plasma/platelet layer as it is being collected to determine when the target amount of platelets has been collected. The yield can be calculated, for example, by comparing a curve plotting a baseline optical density (of a plasma layer containing substantially no cellular components) to a curve plotting the detected optical density. The difference between the two values is indicative of the platelet concentration of the plasma/platelet layer, so the amount of platelets collected can be calculated by comparing the two values during the platelet harvesting stage and then integrating the area between the curves periodically. If the optical reading differs from that which is expected, the spin speed of the chamber may be changed to bring it back in line (e.g., by increasing the spin speed to sediment platelets from the plasma/platelet layer and decrease the optical density of the plasma/platelet layer or decreasing the spin speed to pull platelets into the plasma/platelet layer from the interface and increase the optical density of the plasma/platelet layer). The optical readings taken during the platelet harvesting stage or the final platelet yield calculated during the recirculation stage (described above) may be used to make on-the-fly adjustments to the amount of storage fluid ultimately added to the platelet collection container.

When the target platelet yield has been reached, the system may operate to flow plasma and/or non-plasma storage solution directly to the platelet collection container (bypassing the chamber) if need be.

Although the majority of leukocytes in the plasma/platelet layer will sediment therefrom during the aforementioned recirculation stages, some leukocytes typically remain in the collected fluid. The illustrated disposable sets 556 and 558 (FIGS. 47 and 48, respectively) show an in-line leukoreduction filter 580 between the cassette 592 and the platelet collection container 574. In such embodiments, the plasma/platelet layer that is pumped out of the chamber 500 by the plasma pump PU2 is pumped through the leukoreduction filter 580 and into the platelet collection container 574 while the chamber 500 is still spinning and processing the blood components. In one example, a reduction of white blood cells from approximately $1.0 \times 10^7$ to approximately $1.0 \times 10^4$ on account of an in-line leukoreduction filter was observed.

J. Red Blood Cell Harvesting Stage

When the platelet harvesting stage is complete, the system continues with a red blood cell harvesting stage, which is illustrated schematically in FIG. 62. During this stage, the valves VAL17 and VAL19 associated with cassette port PO6 are closed, effectively closing the plasma outlet 542, and the spin speed of the chamber 500 is increased to a "hard spin" of, for example, approximately 4500 RPM. The in-process pump PU1 delivers platelet poor plasma from the plasma collection container 576 (which is connected via tubing to port PO3 of the cassette 592) to the chamber 500 via the whole blood inlet 510 (which is connected via tubing to port PO5 of the cassette 592). The incoming plasma forces the packed red blood cells out of the red blood cell outlet 544 and into the cassette flow circuit 600 via port PO7. The red blood cells are directed through the cassette flow circuit 600, out of port PO2, and to the red blood cell collection container 578.

K. Post-Processing Stage

After the platelets and red blood cells have been collected, any of a number of post-processing procedures may be initiated, a number of which are described below.

1. Burping the Platelet Product

As a result of the manufacturing process, there may be some air present in the tubing leading from the cassette 592 to the platelet collection container 574 or in the associated leukoreduction filter 580, which means that the plasma/platelet layer passing through the filter 580 will force the air into the platelet collection container 574. For a number of well-known reasons, it is desirable to avoid air in the collection container. Accordingly, the platelet collection container 574 may include a length of tubing leading to a gas exhaust or air burp bag 582, as shown in FIGS. 47 and 48. Air is removed from the collected platelet product by closing the inlet tubing (typically with a clamp) and squeezing the flexible container 574, thereby forcing air out of the container 574 and into the air burp bag 582. The operator watches the tubing to the air burp bag 582 to ensure that little to no platelet product leaves the container 574 during this de-aeration or "burping" process.

Alternatively, rather than employing a manual burping process, an automated burping process is possible. FIGS. 63A-63D show an illustrative automated de-aeration or burping process. First, a pump 612 is operated in a forward direction to pump fluid "F" through a conduit 614 to a flexible collection container 616 (FIG. 63A). This first step is optional, as the following operations may be performed with any flexible container with an amount of fluid and gas, regardless of how the fluid and gas were transferred into the container. When all of the fluid "F" has been pumped into the collection container 616, there will be an amount of air "A" above the fluid "F." To remove the air, the pump 612 is operated in a reverse direction to pull the air "A" and fluid "F" back out of the collection container 616 (FIG. 63B). As air "A" and fluid "F" are being removed from the collection container 616, an optical sensor 618 (e.g., a QProx™ sensor from Quantum Research Group Ltd. of Hamble, England) monitors the conduit 614. The optical sensor 618 is adapted to distinguish between air and fluid in the conduit 614 and may be configured according to known design.

When the optical sensor 618 detects the air-fluid interface "I" in the conduit 614 (FIG. 63C), it signals for the pump 612 (or signals to an intermediary, such as a controller, that commands the pump) to stop operating in the reverse direction and switch to operating in the forward direction. The pump 612 continues to run in the forward direction until the fluid "F" in the conduit 614 has been returned to the collection container 616, with the air "A" remaining in the conduit 614 (FIG. 63D). The volume of fluid "F" in the conduit 614 can be calculated, based on the geometry of the conduit 614 and the distance between the collection container 616 and the sensor 618, so the pump 612 may be operated for a predetermined number of forward cycles (each of which returns a calculable volume of fluid "F" to the collection container 616) to return the fluid "F" to the collection container 616. It will be appreciated that such an automated process may be employed to remove air from the collected blood component(s) in any of the collection containers described herein.

This automated burping process may be variously modified without departing from the scope of the present disclosure. For example, rather than performing a predetermined number of pump cycles to return fluid from the conduit 614 to the collection container 616, the operator may be given the option (via a touch screen or other user interface system) to enter the number of cycles to perform. In another embodiment, the operator may be given the option to order a pump cycle (either a forward or reverse cycle) at the touch of a button or icon. In yet another embodiment, the system controller may automatically burp the collection container and thereafter give the operator the option of confirming that there has been sufficient purgation and, if not, allow the operator to order individual or multiple pump cycles.

2. Red Blood Cell Storage and Filtration

The disposable sets 556 and 558 illustrated in FIGS. 47 and 48 include a red blood cell storage container 586, which is distinct from the red blood cell collection container 578. For reasons that are well-known, it is beneficial to add an additive solution (e.g., Adsol® or SAG-M) to packed red cells. While it is possible to add an additive solution from an additive solution container 564 to the packed red cells in the red blood cell collection container 578 after processing, doing so requires an additional mixing step that is typically performed manually. Rather than carrying out such a procedure, it may be advantageous to automatically mix the packed red cells and additive solution as they are flowing into the red blood cell storage container 586. This can be achieved, for example, by an interleaving process whereby a first phase of pumping an amount of packed red cells from the red blood cell collection container 578 to the red blood cell storage container 586 is alternated with a phase of pumping an amount of additive solution from the additive solution container 564 to the red blood cell storage container 586. By alternating the two phases, the contents of the red blood cell storage container 586 are automatically mixed without requiring manual intervention.

Figure 64A:
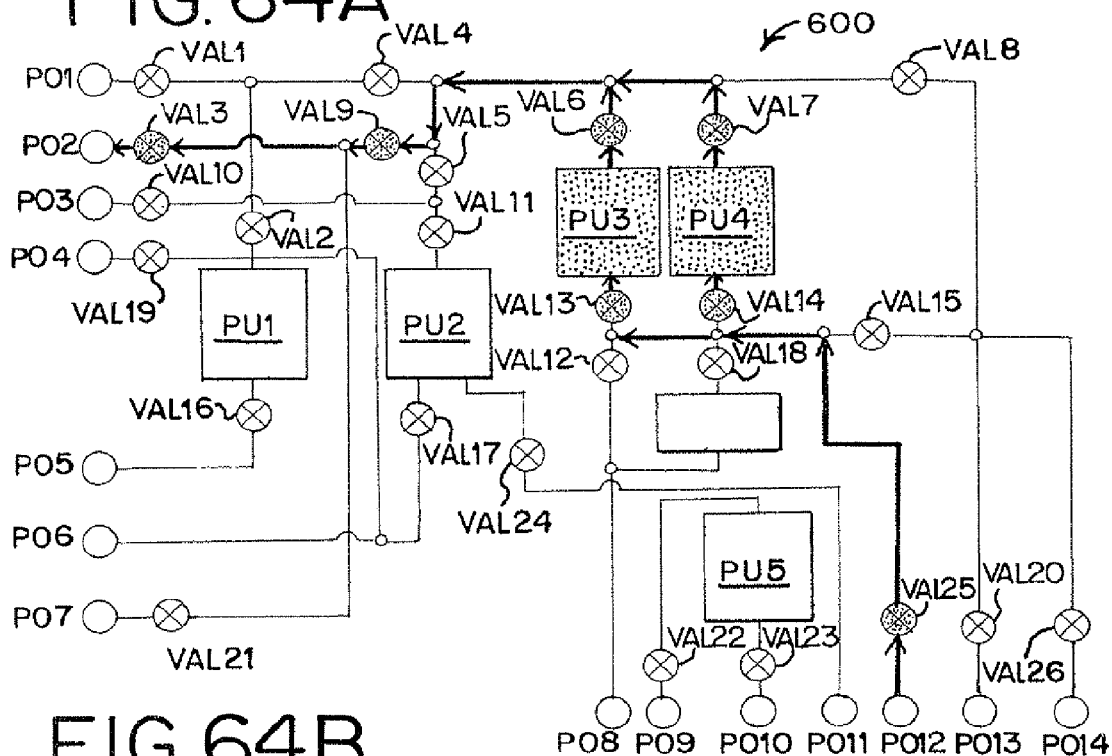
Figure 64B:
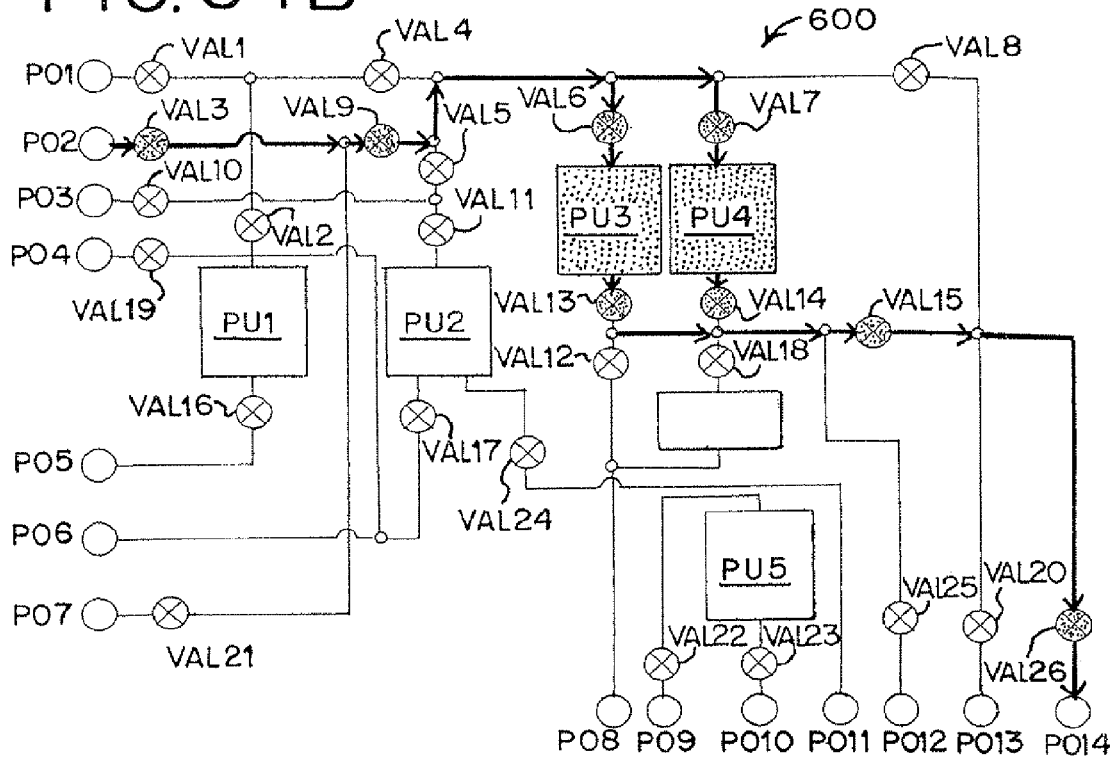

The above mixing procedure is illustrated in greater detail in FIGS. 64A-64C. FIG. 64A shows an additive solution prime stage, whereby the donor pumps PU3 and PU4 are operated to flow additive solution from the additive solution container 564 into the cassette flow circuit 600 via port PO12. The solution is pumped through the cassette flow circuit 600 by the donor pumps PU3 and PU4 to port PO2 and out of the cassette 592 to the red blood cell collection container 578. This phase acts to prime the tubing between the additive solution container 564 and the cassette 592. Next, FIG. 64B shows the donor pumps PU3 and PU4 operating to flow packed red cells from the red blood cell collection container 578 into the cassette flow circuit 600 via port PO2, through the cassette 592, and then out port PO14 to the red blood cell storage container 586.

As shown in the disposable sets 556 and 558 of FIGS. 47 and 48, there may be an in-line leukoreduction filter 590 associated with the tubing between the cassette 592 and the red blood cell storage container 586, thereby filtering the packed red cells as they are pumped through the leukofilter 590 and to the red blood cell storage container 586.

After a certain number of red blood cell pumping cycles, the system switches to an additive solution pumping phase illustrated in FIG. 64C. In this phase, additive solution is pumped from the additive solution container 564, through the cassette flow circuit 600, and into the red blood cell storage container 586 (i.e., into the cassette 592 through port PO12 and out through port PO14). This phase continues for a certain number of pump cycles and then the phases of pumping packed red cells (FIG. 64B) and additive solution (FIG. 64C) to the red blood cell storage container 586 are alternated until the red blood cell collection container 578 is empty.

If the amount of additive solution required to achieve a target ratio (2.1:1 in one embodiment) has not been pumped to the red blood cell storage container 586 by the time the red blood cell collection container 578 is empty, a final phase of pumping additional additive solution to the red blood cell storage container 586 may be initiated.

3. Platelet Poor Plasma Storage and Filtration

In addition to filtering the collected packed red cells, any platelet poor plasma remaining in the plasma collection container 576 may be similarly pumped through a leukoreduction filter and stored in a plasma storage container (not illustrated).

A manual or automated burping process (e.g., the automated process described above with regard to the collected platelets) may be employed to remove any excess air from the filtered plasma and/or packed red cells. If the disposable set is not provided with an air burp bag for a particular filtered blood component, the air may be directed to one of the empty containers, for example, to the empty red blood cell collection container 578.

When the various blood components are in their final storage containers, the containers are typically weighed or otherwise analyzed to confirm that the target yield has been achieved and thereafter separated from the disposable set, which is discarded. Depending on the configuration of the disposable set, samples of the various components may also be taken using, for example in the disposable sets 556 and 558 of FIGS. 47 and 48, a sampling pack 584 for the harvested platelets and a length of segmented tubing 588 for the harvested packed red cells.

L. Other Modifications

Various modifications to the above-described method are possible. One modification includes operating the in-process pump PU1 between at least two different pumping rates to effect recombination of the blood components. For example, fluid may be pumped into the chamber 500 by the in-process pump PU1 at a first flow rate while the chamber 500 is being rotated in a clockwise or counterclockwise direction, and then the rotation in either direction is repeated at a second flow rate. The centrifugal force may be decreased, such as by decreasing the rotor speed, where more than one flow rate is used.

Another modification includes operating the plasma pump PU2 during recombination. Plasma exits the chamber 500 via the plasma outlet 542 and is pumped through the cassette 592 into the in-process container 594. Simultaneously, the flow at the whole blood inlet 510 is reversed using the in-process pump PU1 so that fluid from the chamber 500 is pulled from the chamber 500 via the whole blood inlet 510, through the cassette 592, and into the in-process container 594. The fluid in the in-process container 594 is then pumped back into the chamber 500 through the whole blood inlet 510 by operation of the cassette 592. Therefore, the fluid components are mixed together outside of the chamber 500 and then re-enter the chamber.

It is further possible to modify the pump ratio between the in-process pump PU1 and the plasma pump PU2 during the collection phase to different ratios at different times during the procedure.

In yet another embodiment, a 13-port cassette (e.g., one according to the foregoing description of the cassettes 28 and 28') may be employed rather than the 14-port cassette 592. This may be achieved, for example, by collecting and storing platelets using only platelet poor plasma, which allows the non-plasma platelet storage solution container to be omitted, thereby alleviating the need for one cassette port. Other modifications are also possible.

IX. Red Blood Cell and Plasma Collection with Enhanced Functionality

Figure 65:
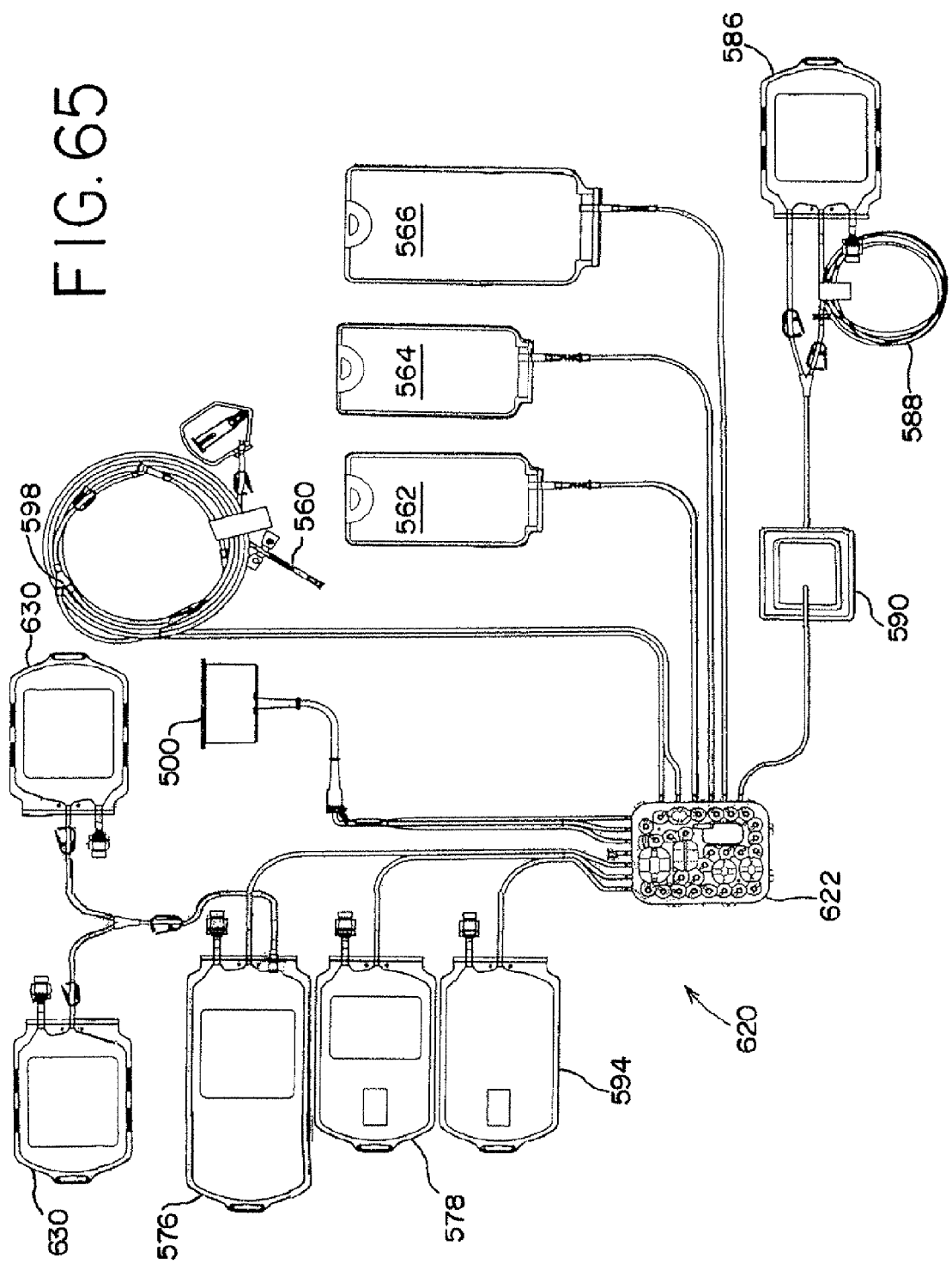
FIG. 65 is a plane view of a disposable set, which can be mounted on the device shown in FIG. 1.

Another benefit of a disposable set incorporating a 14-port cassette is that it can be used to provide enhanced functionality to procedures typically carried out with a 13-port cassette. For example, FIG. 65 illustrates a disposable set 620 with a 13-port cassette 622 that is suitable for use in practicing the previously described red blood cell and plasma collection process. The disposable set 620 is adequate when there is no need to filter the collected plasma, such as for procedures that are carried out in the United States. However, European standards for plasma purity are higher than in the United States, and it is advantageous to filter the collected plasma to remove cellular blood components (particularly white blood cells). Hence, a disposable set 624 (FIG. 66) incorporating a 14-port cassette 592 may be provided. The additional port allows for the inclusion of tubing leading to an in-line filter 626, a gas exhaust or air burp bag 628, and a pair of plasma storage containers 630. It will be seen that the disposable set 624 is similar to the sets illustrated in FIGS. 47 and 48, differing principally in the omission of a platelet collection container and a platelet storage solution container, and the inclusion of the aforementioned filter 626, air burp bag 628, and storage containers 630 associated with cassette port PO11. However, the disposable set 624 of FIG. 66 may be provided with a platelet collection container or other container associated with port PO4 without departing from the scope of the present disclosure.

A. Draw Stage

In an exemplary procedure for harvesting red blood cells and plasma using the disposable set 624 of FIG. 66 (in combination with a suitable blood processing device, such as the one illustrated in FIG. 1), whole blood is pumped from a blood source to a separation device (e.g., the chamber 500 of FIGS. 44-46) and the in-process container 594. Anticoagulant from the anticoagulant container 562 is added to the whole blood by operation of the anticoagulant pump PU5 of the cassette 592. The anticoagulated blood may flow into the chamber 500 either from the blood source, or may flow from the in-process container 594, where the blood from the blood source is temporarily stored for subsequent processing by the chamber 500. The draw procedure can be understood with further reference to the flow diagrams illustrated in FIGS. 52A and 52B and the corresponding description from above.

B. Separation and Collection Stage

Next, within the chamber 500, the fluid components are separated based on density, as shown in FIG. 46, while the chamber spins at a "hard spin" rate of, for example, approximately 4500 RPM. As the interface 554 is pooling upstream of the barrier 516, fluid may be collected separately from either side of the interface—or both sides thereof—through the respective outlet 542 or 544 depending on the requirements of the procedure. For example, in one embodiment (corresponding generally to the flow diagram of FIG. 53 and the accompanying description from above), some platelet poor plasma 550 is collected radially inward of the interface 554 through the plasma outlet 542 and into the plasma collection container 576. Simultaneously, some red blood cells 552 are collected radially outward of the interface 554 through the red blood cell outlet 544 and flow into the red blood cell collection container 578.

1. Reactive Spill Prevention and Control

In one embodiment, the plasma collection rate is determined by the operating rate of the plasma pump PU2 of the cassette 592. The operating rate of the plasma pump PU2 may be constantly ramped to bias the system toward an overspill condition. This may be advantageous because an overspill condition can typically be corrected more quickly than an underspill condition. In particular, an overspill condition can be corrected by stopping the plasma pump PU2, thereby placing the red blood cell outlet 544 of the chamber 500 in a "flow-through" condition (in which any fluid exiting the chamber 500 does so through the red blood cell outlet 544 and not the plasma outlet 542) until a calculated volume of blood has been pumped into the chamber 500. Thereafter, the fluid in the plasma and red blood cell outlets 542 and 544 may be recirculated back into the chamber 500 (by operation of the in-process pump PU1) to flush the associated outlet tubing lines of undesirable material.

In contrast, an underspill condition can be corrected by closing the red blood cell outlet 544 and operating the plasma pump PU2 in a "flow-through" state (in which any fluid exiting the chamber 500 does so through the plasma outlet 542 and not the red blood cell outlet 544) until a set volume of blood has been pumped into the chamber 500 or an overspill condition is detected. The underspill condition is finally corrected by opening the red blood cell outlet 544 and operating the plasma pump PU2 at a lower rate until a set volume of fluid has flown through the red blood cell outlet 544 or an overspill condition is detected.

If the plasma is deemed to be lipemic, it may be advantageous to instead operate the plasma pump PU2 at a constantly decreasing rate to bias the system toward an underspill condition. Such bias protects the collected plasma product from platelet contamination, as it may be difficult for the optical sensor associated with the plasma outlet line to distinguish between platelets and lipemic plasma.

2. Predictive Spill Prevention and Control

In an alternative embodiment, the hematocrit of the fluid exiting the red blood cell outlet 544 may be monitored by an optical sensor. The hematocrit is indicative of the radial location of the interface 554, so the detected hematocrit may be employed to assess the location of the interface 554 and change the chamber spin speed to avoid a spill condition. For example, if the detected hematocrit is greater than a particular value, it is an indication that the red blood cell layer in the chamber 500 is too thick, which may create the risk of an overspill condition. On the other hand, if the detected hematocrit is less than a particular value, it is an indication that the red blood cell layer in the chamber 500 is too thin, which may create the risk of an underspill condition. Increasing the chamber spin speed moves the interface 554 closer toward the high-g wall 504 (for responding to a high hematocrit reading and avoiding an overspill) while decreasing the chamber spin speed moves the interface 554 closer toward the low-g wall 502 (for responding to a low hematocrit reading and avoiding an underspill).

The reactive and predictive spill control systems may also be practiced together, for example, with the detected hematocrit being the primary means of controlling the location of the interface 554 and the biased pumping system being used as a back-up.

C. Return Stage

The separation and collection stage typically will continue until the desired amount of plasma and red blood cells have been collected or are present in the system. For example, in one embodiment, the amount of red blood cells includes the packed red cells in the red blood cell collection container 578, the red blood cells present in the whole blood remaining in the in-process container 594, and the red blood cells in the chamber 500 that have yet to be collected.

Depending on the target yields, the target amount of one component (typically red blood cells) may be present in the system before the target amount of the other component (typically plasma) has been collected, so the duration of the separation and collection stage will be determined by the time required to collect one of the components. In the event that the target volume of one of the components (e.g., red blood cells) is obtained before the other (or is expected to be obtained before the other), that component may be periodically returned to the blood source during the separation and collection stage. Most advantageously, such return phase is carried out while blood is being pumped from the in-process container 594 to the chamber 500, as described above with regard to the Red Blood Cell/Platelet/Plasma collection procedure, to allow for simultaneous processing and fluid return.

D. Final Return and Collection Stage

Figure 67A:
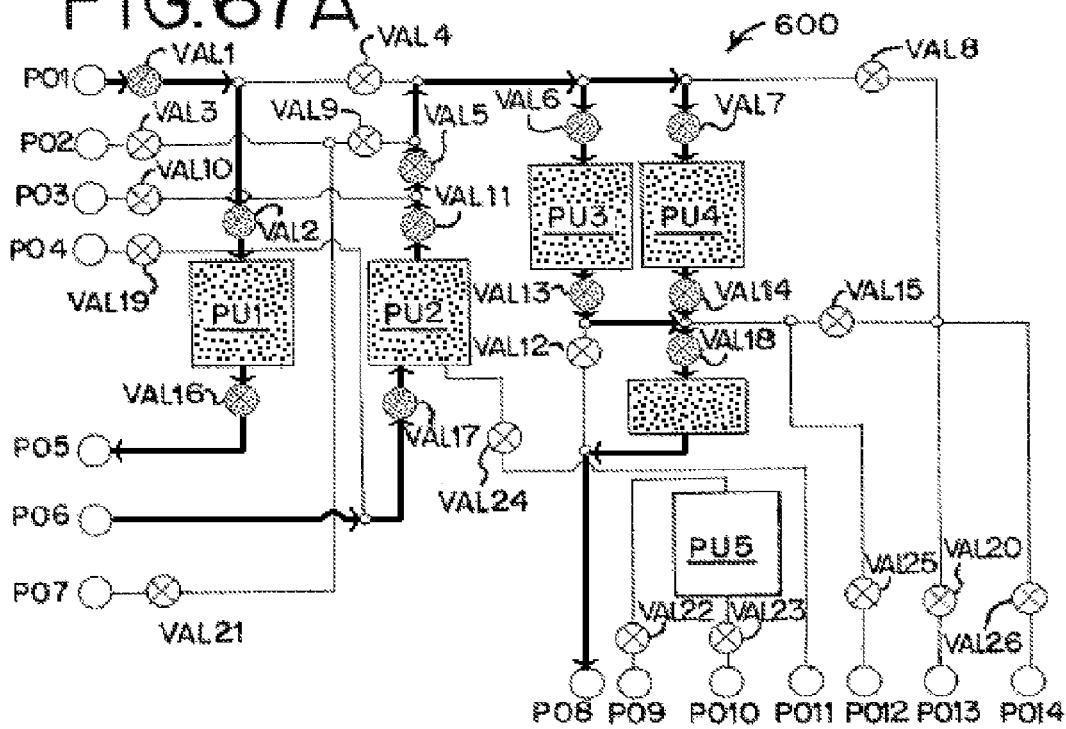
FIGS. 67A-67E are schematic views of the blood processing circuit of FIG. 51, showing the programming of the cassette to carry out different fluid flow tasks in connection with collecting a separated blood component and flushing excess separated blood components from a processing system to a blood source.

With the target amounts of red blood cells and plasma present in the system, the system may move into a final return and collection stage. In one embodiment, any plasma remaining in the chamber 500 is first returned to the blood source. This is achieved by maintaining the chamber at a "hard spin" speed while operating the in-process pump PU1 to convey blood from the in-process container 594, through the cassette flow circuit 600 (in through port PO1 and out through port P5), and into the chamber 500 via the whole blood inlet 510, as shown in FIG. 67A. The blood entering the chamber 500 forces plasma out of the plasma outlet 542, into the cassette flow circuit 600 via port PO6, and then out cassette port PO8 to the blood source by operation of the plasma pump PU2 and the donor pumps PU3 and PU4.

Returning the plasma to the blood source has the effect of moving the interface closer to the low-g wall 502 of the chamber 500. To return the interface layer to the blood source, the spin speed of the chamber 500 is reduced while the in-process pump PU1 continues to convey blood from the in-process container 594, through the cassette flow circuit 600 (in through port PO1 and out through port PO5), and into the chamber 500 via the inlet 510, as shown in FIG. 67A. At the lower spin speed, the interface will be close to the low-g wall 502, so the blood entering the chamber 500 forces the interface out of the plasma outlet 542, through the cassette flow circuit 600 (in through port PO6 and out through port PO8), and to the blood source by operation of the plasma pump PU2 and the donor pumps PU3 and PU4. This "flush interface" phase continues until the in-process container 594 falls below a set volume, as may be determined by a weight sensor associated with the in-process container 594. In one embodiment, the "flush interface" phase continues until the in-process container 594 is empty.

Figure 67B:
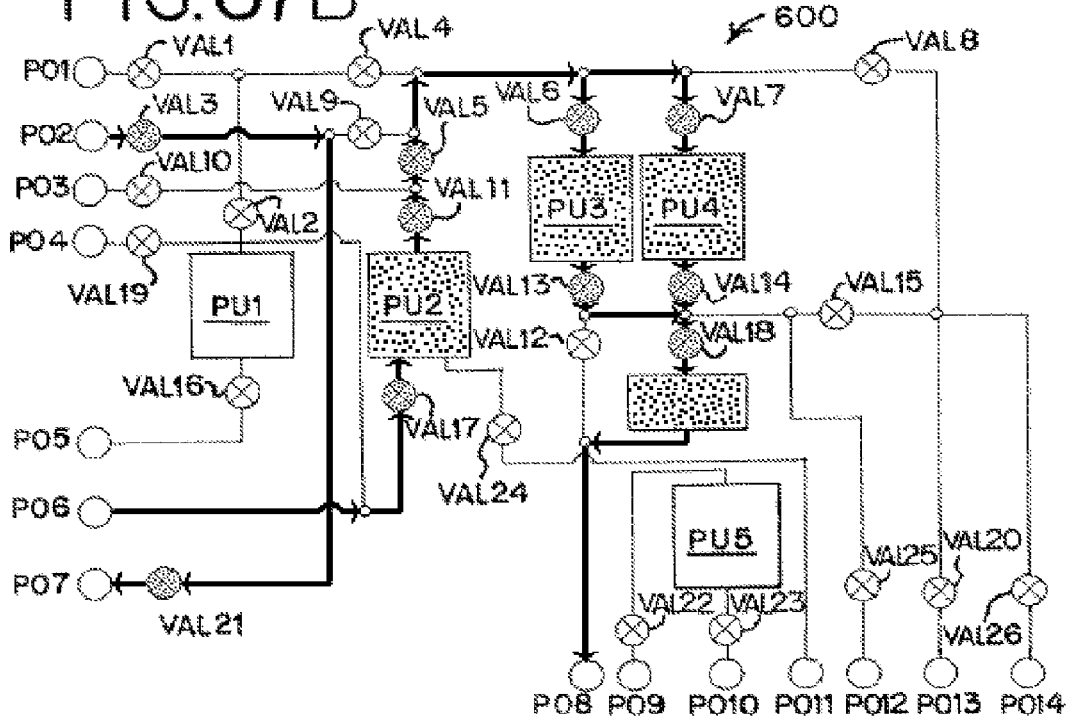

When the interface has been flushed from the chamber 500, the volume of packed red cells in the red blood cell collection container 578 is assessed to determine whether there are any excess red blood cells in the system. If so, the in-process pump PU1 is stopped, while the plasma pump PU2 and the donor pumps PU3 and PU4 continue to operate, thereby pulling some packed red cells from the red blood cell collection container 578, through the cassette flow circuit 600 (in through port PO2 and out through port PO7), and into the chamber 500 via the red blood cell outlet 544, as shown in FIG. 67B. The red blood cells entering the chamber 500 force excess red blood cells in the chamber 500 out the plasma outlet 542, though the cassette flow circuit 600 (in through port PO6 and out through port PO8), to be returned to the blood source. It will be appreciated that the hematocrit of the packed red cells entering the chamber 500 from the red blood cell collection container 578 is greater than that of the red blood cells exiting the chamber 500, thereby effectively increasing the hematocrit of the fluid in the chamber 500.

Figure 67C:
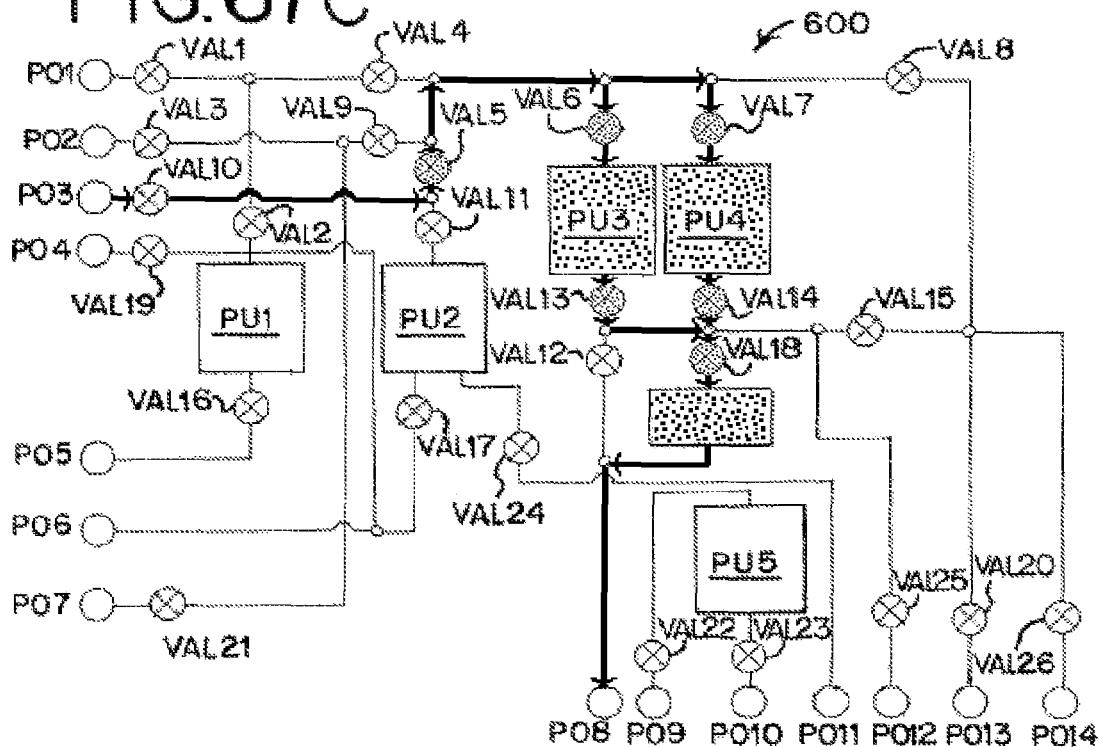

Next, the volume of plasma in the plasma collection container 576 is assessed to determine whether there is any excess plasma in the system. If so, the plasma pump PU2 is stopped, while the donor pumps PU3 and PU4 continue to operate, and the flow path through the cassette 592 is modified to direct any excess plasma from the plasma collection container 576, through the cassette flow circuit 600 (in through port PO3 and out through port PO8), and to the blood source, entirely bypassing the chamber 500 to avoid lowering the hematocrit of the fluid therein. This phase is illustrated in FIG. 67C. The blood source may be disconnected from the system at this time.

Figure 67D:
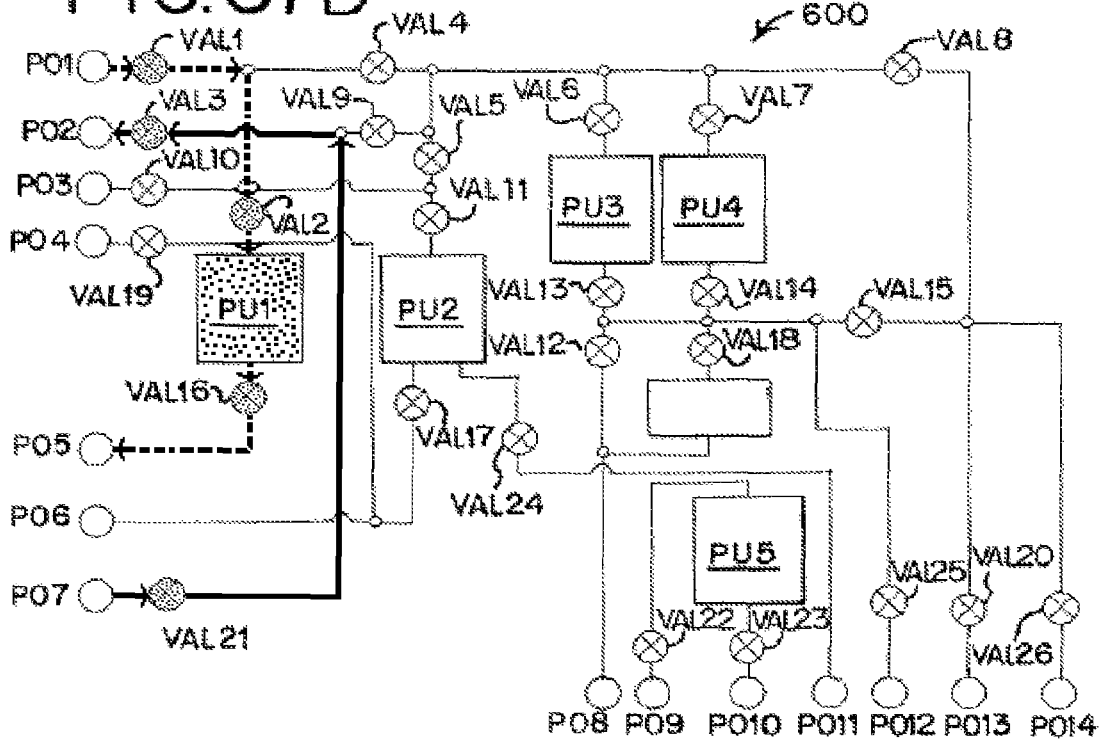

Next, air from the empty in-process container 594 is pumped through the cassette flow circuit 600 (in through port PO1 and out through port PO5) and into the chamber 500 by the in-process pump PU1, as shown in FIG. 67D. The valves VAL17 and VAL19 associated with the plasma outlet port PO6 are closed, thereby causing the air entering the chamber 500 to force the red blood cells therein out the red blood cell outlet 544, through the cassette flow circuit 600 (in through port PO7 and out through port PO2), and to the red blood cell collection container 578. This phase continues until the red blood cells in the chamber 500 have been conveyed to the red blood cell collection container 578, which may be identified when the weight sensor associated with the red blood cell collection container 578 stops registering an increase in volume.

Figure 67E:
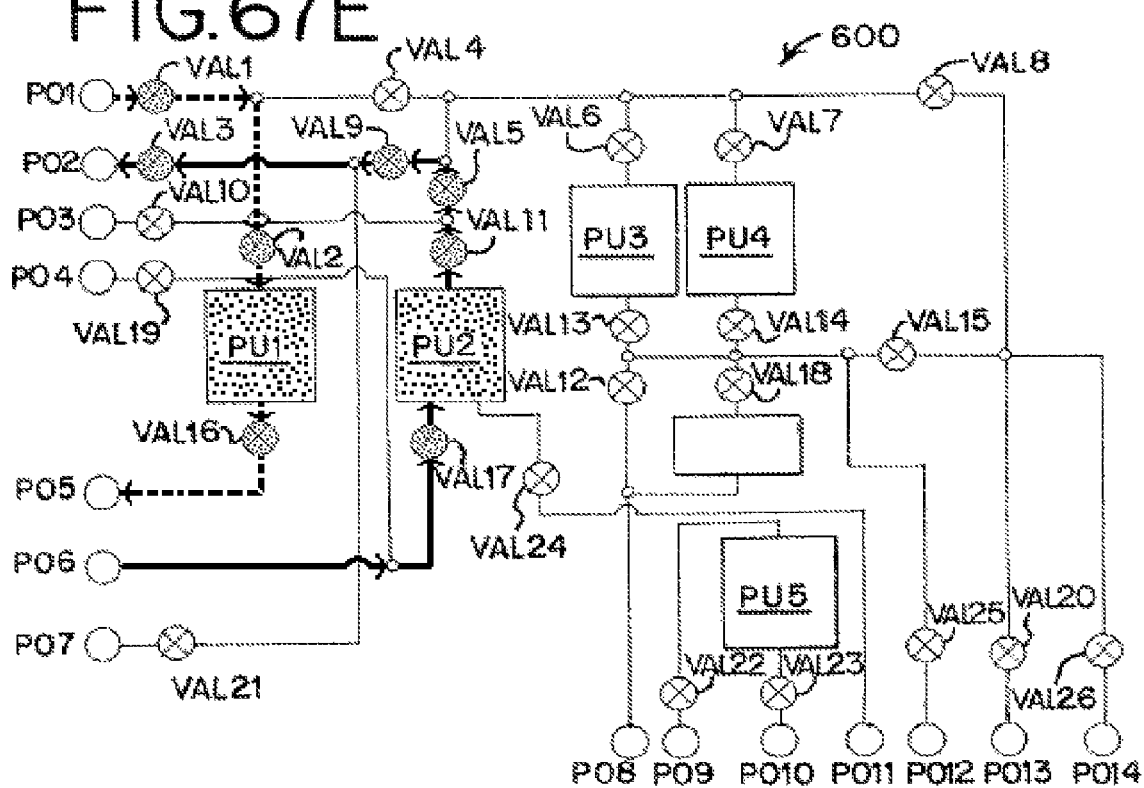

When the red blood cells have been conveyed from the chamber 500 to the red blood cell collection container 578, the valve VAL21 associated with the red blood cell outlet port PO7 is closed and valve VAL17 is opened, thereby effectively re-opening the plasma outlet port PO6, as shown in FIG. 67E. Air is still being pumped into the chamber 500 from the in-process container 594, and the air pumped through the chamber 500 is directed out the plasma outlet 542 and associated plasma outlet port PO6, thereby flushing any red blood cells in the plasma pump PU2 or outlet line to the red blood cell collection container 578 (via port PO2) and completing collection of the red blood cells. If the blood source is still attached to the system, saline from a saline container may be pumped to the blood source to flush any blood components in the return line (typically red blood cells) to the blood source, and then the blood source is finally disconnected from the system.

E. Flush Stage

The above final return and collection stage may be replaced by a conditional "flush" stage that is employed if the collection procedure is stopped prematurely or otherwise interrupted.

The "flush" stage operates to return fluid to the blood source. In one embodiment, the chamber spin speed is ramped down to zero while blood from the in-process container 594 is conveyed to the blood source and excess red blood cells and plasma are returned from their respective collection container, with the material being returned using the donor pumps PU3 and PU4 of the cassette 592. Most advantageously, the contents of the containers are returned to the blood source while bypassing the chamber 500, which can be achieved by properly programming the valves VAL1-VAL26 of the cassette 592. If the plasma or red blood cell level is below the target volume (e.g., if the procedure was stopped prematurely), the operator may be given the option to convey the entire contents of the associated collection container to the blood source. Alternatively, the system may attempt to salvage some of the components by retaining an amount less than the target volume, such as by retaining one unit of a component after an interruption prevents collection of the targeted two units.

Figure 68:
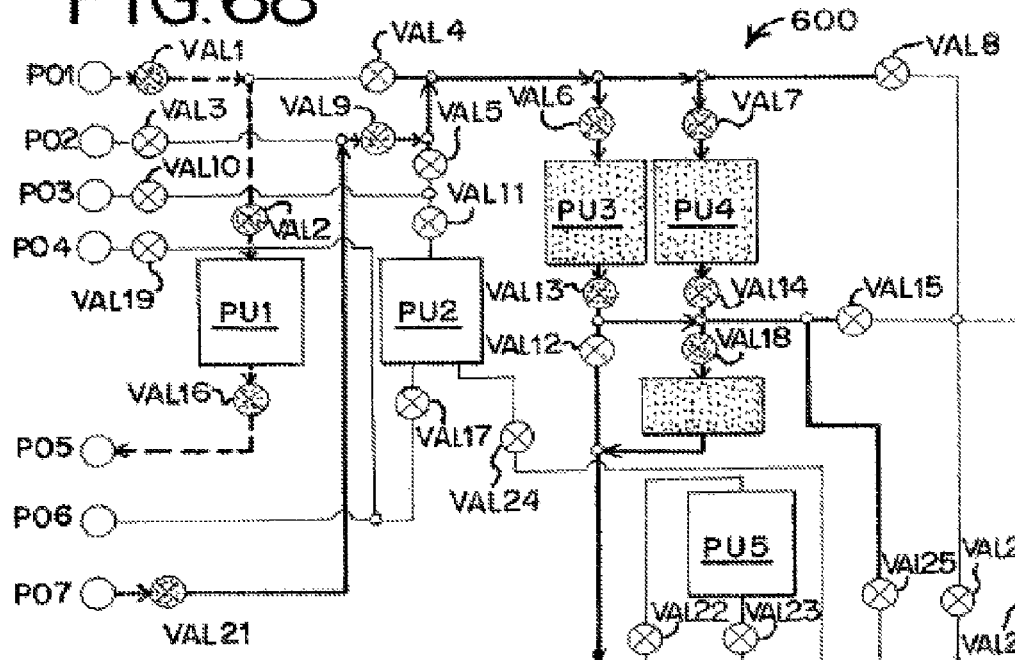
FIG. 68 is a schematic view of the blood processing circuit of FIG. 51, showing the programming of the cassette to carry out different fluid flow tasks in connection with flushing blood components from a processing chamber.

When the chamber 500 has stopped spinning, the system moves to an "air flush" phase to begin flushing any excess fluid remaining in the system to the blood source. In this phase, the in-process pump PU1 conveys air from the in-process container 594, through the cassette flow circuit 600 (in through port PO1 and out through port PO5), and into the chamber 500 (FIG. 68). The air forces some (about half) of the contents of the chamber 500 out of the red blood cell outlet 544, through the cassette flow circuit 600 (entering via port PO7), before the donor pumps PU3 and PU4 are operated to return the flushed contents to the blood source (via port PO8).

Next, the various pumps are stopped and the chamber spin speed is increased to a "flush chamber" speed of, for example, about 1000 RPM. When the spin speed has reached the target level, the above "air flush" phase (FIG. 68) is repeated to flush more of the contents of the chamber 500 to the blood source. This may be followed by a "saline return" stage, whereby the donor pumps PU3 and PU4 of the cassette 592 pump saline from a saline container (not illustrated) to the blood source, thereby flushing cells in the tubing back to the blood source.

Figure 69A:
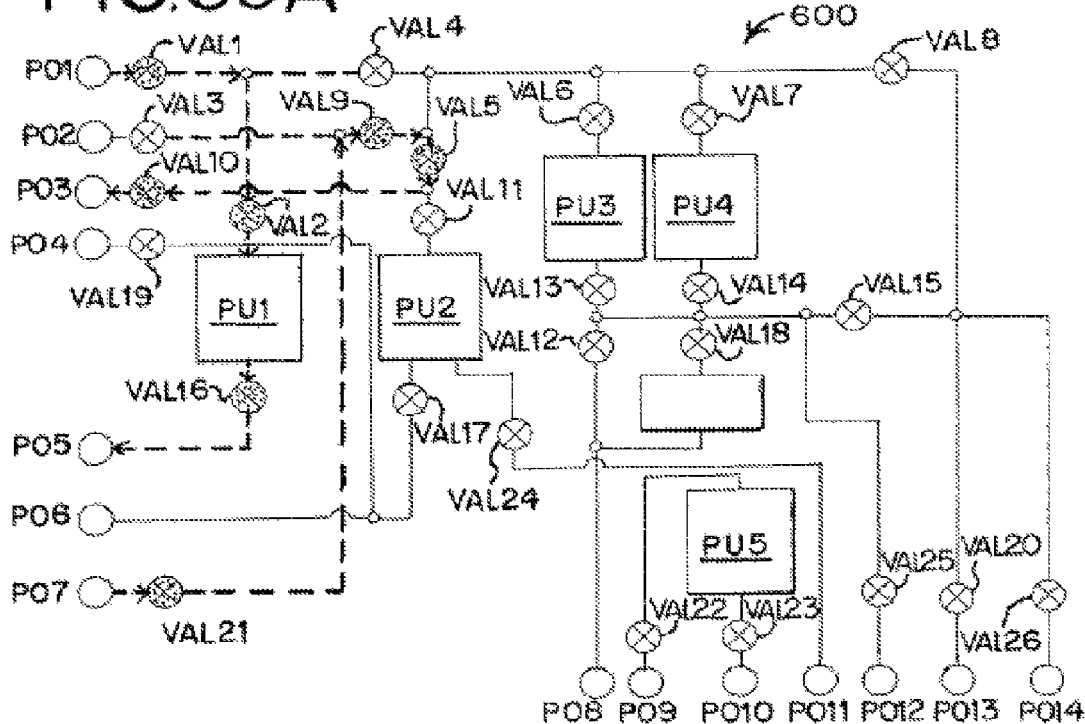
FIGS. 69A-69C are schematic views of the blood processing circuit of FIG. 51, showing the programming of the cassette to carry out different fluid flow tasks in connection with returning blood components from a processing chamber to a blood source.
Figure 69B:
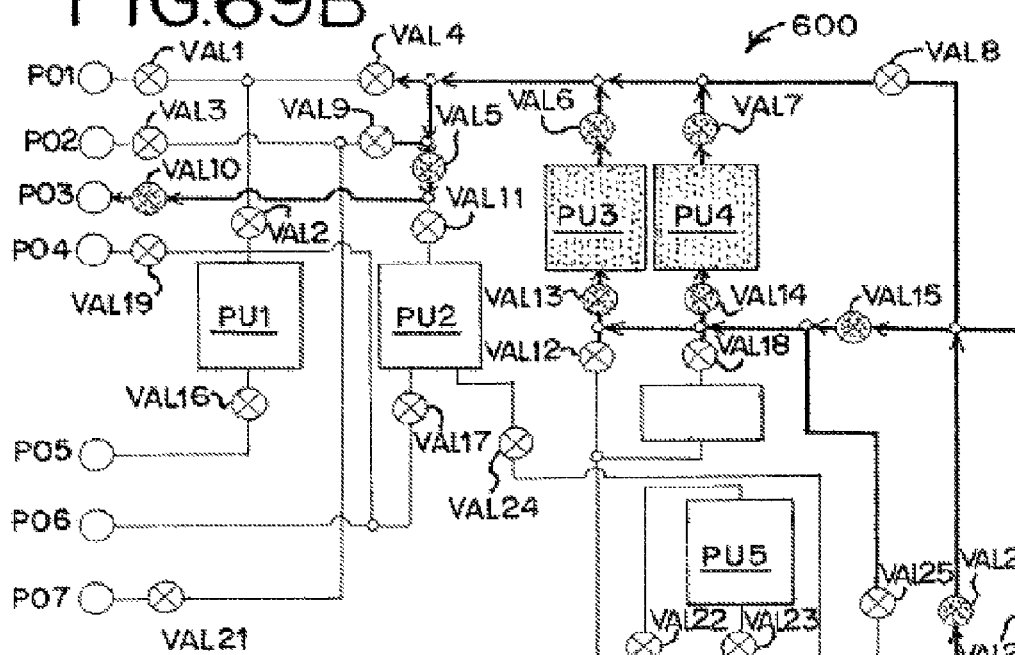
Figure 69C:
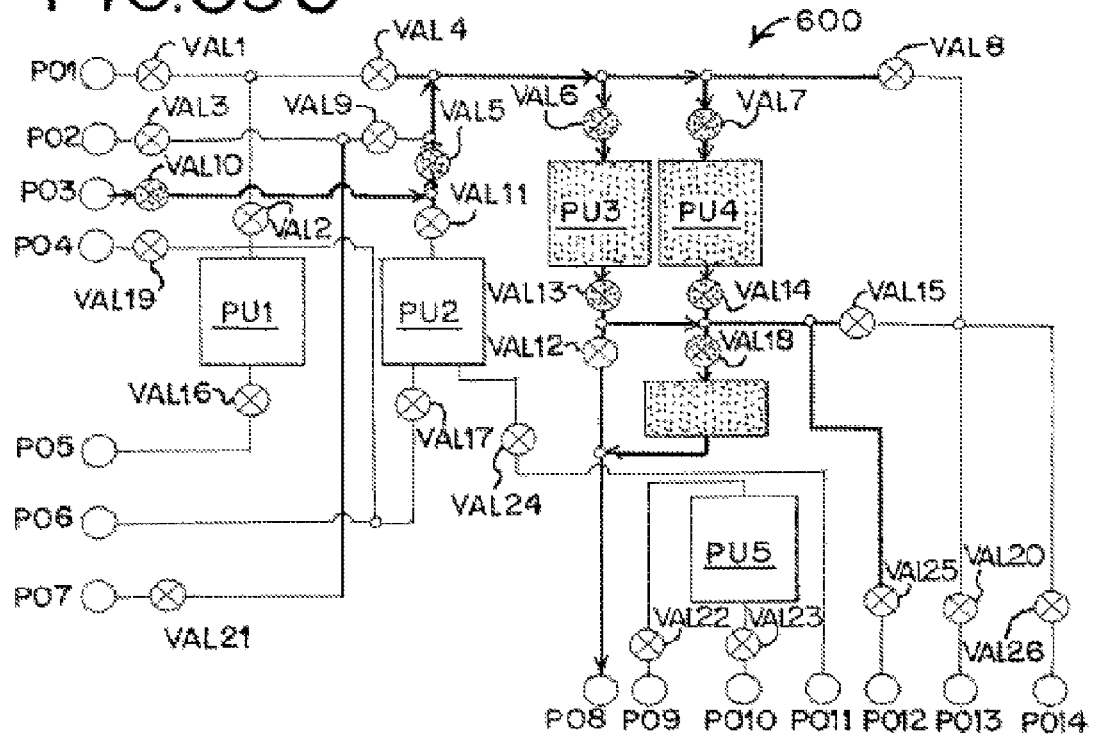

However, if the contents of the plasma collection container 576 were previously returned to the blood source (e.g., when the decision has been made to not salvage any of the collected plasma), the "saline return" stage may be preceded by an additional "air flush" phase. Such a third "air flush" phase is illustrated in FIGS. 69A-69C. First, the above "air flush" phase is repeated, with the contents of the chamber 500 being flushed through the cassette flow circuit 600 (in through port PO7 and out through port PO3) to the plasma collection container 576, rather than being returned to the blood source (FIG. 69A). This additional "air flush" phase substantially empties the chamber 500.

Next, saline is pumped from a saline container, through the cassette flow circuit 600 (in through port PO13 and out through port PO3), and into the plasma collection container 576 to prime the flow path to the plasma collection container 576 (FIG. 69B).

Finally, the contents of the plasma collection container 576 are pumped through the cassette flow circuit 600 (in through port PO3 and out through port PO8) and returned to the blood source (FIG. 69C). Thereafter, the blood source may be disconnected from the system.

F. Filtration Stage

If at least one of the collected components (i.e., plasma or packed red cells) is being retained, the final return and collection of the "flush" stage may be followed by a leukoreduction stage. As shown in FIG. 66, the disposable set 624 may include a red blood cell storage container 586 and at least one plasma storage container 630. Each storage container includes an associated in-line leukoreduction filter 590/626, such that the component is filtered as it is pumped from the collection container to the storage container by the cassette 592. The leukoreduction of the packed red cells and/or plasma can be understood with reference to the corresponding stage of the Red Blood Cell/Platelet/Plasma collection procedure, described above.

X. Other Blood Processing Functions

The many features of the present subject matter have been demonstrated by describing their use in separating whole blood into component parts for storage and blood component therapy. This is because the present subject matter is well adapted for use in carrying out these blood processing procedures. It should be appreciated, however, that the described features equally lend themselves to use in other blood processing procedures.

For example, the systems and methods described, which make use of a programmable cassette in association with a blood processing chamber, can be used for the purpose of washing or salvaging blood cells during surgery, or for the purpose of conducting therapeutic plasma exchange, or in any other procedure where blood is circulated in an extracorporeal path for treatment.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A method for conveying an amount of red blood cells from a red blood cell source and an amount of plasma from a plasma source to a living recipient comprising:
  conveying a volume of the red blood cells from the red blood cell source to the living recipient; and
  separately conveying a volume of the plasma from the plasma source to the living recipient without pooling said volumes of red blood cells and plasma, wherein said conveying a volume of the red blood cells to the living recipient and said separately conveying a volume of the plasma to the living recipient are alternated repeatedly during conveyance of said amounts of red blood cells and plasma.

2. The method of claim 1, wherein said conveying a volume of the red blood cells from the red blood cell source to the living recipient includes simultaneously conveying plasma into the plasma source and conveying red blood cells from a plurality of red blood cell sources to the living recipient, and wherein said separately conveying a volume of the plasma from the plasma source to the living recipient includes simultaneously conveying red blood cells into the red blood cell source and conveying plasma from a plurality of plasma sources to the living recipient.

3. The method of claim 1, further comprising
  calculating said amount of red blood cells to convey to the living recipient;
  calculating said amount of plasma to convey to the living recipient; and
  calculating an interleaving ratio based, at least in part, on the calculated amounts of red blood cells and plasma to convey to the living recipient, and wherein
  said conveying a volume of the red blood cells from the red blood cell source to the living recipient includes pumping red blood cells to the living recipient during a red blood cell pumping interval,
  said separately conveying a volume of the plasma from the plasma source to the living recipient includes pumping plasma to the living recipient during a plasma pumping interval, and
  the durations of said red blood cell and plasma pumping intervals are based, at least in part, on said interleaving ratio.

4. The method of claim 1, further comprising
  conveying blood from the living recipient into a separation device;
  operating said separation device to separate the blood into a layer containing red blood cells and a layer containing plasma;
  removing separated red blood cells from the separation device; and
  removing separated plasma from the separation device prior to said conveying a volume of the red blood cells from the red blood cell source to the living recipient and said separately conveying a volume of the plasma from the plasma source to the living recipient.

5. The method of claim 4, wherein said conveying a volume of the red blood cells from the red blood cell source to the living recipient and said separately conveying a volume of the plasma from the plasma source to the living recipient include simultaneously conveying blood into the separation device.

6. The method of claim 4, wherein said conveying a volume of the red blood cells from the red blood cell source to the living recipient includes simultaneously conveying separated plasma from the separation device into a plasma collection container and wherein said separately conveying a volume of the plasma from the plasma source to the living recipient includes simultaneously conveying separated red blood cells from the separation device into a red blood cell collection container.

7. The method of claim 4, wherein said removing separated red blood cells from the separation device includes conveying said separated red blood cells to a red blood cell collection container, and wherein said conveying a volume of the red blood cells from the red blood cell source to the living recipient includes conveying red blood cells from the red blood cell collection container and from the separation device to the living recipient.

8. The method of claim 4, wherein said removing separated plasma from the separation device includes conveying said separated plasma to a plasma collection container, and wherein said separately conveying a volume of the plasma from the plasma source to the living recipient includes conveying plasma from the plasma collection container and from the separation device to the living recipient.

9. The method of claim 1 employing a blood separation system comprising:
  a pump system; and
  a controller, wherein
    said conveying a volume of the red blood cells from the red blood cell source to the living recipient includes conveying said volume of the red blood cells from the red blood cell source to the living recipient using the pump system;
    said separately conveying a volume of the plasma from the plasma source to the living recipient includes conveying said volume of the plasma from the plasma source to the living recipient using the pump system; and
    the controller repeatedly alternates between actuating the pump system to convey the red blood cells and the plasma to the living recipient during conveyance of said amounts of red blood cells and plasma.

10. The method of claim 9, wherein the system further comprises a second red blood cell source and wherein the pump system simultaneously conveys plasma into the plasma source and red blood cells from the red blood cell source and/or the second red blood cell source to the living recipient.

11. The method of claim 9, wherein the system further comprises a second plasma source and the pump system simultaneously conveys red blood cells into the red blood cell source and plasma from the plasma source and/or the second plasma source to the living recipient.

12. The method of claim 9, wherein the controller
calculates said amount of red blood cells to convey to the living recipient;
calculates said amount of plasma to convey to the living recipient; and
calculates an interleaving ratio based, at least in part, on the calculated amounts of red blood cells and plasma to convey to the living recipient,
actuates the pump system to convey a volume of the red blood cells from the red blood cell source to the living recipient during a red blood cell pumping interval, and
actuates the pump system to convey a volume of the plasma from the plasma source to the living recipient during a plasma pumping interval, wherein the durations of said red blood cell and plasma pumping intervals are based, at least in part, on said interleaving ratio.

13. The method of claim 1 employing a blood separation system comprising:
a separation device adapted to separate blood into a layer containing red blood cells and a layer containing plasma;
a pump system; and
a controller, wherein
the pump system conveys blood into the separation device;
the separation device separates the blood therein into a layer containing red blood cells and a layer containing plasma;
the pump system removes separated red blood cells from the separation device;
the pump system removes separated plasma from the separation device;
the pump system implements said conveying a volume of the red blood cells from the red blood cell source to the living recipient by conveying a volume of said removed red blood cells to the living recipient;
the pump system implements said separately conveying a volume of the plasma from the plasma source to the living recipient by conveying a volume of said removed plasma to the living recipient; and
the controller repeatedly alternates between actuating the pump system to convey the red blood cells and the plasma to the living recipient during conveyance of said amounts of red blood cells and plasma.

14. The method of claim 13, wherein the pump system simultaneously conveys blood into the separation device while conveying red blood cells to the living recipient and simultaneously conveys blood into the separation device while conveying plasma to the living recipient.

15. The method of claim 13, wherein the system further comprises a plasma collection container, and wherein the pump system conveys plasma into the plasma collection container while conveying red blood cells to the living recipient.

16. The method of claim 13, wherein the system further comprises a red blood cell collection container containing red blood cells, and wherein the pump system conveys red blood cells from the red blood cell collection container and the separation device to the living recipient.

17. The method of claim 13, wherein the system further comprises a red blood cell collection container, and wherein the pump system conveys red blood cells into the red blood cell collection container while conveying plasma to the living recipient.

18. The method of claim 13, wherein the system further comprises a plasma collection container containing plasma, and wherein the pump system conveys plasma from the plasma collection container and the separation device to the living recipient.

19. The method of claim 13, wherein the controller
calculates said amount of red blood cells to convey to the living recipient;
calculates said amount of plasma to convey to the living recipient; and
calculates an interleaving ratio based, at least in part, on the calculated amounts of red blood cells and plasma to convey to the living recipient, wherein said volumes of red blood cells and plasma are based, at least in part, on said interleaving ratio.

20. The method of claim 19, wherein the pump system conveys red blood cells to the living recipient during a red blood cell pumping interval and conveys plasma to the living recipient during a plasma pumping interval, and wherein said volume of red blood cells is determined by the duration of the red blood cell pumping interval, said volume of plasma is determined by the duration of the plasma pumping interval, and the durations of said red blood cell and plasma pumping intervals are based, at least in part, on said interleaving ratio.

* * * * *